(12) United States Patent
Fujita et al.

(10) Patent No.: US 7,318,965 B2
(45) Date of Patent: *Jan. 15, 2008

(54) PERYLENE DERIVATIVE SYNTHESIS PROCESS, PERYLENE DERIVATIVE AND ORGANIC EL DEVICE

(75) Inventors: Tetsuji Fujita, Tokyo (JP); Kensuke Ara, Tokyo (JP); Tetsushi Inoue, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/189,248

(22) Filed: Jul. 5, 2002

(65) Prior Publication Data

US 2003/0137241 A1    Jul. 24, 2003

(30) Foreign Application Priority Data

Jul. 4, 2001    (JP) .............................. 2001-203926

(51) Int. Cl.
*H01L 51/50*    (2006.01)
*C07C 13/28*    (2006.01)

(52) U.S. Cl. ...................... 428/690; 428/917; 313/504; 313/506; 585/26

(58) Field of Classification Search ................ 428/690, 428/917; 313/504; 558/357; 562/405; 568/58, 568/774, 732; 570/143
See application file for complete search history.

(56) References Cited

U.S. PATENT DOCUMENTS

| 5,141,671 | A | * | 8/1992 | Bryan et al. ............ 252/301.16 |
| 6,004,685 | A | | 12/1999 | Antoniadis et al. .......... 428/690 |
| 6,613,454 | B2 | * | 9/2003 | Ara et al. .................... 428/690 |
| 6,689,493 | B2 | * | 2/2004 | Motomatsu et al. ........ 428/690 |

FOREIGN PATENT DOCUMENTS

| JP | 10-330295 | 12/1998 |
| JP | 2000-86549 | 3/2000 |
| JP | 2000-133457 | 5/2000 |

OTHER PUBLICATIONS

Debad et al., Journal of the American Chemical Society, (1996), vol. 118, pp. 2374-2379.*
English translation of Japanese Patent 10-330295, published Dec. 15, 1998.*
N. Miyaura, et al., Tetrahedron Letters 1979, 3437; N. Miyaura, A. Suzuki, Chem. Commun. 1979, 866, no month.

* cited by examiner

Primary Examiner—Dawn L. Garrett
(74) Attorney, Agent, or Firm—Oblon, Spivak, McClelland, Maier & Neustadt, P.C.

(57) ABSTRACT

The invention aims to provide a perylene derivative preparation process featuring satisfactory yields and improved preparation efficiency, a perylene derivative obtained by the process, and an organic EL device using the same.

2 Claims, 1 Drawing Sheet

PERYLENE DERIVATIVE SYNTHESIS PROCESS, PERYLENE DERIVATIVE AND ORGANIC EL DEVICE

BACKGROUND OF THE INVENTION

1. Field of the Invention

This invention relates to an organic electro-luminescent (EL) device, and more particularly, to a compound for use in a device of the type wherein an electric field is applied across a thin film of an organic compound to emit light.

2. Background Art

Organic electroluminescent (EL) devices include a thin film containing a luminescent organic compound interleaved between an electron injecting electrode and a hole injecting electrode. Electrons and holes are injected into the thin film where they are recombined to create excitons. Light is emitted by utilizing luminescence (phosphorescence or fluorescence) upon deactivation of excitons.

The organic EL devices are characterized by plane light emission at a high luminance of about 100 plus to about 10,000 plus cd/m² with a voltage of about 10 volts and light emission in a spectrum from blue to red color by a simple choice of the type of fluorescent material.

Doping is one technique for producing light emission of any desired color from organic EL devices. It was reported in Jpn. J. Appl. Phys., 10, 527 (1971) to change emission color from blue to green by doping anthracene crystals with a minor level of tetracene. With respect to organic thin film EL devices having a multilayer structure, it was reported in JP-A 63-264692 to incorporate in a host material having a light emitting function a minor amount of a fluorescent dye capable of emitting light different from that of the host material in response to light emission from the host material as a dopant to form a light emitting layer, thereby changing the color of light emission from green to orange or red.

With respect to long wavelength light emission of yellow to red, known light emitting materials or dopant materials include laser dyes capable of red oscillation (EPO 281381), compounds capable of exciplex emission (JP-A 2-255788), coumarin compounds (JP-A 3-792), dicyano-methylene compounds (JP-A 3-162481), thioxanthene compounds (JP-A 3-177486), mixtures of a conjugated polymer and an electron transporting compound (JP-A 6-73374), squalirium compounds (JP-A 6-93257), oxadiazole compounds (JP-A 6-136359), oxynate derivatives (JP-A 6-145146), and pyrene compounds (JP-A 6-240246).

It is reported in J. Am. Chem. Soc., 118, 2374-2379, 1996, that benzofluoranthene derivatives have a very high fluorescent quantum yield. JP-A 10-330295 and JP-A 11-233261 disclose organic EL devices having a light emitting layer in which a variety of host materials are doped with dibenzo[f,f']diindeno[1,2,3-cd:1',2',3'-lm]perylene derivatives derived from benzofluoranthene.

For the synthesis of perylene derivatives encompassing such benzofluoranthene derivatives, it is a common practice to conduct synthesis using starting reactants of the following formulae (A), (B) and (C) and catalysts.

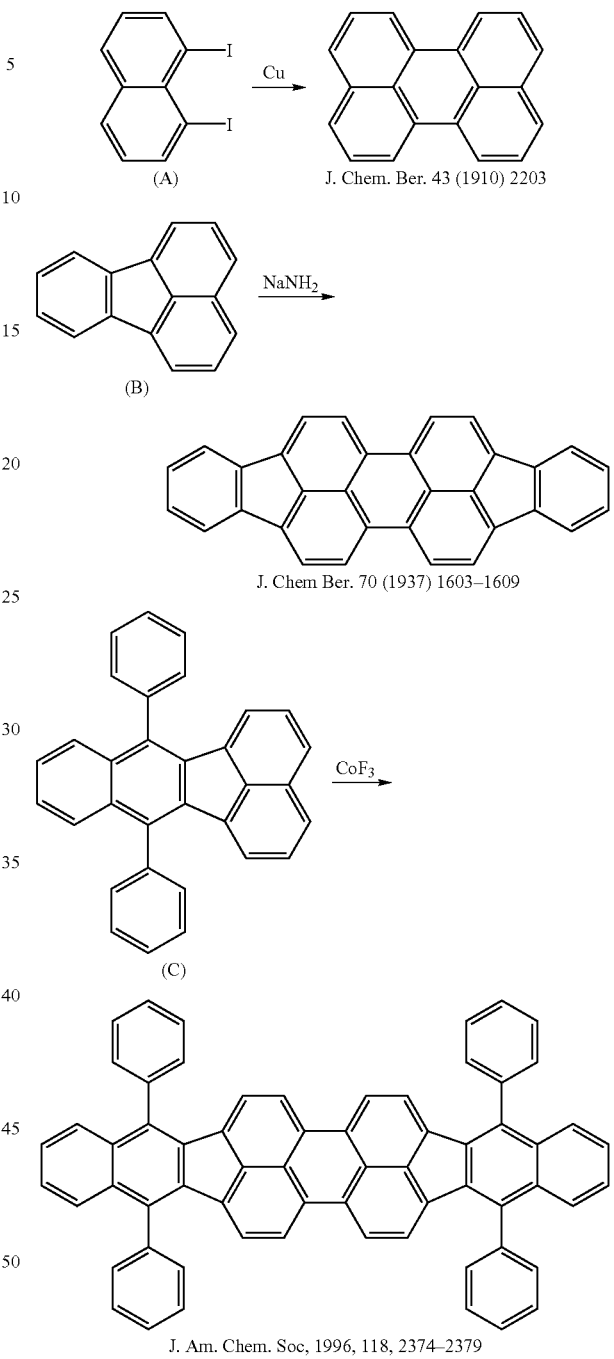

However, these prior art synthesis procedures suffer from the problem of very low efficiency because the end products are obtained in yields of at most 20%. Although the prior art synthesis procedures are relatively easy to synthesize an end product having symmetry, they encounter a problem when it is desired to obtain an end product having no symmetry. That is, since it is difficult to directly synthesize the asymmetric end product, the asymmetric end product must be separated from a variety of reaction products, which indicates a very low preparation efficiency and restricts the degree of freedom of compound design.

SUMMARY OF THE INVENTION

An object of the invention is to provide a perylene derivative synthesis process featuring a satisfactory yield and improved preparation efficiency, a perylene derivative obtained by the process, and an organic EL device using the same.

The above objects are achieved by the construction which is defined below as [1] to [22].

[1] A process for synthesizing a perylene derivative comprising the steps of halogenating a reactant and subjecting the halogenated reactant at its halogenated site to coupling reaction or the steps of using a halogenated reactant and a boronized reactant and subjecting them at their halogenated and boronized sites to Suzuki coupling reaction, or combining the foregoing steps.

[2] A process for synthesizing a perylene derivative according to [1] wherein a 1,8-dihalogenated naphthalene derivative of the following formula (1):

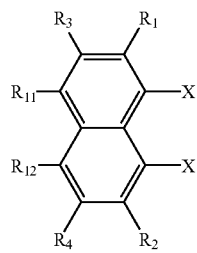

(1)

wherein X is Cl, Br or I, $R_1$ to $R_4$, $R_{11}$ and $R_{12}$ each are a hydrogen atom, a straight, branched or cyclic alkyl radical which may be substituted, a straight, branched or cyclic alkoxy radical which may be substituted, a straight, branched or cyclic alkylthio radical which may be substituted, a straight, branched or cyclic alkenyl radical which may be substituted, a straight, branched or cyclic alkenyloxy radical which may be substituted, a straight, branched or cyclic alkenylthio radical which may be substituted, a substituted or unsubstituted aralkyl radical, a substituted or unsubstituted aralkyloxy radical, a substituted or unsubstituted aralkylthio radical, a substituted or unsubstituted aryl radical, a substituted or unsubstituted aryloxy radical, a substituted or unsubstituted arylthio radical, a substituted or unsubstituted amino radical, a cyano radical, a hydroxyl radical, a —$COOM_1$ radical (wherein $M_1$ is a hydrogen atom, a straight, branched or cyclic alkyl radical which may be substituted, a straight, branched or cyclic alkenyl radical which may be substituted, a substituted or unsubstituted aralkyl radical, or a substituted or unsubstituted aryl radical), a —$COM_2$ radical (wherein $M_2$ is a hydrogen atom, a straight, branched or cyclic alkyl radical which may be substituted, a straight, branched or cyclic alkenyl radical which may be substituted, a substituted or unsubstituted aralkyl radical, a substituted or unsubstituted aryl radical, or an amino radical), or a —$OCOM_3$ radical (wherein $M_3$ is a straight, branched or cyclic alkyl radical which may be substituted, a straight, branched or cyclic alkenyl radical which may be substituted, a substituted or unsubstituted aralkyl radical, or a substituted or unsubstituted aryl radical), and at least two adjoining radicals selected from among $R_1$ to $R_4$, $R_{11}$ and $R_{12}$ may bond or fuse together to form a substituted or unsubstituted carbocyclic aliphatic ring, aromatic ring or fused aromatic ring with the carbon atoms on which they substitute, with the proviso that when the carbocyclic aliphatic ring, aromatic ring or fused aromatic ring has substituent radicals, the substituent radicals are the same as $R_1$ to $R_4$, $R_{11}$ and $R_{12}$, is subjected to coupling reaction to synthesize a perylene derivative of the following formula (2):

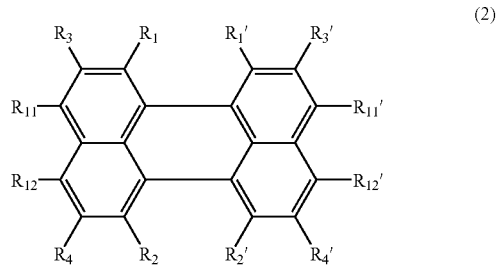

(2)

wherein $R_1'$ to $R_4'$, $R_{11}'$ and $R_{12}'$ are as defined for $R_1$ to $R_4$, $R_{11}$ and $R_{12}$ in formula (1), and $R_1$ to $R_4$, $R_{11}$ and $R_{12}$ and $R_1'$ to $R_4'$, $R_{11}'$ and $R_{12}'$ may be the same or different.

[3] A process for synthesizing a perylene derivative according to [1] wherein a 3,4-dihalogenated fluoranthene derivative of the following formula (3):

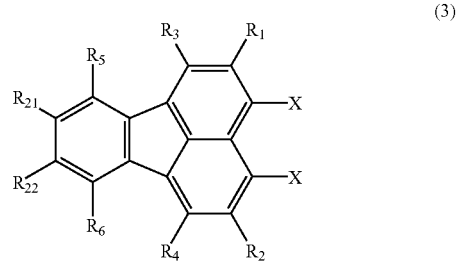

(3)

wherein X is Cl, Br or I, $R_1$ to $R_6$, $R_{21}$ and $R_{22}$ each are a hydrogen atom, a straight, branched or cyclic alkyl radical which may be substituted, a straight, branched or cyclic alkoxy radical which may be substituted, a straight, branched or cyclic alkylthio radical which may be substituted, a straight, branched or cyclic alkenyl radical which may be substituted, a straight, branched or cyclic alkenyloxy radical which may be substituted, a straight, branched or cyclic alkenylthio radical which may be substituted, a substituted or unsubstituted aralkyl radical, a substituted or unsubstituted aralkyloxy radical, a substituted or unsubstituted aralkylthio radical, a substituted or unsubstituted aryl radical, a substituted or unsubstituted aryloxy radical, a substituted or unsubstituted arylthio radical, a substituted or unsubstituted amino radical, a cyano radical, a hydroxyl radical, a —$COOM_1$ radical (wherein $M_1$ is a hydrogen atom, a straight, branched or cyclic alkyl radical which may be substituted, a straight, branched or cyclic alkenyl radical which may be substituted, a substituted or unsubstituted aralkyl radical, or a substituted or unsubstituted aryl radical), a —$COM_2$ radical (wherein $M_2$ is a hydrogen atom, a straight, branched or cyclic alkyl radical which may be substituted, a straight, branched or cyclic alkenyl radical which may be substituted, a substituted or unsubstituted aralkyl radical, a substituted or unsubstituted aryl radical, or an amino radical), or a —OCOM$_3$ radical (wherein M$_3$ is a straight, branched or cyclic alkyl radical which may be substituted, a straight, branched or cyclic alkenyl radical which may be substituted, a substituted or unsubstituted aralkyl radical, or a substituted or unsubstituted aryl radical), and at least two adjoining radicals selected from among R$_1$ to R$_6$, R$_{21}$ and R$_{22}$ may bond or fuse together to form a substituted or unsubstituted carbocyclic aliphatic ring, aromatic ring or fused aromatic ring with the carbon atoms on which they substitute, is subjected to coupling reaction to synthesize a perylene derivative of the following formula (4):

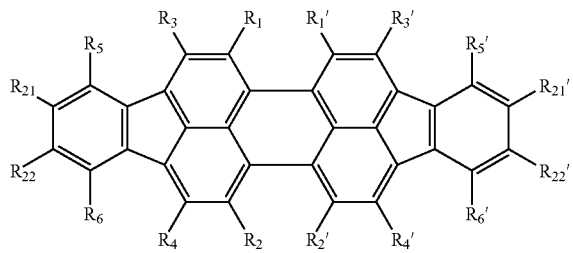

(4)

wherein R$_1'$ to R$_6'$, R$_{21}'$ and R$_{22}'$ are as defined for R$_1$ to R$_6$, R$_{21}$ and R$_{22}$ in formula (3), and R$_1$ to R$_6$, R$_{21}$ and R$_{22}$ and R$_1'$ to R$_6'$, R$_{21}'$ and R$_{22}'$ may be the same or different.

[4] A process for synthesizing a perylene derivative according to [1] wherein a 3,4-dihalogenated benzofluoranthene derivative of the following formula (5):

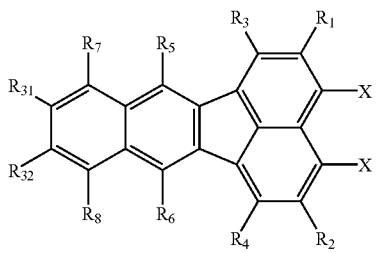

(5)

wherein X is Cl, Br or I, R$_1$ to R$_8$, R$_{31}$ and R$_{32}$ each are a hydrogen atom, a straight, branched or cyclic alkyl radical which may be substituted, a straight, branched or cyclic alkoxy radical which may be substituted, a straight, branched or cyclic alkylthio radical which may be substituted, a straight, branched or cyclic alkenyl radical which may be substituted, a straight, branched or cyclic alkenyloxy radical which may be substituted, a straight, branched or cyclic alkenylthio radical which may be substituted, a substituted or unsubstituted aralkyl radical, a substituted or unsubstituted aralkyloxy radical, a substituted or unsubstituted aralkylthio radical, a substituted or unsubstituted aryl radical, a substituted or unsubstituted aryloxy radical, a substituted or unsubstituted arylthio radical, a substituted or unsubstituted amino radical, a cyano radical, a hydroxyl radical, a —COOM$_1$ radical (wherein M$_1$ is a hydrogen atom, a straight, branched or cyclic alkyl radical which may be substituted, a straight, branched or cyclic alkenyl radical which may be substituted, a substituted or unsubstituted aralkyl radical, or a substituted or unsubstituted aryl radical), a —COM$_2$ radical (wherein M$_2$ is a hydrogen atom, a straight, branched or cyclic alkyl radical which may be substituted, a straight, branched or cyclic alkenyl radical which may be substituted, a substituted or unsubstituted aralkyl radical, a substituted or unsubstituted aryl radical, or an amino radical), or a —OCOM$_3$ radical (wherein M$_3$ is a straight, branched or cyclic alkyl radical which may be substituted, a straight, branched or cyclic alkenyl radical which may be substituted, a substituted or unsubstituted aralkyl radical, or a substituted or unsubstituted aryl radical), and at least two adjoining radicals selected from among R$_1$ to R$_8$, R$_{31}$ and R$_{32}$ may bond or fuse together to form a substituted or unsubstituted carbocyclic aliphatic ring, aromatic ring or fused aromatic ring with the carbon atoms on which they substitute, is subjected to coupling reaction to synthesize a perylene derivative of the following formula (6):

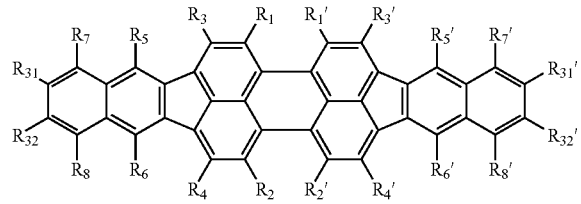

(6)

wherein R$_1'$ to R$_8'$, R$_{31}'$ and R$_{32}'$ are as defined for R$_1$ to R$_8$, R$_{31}$ and R$_{32}$ in formula (5), and R$_1$ to R$_8$, R$_{31}$ and R$_{32}$ and R$_1'$ to R$_8'$, R$_{31}'$ and R$_{32}'$ may be the same or different.

[5] A process for synthesizing a perylene derivative according to any one of [1] to [4] wherein the coupling reaction is homo- or hetero-coupling reaction using a catalyst.

[6] A process for synthesizing a perylene derivative according to [5] wherein the catalyst is a metal catalyst, metal complex catalyst or metal compound (exclusive of metallic copper) containing at least one element selected from among the Group VIII elements of Ni, Pd, Pt, Fe, Co, Ru and Rh, and the Group IB elements.

[7] A process for synthesizing a perylene derivative according to [5] or [6] wherein said catalyst is NiCl$_2$(dppe), NiCl$_2$(dppp) or Ni(COD)$_2$.

[8] A process for synthesizing a perylene derivative according to [1], including the steps of using a 1,8-dihalogenated naphthalene derivative of formula (1) as set forth in above [2] and a naphthyl-1,8-diboronic acid derivative of the following formula (7):

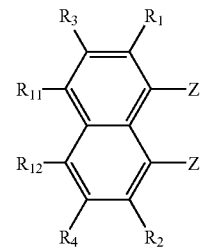

(7)

wherein Z is a boronic acid derivative, and $R_1$ to $R_4$, $R_{11}$ and $R_{12}$ are as defined in formula (1), and subjecting them to Suzuki coupling reaction, thereby synthesizing a perylene derivative of formula (2).

[9] A process for synthesizing a perylene derivative according to [1], including the steps of using a 3,4-dihalogenated fluoranthene derivative of formula (3) as set forth in above [3] and a fluorantheno-1,8-diboronic acid derivative of the following formula (8):

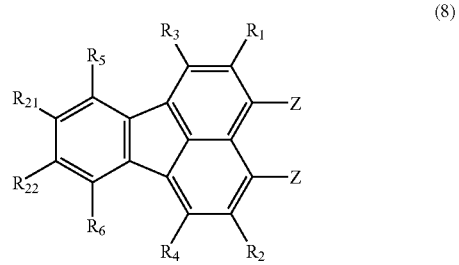

(8)

wherein Z is a boronic acid derivative, and $R_1$ to $R_6$, $R_{21}$ and $R_{22}$ are as defined in formula (3), and subjecting them to Suzuki coupling reaction, thereby synthesizing a perylene derivative of formula (4).

[10] A process for synthesizing a perylene derivative according to [1], including the steps of using a 3,4-dihalogenated benzofluoranthene derivative of formula (5) as set forth in above [4] and a dibenzofluorantheno-1,8-diboronic acid derivative of the following formula (9):

(9)

wherein Z is a boronic acid derivative, and $R_1$ to $R_8$, $R_{31}$ and $R_{32}$ are as defined in formula (5), and subjecting them to Suzuki coupling reaction, thereby synthesizing a perylene derivative of formula (6).

[11] A process for synthesizing a perylene derivative according to [1], including the steps of using a naphthalene derivative of the following formula (13):

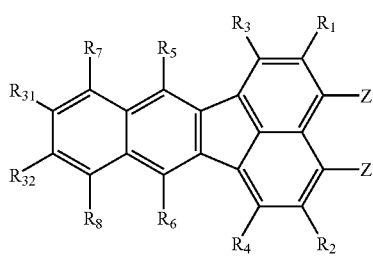

(13)

wherein X is Cl, Br or I, Z is a boronic acid derivative, and $R_1$ to $R_4$, $R_{11}$ and $R_{12}$ are as defined in formula (1), and subjecting it to Suzuki coupling reaction, thereby synthesizing a perylene derivative.

[12] A perylene derivative synthesizing process comprising the steps of using a fluoranthene derivative of the following formula (14):

(14)

wherein X is Cl, Br or I, Z is a boronic acid derivative, and $R_1$ to $R_6$, $R_{21}$ and $R_{22}$ are as defined in formula (3), and subjecting it to Suzuki coupling reaction, thereby synthesizing a perylene derivative.

[13] A perylene derivative synthesizing process comprising the steps of using a benzofluoranthene derivative of the following formula (15):

(15)

wherein X is Cl, Br or I, Z is a boronic acid derivative, and $R_1$ to $R_8$, $R_{31}$ and $R_{32}$ are as defined in formula (5), and subjecting it to Suzuki coupling reaction, thereby synthesizing a perylene derivative.

[14] A perylene derivative synthesizing process wherein at least one derivative selected from among 1,8-dihalogenated naphthalene derivatives of formula (1), 3,4-dihalogenated fluoranthene derivatives of formula (3), and 3,4-dihalogenated benzofluoranthene derivatives of formula (5) as set forth in [2] to [4] is used to form an asymmetric compound.

[15] A perylene derivative synthesizing process according to [14] wherein the asymmetric compound is a compound of the following formula (10):

(10)

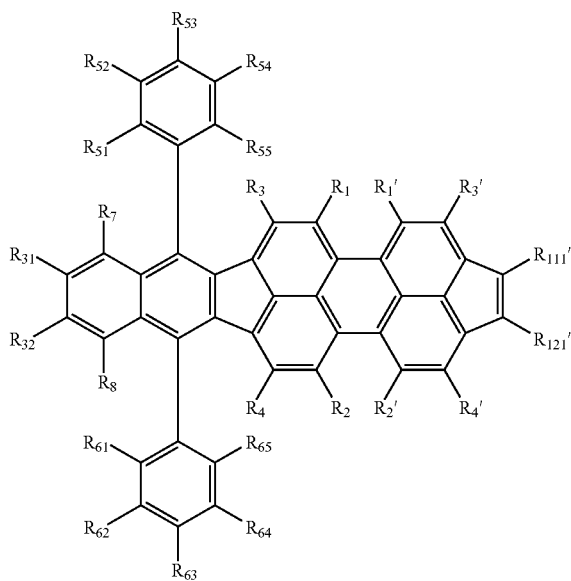

wherein $R_{51}$ to $R_{55}$, $R_{61}$ to $R_{65}$, $R_{111}$ and $R_{121}$ are as defined for $R_1$ to $R_4$, $R_{11}$ and $R_{12}$ in formula (1).

[16] A perylene derivative synthesizing process according to [1] wherein the perylene derivative is a compound of the following formula (11):

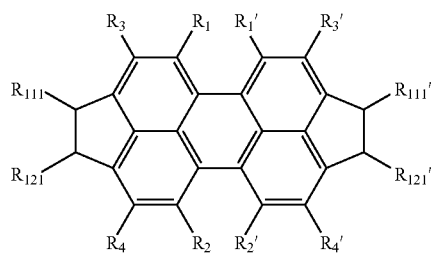

(11)

wherein $R_{111}$, $R_{121}$, $R_{111}'$ and $R_{121}'$ are as defined for $R_1$ to $R_4$, $R_{11}$, and $R_{12}$ in formula (1).

[17] A perylene derivative synthesizing process according to [1] wherein said perylene derivative is a compound of the following formula (12):

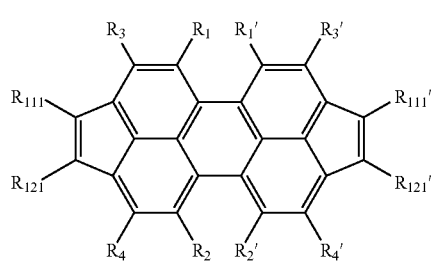

(12)

wherein $R_{111}$, $R_{121}$, $R_{111}'$ and $R_{121}'$ are as defined for $R_1$ to $R_4$, $R_{11}$ and $R_{12}$ in formula (1).

[18] A perylene derivative synthesizing process according to any one of [4] to [7] wherein at least $R_5$ and $R_6$ and/or $R_5'$ and $R_6'$ are different.

[19] A process for synthesizing a perylene derivative according to [1] wherein
a bisnaphthalene derivative of the following formula (16):

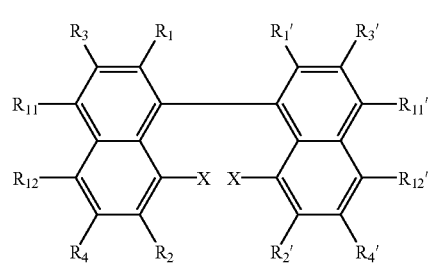

(16)

wherein X is Cl, Br or I, $R_1$ to $R_4$, $R_{11}$ and $R_{12}$ each are a hydrogen atom, a straight, branched or cyclic alkyl radical which may be substituted, a straight, branched or cyclic alkoxy radical which may be substituted, a straight, branched or cyclic alkylthio radical which may be substituted, a straight, branched or cyclic alkenyl radical which may be substituted, a straight, branched or cyclic alkenyloxy radical which may be substituted, a straight, branched or cyclic alkenylthio radical which may be substituted, a substituted or unsubstituted aralkyl radical, a substituted or unsubstituted aralkyloxy radical, a substituted or unsubstituted aralkylthio radical, a substituted or unsubstituted aryl radical, a substituted or unsubstituted aryloxy radical, a substituted or unsubstituted arylthio radical, a substituted or unsubstituted amino radical, a cyano radical, a hydroxyl radical, a —COOM$_1$ radical (wherein M$_1$ is a hydrogen atom, a straight, branched or cyclic alkyl radical which may be substituted, a straight, branched or cyclic alkenyl radical which may be substituted, a substituted or unsubstituted aralkyl radical, or a substituted or unsubstituted aryl radical), a —COM$_2$ radical (wherein M$_2$ is a hydrogen atom, a straight, branched or cyclic alkyl radical which may be substituted, a straight, branched or cyclic alkenyl radical which may be substituted, a substituted or unsubstituted aralkyl radical, a substituted or unsubstituted aryl radical, or an amino radical), or a —OCOM$_3$ radical (wherein M$_3$ is a straight, branched or cyclic alkyl radical which may be substituted, a straight, branched or cyclic alkenyl radical which may be substituted, a substituted or unsubstituted aralkyl radical, or a substituted or unsubstituted aryl radical), and at least two adjoining radicals selected from among $R_1$ to $R_4$, $R_{11}$ and $R_{12}$ may bond or fuse together to form a substituted or unsubstituted carbocyclic aliphatic ring, aromatic ring or fused aromatic ring with the carbon atoms on which they substitute, with the proviso that when the carbocyclic aliphatic ring, aromatic ring or fused aromatic ring has substituent radicals, the substituent radicals are the same as $R_1$ to $R_4$, $R_{11}$ and $R_{12}$, is subjected to coupling reaction to synthesize a perylene derivative of the following formula (2):

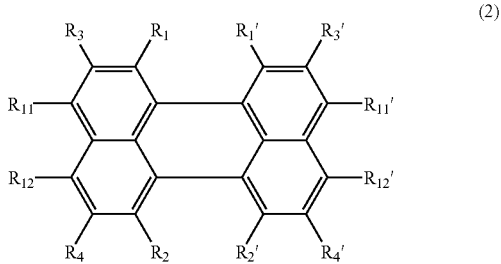

(2)

wherein $R_1'$ to $R_4'$, $R_{11}'$ and $R_{12}'$ are as defined for $R_1$ to $R_4$, $R_{11}$ and $R_{12}$ in formula (1), and $R_1$ to $R_4$, $R_{11}$ and $R_{12}$ and $R_1'$ to $R_4'$, $R_{11}'$ and $R_{12}'$ may be the same or different.

[20] An organic EL device comprising the perylene derivative obtained by the process of any one of [1] to [19].

[21] An organic EL device according to [20] wherein the perylene derivative is contained in a light emitting layer.

[22] A perylene derivative having a structure of the following formula (10):

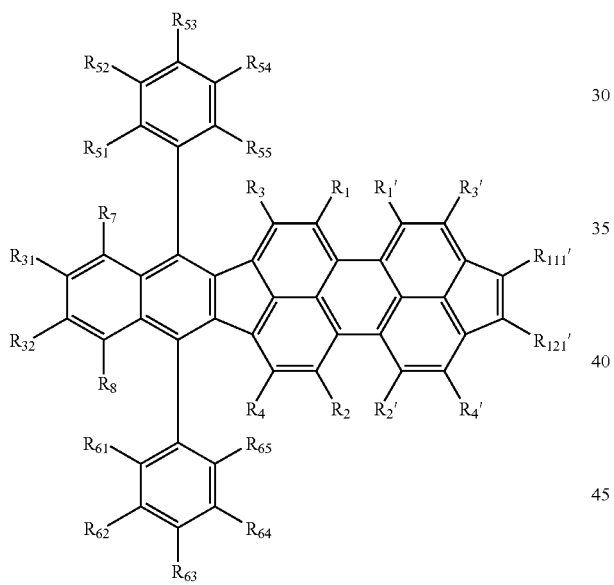

(10)

wherein $R_{51}$ to $R_{55}$, $R_{61}$ to $R_{65}$, $R_{111}$ and $R_{121}$ are as defined for $R_1$ to $R_4$, $R_{11}$ and $R_{12}$ in formula (1).

DESCRIPTION OF THE PREFERRED EMBODIMENTS

Figure 1:
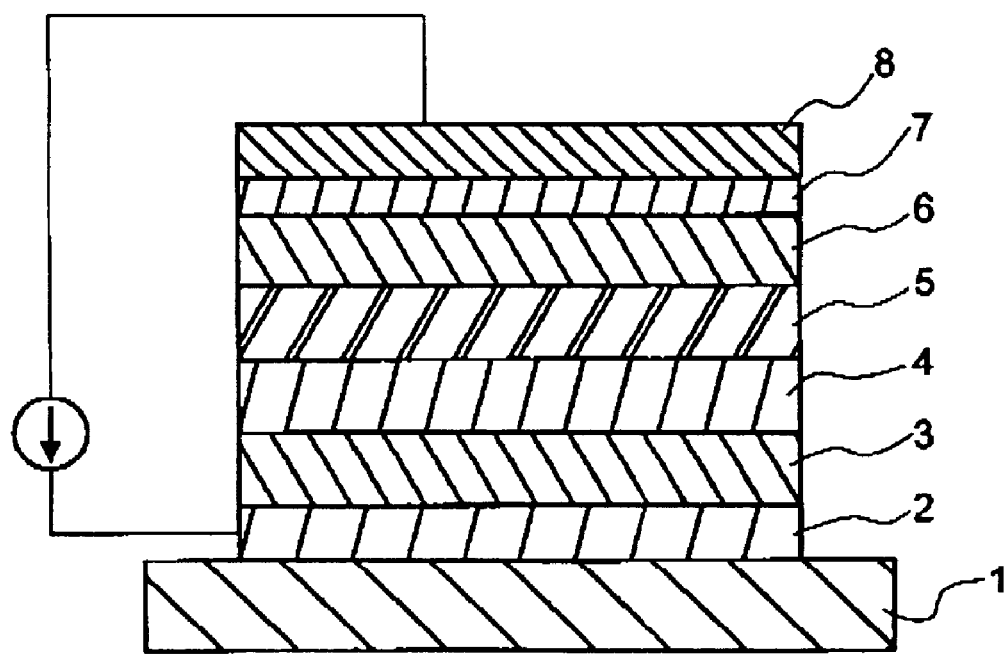
FIG. 1 is a schematic cross-sectional view showing the basic construction of an organic EL device according to the invention.

The synthesis process of the invention is to produce a perylene derivative by halogenating a starting reactant and subjecting the halogenated reactant to coupling reaction or using a halogenated reactant and a boronized reactant and subjecting them to Suzuki coupling reaction, or combining the foregoing routes.

By these synthesis processes, the desired perylene derivatives can be quite efficiently synthesized and their yield can reach 90% or higher. Even asymmetric end products can be synthesized in a relatively simple manner by either of the synthesis processes or a combination thereof, indicating a spreading of the use and application of asymmetric compounds which found little use in the prior art.

Now the respective embodiments of the inventive synthesis process are described in detail.

First Embodiment: Halogenation Followed by Coupling

The first embodiment of the inventive synthesis process involves halogenating a 1,8-dihalogenated naphthalene derivative of the following formula (1), and subjecting it to coupling reaction for thereby synthesizing a perylene derivative of the following formula (2).

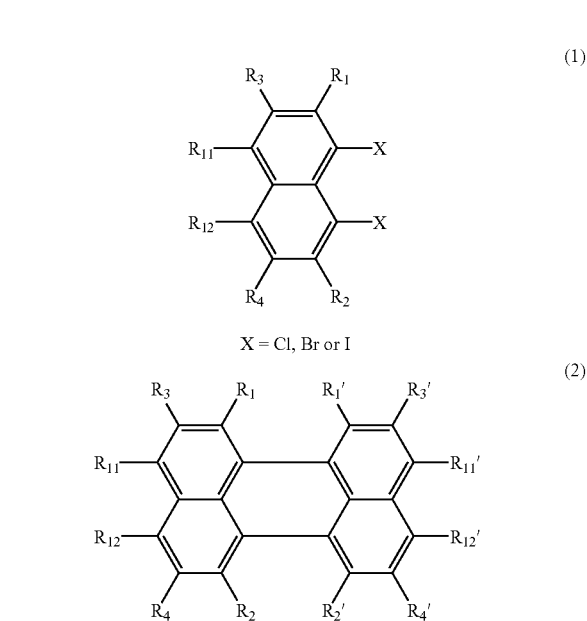

Referring to formula (1), $R_1$ to $R_4$, $R_{11}$ and $R_{12}$ each are a hydrogen atom, a straight, branched or cyclic alkyl radical which may be substituted, a straight, branched or cyclic alkoxy radical which may be substituted, a straight, branched or cyclic alkylthio radical which may be substituted, a straight, branched or cyclic alkenyl radical which may be substituted, a straight, branched or cyclic alkenyloxy radical which may be substituted, a straight, branched or cyclic alkenylthio radical which may be substituted, a substituted or unsubstituted aralkyl radical, a substituted or unsubstituted aralkyloxy radical, a substituted or unsubstituted aralkylthio radical, a substituted or unsubstituted aryl radical, a substituted or unsubstituted aryloxy radical, a substituted or unsubstituted arylthio radical, a substituted or unsubstituted amino radical, a cyano radical, a hydroxyl radical, a —COOM$_1$ radical (wherein M$_1$ is a hydrogen atom, a straight, branched or cyclic alkyl radical which may be substituted, a straight, branched or cyclic alkenyl radical which may be substituted, a substituted or unsubstituted aralkyl radical, or a substituted or unsubstituted aryl radical), a —COM$_2$ radical (wherein M$_2$ is a hydrogen atom, a straight, branched or cyclic alkyl radical which may be substituted, a straight, branched or cyclic alkenyl radical which may be substituted, a substituted or unsubstituted aralkyl radical, a substituted or unsubstituted aryl radical, or an amino radical), or a —OCOM$_3$ radical (wherein M$_3$ is a straight, branched or cyclic alkyl radical which may be substituted, a straight, branched or cyclic alkenyl radical which may be substituted, a substituted or unsubstituted aralkyl radical, or a substituted or unsubstituted aryl radical), and at least two adjoining radicals selected from among R$_1$ to R$_4$, R$_{11}$ and R$_{12}$ may bond or fuse together to form a substituted or unsubstituted carbocyclic aliphatic ring, aromatic ring or fused aromatic ring with the carbon atoms on which they substitute, with the proviso that when the carbocyclic aliphatic ring, aromatic ring or fused aromatic ring has substituent radicals, the substituent radicals are the same as R$_1$ to R$_4$, R$_{11}$ and R$_{12}$.

As used herein, the term "aryl radical" represents carbocyclic aromatic radicals such as phenyl and naphthyl and heterocyclic aromatic radicals such as furyl, thienyl and pyridyl.

In formula (1), when R$_1$ to R$_4$, R$_{11}$ and R$_{12}$ stand for straight, branched or cyclic alkyl radicals, straight, branched or cyclic alkoxy radicals, straight, branched or cyclic alkylthio radicals, straight, branched or cyclic alkenyl radicals, straight, branched or cyclic alkenyloxy radicals, and straight, branched or cyclic alkenylthio radicals, these radicals may have substituent radicals. For example, they may be mono- or multi-substituted with halogen atoms, aryl radicals of 4 to 20 carbon atoms, alkoxy radicals of 1 to 20 carbon atoms, alkoxyalkoxy radicals of 2 to 20 carbon atoms, alkenyloxy radicals of 2 to 20 carbon atoms, aralkyloxy radicals of 4 to 20 carbon atoms, aralkyloxyalkoxy radicals of 5 to 20 carbon atoms, aryloxy radicals of 3 to 20 carbon atoms, aryloxyalkoxy radicals of 4 to 20 carbon atoms, arylalkenyl radicals 5 to 20 carbon atoms, aralkylalkenyl radicals of 6 to 20 carbon atoms, alkylthio radicals of 1 to 20 carbon atoms, alkoxyalkylthio radicals of 2 to 20 carbon atoms, alkylthioalkylthio radicals of 2 to 20 carbon atoms, alkenylthio radicals of 2 to 20 carbon atoms, aralkylthio radicals of 4 to 20 carbon atoms, aralkyloxyalkylthio radicals of 5 to 20 carbon atoms, aralkylthioalkylthio radicals of 5 to 20 carbon atoms, arylthio radicals of 3 to 20 carbon atoms, aryloxyalkylthio radicals of 4 to 20 carbon atoms, arylthioalkylthio radicals of 4 to 20 carbon atoms, heteroatom-containing cyclic alkyl radicals of 4 to 20 carbon atoms, and halogen atoms. The aryl radicals in these substituent radicals may have further substituted thereon alkyl radicals of 1 to 10 carbon atoms, alkoxy radicals of 1 to 10 carbon atoms, aryl radicals of 3 to 10 carbon atoms, aralkyl radicals of 4 to 10 carbon atoms or the like.

In formula (1), when R$_1$ to R$_4$, R$_{11}$ and R$_{12}$ stand for aralkyl, aralkyloxy, aralkylthio, aryl, aryloxy and arylthio radicals, the aryl radicals in these radicals may have substituent radicals. For example, they may be mono- or multi-substituted with alkyl radicals of 1 to 20 carbon atoms, alkenyl radicals of 2 to 20 carbon atoms, aralkyl radicals of 4 to 20 carbon atoms, aryl radicals of 3 to 20 carbon atoms, alkoxy radicals of 1 to 20 carbon atoms, alkoxyalkyl radicals of 2 to 20 carbon atoms, alkoxyalkyloxy radicals of 2 to 20 carbon atoms, alkenyloxy radicals of 2 to 20 carbon atoms, alkenyloxyalkyl radicals of 3 to 20 carbon atoms, alkenyloxyalkyloxy radicals of 3 to 20 carbon atoms, aralkyloxy radicals of 4 to 20 carbon atoms, aralkyloxyalkyl radicals of 5 to 20 carbon atoms, aralkyloxyalkyloxy radicals of 5 to 20 carbon atoms, aryloxy radicals of 3 to 20 carbon atoms, aryloxyalkyl radicals of 4 to 20 carbon atoms, aryloxyalkyloxy radicals of 4 to 20 carbon atoms, alkylcarbonyl radicals of 2 to 20 carbon atoms, alkenylcarbonyl radicals of 3 to 20 carbon atoms, aralkylcarbonyl radicals of 5 to 20 carbon atoms, arylcarbonyl radicals of 4 to 20 carbon atoms, alkoxycarbonyl radicals of 2 to 20 carbon atoms, alkenyloxycarbonyl radicals of 3 to 20 carbon atoms, aralkyloxycarbonyl radicals of 5 to 20 carbon atoms, aryloxycarbonyl radicals of 4 to 20 carbon atoms, alkylcarbonyloxy radicals of 2 to 20 carbon atoms, alkenylcarbonyloxy radicals of 3 to 20 carbon atoms, aralkylcarbonyloxy radicals of 5 to 20 carbon atoms, arylcarbonyloxy radicals of 4 to 20 carbon atoms, alkylthio radicals of 1 to 20 carbon atoms, aralkylthio radicals of 4 to 20 carbon atoms, arylthio radicals of 3 to 20 carbon atoms, nitro radicals, cyano radicals, formyl radicals, halogen atoms, halogenated alkyl radicals, hydroxyl radicals, amino radicals, N-mono-substituted amino radicals of 1 to 20 carbon atoms, and N,N-di-substituted amino radicals of 2 to 40 carbon atoms.

The aryl radicals in these substituent radicals may have further substituted thereon alkyl radicals of 1 to 10 carbon atoms, alkoxy radicals of 1 to 10 carbon atoms, aryl radicals of 6 to 10 carbon atoms, aralkyl radicals of 7 to 10 carbon atoms or the like.

In formula (1), the amino radicals represented by R$_1$ to R$_4$, R$_{11}$ and R$_{12}$ may have substituent radicals. For example, they may be mono- or di-substituted with alkyl radicals of 1 to 20 carbon atoms, aralkyl radicals of 4 to 20 carbon atoms, or aryl radicals of 3 to 20 carbon atoms.

Further, two adjoining radicals selected from among R$_1$ to R$_4$, R$_{11}$ and R$_{12}$ may bond or fuse together to form a substituted or unsubstituted carbocyclic aliphatic ring, aromatic ring or fused aromatic ring with the carbon atoms on which they substitute.

The naphthalene derivative of formula (1) is halogenated with halogen atoms X which are bonded at the 1, 8 positions thereof. The halogen atoms X used for halogenation may be Cl, Br or I, with Br being especially preferred. Two halogen atoms X may be the same or different although they are often the same.

After the compound of formula (1) is modified with halogen atoms, it is subjected to coupling reaction. The coupling reaction may be conducted by various well-known techniques although the present invention favors a technique of conducting homo- or hetero-coupling reaction using a catalyst.

The catalyst used in the reaction is not critical as long as it can promote the coupling reaction, and various catalysts may be used. Examples of the catalyst include metal catalysts, metal complex catalysts and metal compounds containing one or more elements selected from among the Group VIII elements of Ni, Pd, Pt, Fe, Co, Ru, Rh, etc. and the Group IB elements. Alternatively, use may also be made of metal complex catalysts and metal compounds of Cu.

Of these, nickel catalysts are preferred. Nickel catalysts in various forms may be used. Examples of suitable nickel catalysts include [1,2-bis(diphenyl-phosphino)ethane] dichloronickel (II), referred to as NiCl$_2$(dppe), [1,3-bis(diphenylphosphino)propane]-dichloronickel (II), referred to as NiCl$_2$(dppp), tetrakis(triphenylphosphine)nickel, and nickel-bis-(1,5-cyclooctadiene), referred to as Ni(COD)$_2$. In this regard, the use of NiCl$_2$(dppe) or NiCl$_2$(dppp) brings about Grignard coupling.

Coupling reaction conditions differ with a particular reactant and catalyst. In one exemplary reaction using Ni(COD)$_2$, a halogenated naphthalene derivative is dissolved in a solvent such as DMF, in a concentration of about 0.01 to 10 mol/l, especially about 0.05 to 1 mol/l, with which the nickel catalyst (Ni(COD)$_2$ etc.) is admixed. The amount of the catalyst used is usually an equimolar amount, but the amount preferred in consideration of the probable event where part of the catalyst loses activity is in the range from equimolar to 1.5 times, and especially equimolar to 1.2 times on a molar basis. Also, if necessary, cyclooctadiene (COD) is added in an amount of 2 to 10 moles per mole of the halogenated naphthalene, and bipyridine is added in an amount of 0.5 to 5 moles per mole of the halogenated derivative. Under such conditions, reaction is effected at a temperature of 50 to 100° C., especially 60 to 90° C. for about 0.5 to 12 hours, especially about 1 to 5 hours. At the end of reaction, aqueous hydrochloric acid, methanol or the like is added whereby the end compound is precipitated for recovery.

Through coupling reaction on the halogenated naphthalene, preferably in the presence of the catalyst, a compound of formula (2) is produced.

In formula (2), $R_1'$ to $R_4'$, $R_{11}'$ and $R_{12}'$ are as defined for $R_1$ to $R_4$, $R_{11}$ and $R_{12}$ in formula (1). $R_1$ to $R_4$, $R_{11}$ and $R_{12}$ and $R_1'$ to $R_4'$, $R_{11}'$ and $R_{12}'$ may be the same or different, and preferably different.

In accordance with the first embodiment of the invention involving coupling reaction on the halogenated naphthalene, preferably in the presence of the catalyst, it is possible to synthesize a perylene derivative of the following formula (4) by subjecting a 3,4-dihalogenated fluoranthene derivative of the following formula (3) to coupling reaction.

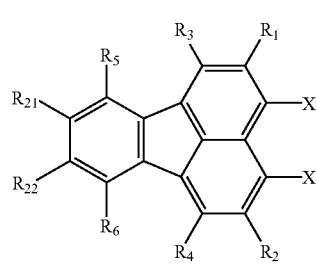

X = Cl, Br or I

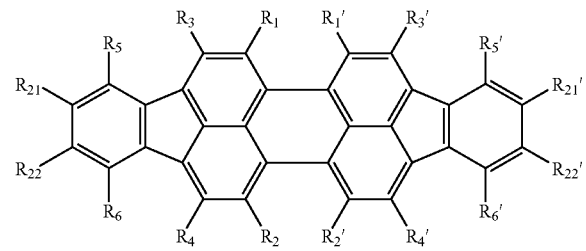

In formula (3), $R_1$ to $R_6$, $R_{21}$ and $R_{22}$ have the same meaning as $R_1$ to $R_4$, $R_{11}$ and $R_{12}$ in formula (1), and their preferred range is also the same.

Namely, $R_1$ to $R_6$, $R_{21}$ and $R_{22}$ in formula (3) each are a hydrogen atom, a straight, branched or cyclic alkyl radical which may be substituted, a straight, branched or cyclic alkoxy radical which may be substituted, a straight, branched or cyclic alkylthio radical which may be substituted, a straight, branched or cyclic alkenyl radical which may be substituted, a straight, branched or cyclic alkenyloxy radical which may be substituted, a straight, branched or cyclic alkenylthio radical which may be substituted, a substituted or unsubstituted aralkyl radical, a substituted or unsubstituted aralkyloxy radical, a substituted or unsubstituted aralkylthio radical, a substituted or unsubstituted aryl radical, a substituted or unsubstituted aryloxy radical, a substituted or unsubstituted arylthio radical, a substituted or unsubstituted amino radical, a cyano radical, a hydroxyl radical, a —$COOM_1$ radical (wherein $M_1$ is a hydrogen atom, a straight, branched or cyclic alkyl radical which may be substituted, a straight, branched or cyclic alkenyl radical which may be substituted, a substituted or unsubstituted aralkyl radical, or a substituted or unsubstituted aryl radical), a —$COM_2$ radical (wherein $M_2$ is a hydrogen atom, a straight, branched or cyclic alkyl radical which may be substituted, a straight, branched or cyclic alkenyl radical which may be substituted, a substituted or unsubstituted aralkyl radical, a substituted or unsubstituted aryl radical, or an amino radical), or a —$OCOM_3$ radical (wherein $M_3$ is a straight, branched or cyclic alkyl radical which may be substituted, a straight, branched or cyclic alkenyl radical which may be substituted, a substituted or unsubstituted aralkyl radical, or a substituted or unsubstituted aryl radical), and at least two adjoining radicals selected from among $R_1$ to $R_6$, $R_{21}$ and $R_{22}$ may bond or fuse together to form a substituted or unsubstituted carbocyclic aliphatic ring, aromatic ring or fused aromatic ring with the carbon atoms on which they substitute.

In formula (4), $R_1'$ to $R_6'$, $R_{21}'$ and $R_{22}'$ are as defined for $R_1$ to $R_6$, $R_{21}$ and $R_{22}$ in formula (3). $R_1$ to $R_6$, $R_{21}$ and $R_{22}$ and $R_1'$ to $R_6'$, $R_{21}'$ and $R_{22}'$ may be the same or different.

In accordance with the first embodiment of the invention involving coupling reaction on the halogenated naphthalene, preferably in the presence of the catalyst, it is possible to synthesize a perylene derivative of the following formula (6) by subjecting a 3,4-dihalogenated benzofluoranthene derivative of the following formula (5) to coupling reaction.

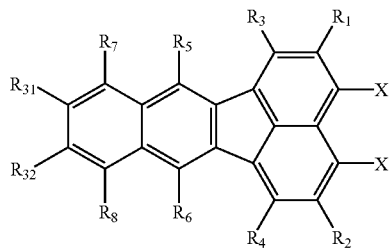

X = Cl, Br or I

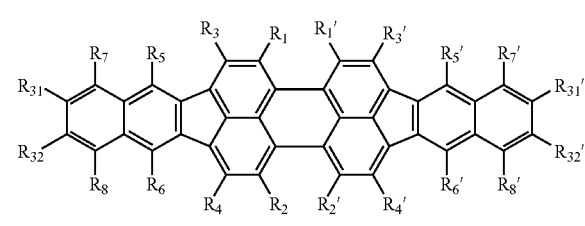

In formula (5), $R_1$ to $R_8$, $R_{31}$ and $R_{32}$ have the same meaning as $R_1$ to $R_4$, $R_{11}$ and $R_{12}$ in formula (1), and their preferred range is also the same.

Namely, $R_1$ to $R_8$, $R_{31}$ and $R_{32}$ in formula (5) each are a hydrogen atom, a straight, branched or cyclic alkyl radical which may be substituted, a straight, branched or cyclic alkoxy radical which may be substituted, a straight, branched or cyclic alkylthio radical which may be substituted, a straight, branched or cyclic alkenyl radical which may be substituted, a straight, branched or cyclic alkenyloxy radical which may be substituted, a straight, branched or cyclic alkenylthio radical which may be substituted, a substituted or unsubstituted aralkyl radical, a substituted or unsubstituted aralkyloxy radical, a substituted or unsubstituted aralkylthio radical, a substituted or unsubstituted aryl radical, a substituted or unsubstituted aryloxy radical, a substituted or unsubstituted arylthio radical, a substituted or unsubstituted amino radical, a cyano radical, a hydroxyl radical, a —COOM$_1$ radical (wherein M$_1$ is a hydrogen atom, a straight, branched or cyclic alkyl radical which may be substituted, a straight, branched or cyclic alkenyl radical which may be substituted, a substituted or unsubstituted aralkyl radical, or a substituted or unsubstituted aryl radical), a —COM$_2$ radical (wherein M$_2$ is a hydrogen atom, a straight, branched or cyclic alkyl radical which may be substituted, a straight, branched or cyclic alkenyl radical which may be substituted, a substituted or unsubstituted aralkyl radical, a substituted or unsubstituted aryl radical, or an amino radical), or a —OCOM$_3$ radical (wherein M$_3$ is a straight, branched or cyclic alkyl radical which may be substituted, a straight, branched or cyclic alkenyl radical which may be substituted, a substituted or unsubstituted aralkyl radical, or a substituted or unsubstituted aryl radical), and at least two adjoining radicals selected from among $R_1$ to $R_8$, $R_{31}$ and $R_{32}$ may bond or fuse together to form a substituted or unsubstituted carbocyclic aliphatic ring, aromatic ring or fused aromatic ring with the carbon atoms on which they substitute.

In formula (6), $R_1'$ to $R_8'$, $R_{31}'$ and $R_{32}'$ are as defined for $R_1$ to $R_8$, $R_{31}$ and $R_{32}$ in formula (5). $R_1$ to $R_8$, $R_{31}$ and $R_{32}$ and $R_1'$ to $R_8'$, $R_{31}'$ and $R_{32}'$ may be the same or different.

It is preferred that at least $R_5$ and $R_6$ and/or $R_5'$ and $R_6'$ in formula (6) be different. The provision of such an asymmetric structure can yield materials capable of emitting orange to red light when used as the organic EL material, and electron or hole transporting materials.

Also the asymmetric structure can improve solubility which makes material purification easy, retard decomposition upon sublimation purification, and improve fluorescence. The asymmetric structure can further reduce the interaction between similar or distinct molecules, improve the fluorescent luminance of EL devices, and suppress the concentration quenching which increases the margin as the EL dopant and improves the freedom of design.

Moreover, an asymmetric compound can be obtained by using one or more derivatives selected from among 1,8-dihalogenated naphthalene derivatives of formula (1), 3,4-dihalogenated fluoranthene derivatives of formula (3), and 3,4-dihalogenated benzofluoranthene derivatives of formula (5) and effecting hetero-coupling reaction.

In this way, asymmetric compounds can be readily and freely produced using the inventive process, while the yield of the desired compounds is dramatically increased.

These asymmetric compounds are not critical as long as they are obtainable from a combination of formulae (1), (3) and (5). In particular, compounds of the following formula (10) are preferred in the practice of the invention.

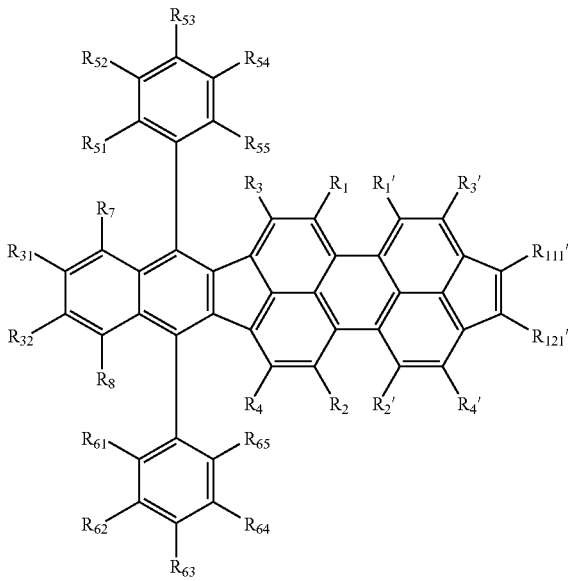

(10)

In formula (10), $R_{51}$ to $R_{55}$, $R_{61}$ to $R_{65}$, $R_{111}'$ and $R_{121}'$ are as defined for $R_1$ to $R_4$, $R_{11}$ and $R_{12}$ in formula (1). Also, $R_1$ to $R_4$, $R_1'$ to $R_4'$, $R_{31}$ and $R_{32}$ are as defined in formula (1).

The provision of such a structure can yield materials capable of emitting orange to green light when used as the organic EL material, and electron or hole transporting materials.

It is further preferred that the perylene derivative of formula (2) be a compound of the following formula (11).

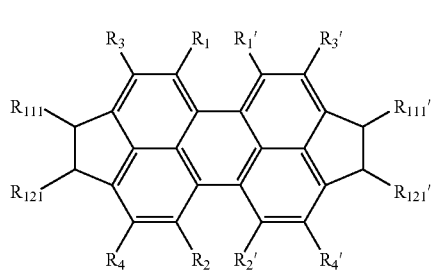

(11)

In formula (11), $R_{111}$, $R_{121}$, $R_{111}'$ and $R_{121}'$ are as defined for $R_1$ to $R_4$, $R_{11}$ and $R_{12}$ in formula (1).

Alternatively, the perylene derivative of formula (2) may be a compound of the following formula (12).

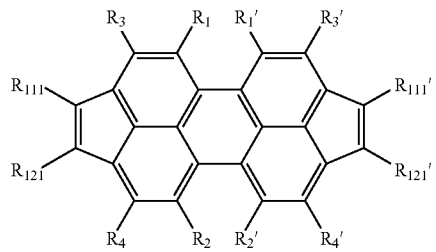
(12)

In formula (12), $R_{111}$, $R_{121}$, $R_{111}'$ and $R_{121}'$ are as defined for $R_1$ to $R_4$, $R_{11}$ and $R_{12}$ in formula (1).

The compound of formula (11) and the compound of formula (12) are not definitely distinguishable. Depending on the conjugated electron state, it may take the form of either the compound of formula (11) or the compound of formula (12). However, the invention favors the form of the compound of formula (12).

Shown below are the synthesis schemes of these synthesis processes.

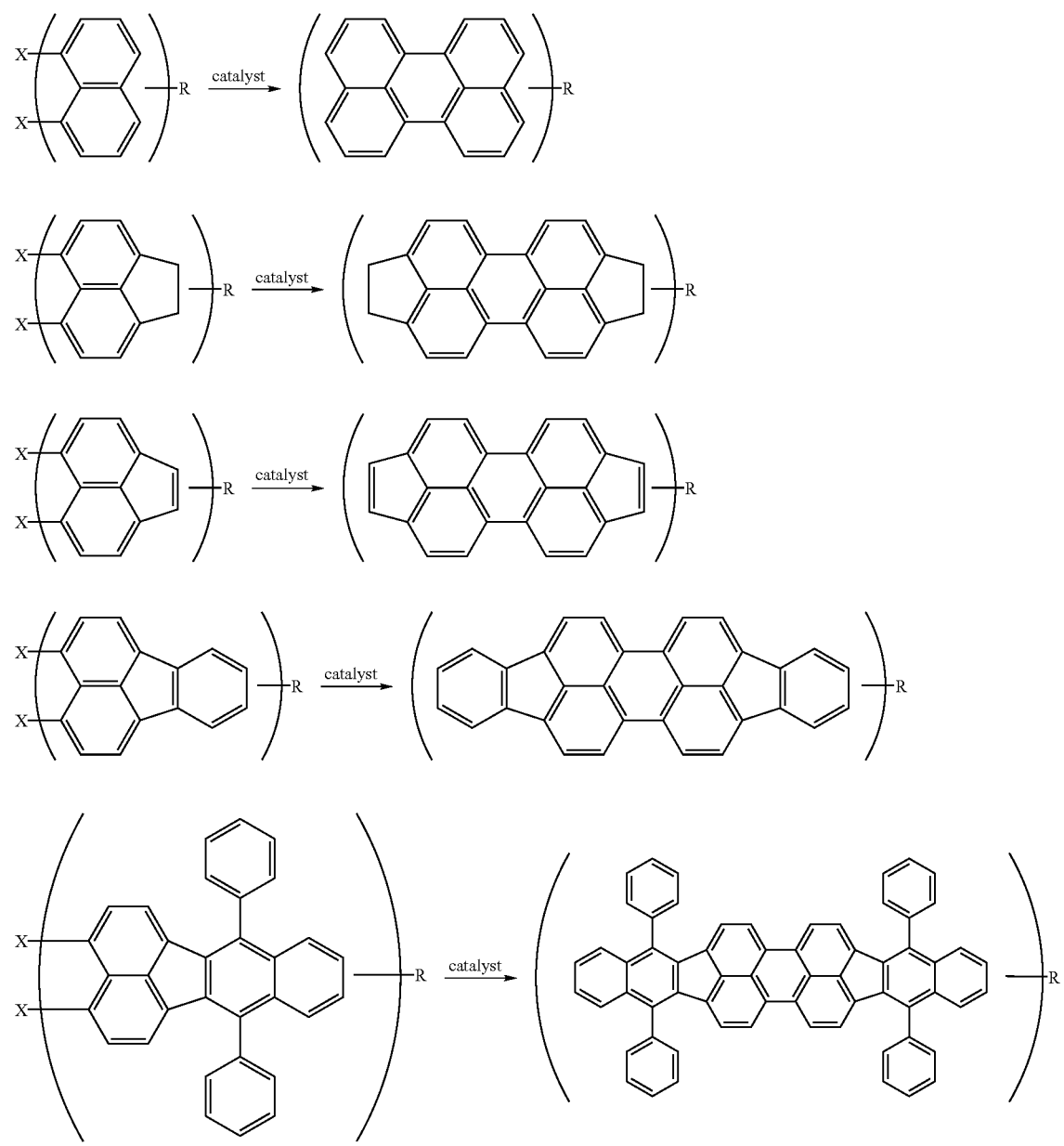

x = Cl, Br, I      catalyst for example: Ni(COD)2
COD
bipyridine

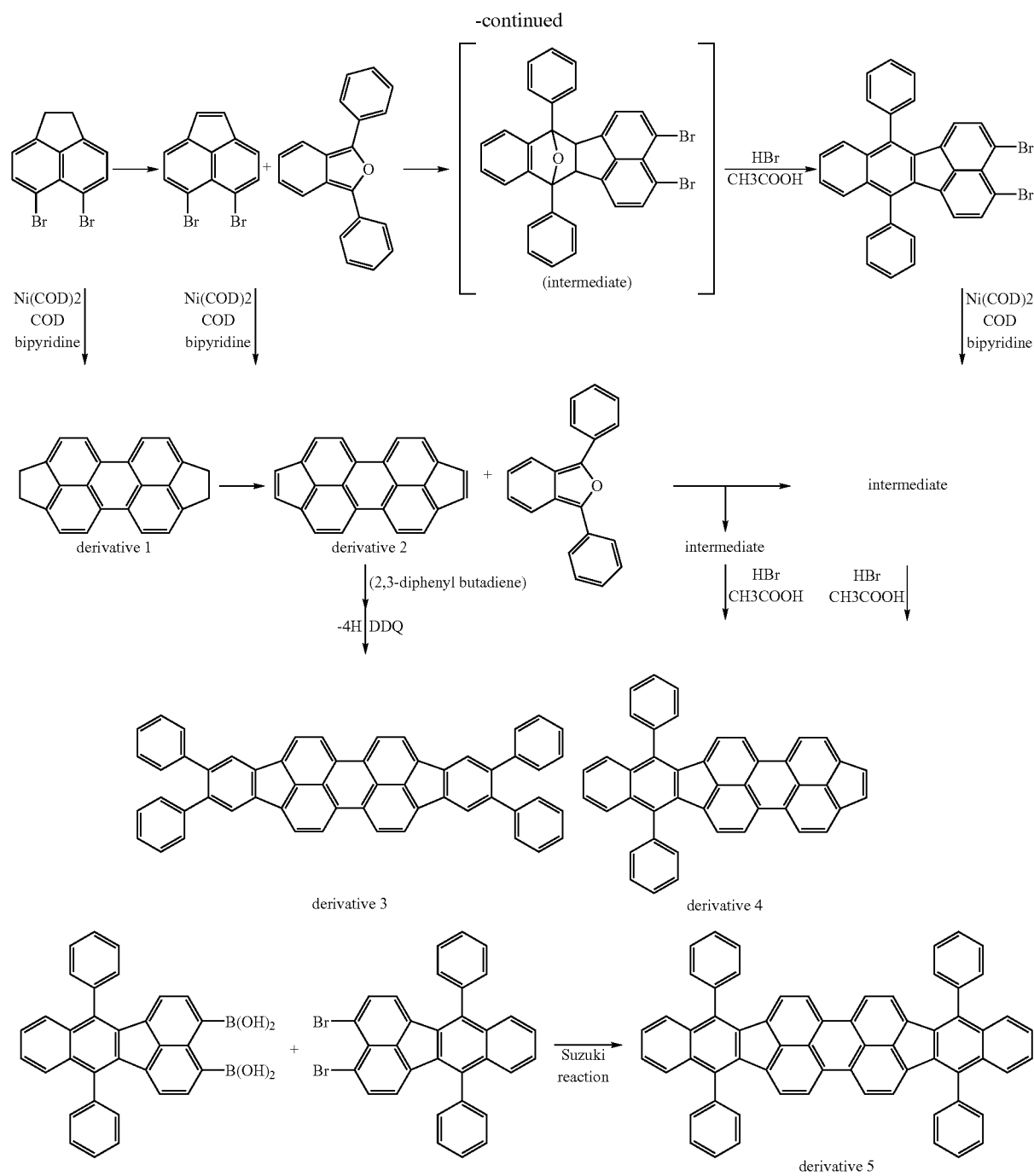
for example.
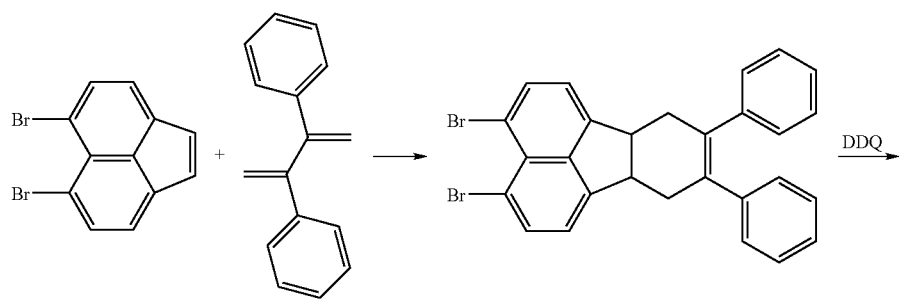

-continued
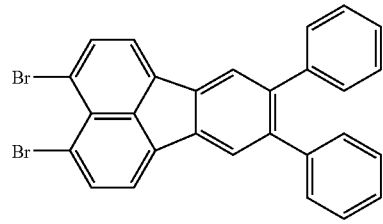
for example.
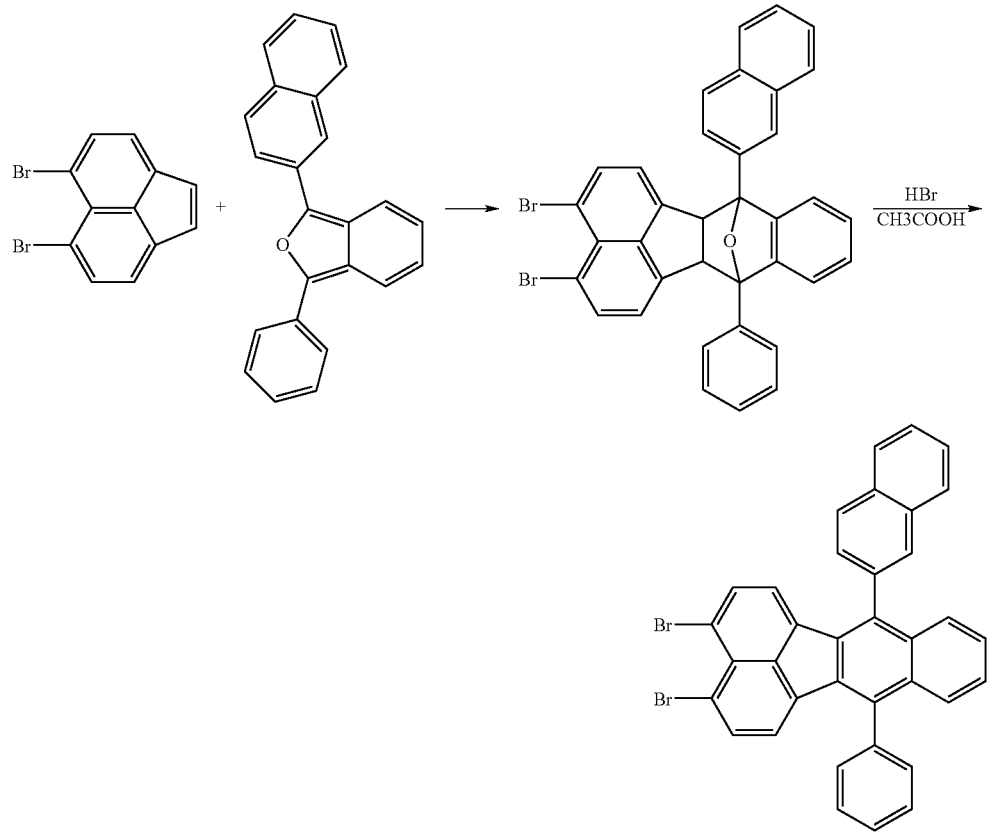
for example.
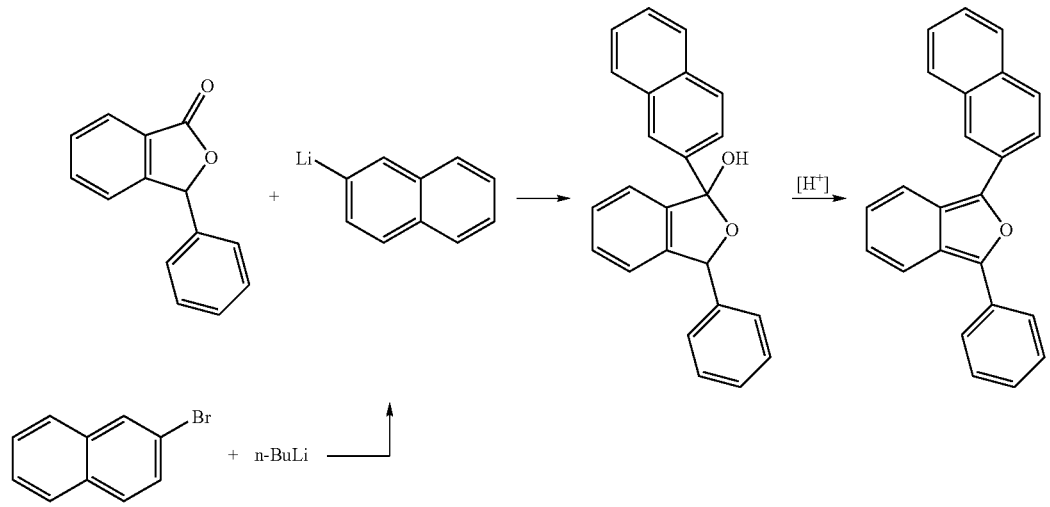

Second Embodiment: Suzuki Coupling via Boronized Derivative

The second embodiment of the inventive synthesis process involves using a 1,8-dihalogenated naphthalene derivative of formula (1) and a naphthyl-1,8-diboronic acid derivative of the following formula (7), and subjecting them to Suzuki coupling reaction for thereby synthesizing a perylene derivative of formula (2).

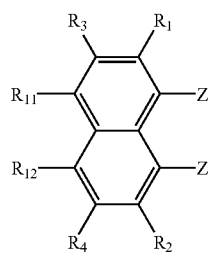
(7)

In formula (7), Z is a boronic acid derivative, and $R_1$ to $R_4$, $R_{11}$ and $R_{12}$ are as defined for $R_1$ to $R_4$, $R_{11}$ and $R_{12}$ in formula (1). As the boronic acid derivative represented by Z, boronic acid $B(OH)_2$ is often used although derivatives having equivalent action are inclusive.

In Suzuki coupling reaction, the compounds of formulae (1) and (7) are treated in a solvent which inert to the reaction, in the presence of a base and a palladium catalyst, and at a temperature of room temperature to 125° C. for 10 minutes to 24 hours, obtaining a reaction product.

The solvent used herein is not critical, and examples thereof include aromatic hydrocarbons (e.g., benzene and toluene), ethers (e.g., tetrahydrofuran and dioxane), amides (e.g., dimethylformamide and dimethylacetamide), esters (e.g., ethyl acetate), alcohols (e.g., methanol), and ketones (e.g., acetone and cyclohexanone).

Alternatively, a perylene derivative of formula (4) can be synthesized by using a 3,4-dihalogenated fluoranthene derivative of formula (3) and a fluorantheno-1,8-diboronic acid derivative of the following formula (8), and subjecting them to Suzuki coupling reaction.

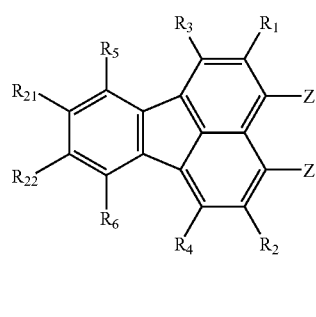
(8)

In formula (8), Z is a boronic acid derivative, and $R_1$ to $R_6$, $R_{21}$ and $R_{22}$ are as defined for $R_1$ to $R_6$, $R_{21}$ and $R_{22}$ in formula (3).

Moreover, a perylene derivative of formula (6) can be synthesized by using a 3,4-dihalogenated benzofluoranthene derivative of formula (5) and a dibenzofluorantheno-1,8-diboronic acid derivative of the following formula (9), and subjecting them to Suzuki coupling reaction.

(9)

In formula (9), Z is a boronic acid derivative.

Shown below are the synthesis schemes of these synthesis processes.

-continued
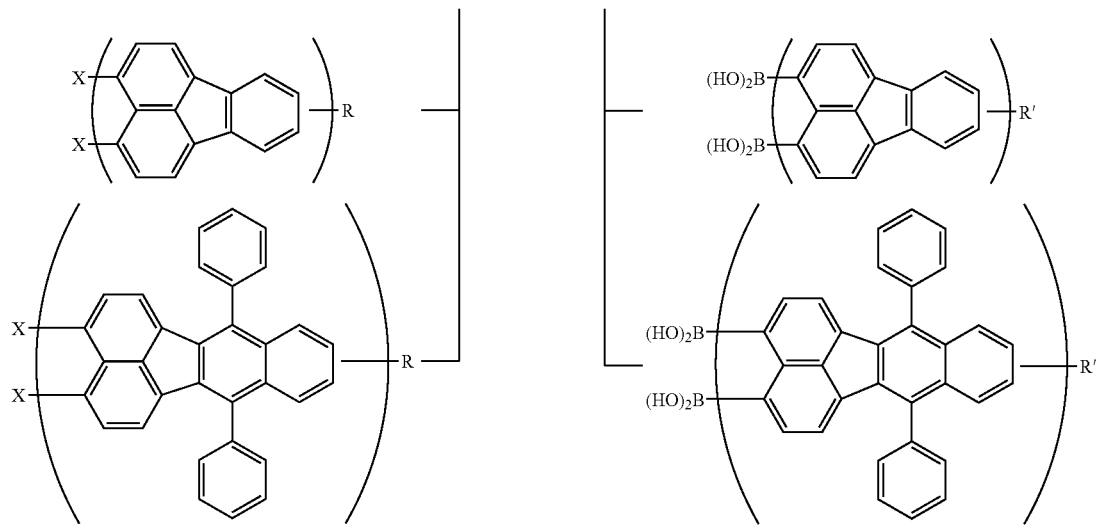
x = Cl, Br, I
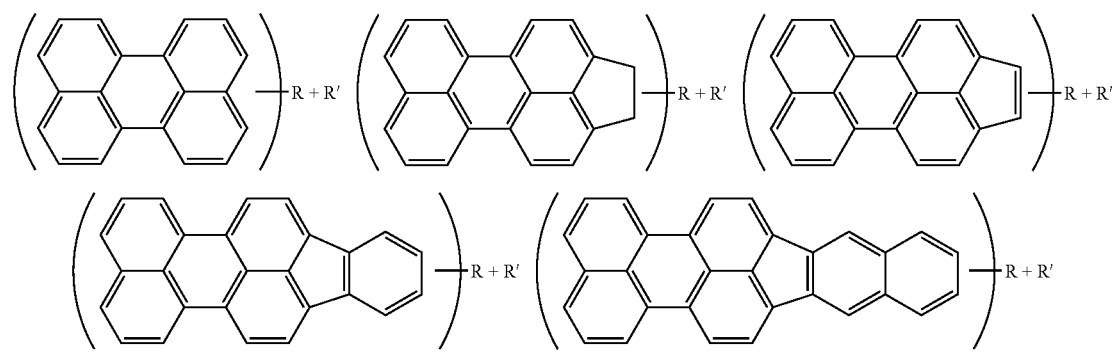
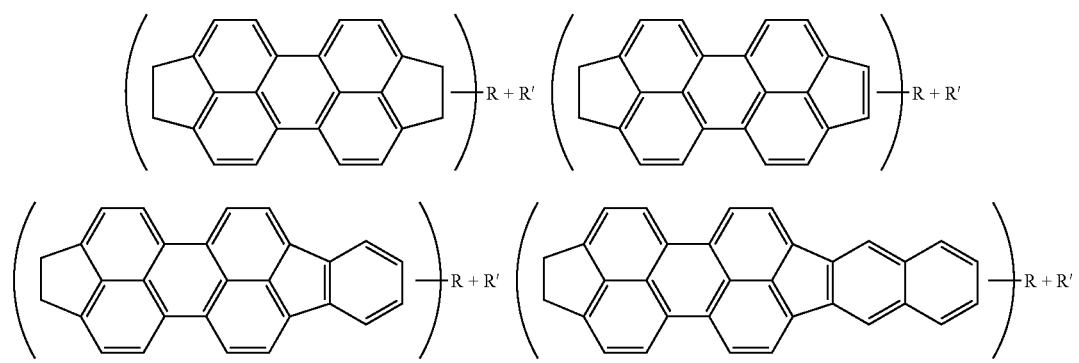

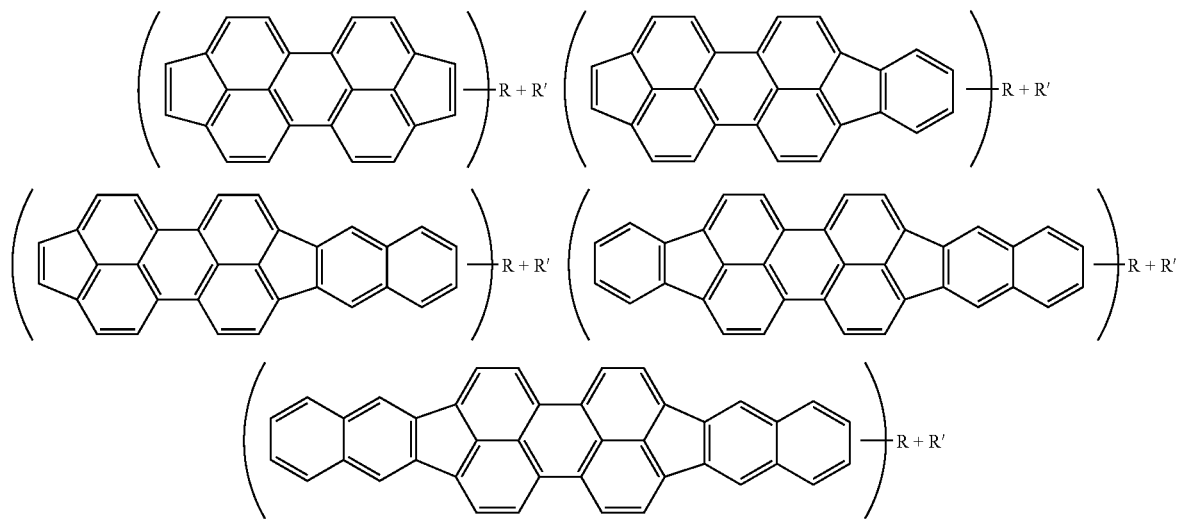

Third Embodiment: Coupling via Halogenation and Boron Derivative

The third embodiment of the invention is a combination of halogenation followed by coupling according to the first embodiment with coupling via boron derivative according to the second embodiment. That is, the third embodiment is a perylene derivative synthesis process involving using a naphthalene derivative of the following formula (13) and subjecting it to Suzuki coupling reaction for thereby synthesizing a desired perylene derivative.

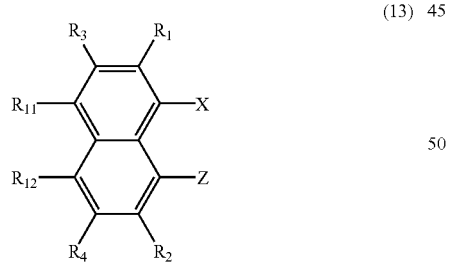

(13)

X is Cl, Br or I, and Z is a boronic acid derivative. $R_1$ to $R_4$, $R_{11}$ and $R_{12}$ in formula (13) are as defined in formula (1). X and Z are the same as in the first and second embodiments, with their preferred examples being also the same. The same applies to formulae (14) and (15) below.

Also, a perylene derivative can be synthesized by using a fluoranthene derivative of the following formula (14), and subjecting it to Suzuki coupling reaction.

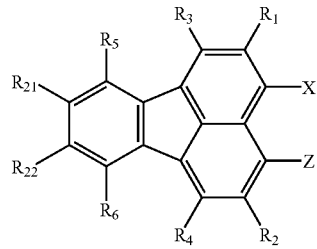

(14)

X is Cl, Br or I, and Z is a boronic acid derivative. $R_1$ to $R_6$, $R_{21}$ and $R_{22}$ in formula (14) are as defined in formula (3).

Further, a perylene derivative can be synthesized by using a benzofluoranthene derivative of the following formula (15), and subjecting it to Suzuki coupling reaction.

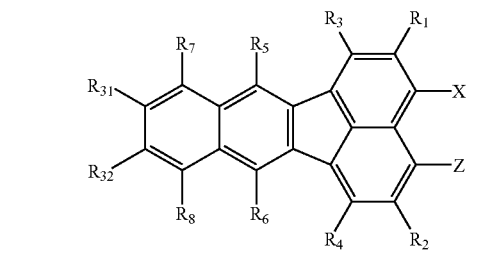

(15)

X is Cl, Br or I, and Z is a boronic acid derivative. $R_1$ to $R_8$, $R_{31}$ and $R_{32}$ in formula (15) are as defined in formula (5).

Fourth Embodiment: Synthesis from Bishalogenated Naphthalene

The inventive process is characterized by coupling reaction using a site modified by halogenation and optionally, a site modified with a boronic acid derivative. For these two bonding sites, it is acceptable whether the two sites are simultaneously bonded, or the two sites are sequentially bonded one by one. Also for the modification sites, it is acceptable whether the two sites are simultaneously modified, or the two sites are sequentially modified one by one.

Accordingly, the inventive process encompasses a process comprising the steps of using a bisnaphthalene derivative of the following formula (16) as a starting reactant or intermediate, and subjecting it to coupling reaction for thereby synthesizing a perylene derivative of the following formula (2).

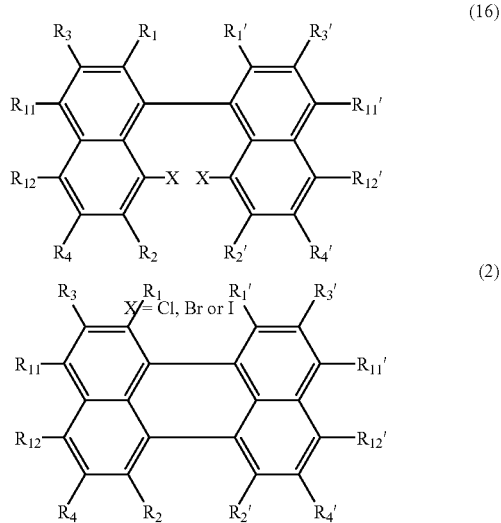

$R_1$ to $R_4$, $R_{11}$ and $R_{12}$ in formula (16) are as defined for $R_1$ to $R_4$, $R_{11}$ and $R_{12}$ in formula (1). $R_1'$ to $R_4'$, $R_{11}'$ and $R_{12}'$ in formula (2) are as defined for $R_1$ to $R_4$, $R_{11}$ and $R_{12}$ in formula (1). $R_1$ to $R_4$, $R_{11}$ and $R_{12}$ and $R_1'$ to $R_4'$, $R_{11}'$ and $R_{12}'$ may be the same or different. X stands for a halogen atom, the detail of which is the same as described in formula (1). In some cases, one X may be a boronic acid derivative represented by Z.

The inventive process is especially effective for synthesizing the compounds of formula (6). It is preferred in formula (6) that $R_1$ to $R_8$, $R_{31}$, $R_{32}$, $R_1'$ to $R_8'$, $R_{31}'$ and $R_{32}'$ stand for substituted or unsubstituted aryl, alkyl, alkenyl, alkoxy or aryloxy radicals.

In the compounds of formula (6), it is further preferred that any one or more of $R_1$ to $R_8$, $R_{31}$, $R_{32}$, $R_1'$ to $R_8'$, $R_{31}'$ and $R_{32}'$ stand for ortho-substituted phenyl radicals. Using the inventive process, those compounds having a substituent radical at a specific position such as ortho-substituted compounds can be readily produced. Similarly, compounds which are vertically or laterally asymmetric can be readily produced.

Especially, the compounds of formula (6) wherein either one or both (vertical) of either one or both (lateral) of $R_5$ and $R_6$, and $R_5'$ and $R_6'$ be ortho-substituted phenyl radicals.

The introduction of a substituent radical at the ortho-position holds down the propensity for the compound to decompose upon sublimation purification. Fluorescence is also improved by introducing a substituent radical at the ortho-position.

The use of the ortho-substituted compound is effective for increasing the fluorescent luminance and holding down the concentration quenching of the EL device, thereby spreading the margin of the EL dopant and improving the freedom of design.

Specifically, the introduction of an ortho-substituted phenyl radical has several advantages. The ortho-substituted phenyl radical introduced makes it possible to control the association of the perylene skeleton by virtue of its steric hindrance, to improve the solubility in solvents and to purify the compound to a high purity. For the same reason, sublimation purification becomes possible at a lower temperature and entails little decomposition. This is also advantageous in obtaining a high purity material. Using such a pure material, an organic EL device having a high emission efficiency is obtainable because the deactivation of excitons by impurities is minimized.

Another reason accounting for the high emission efficiency is that the association between similar or distinct molecules in the light emitting layer is suppressed whereby concentration quenching is restrained.

Illustrative, preferred examples of the compounds having formulae (2), (4) and (6) are given below.

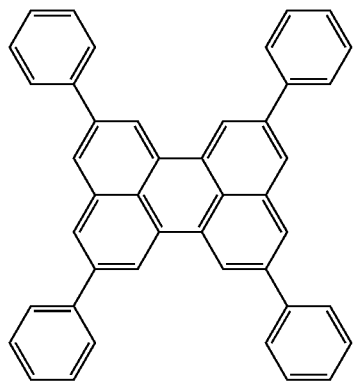

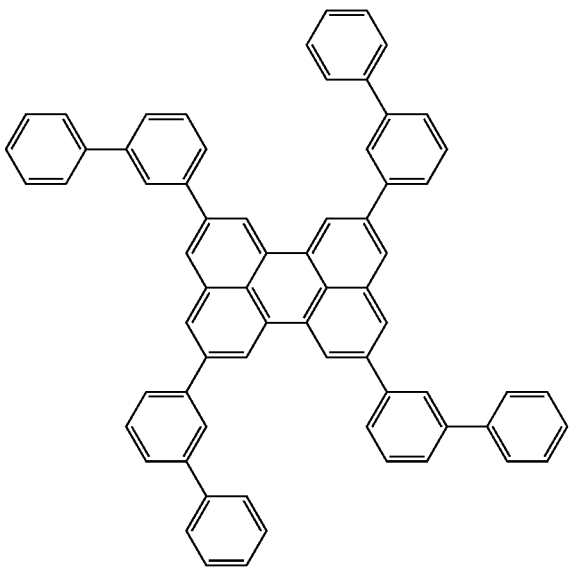

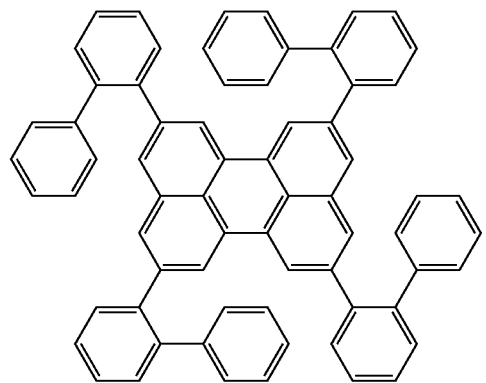
-continued

-continued
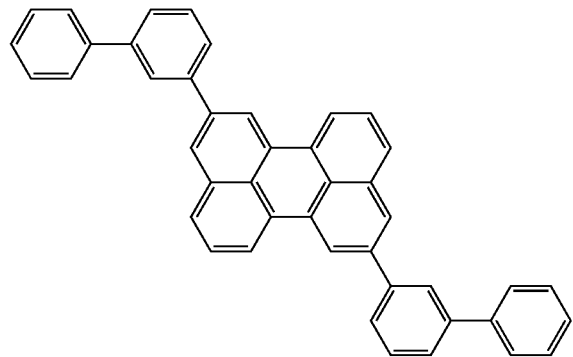
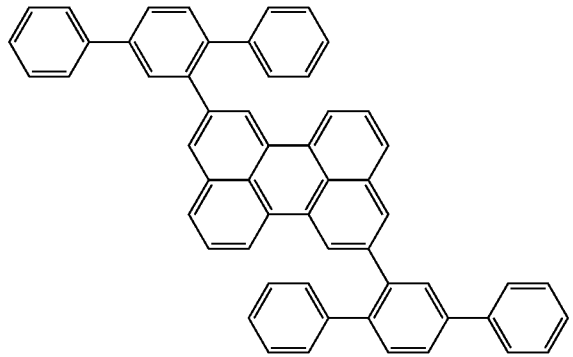
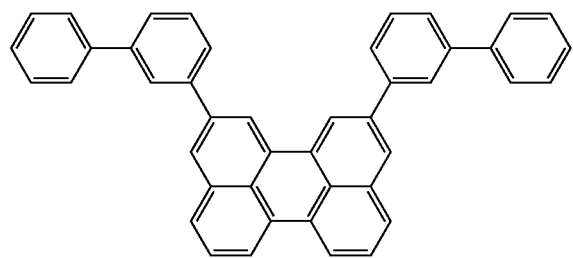
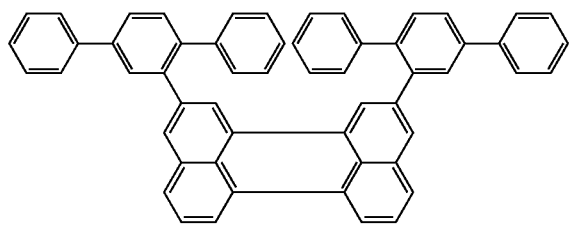
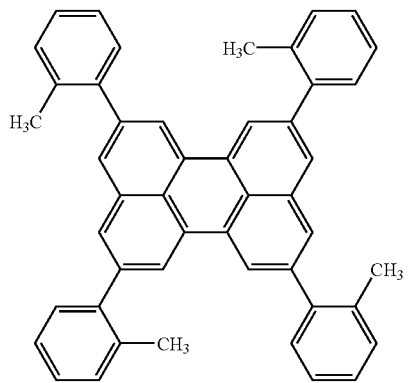
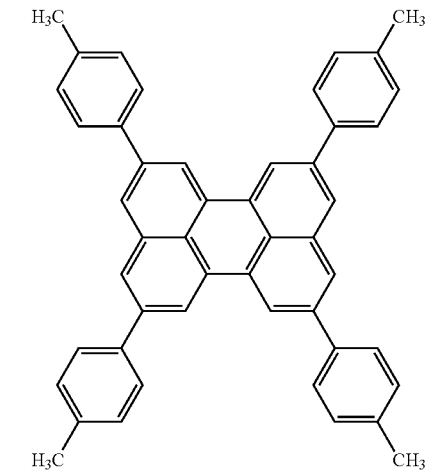
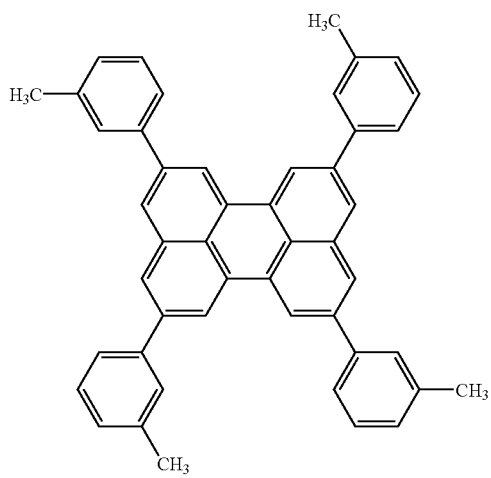
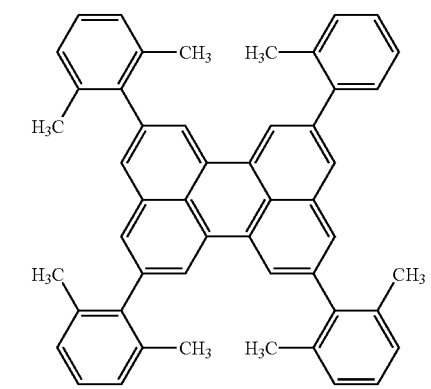

-continued
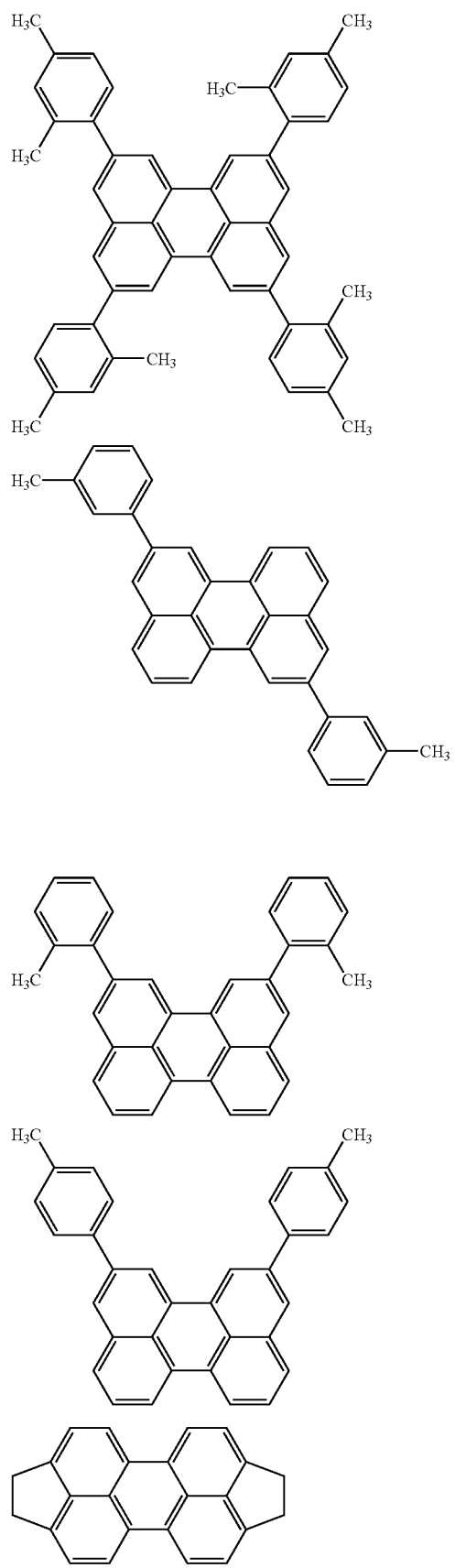
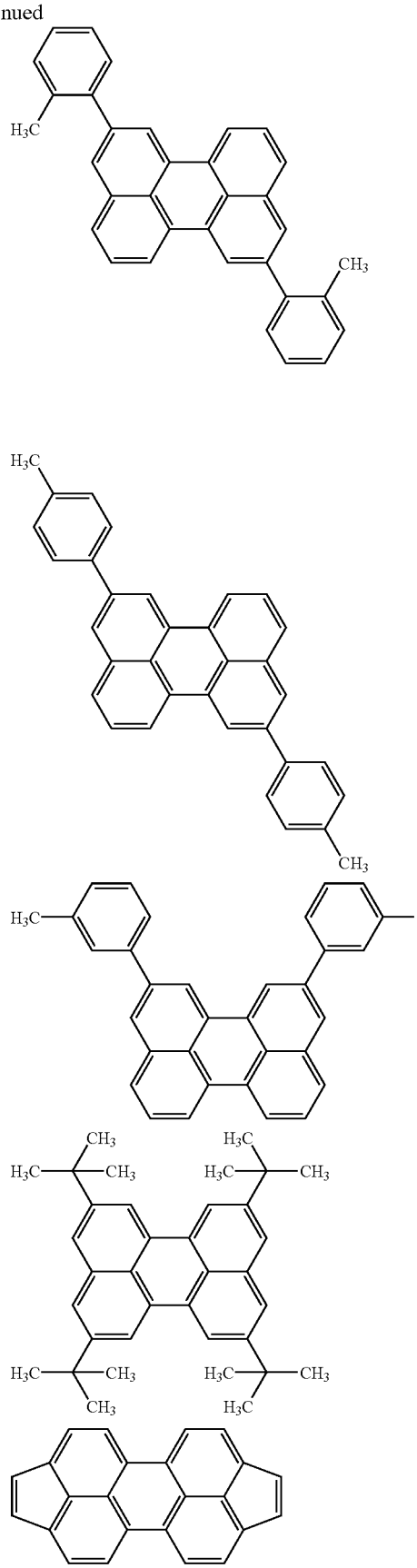

-continued
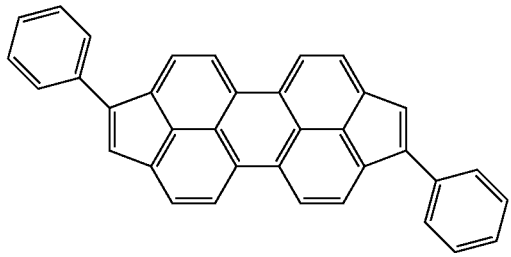
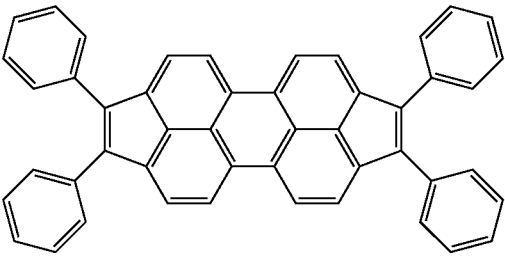
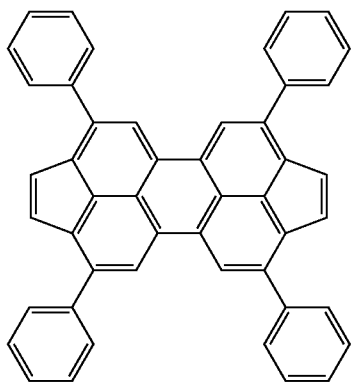
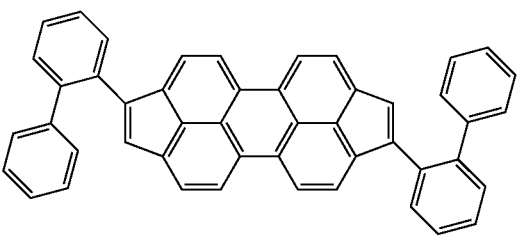
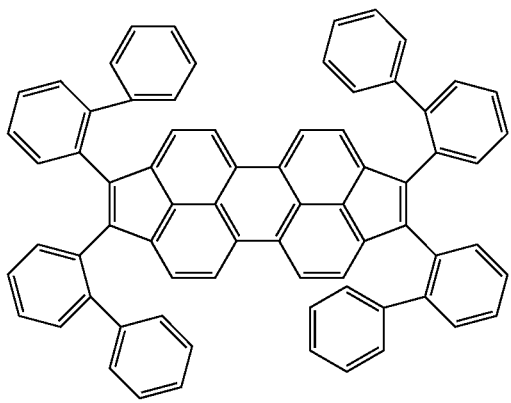
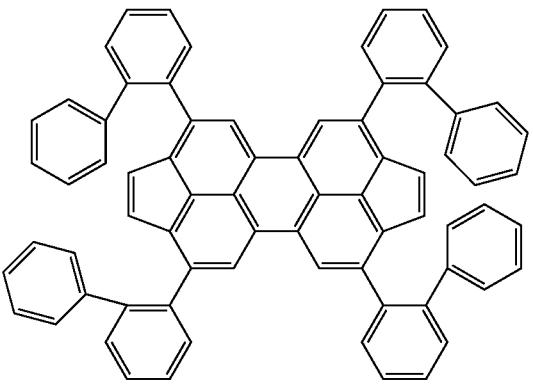
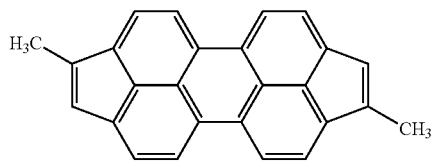
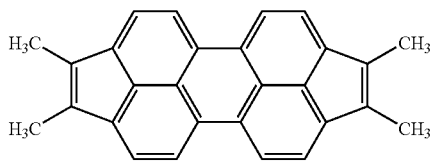
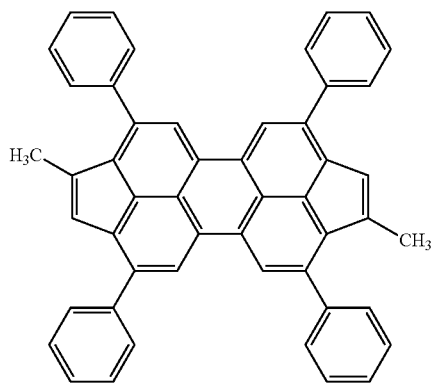
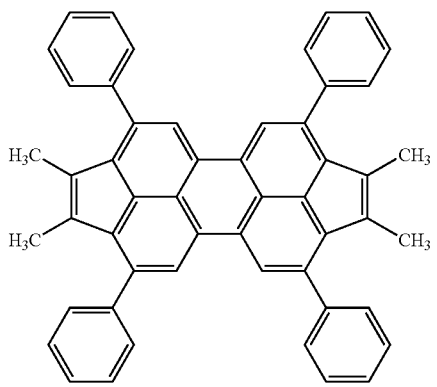

-continued
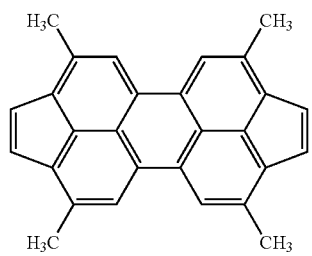
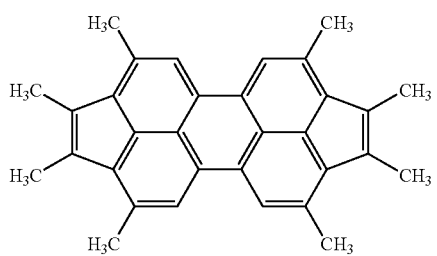
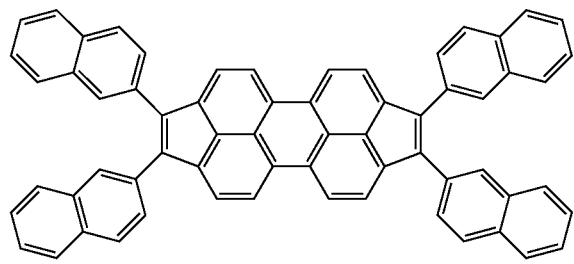
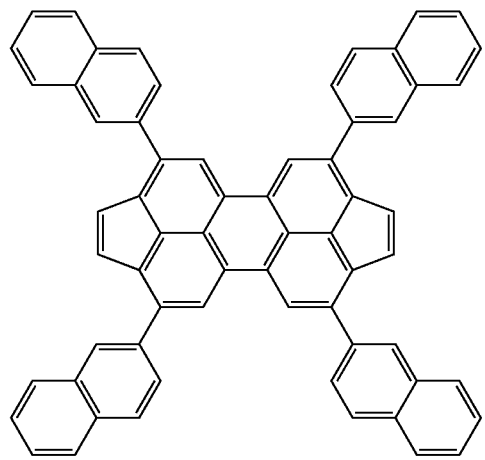
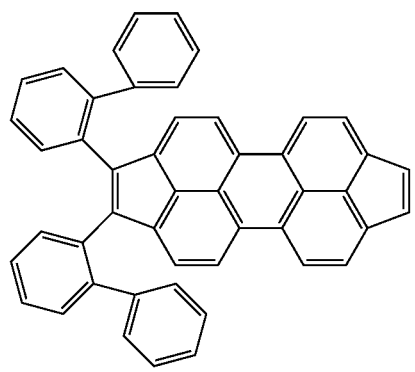
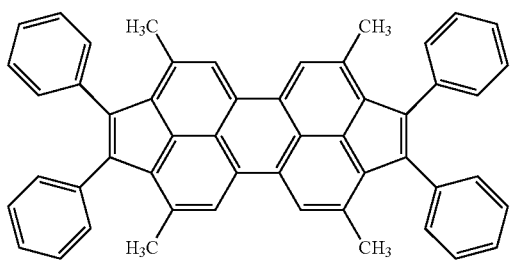
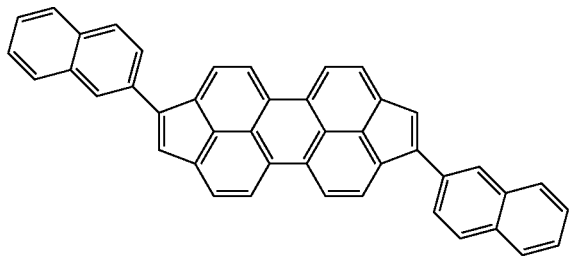
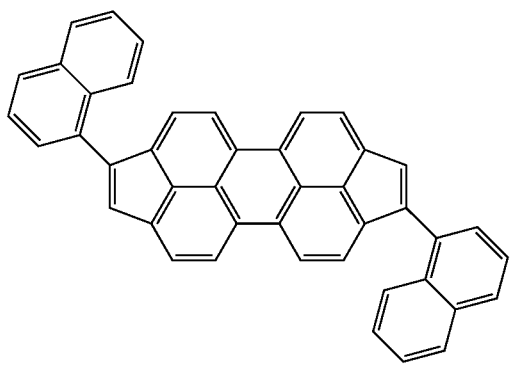
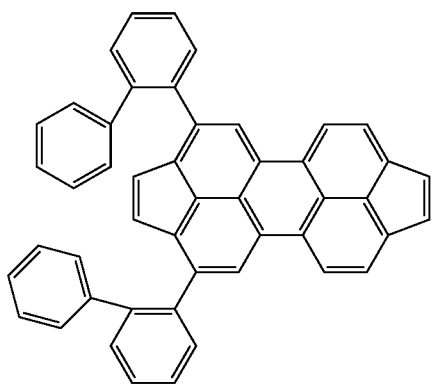

-continued
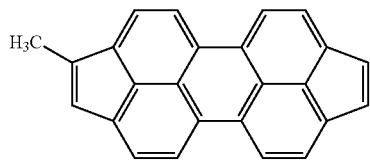
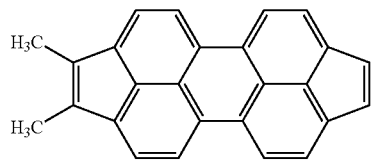
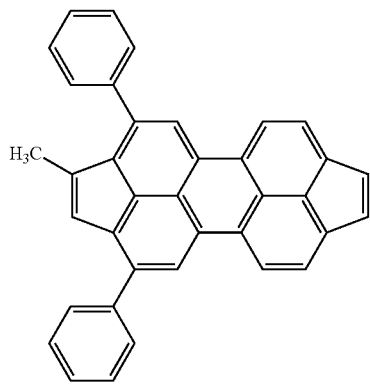
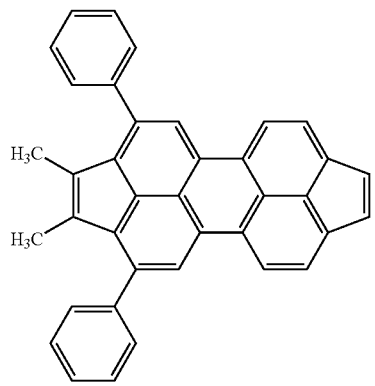
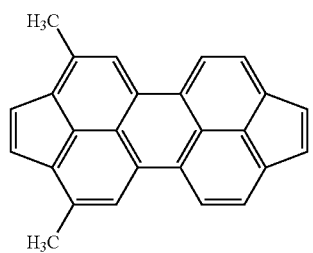
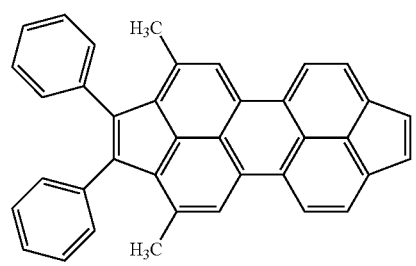
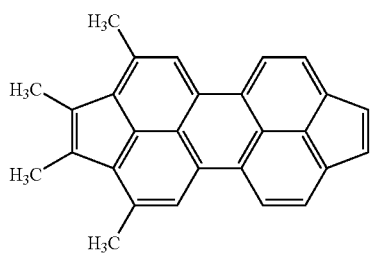
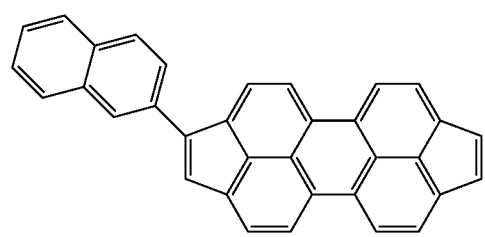
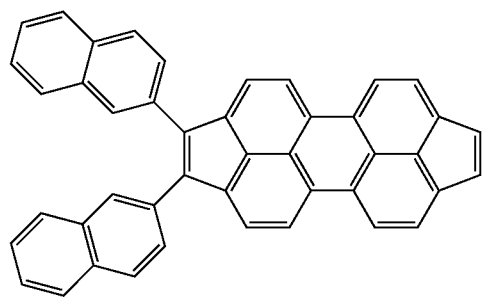
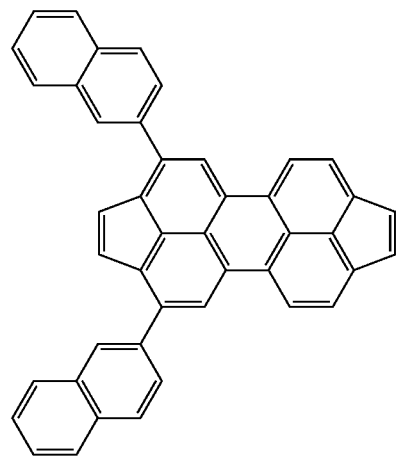

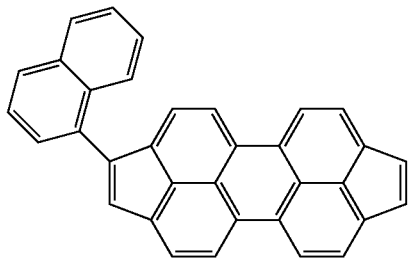
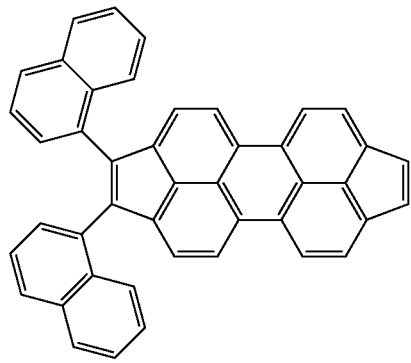
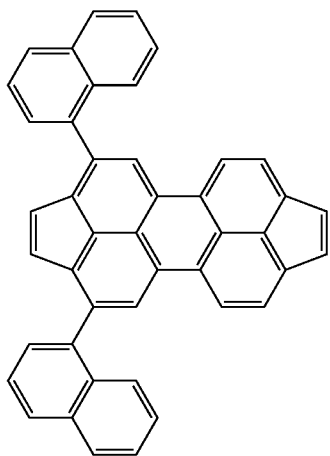
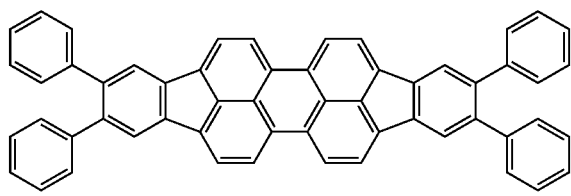
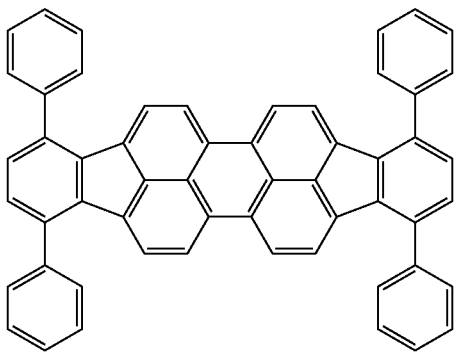
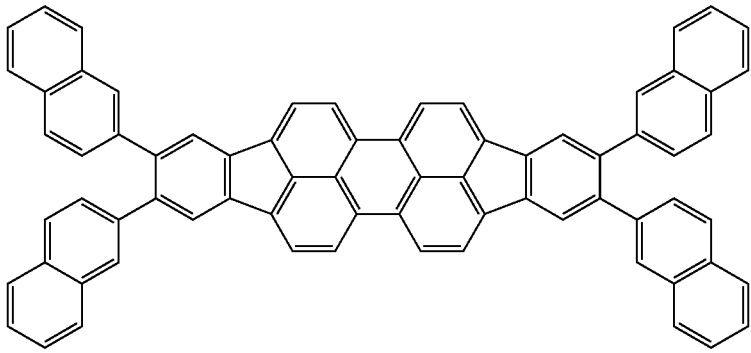
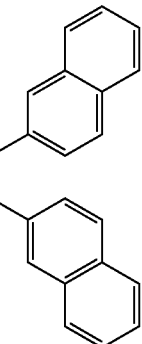

-continued
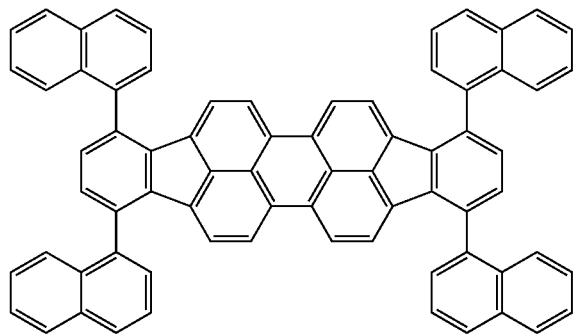
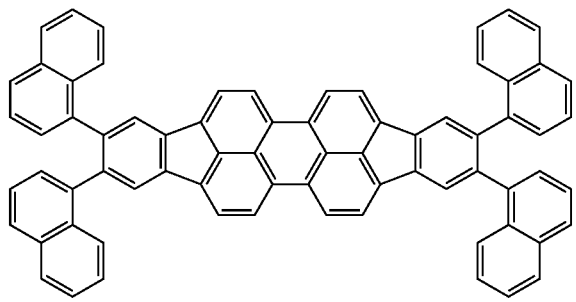
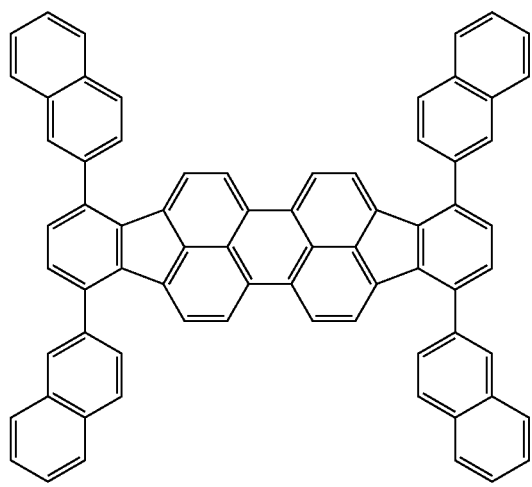
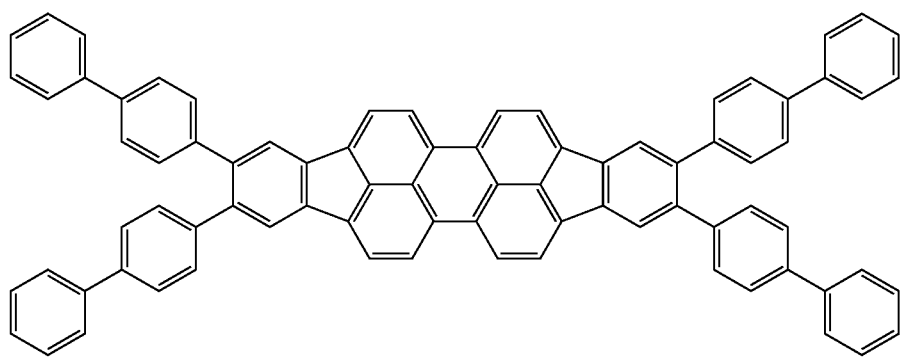

-continued
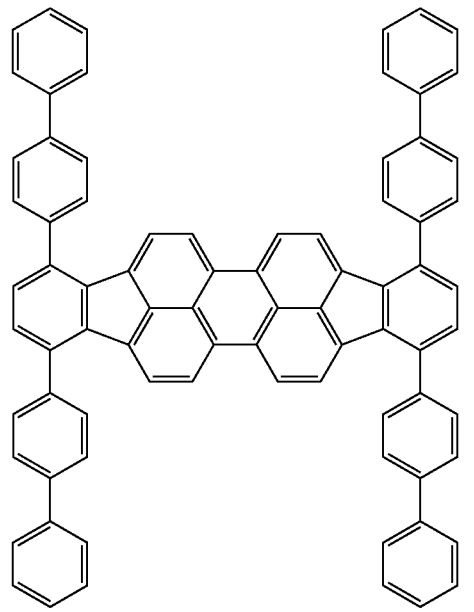
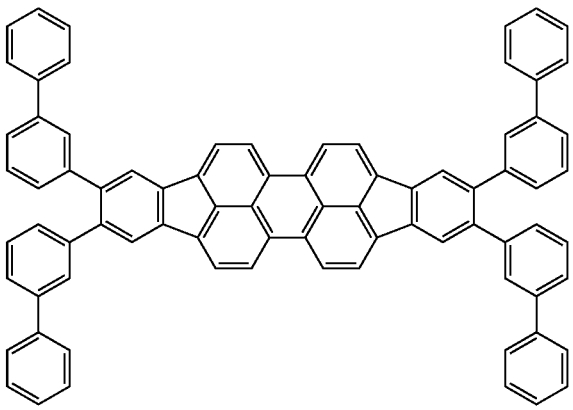
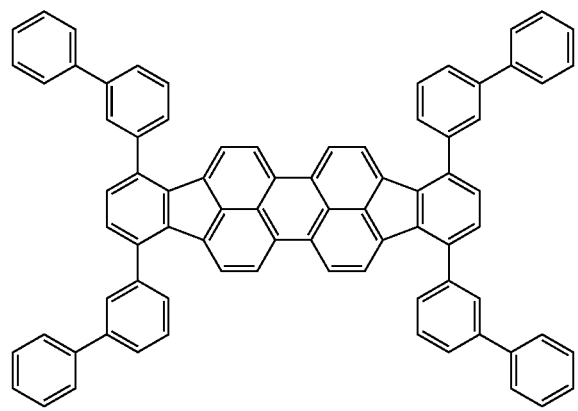
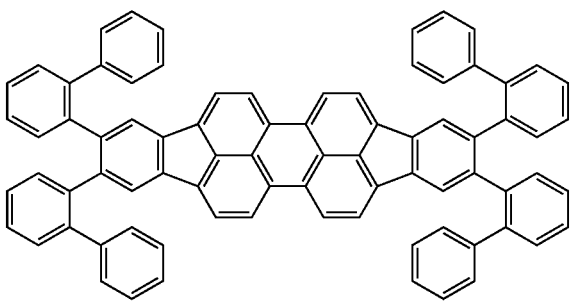
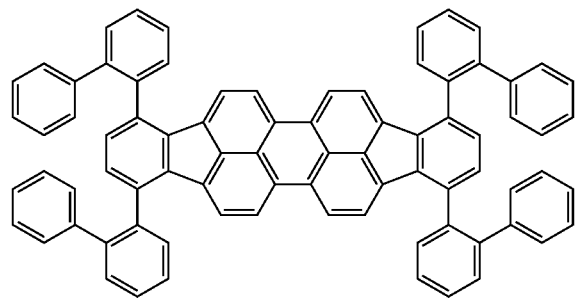
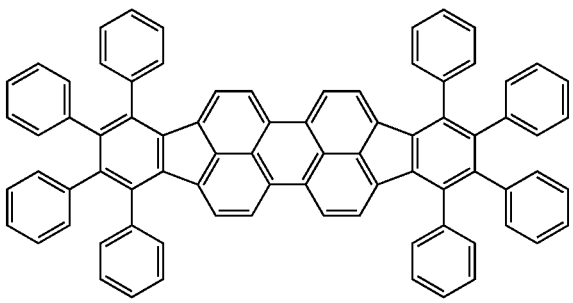
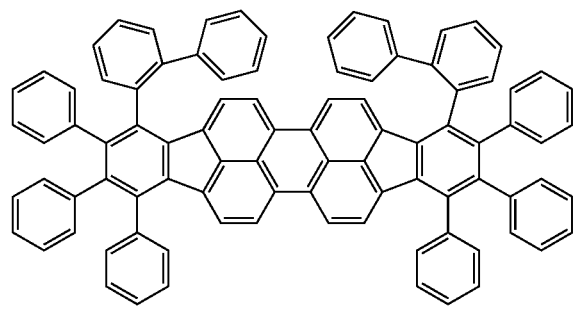
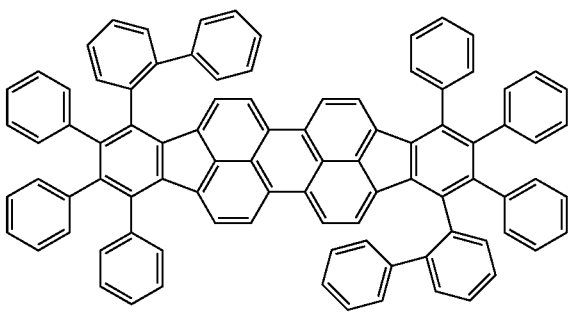

-continued
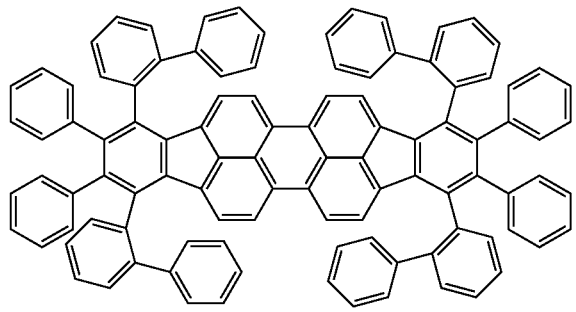
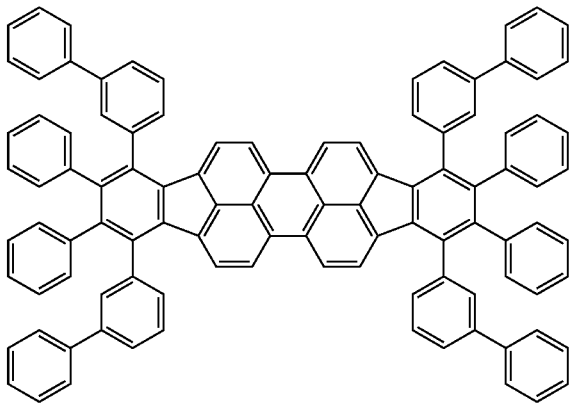
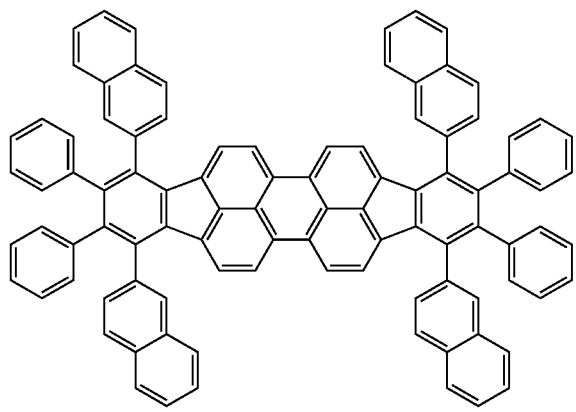
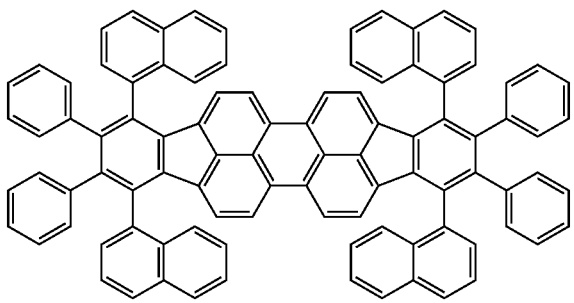
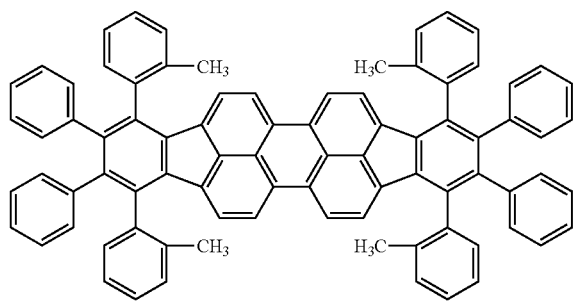
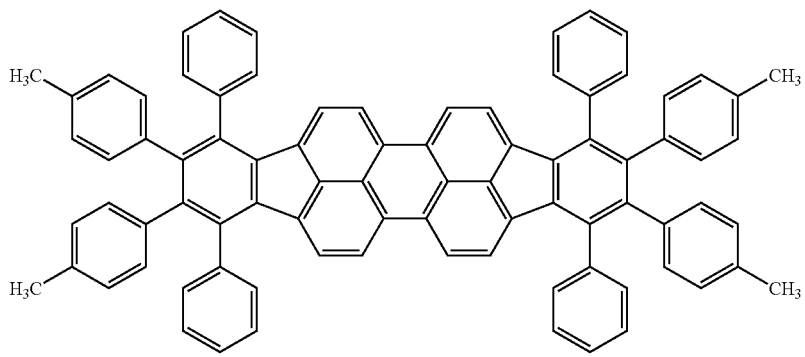

-continued
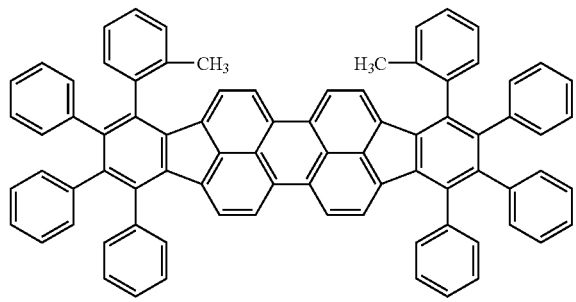
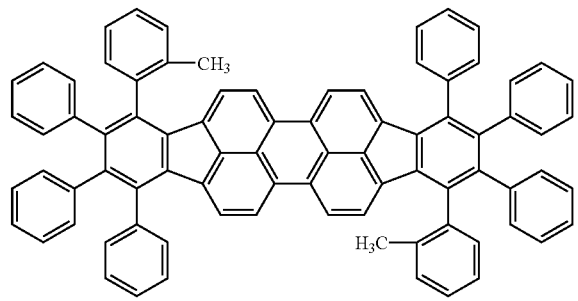
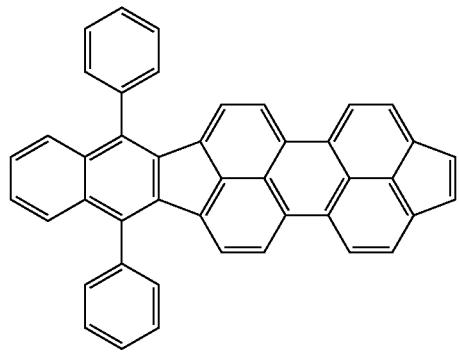
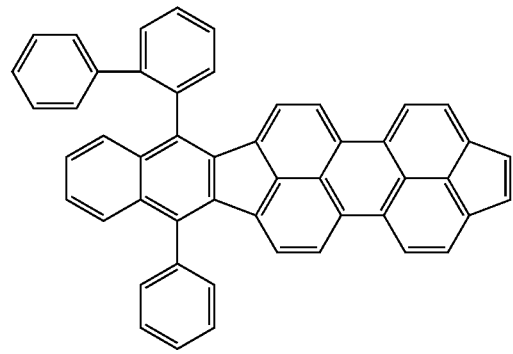
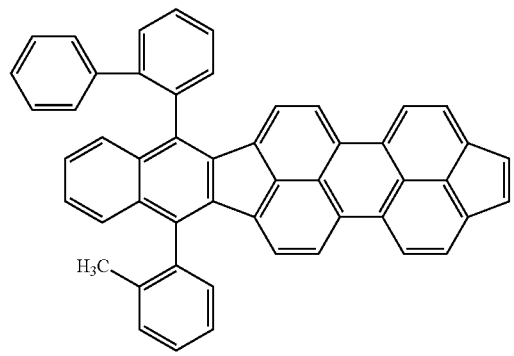
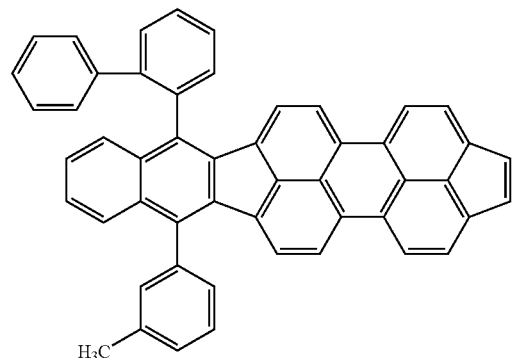
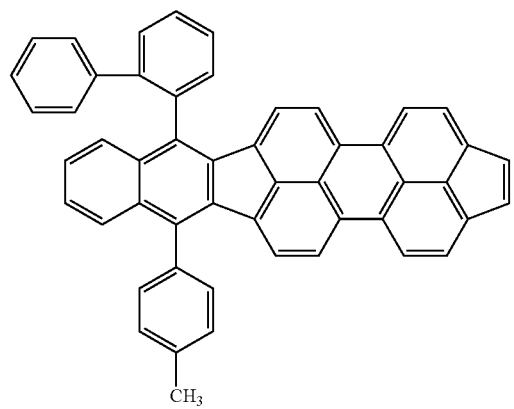
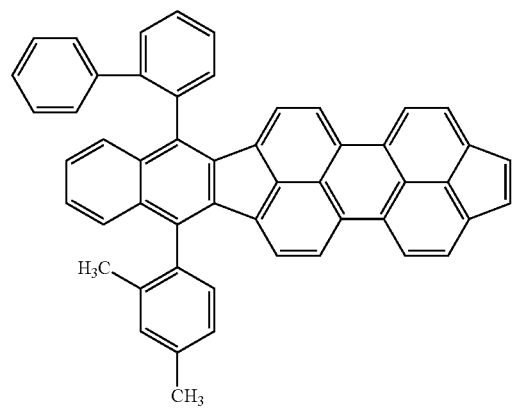

-continued
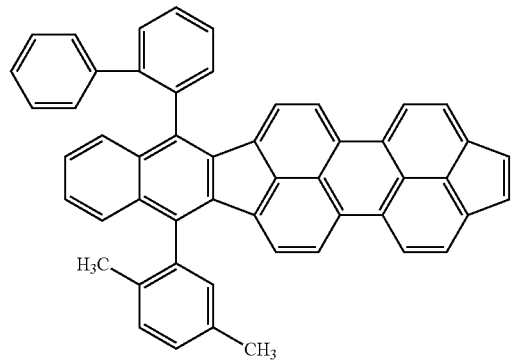
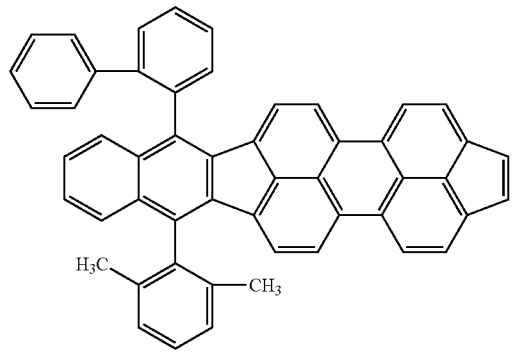
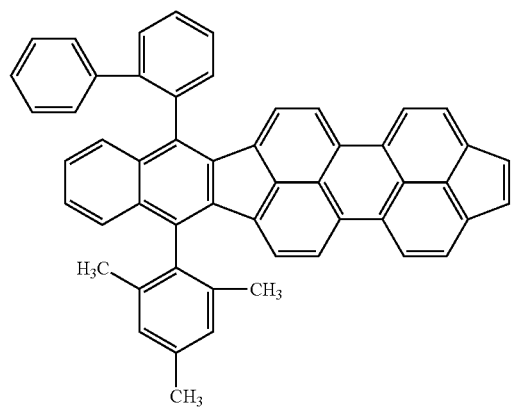
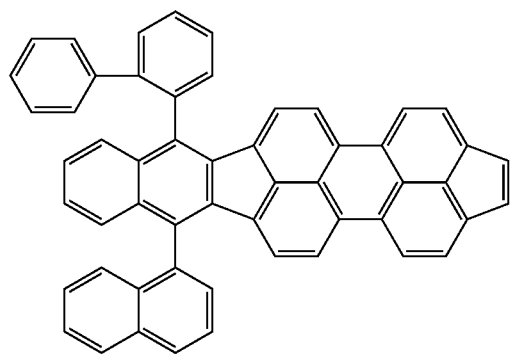
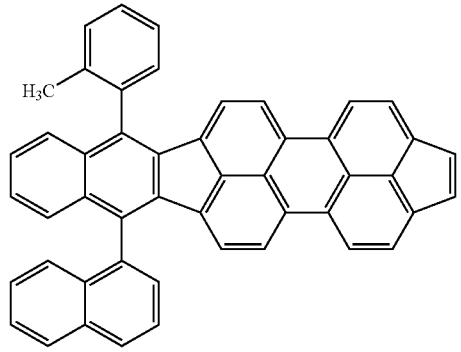
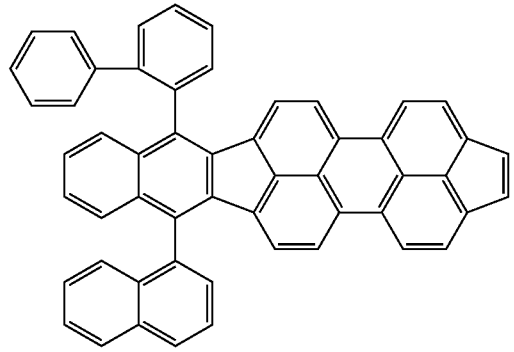
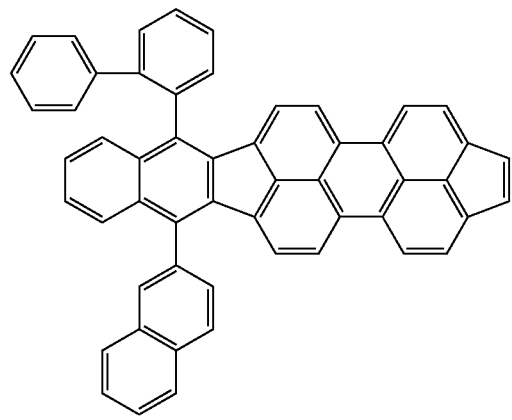
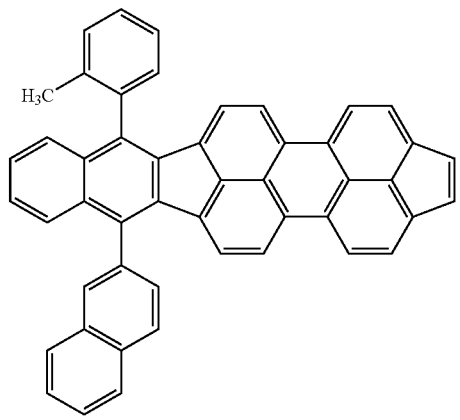

-continued
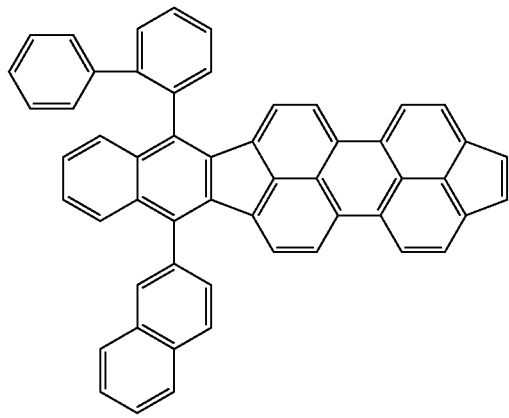
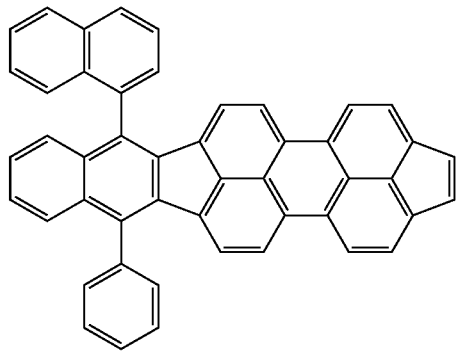
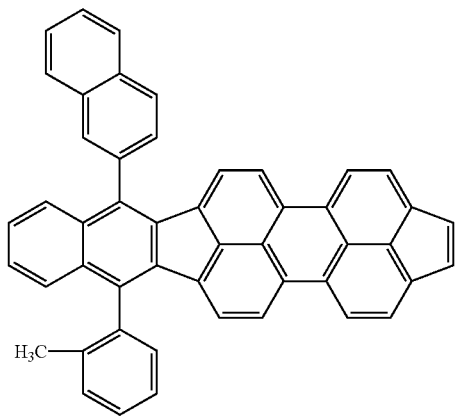
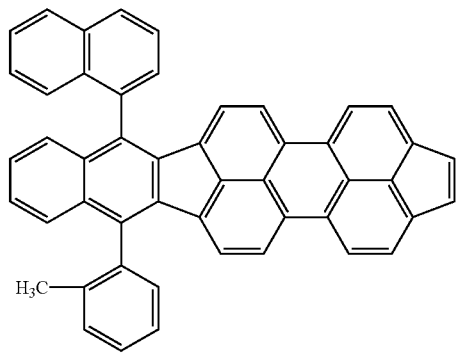
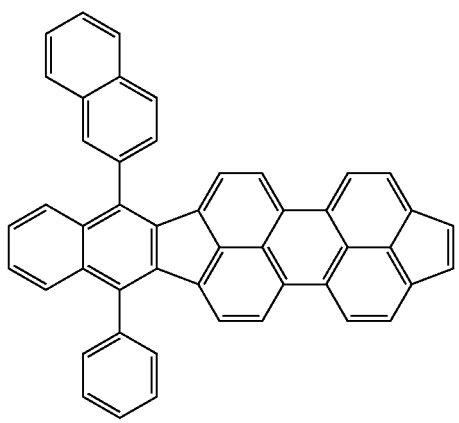
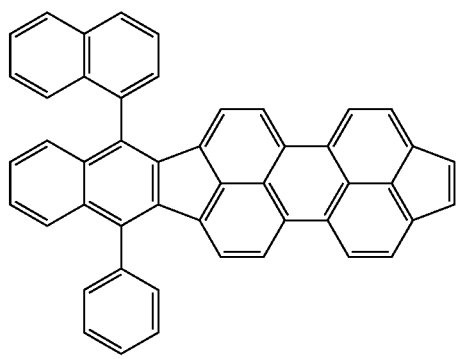

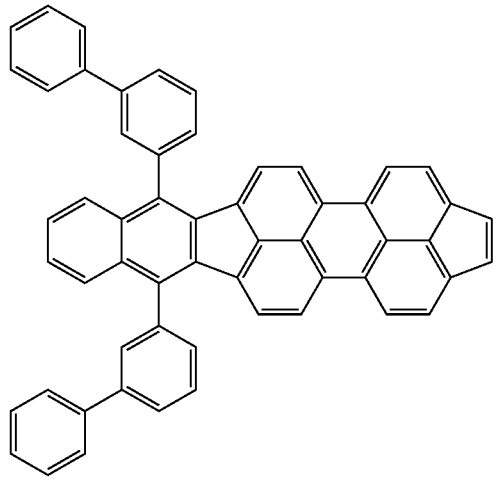
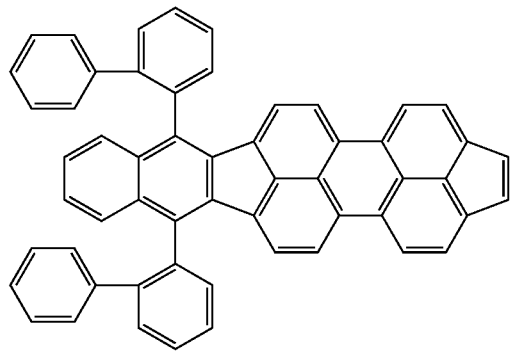
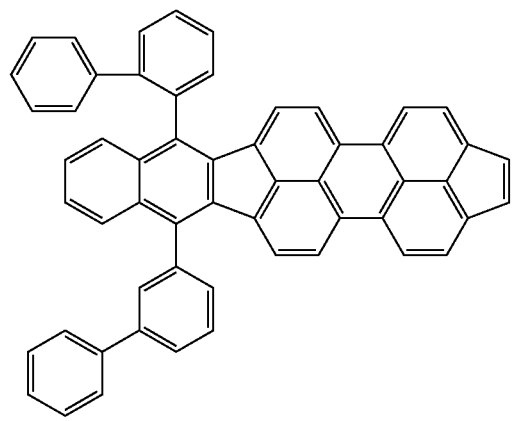
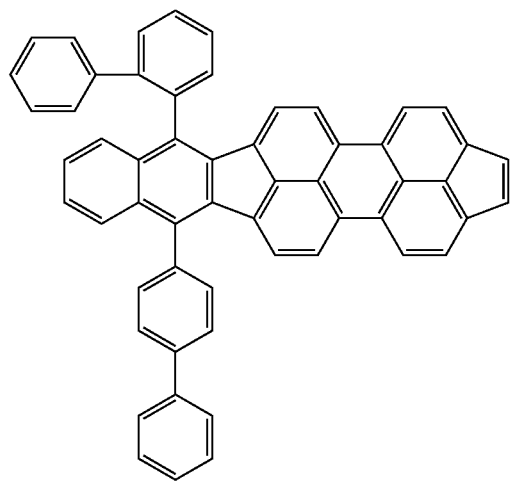
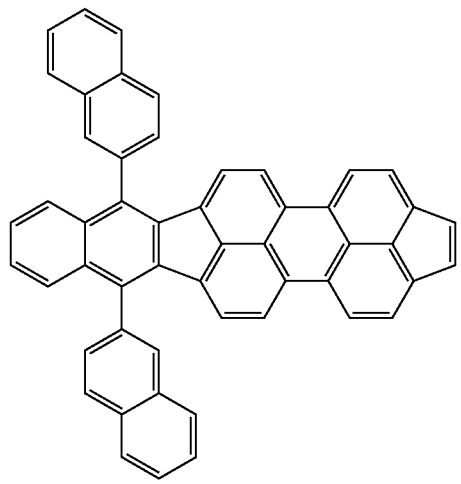
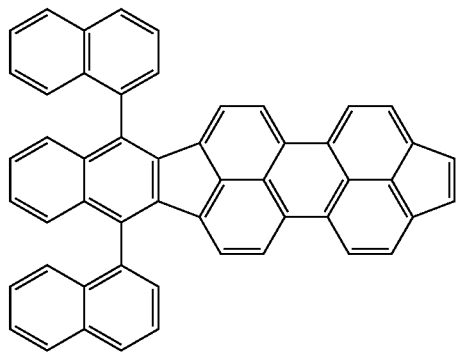

-continued
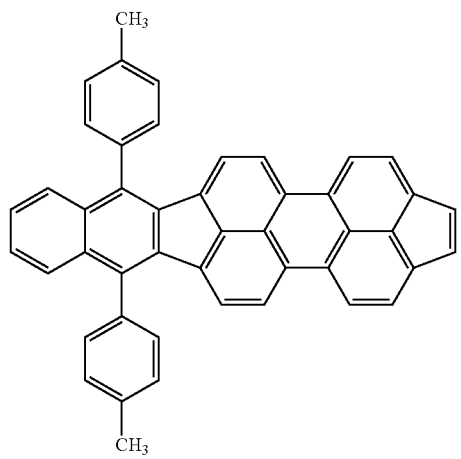
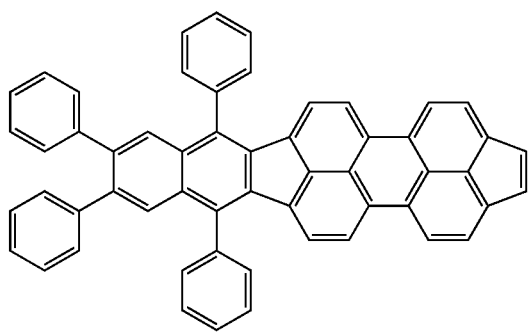
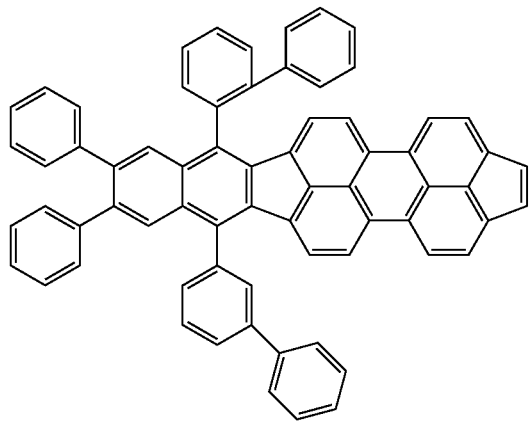
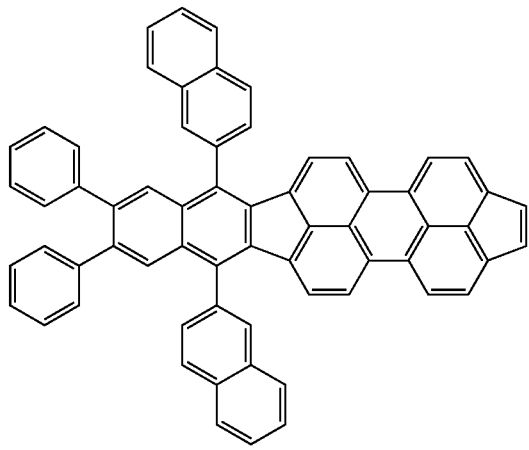
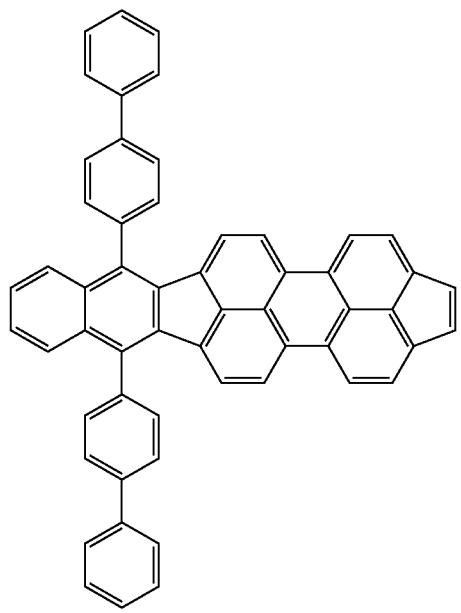
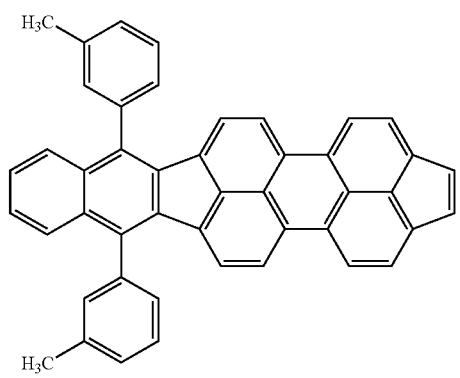

-continued
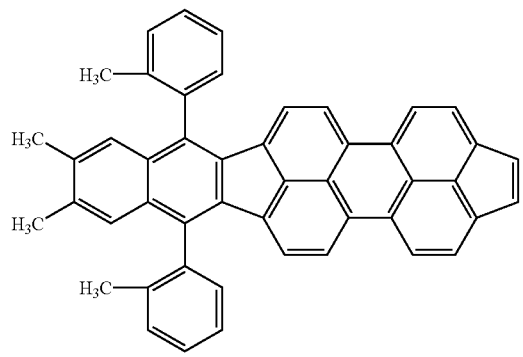
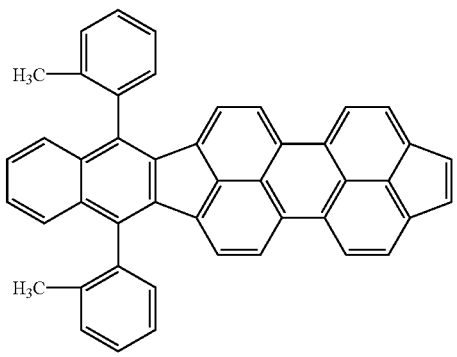
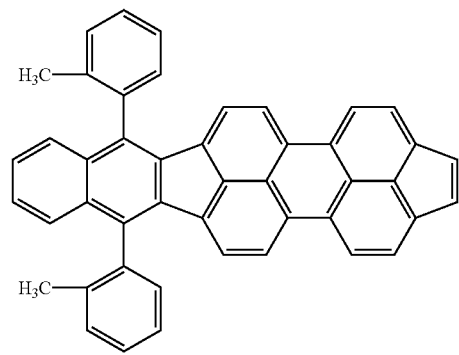
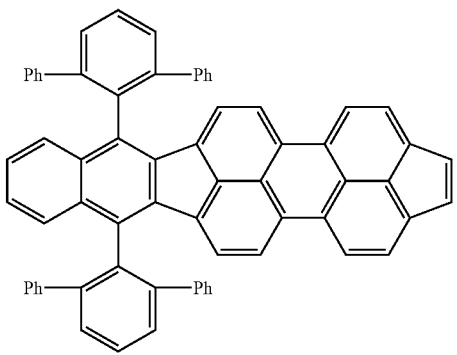
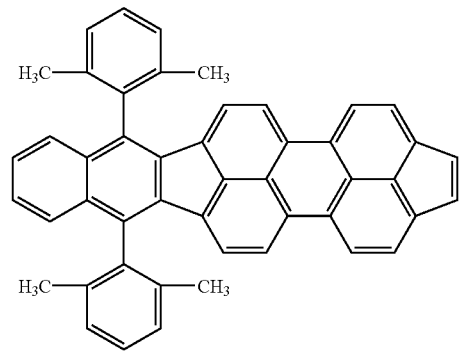
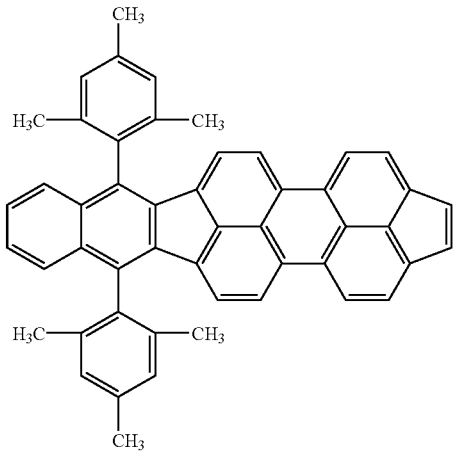
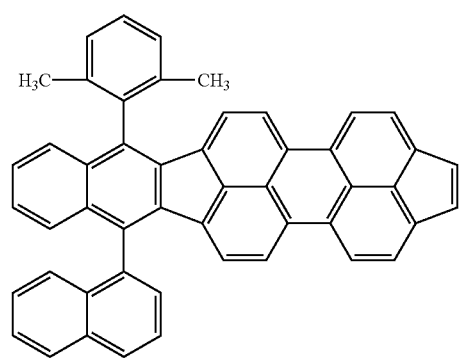
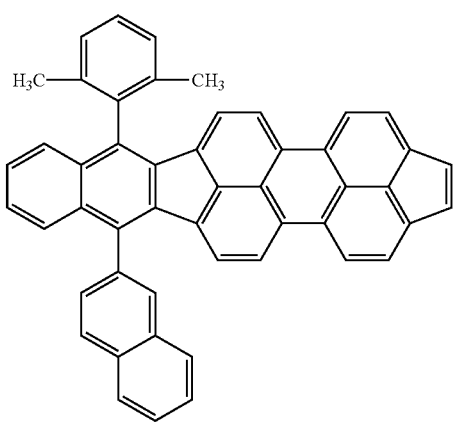

-continued
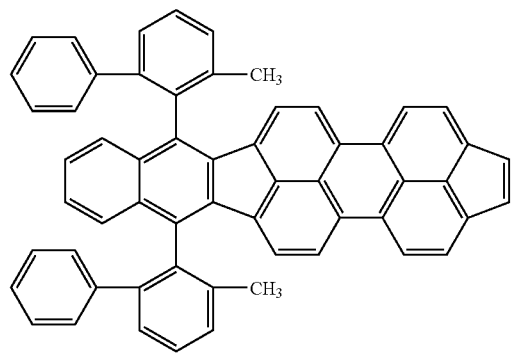
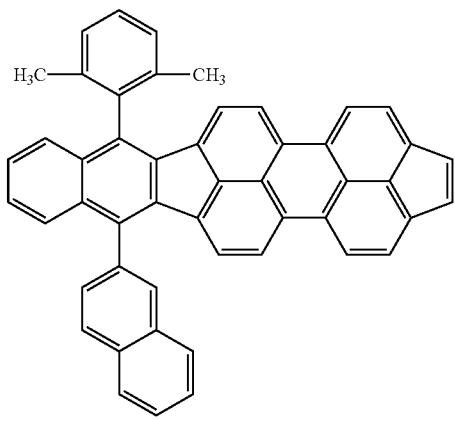
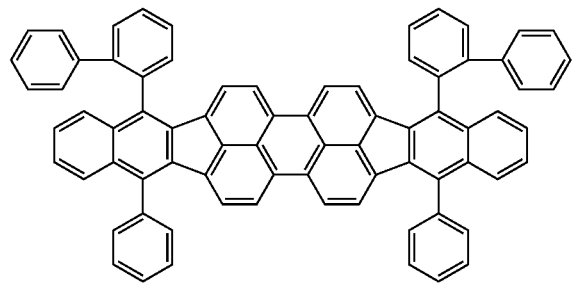
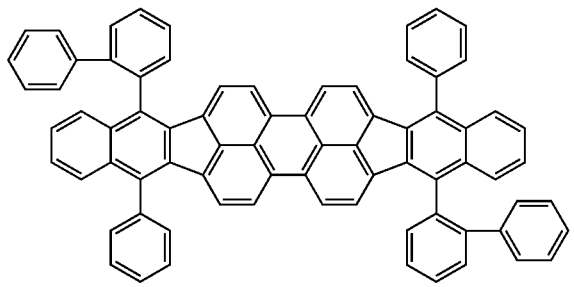
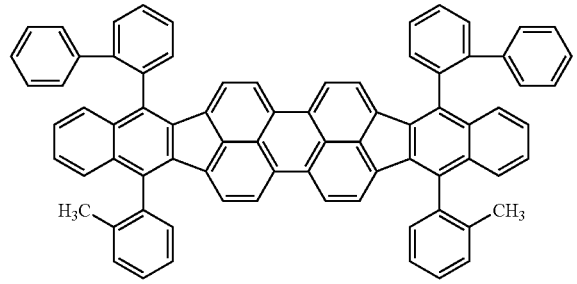
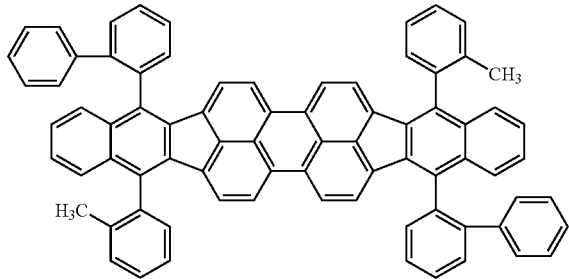
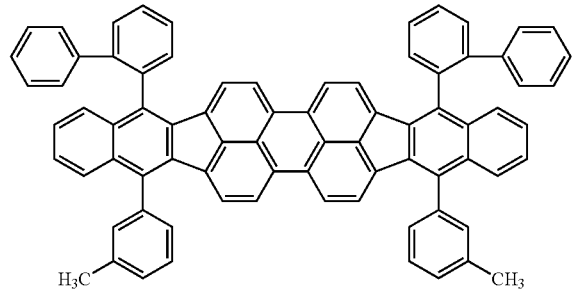
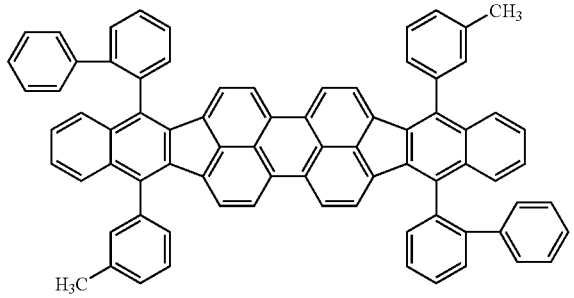
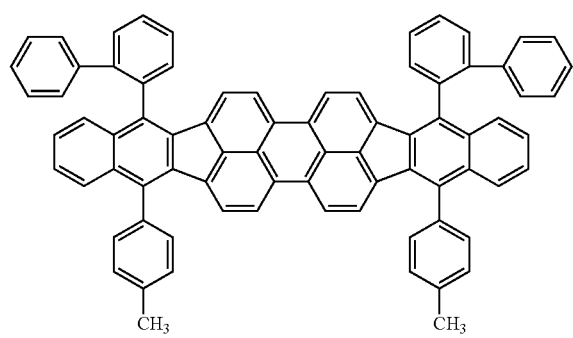
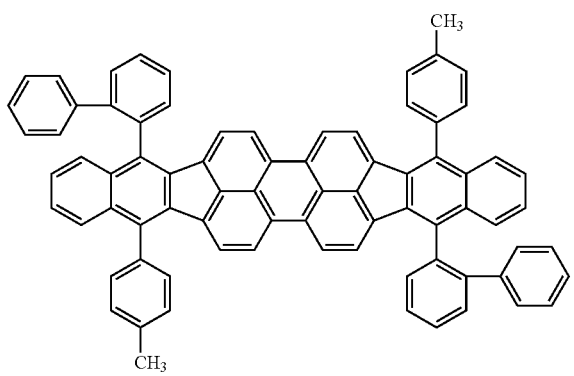

-continued
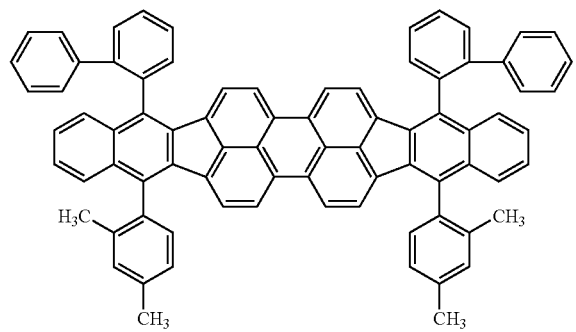
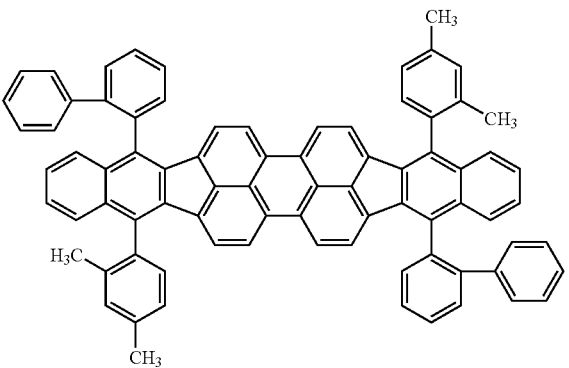
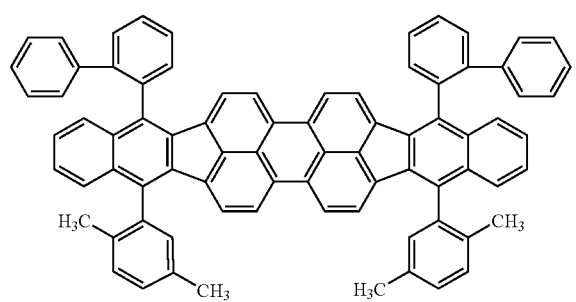
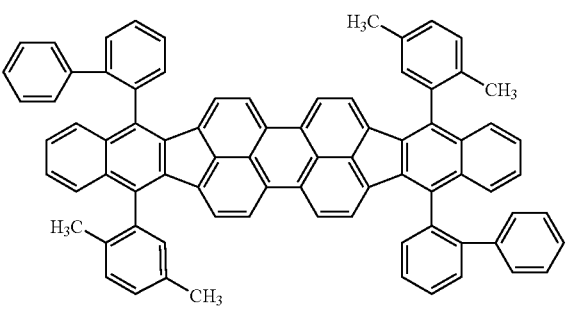
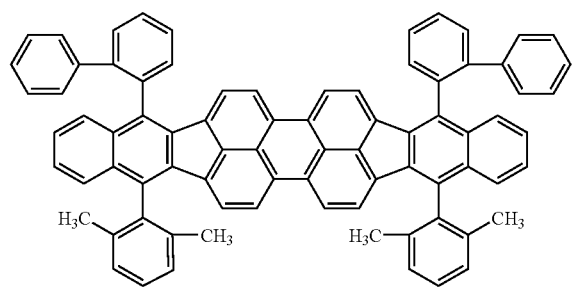
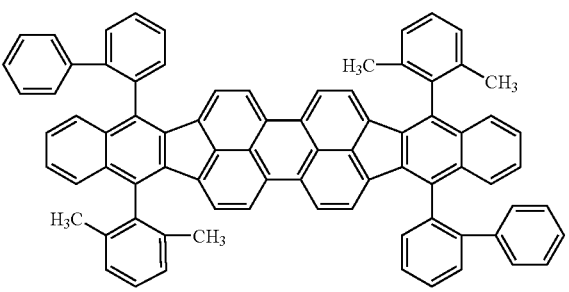
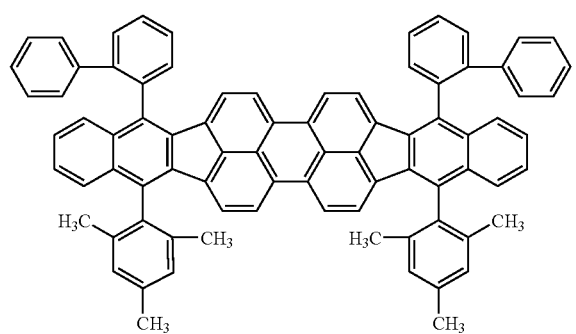
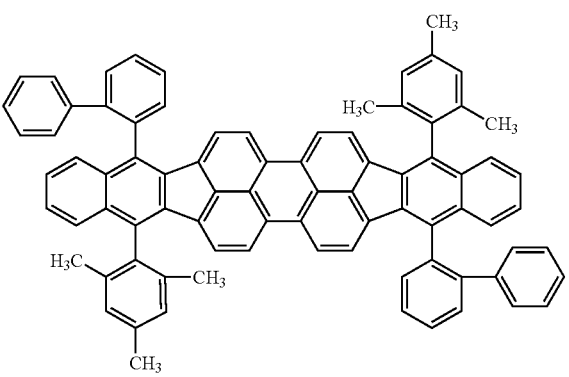
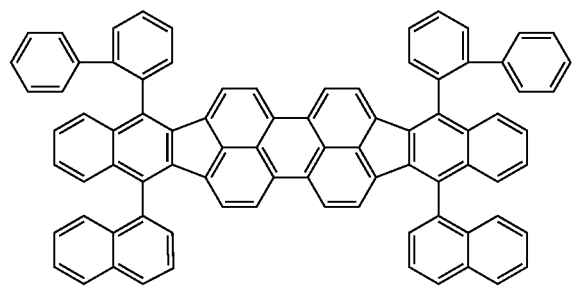
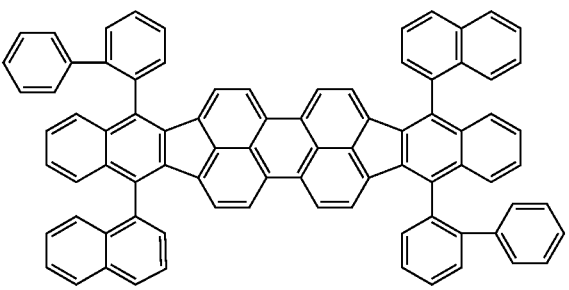

-continued
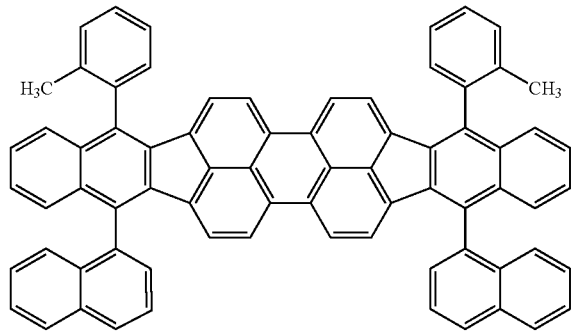
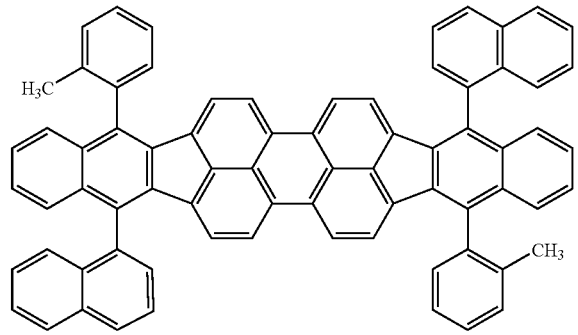
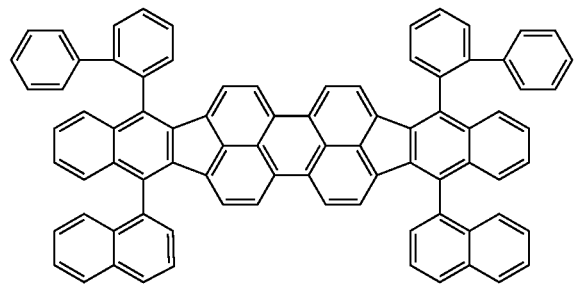
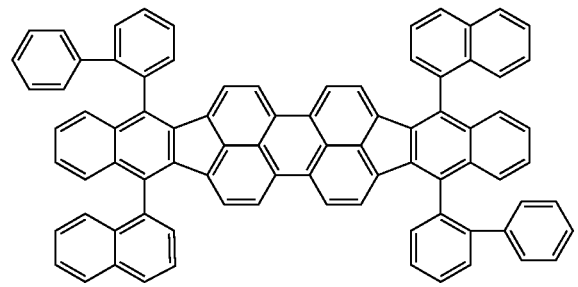
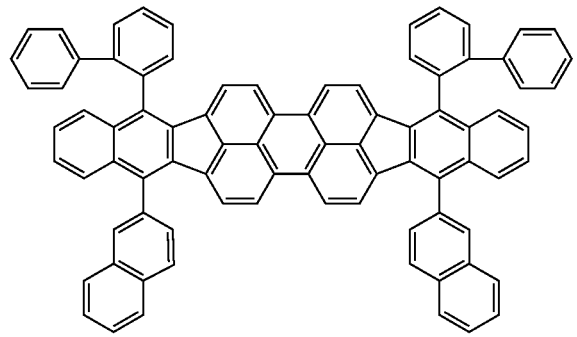
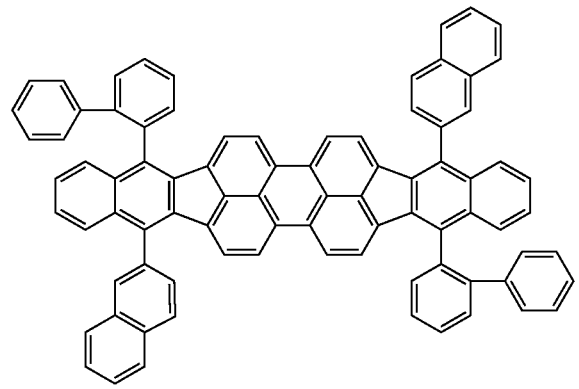
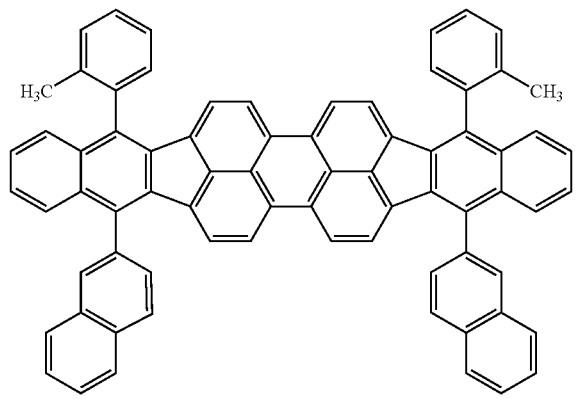
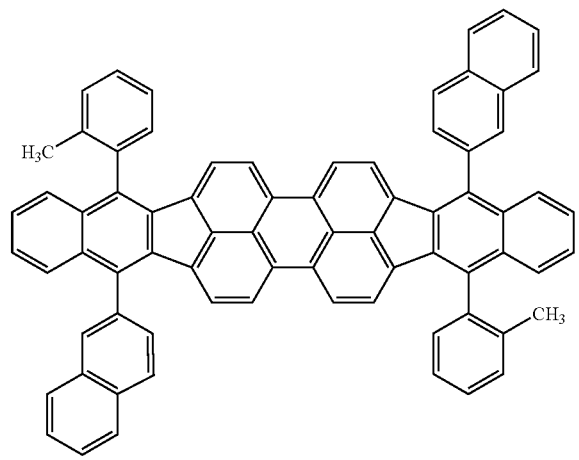

-continued
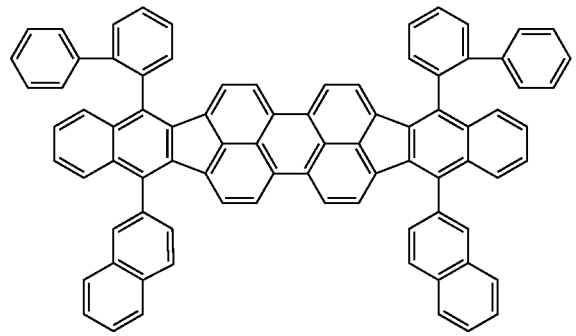
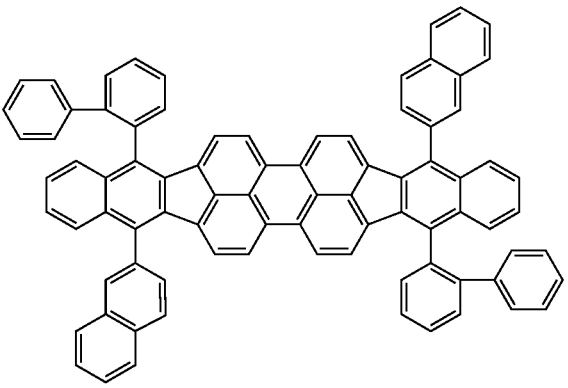
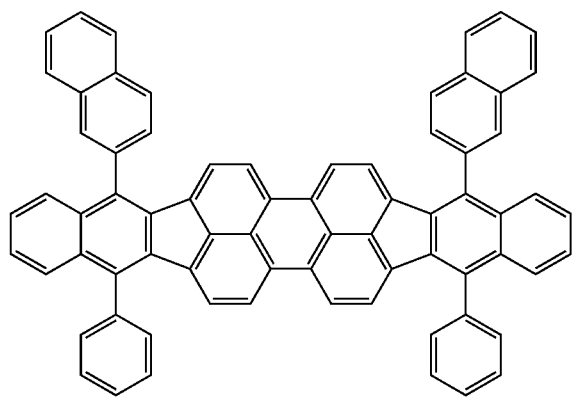
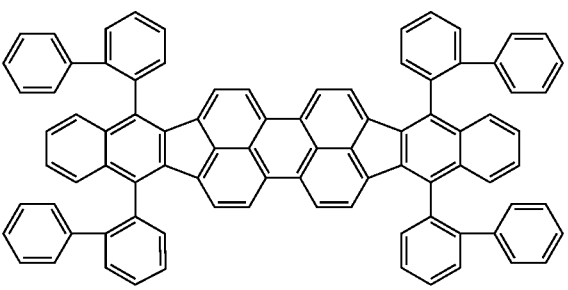
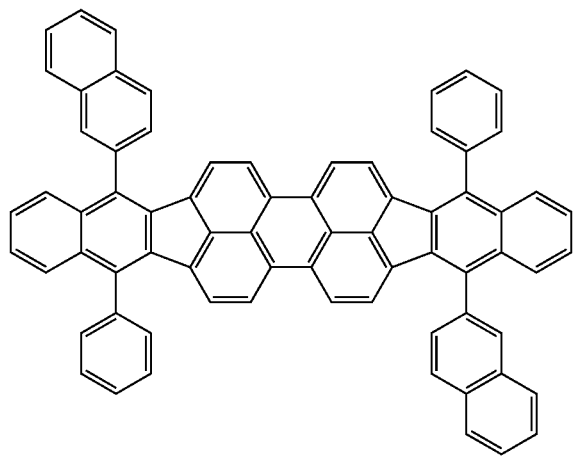
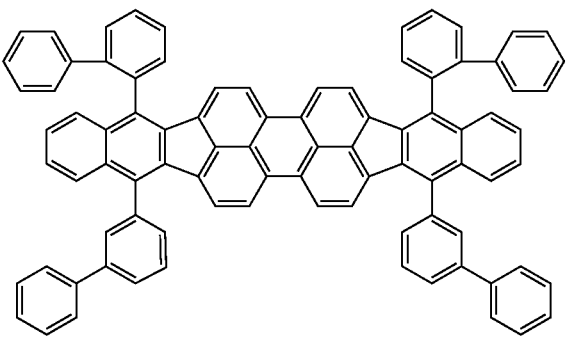
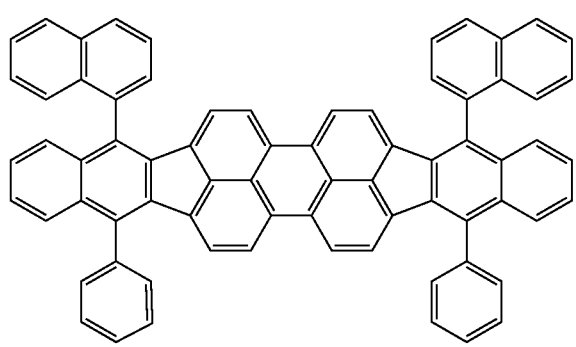
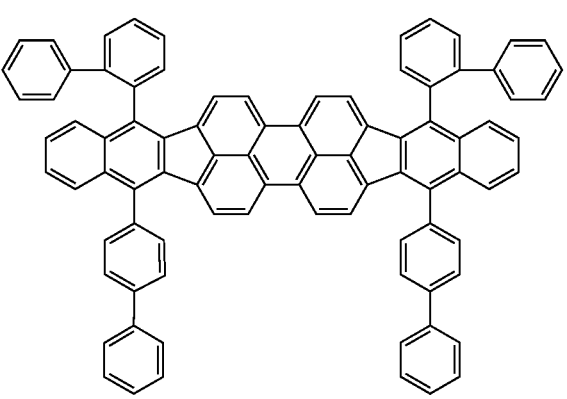

-continued
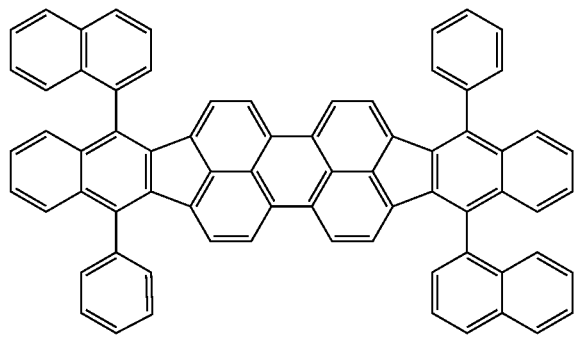
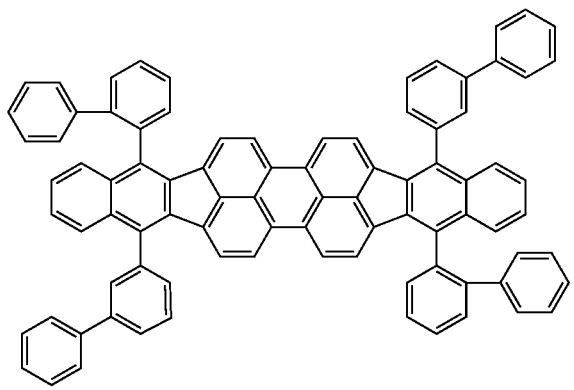
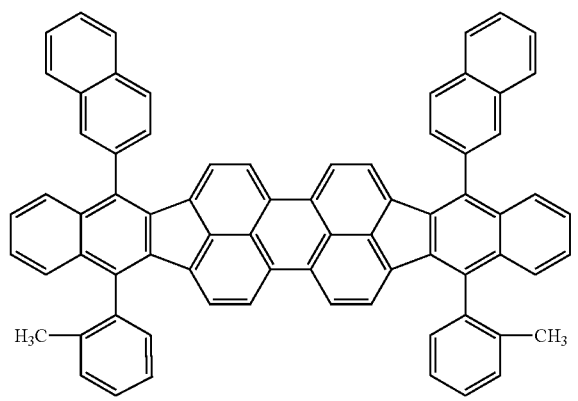
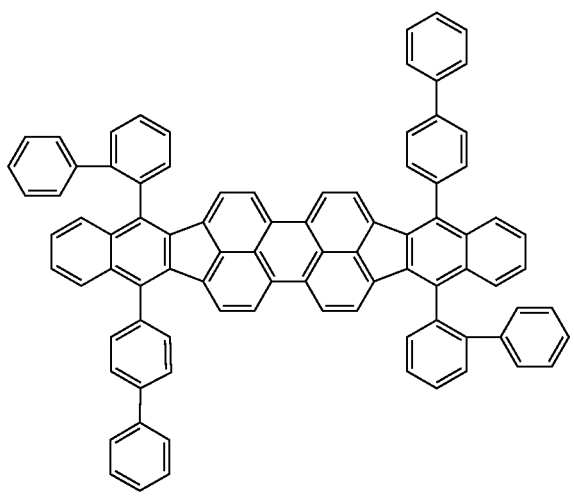
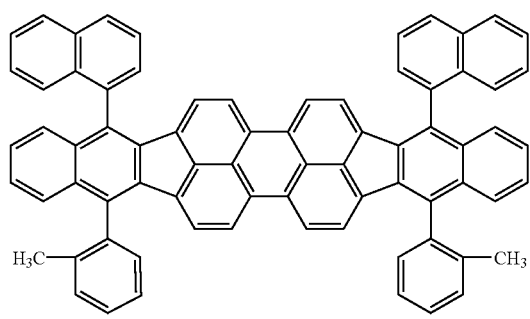
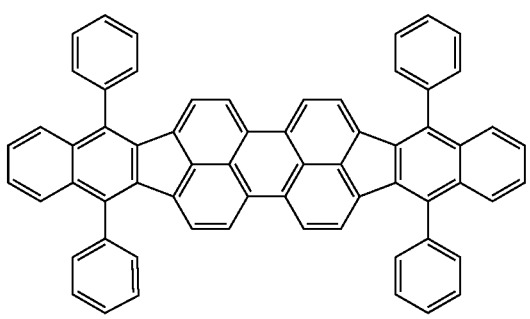
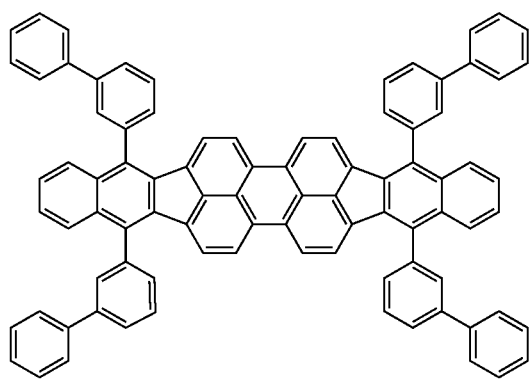
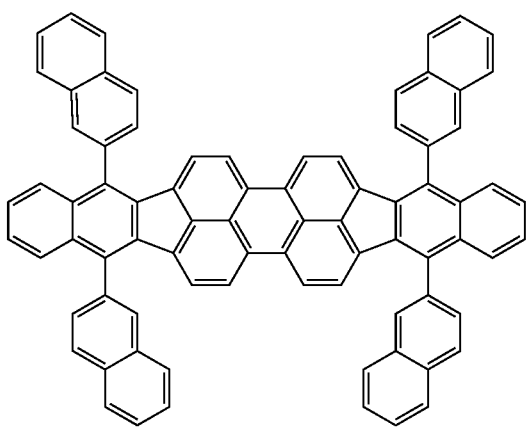

-continued
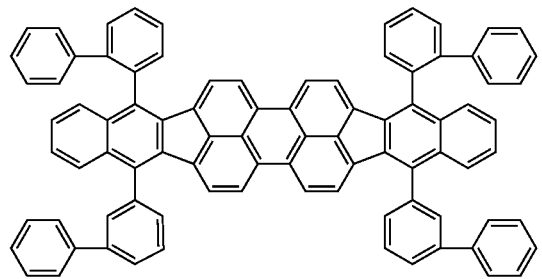
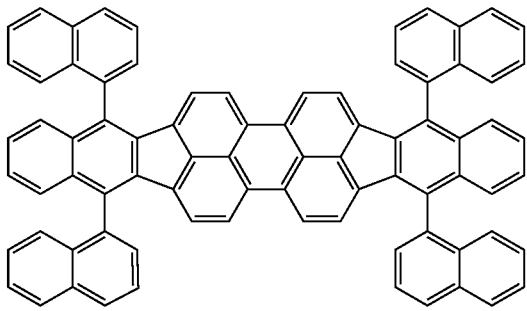
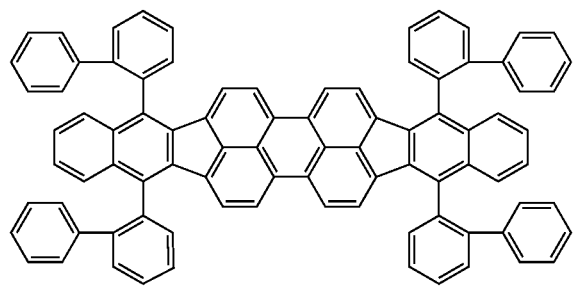
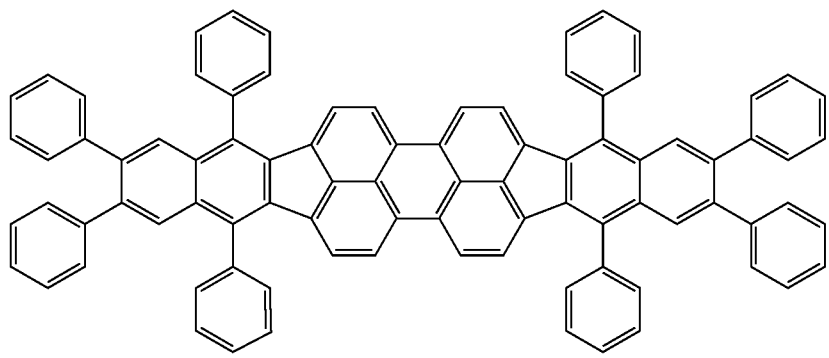
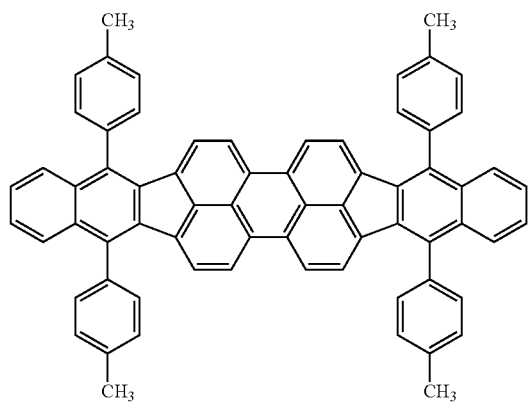
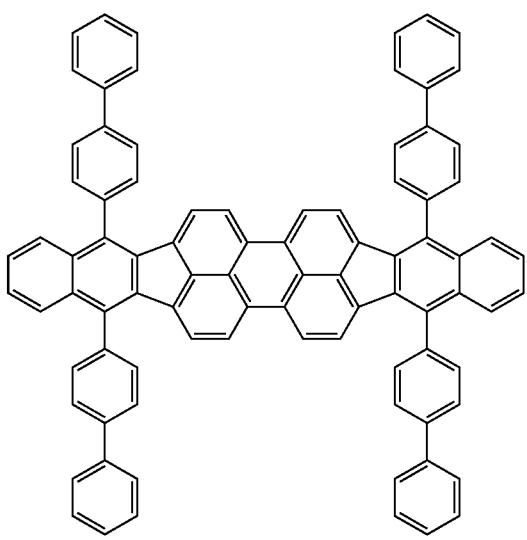

-continued
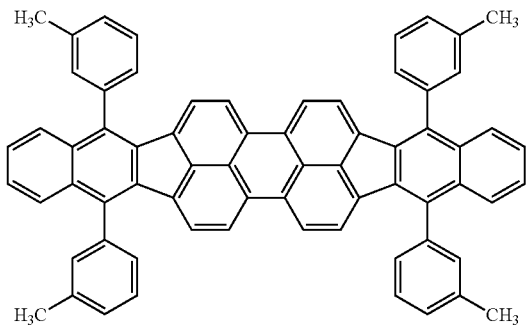
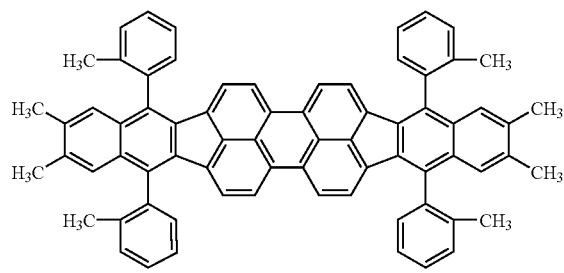
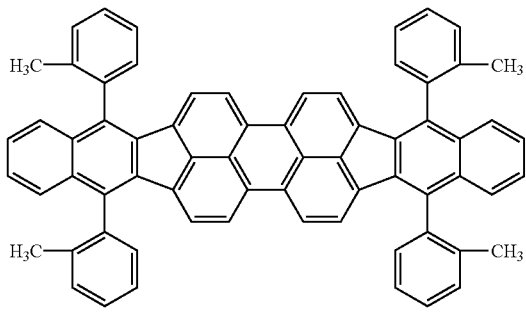
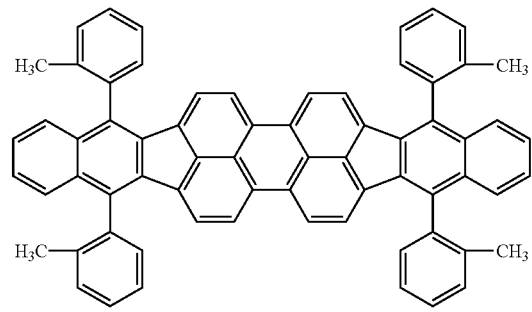
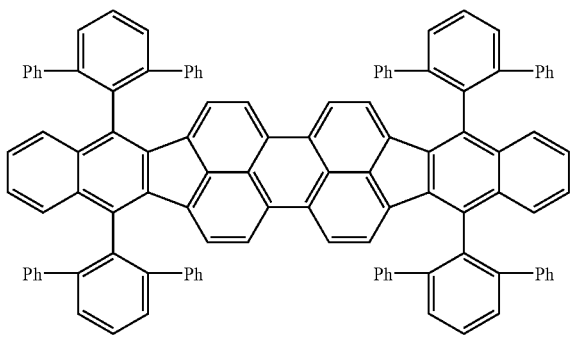
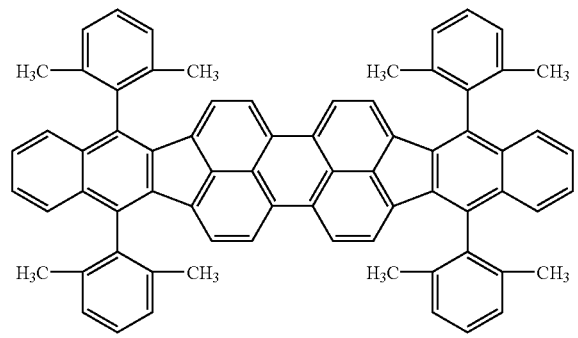
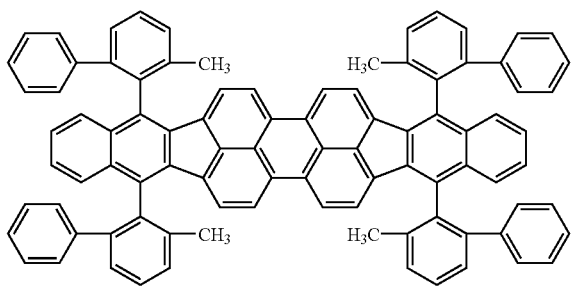
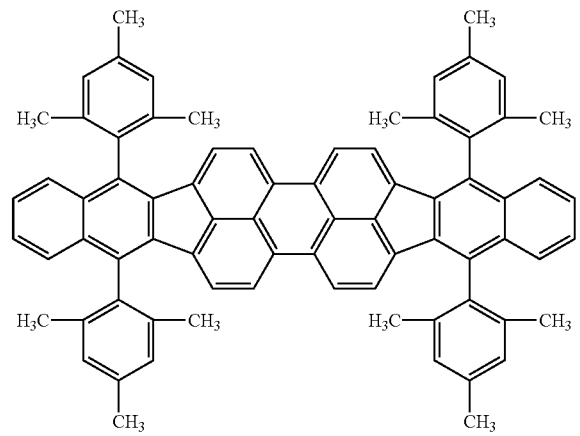

-continued
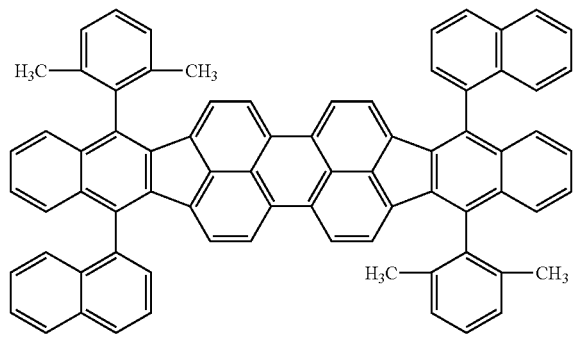
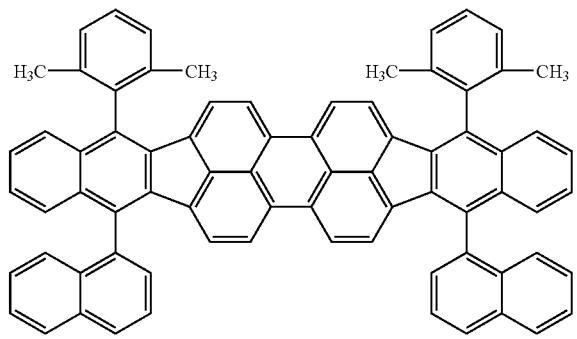
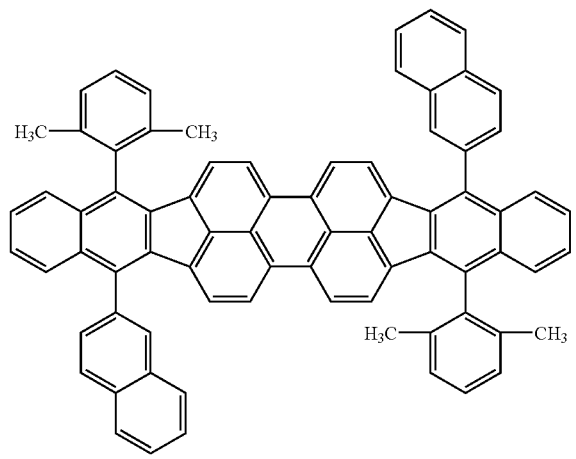
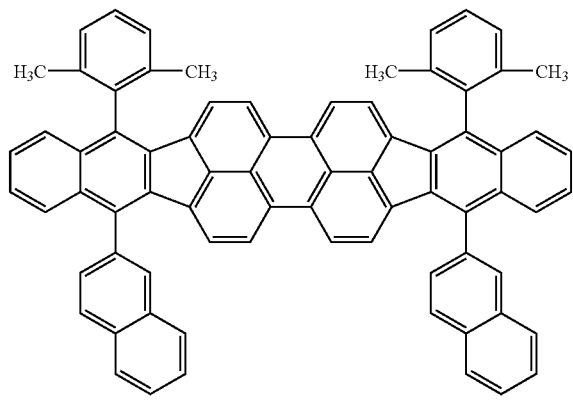
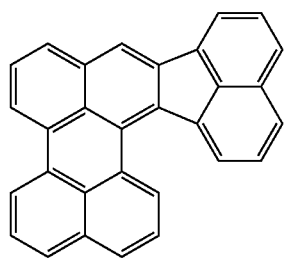
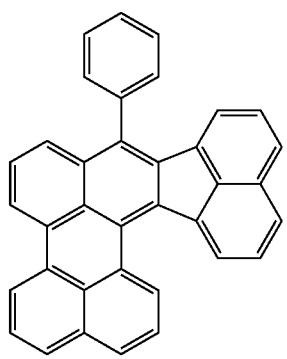
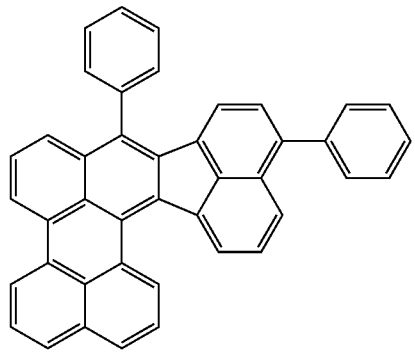
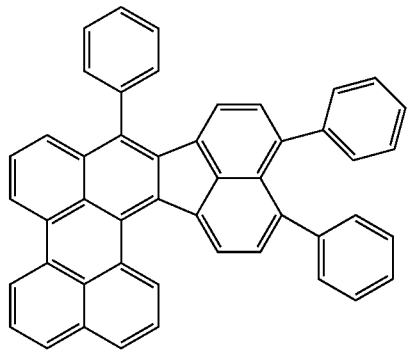

-continued
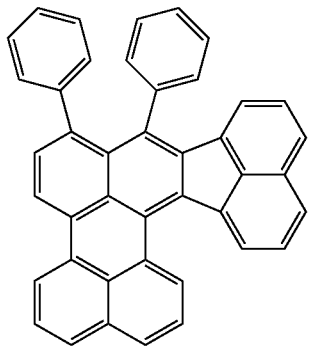
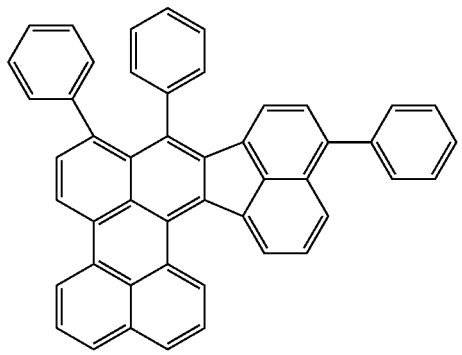
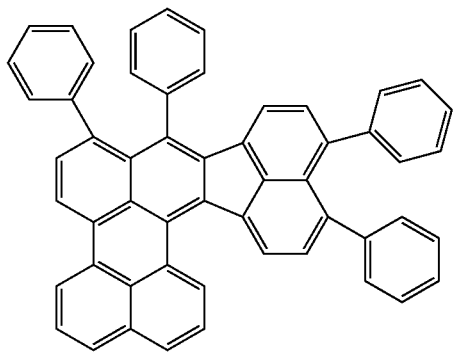
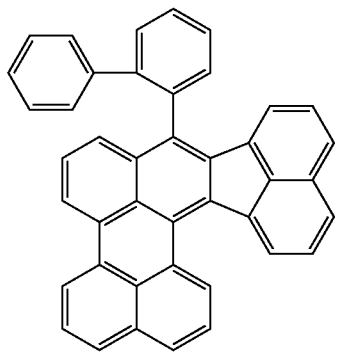
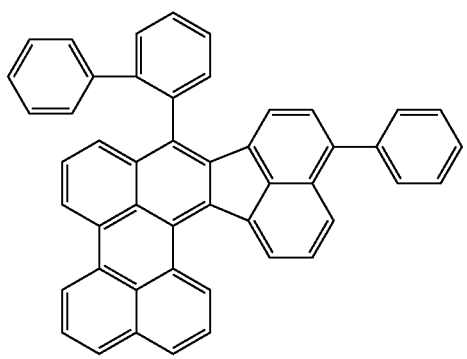
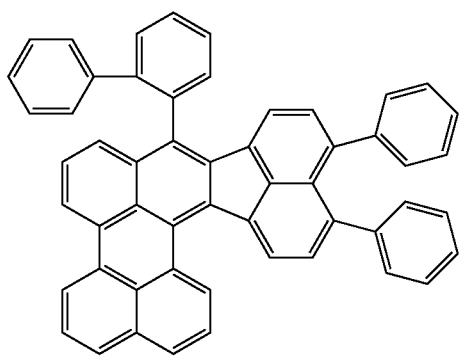
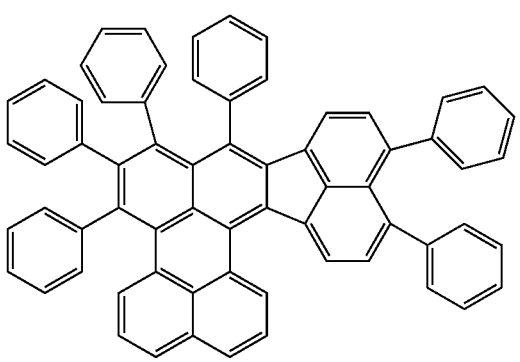
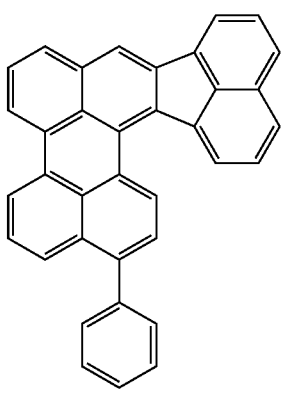

-continued
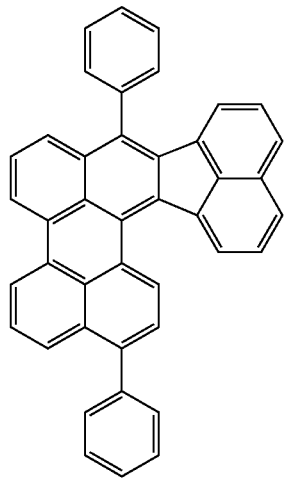
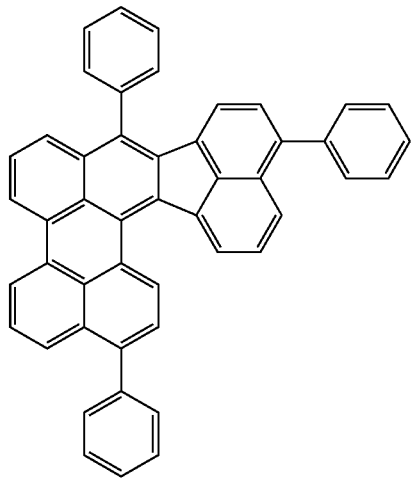
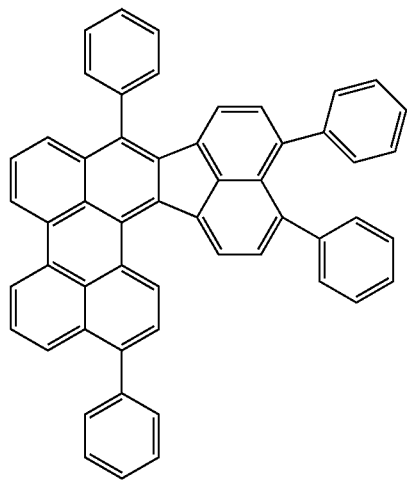
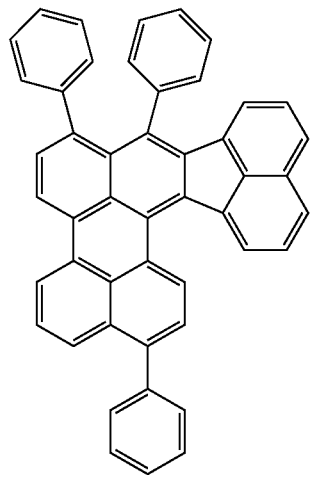
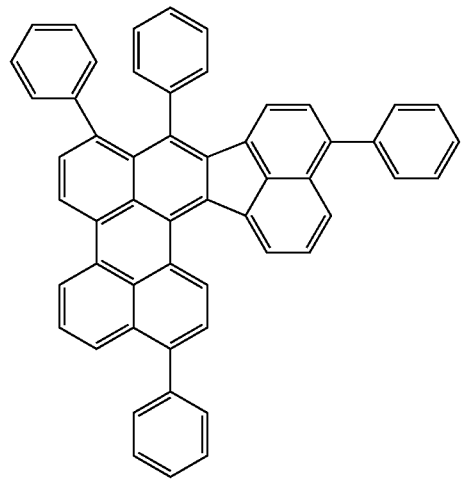
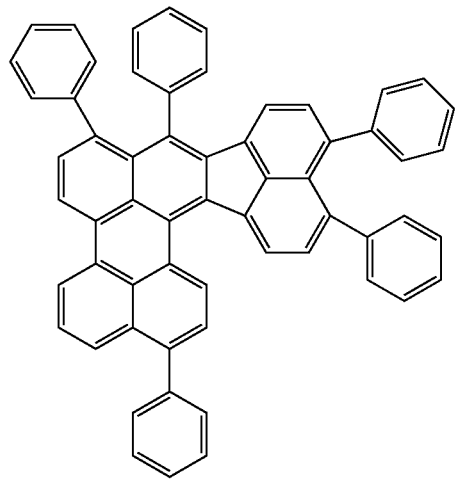

-continued
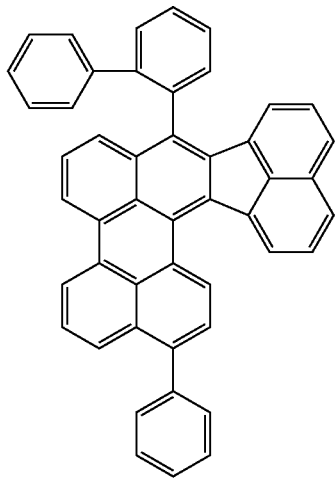
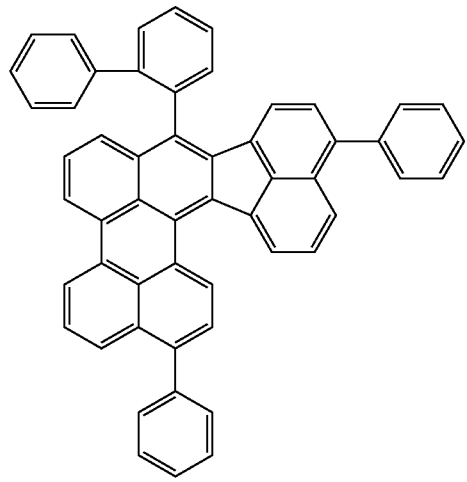
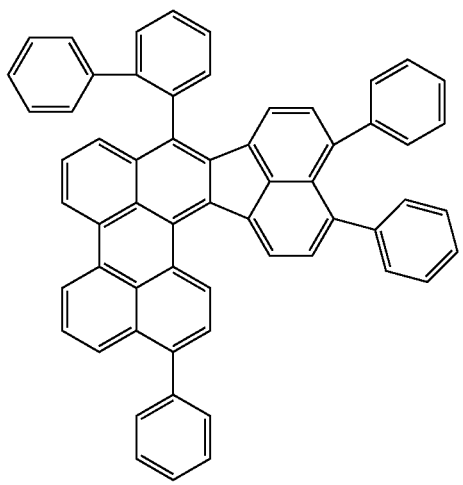
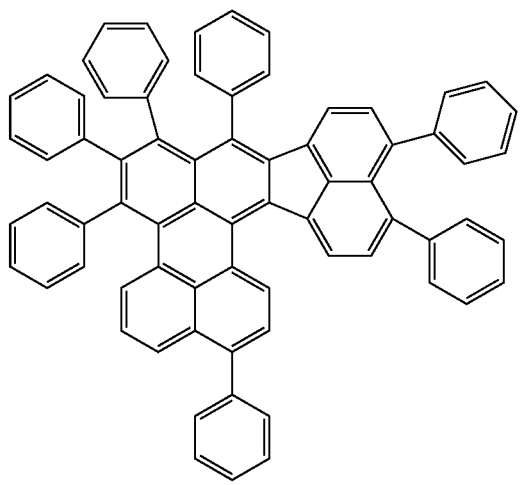
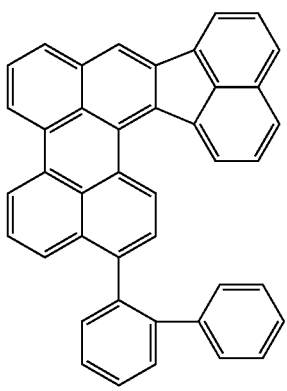
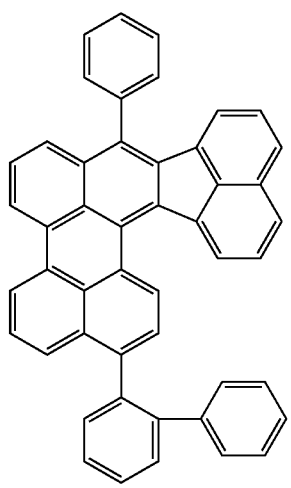

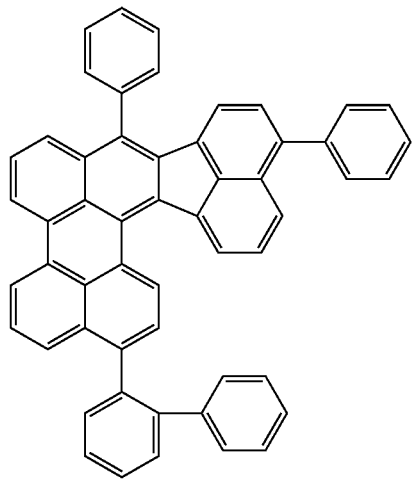
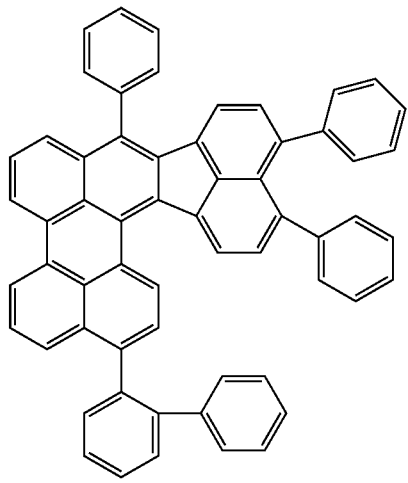
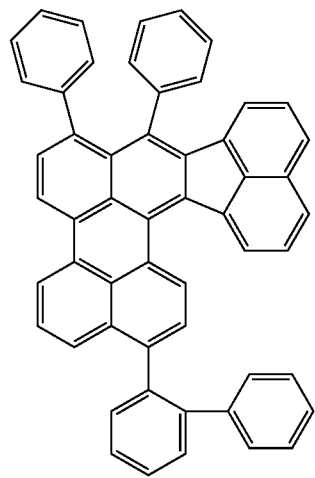
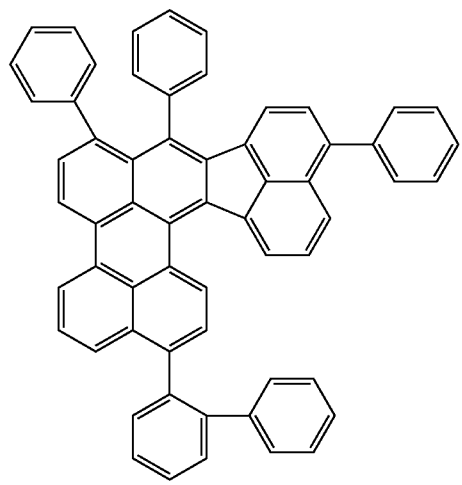
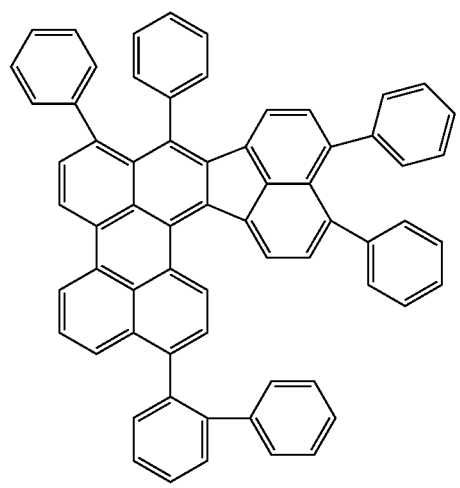
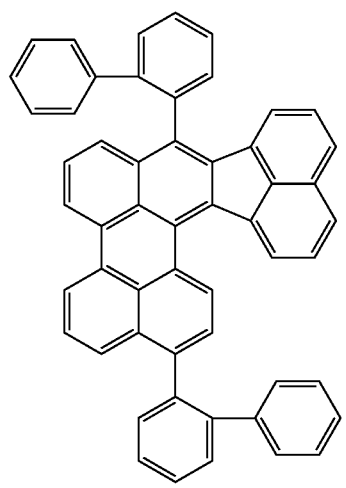

-continued
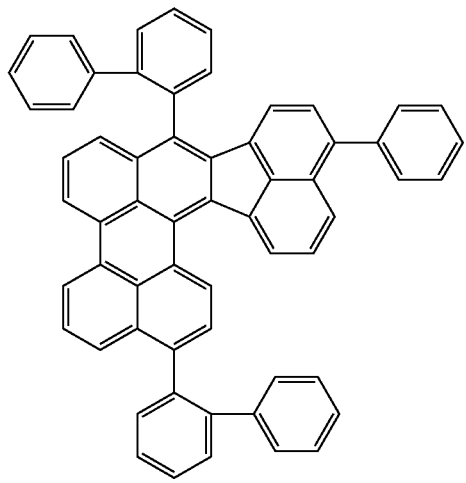
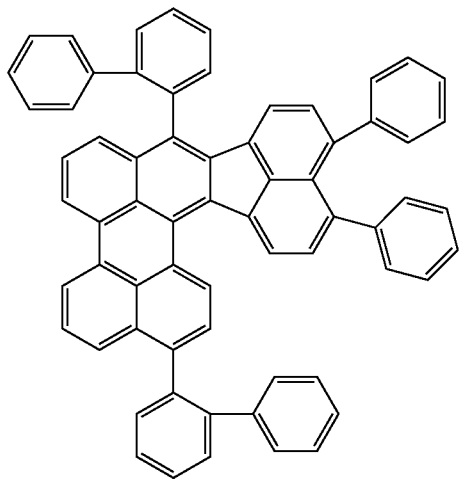
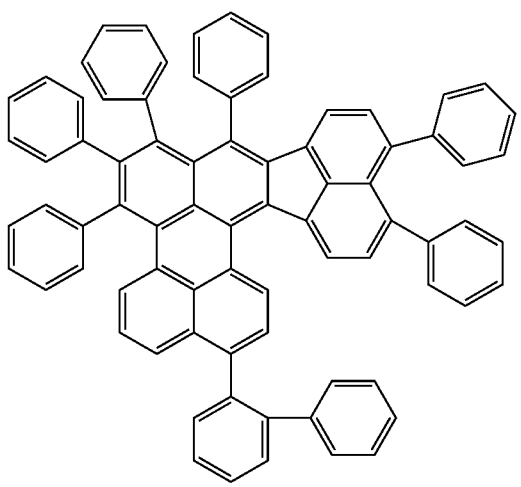
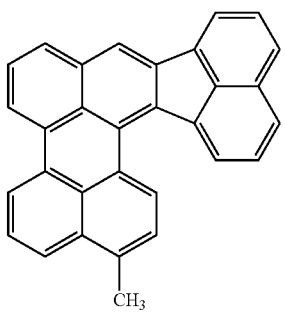
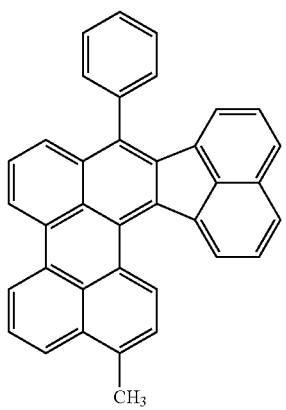
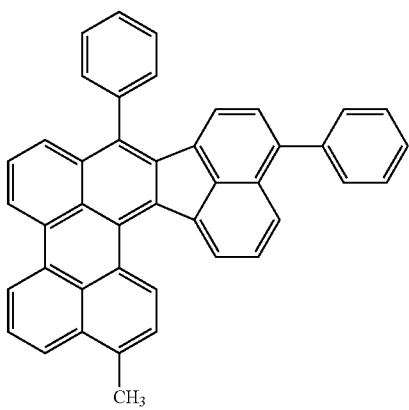

-continued
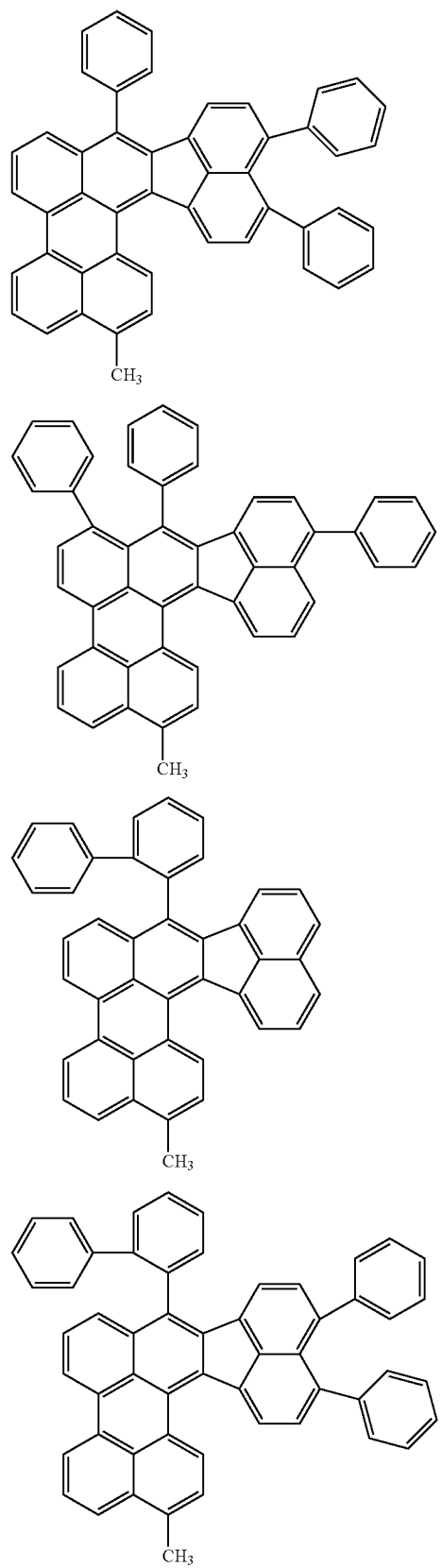
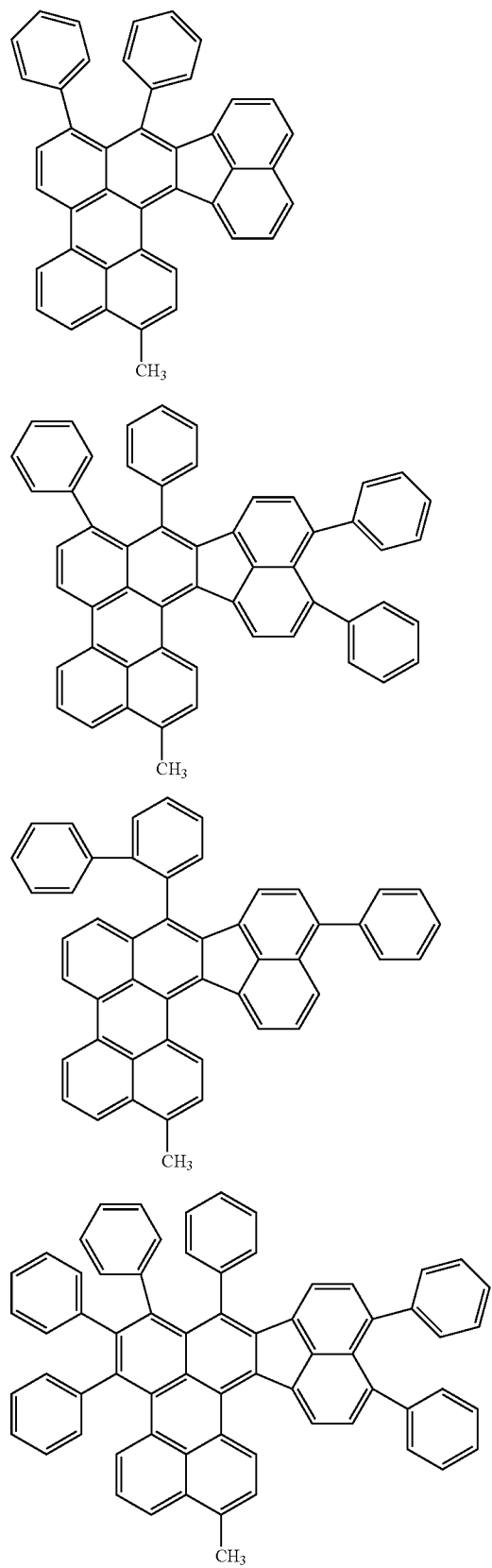

-continued
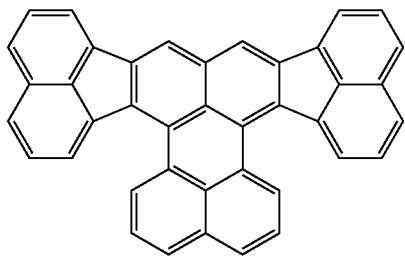
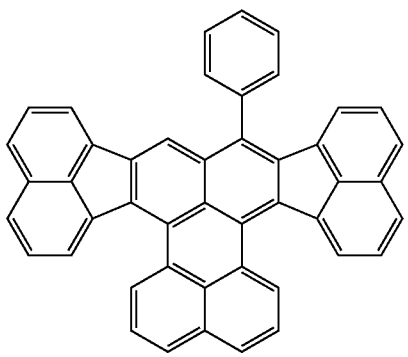
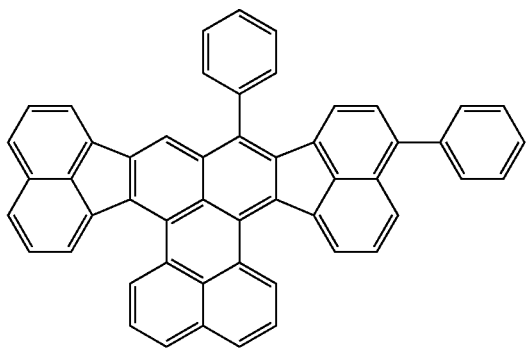
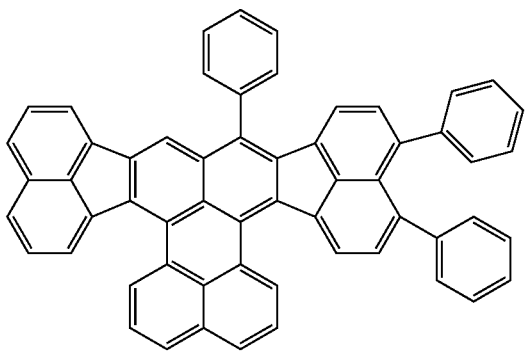
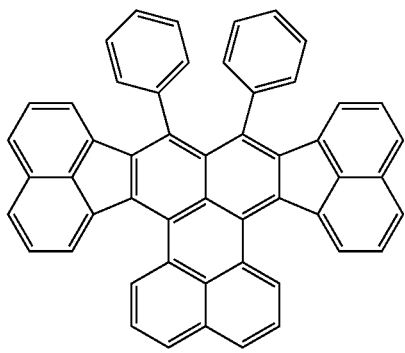
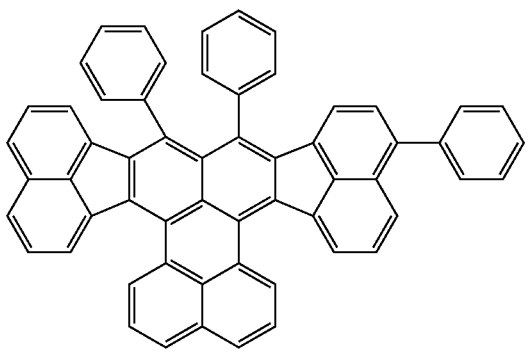
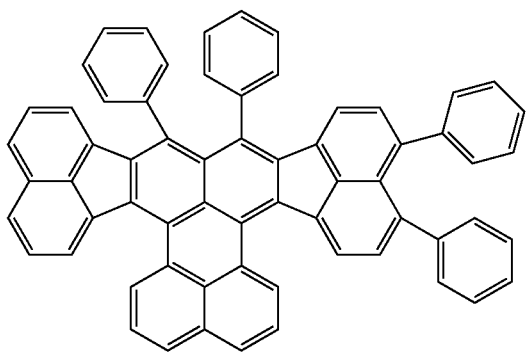
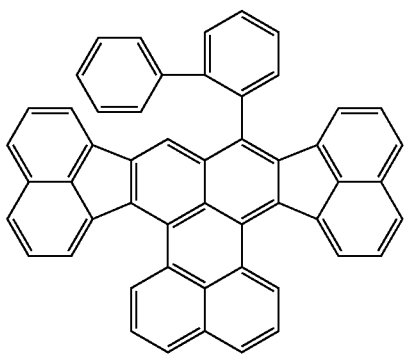

-continued
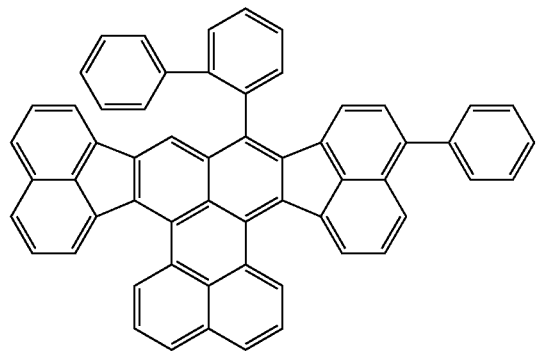
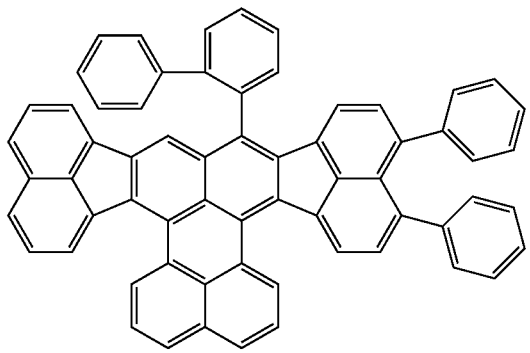
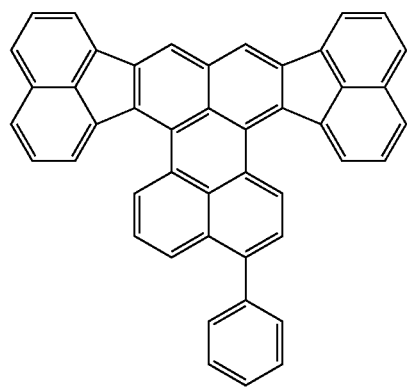
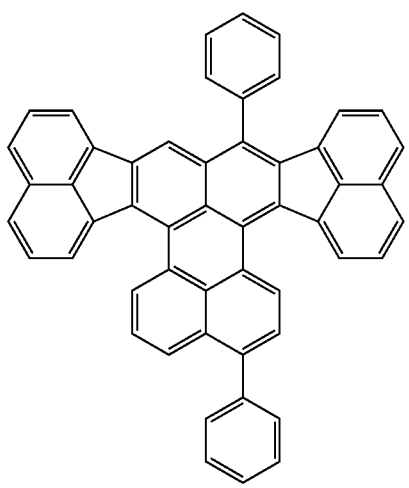
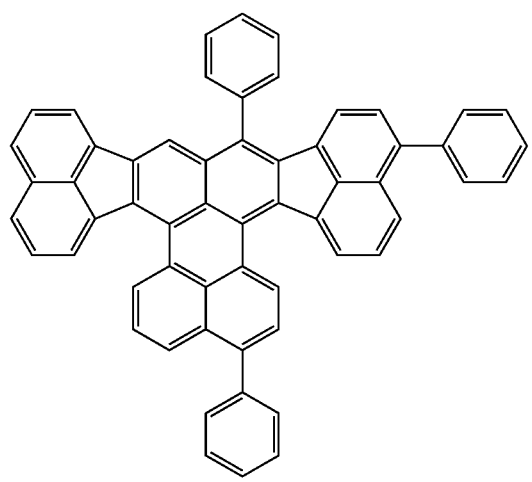
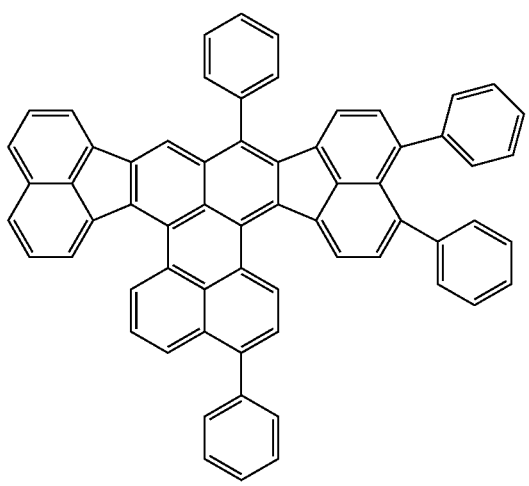

-continued
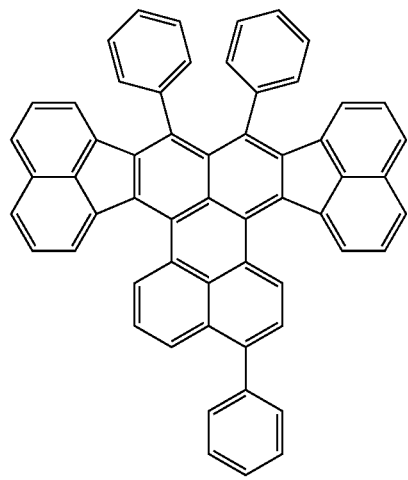
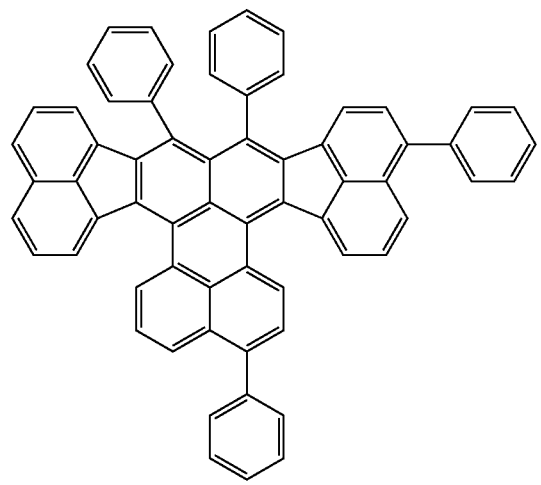
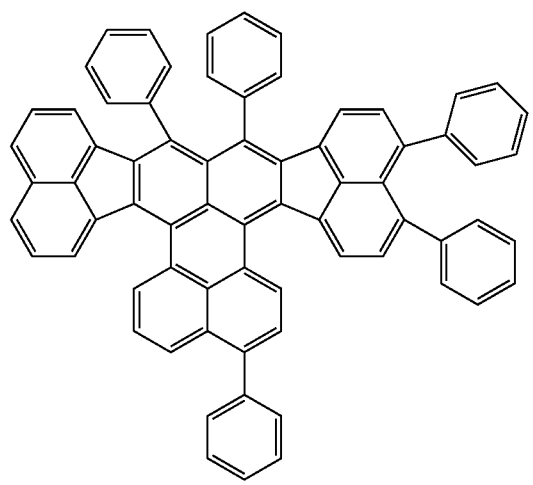
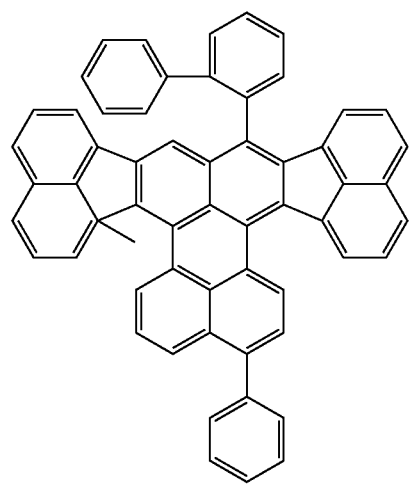
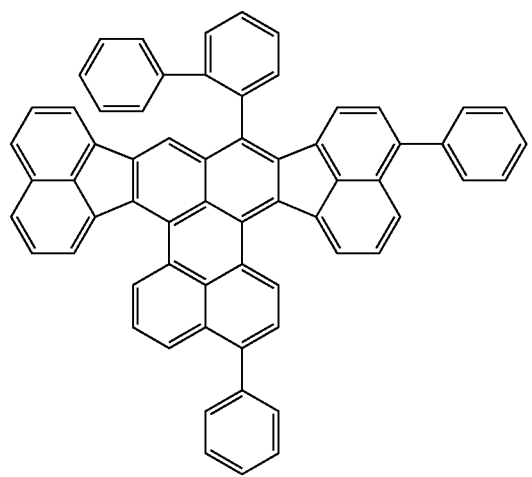
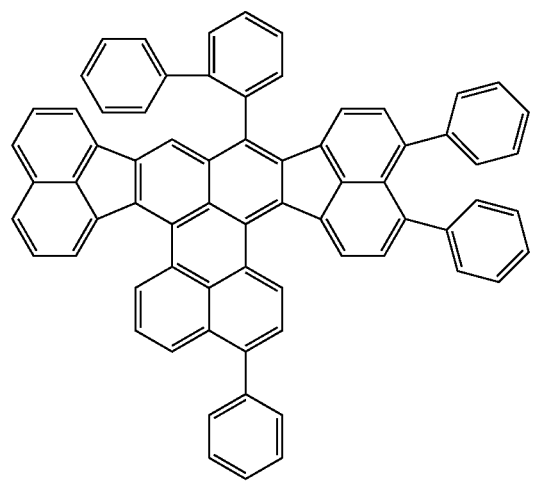

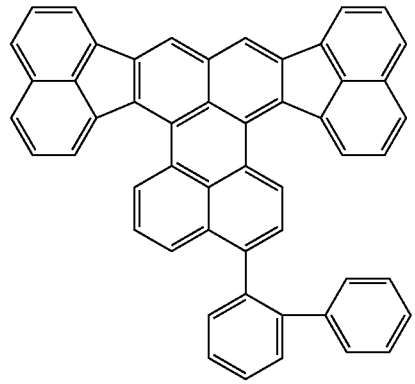
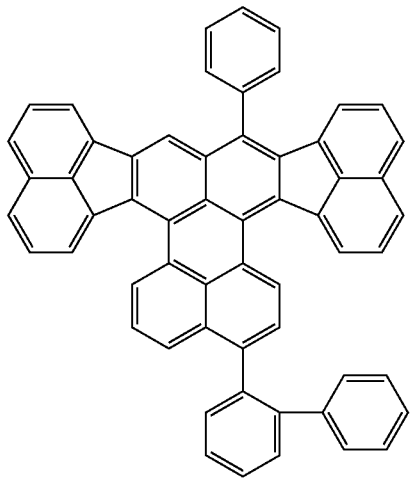
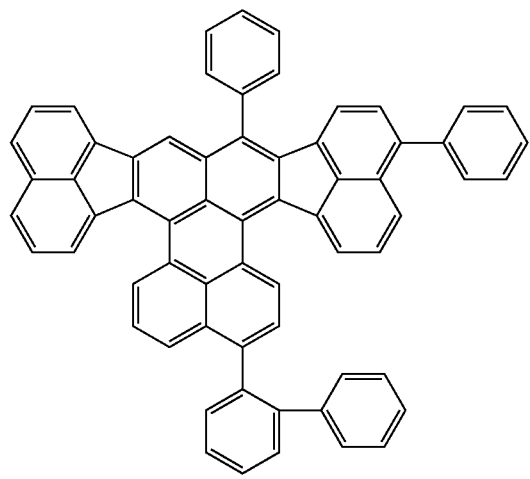
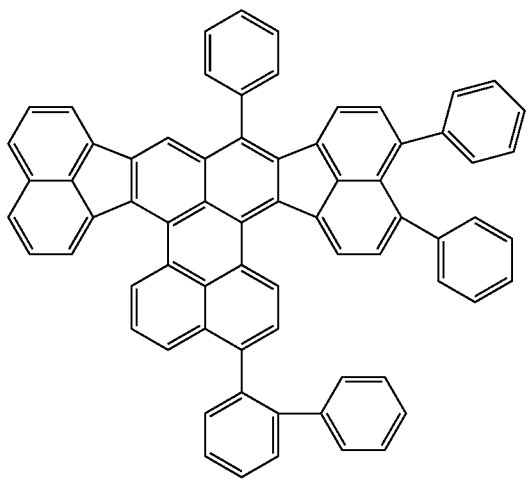
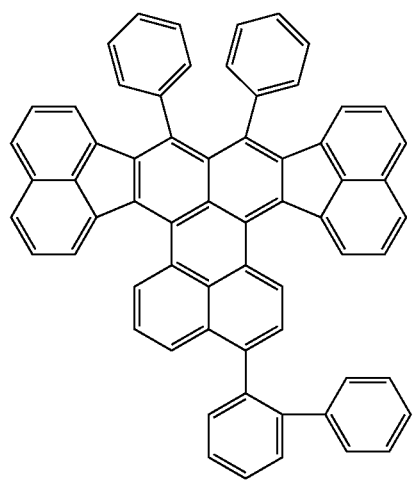
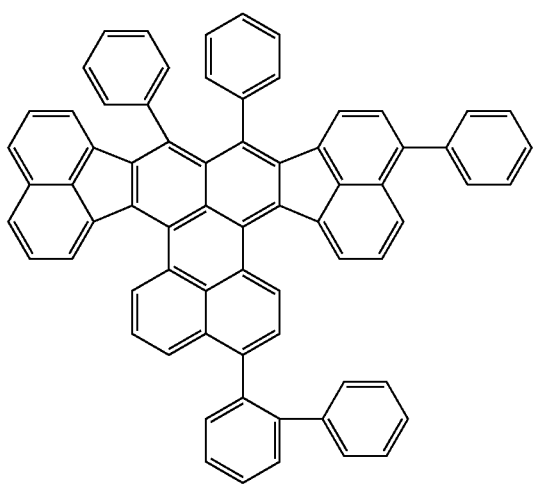

-continued
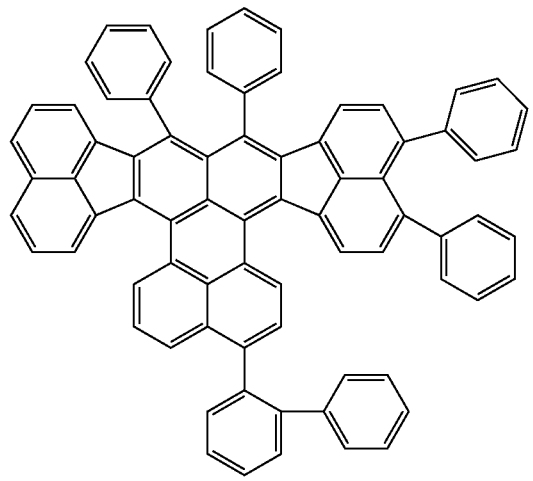
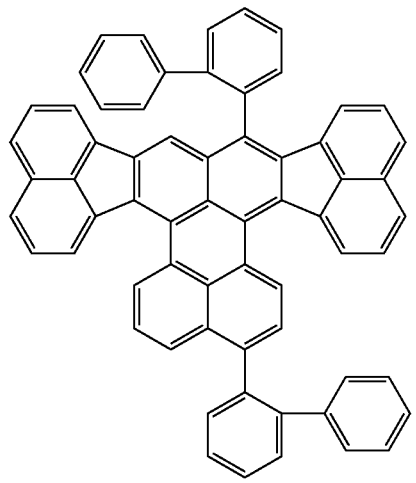
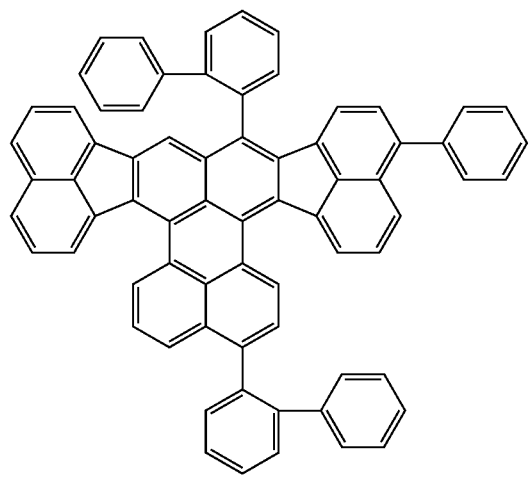
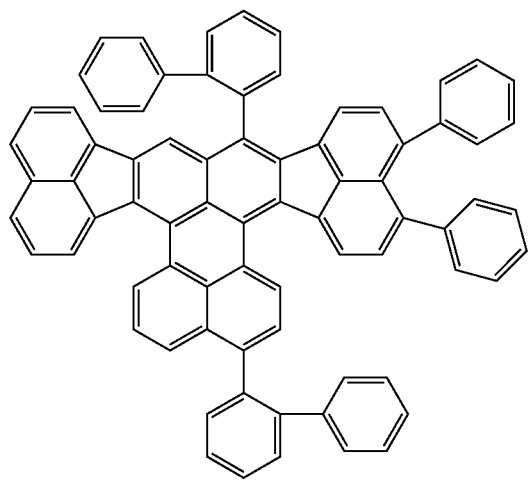
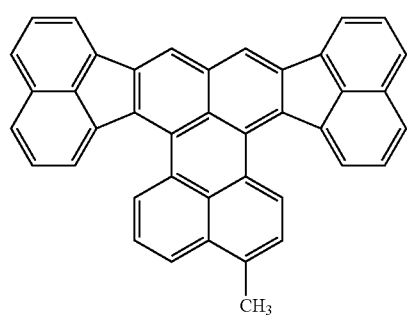
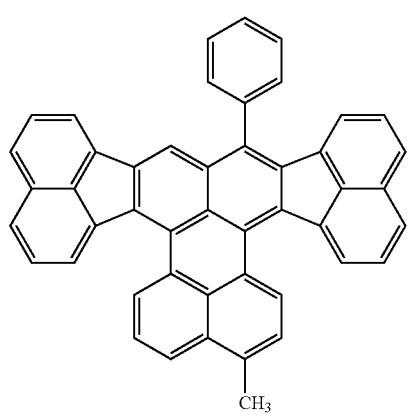

-continued
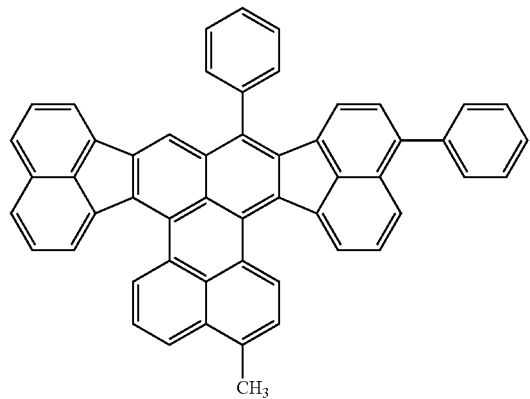
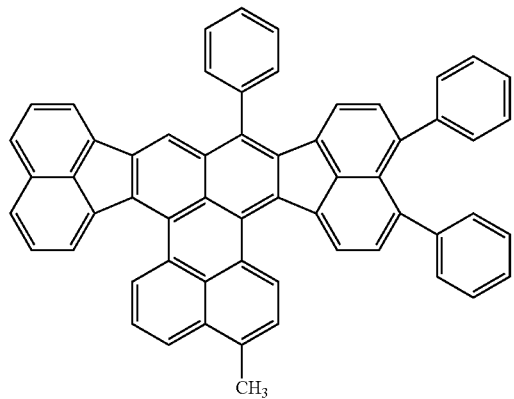
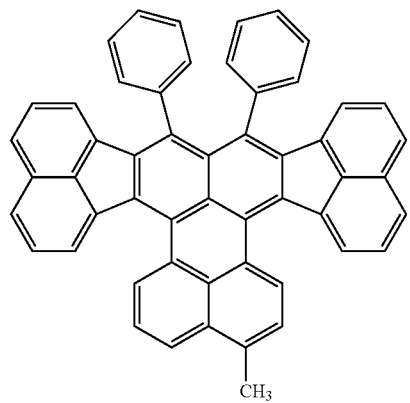
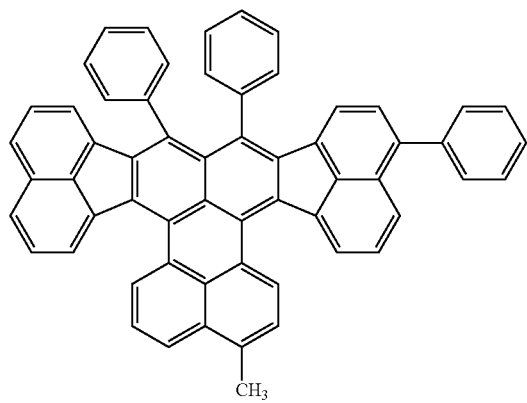
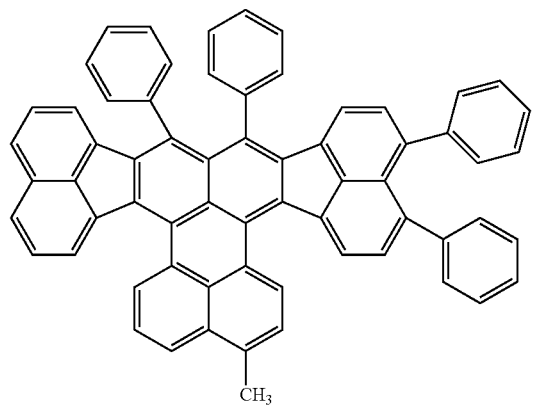
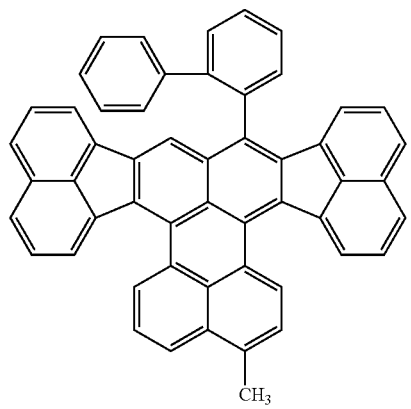
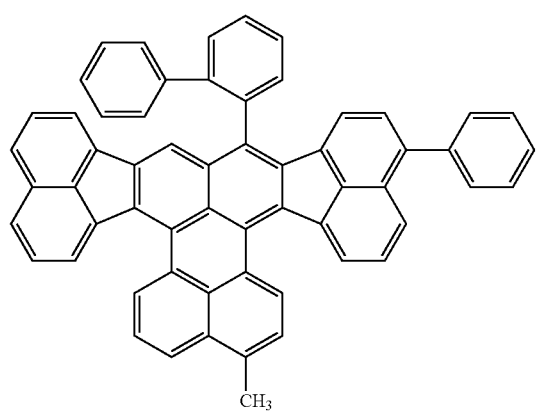
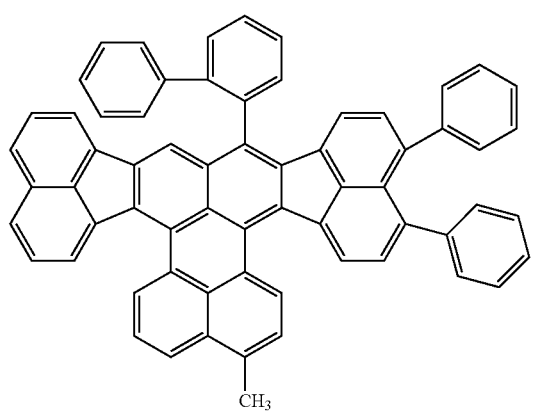

-continued
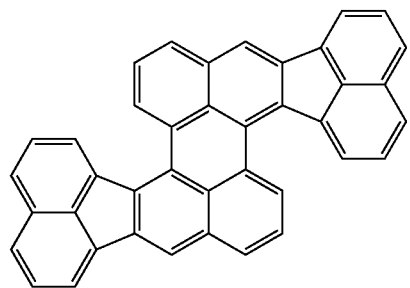
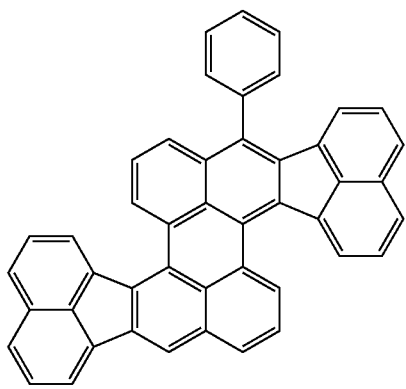
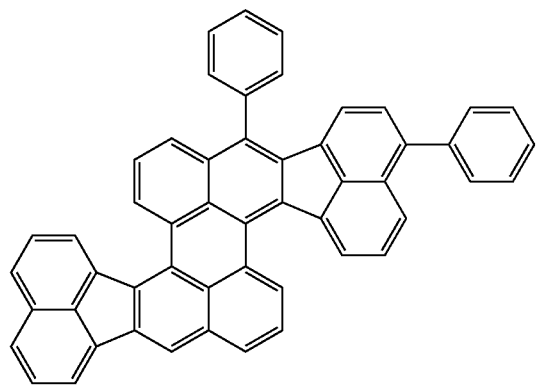
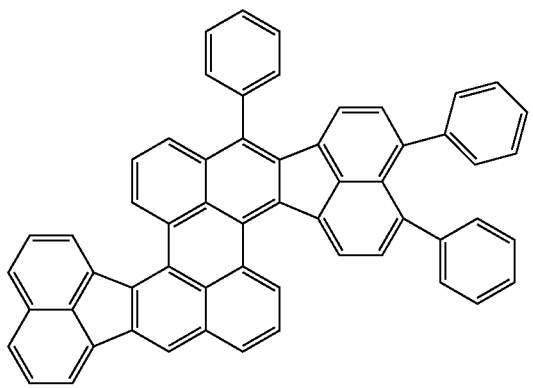
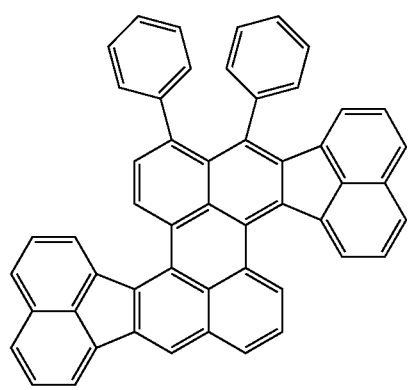
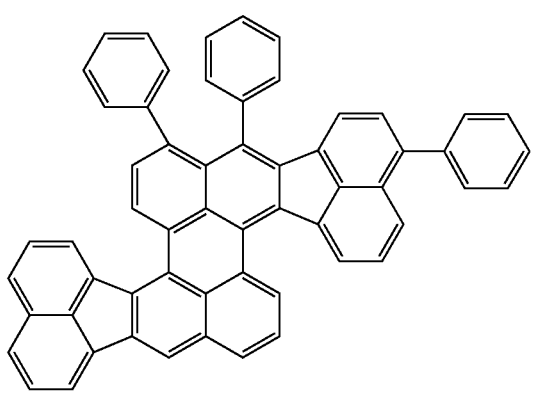
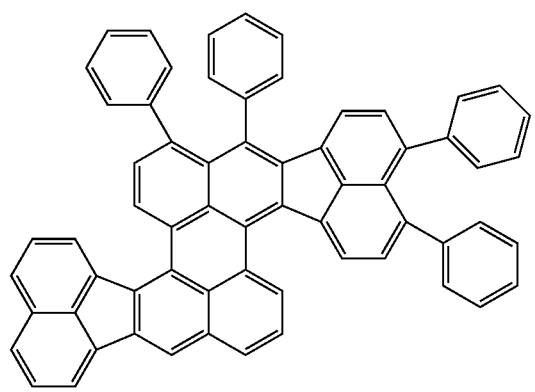
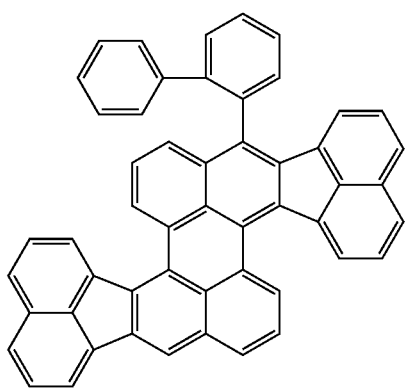

-continued
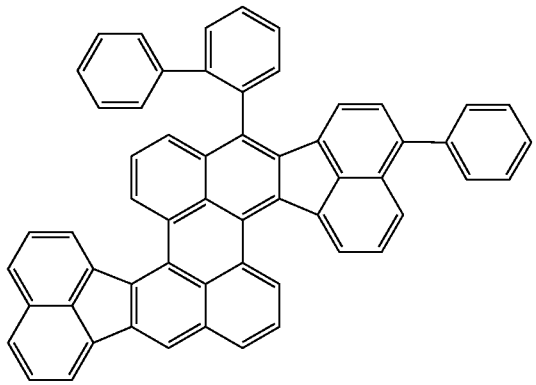
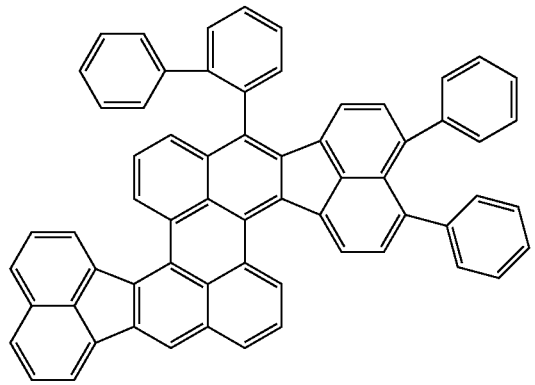
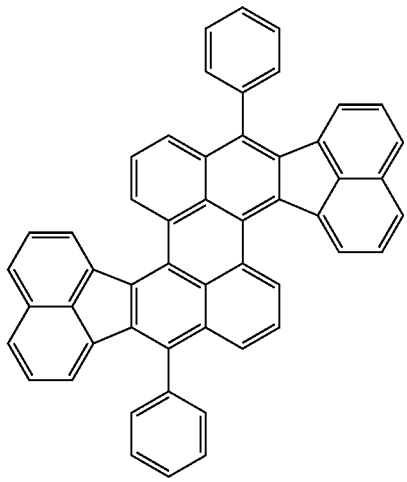
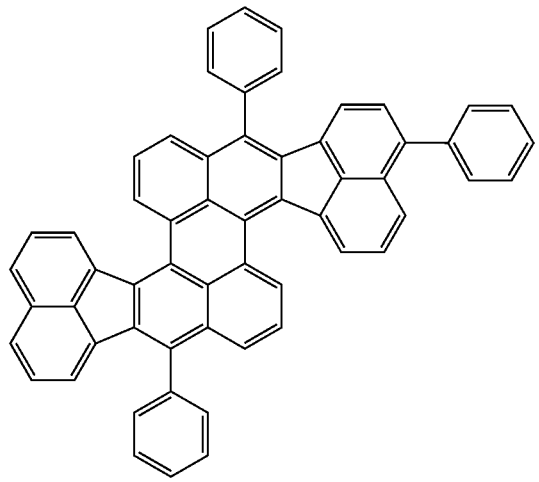
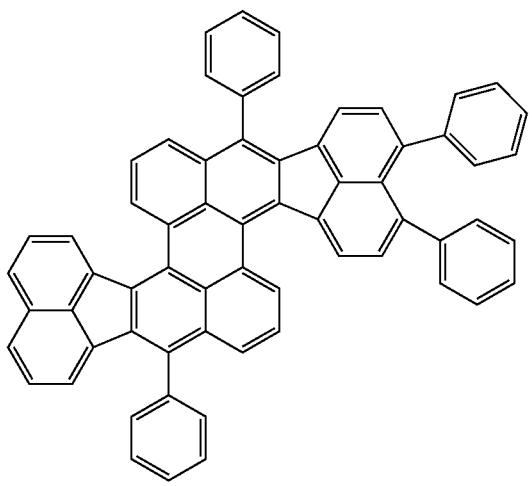
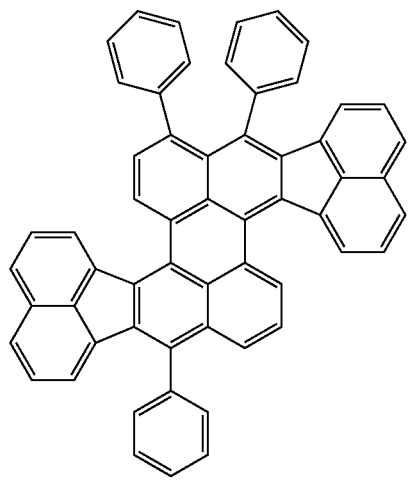

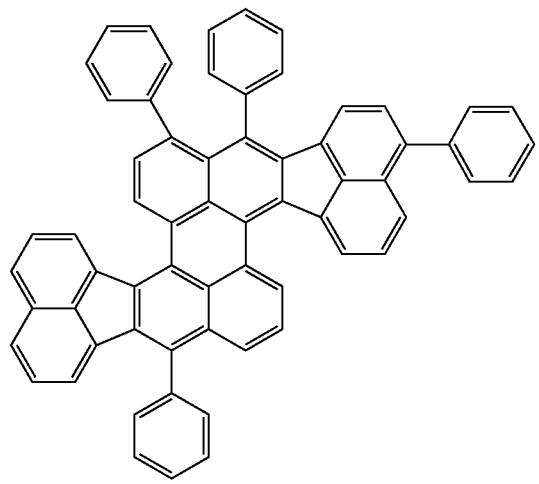
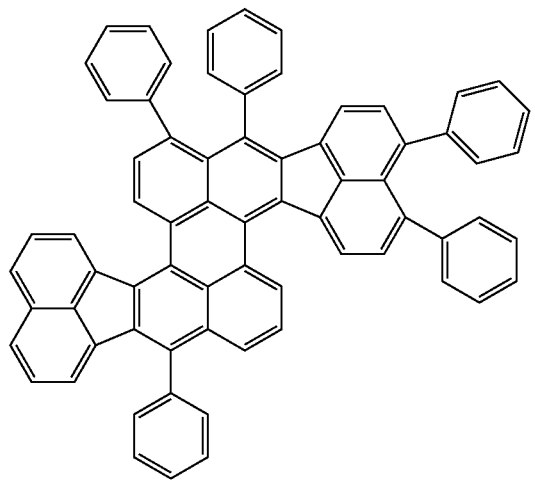
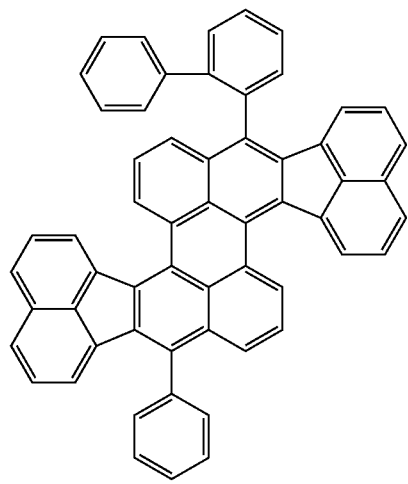
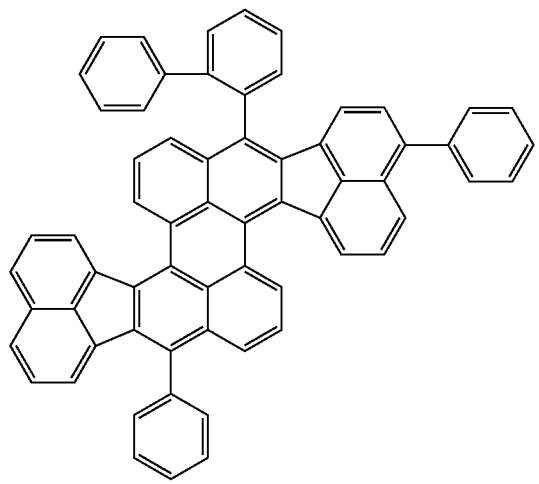
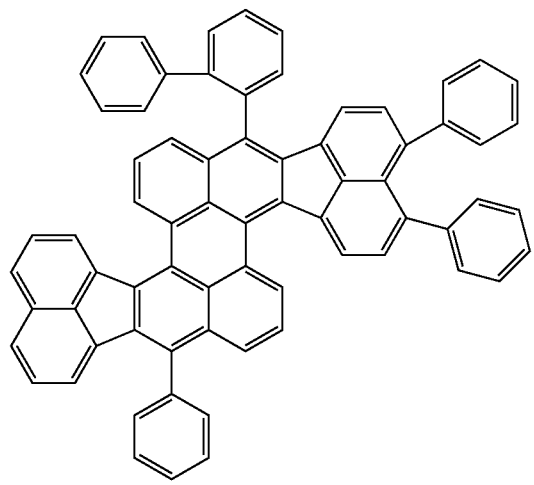
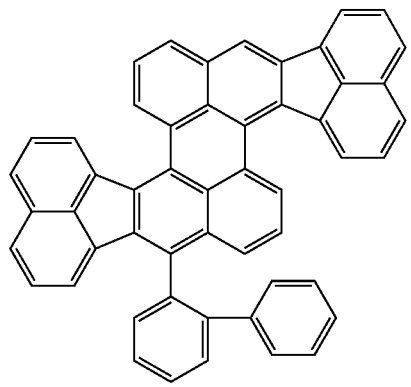

-continued
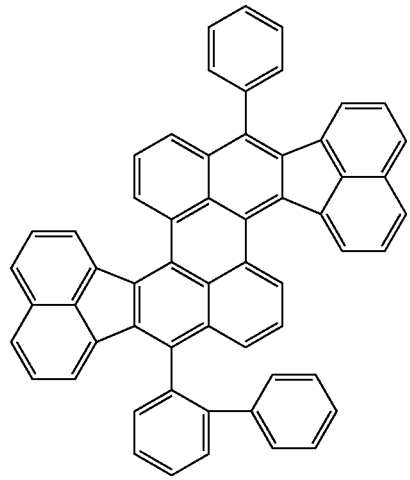
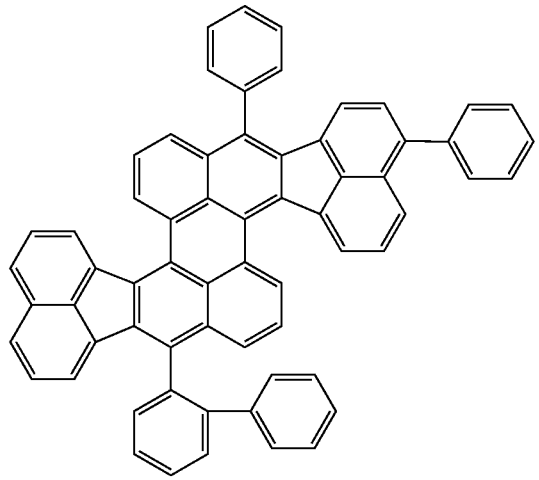
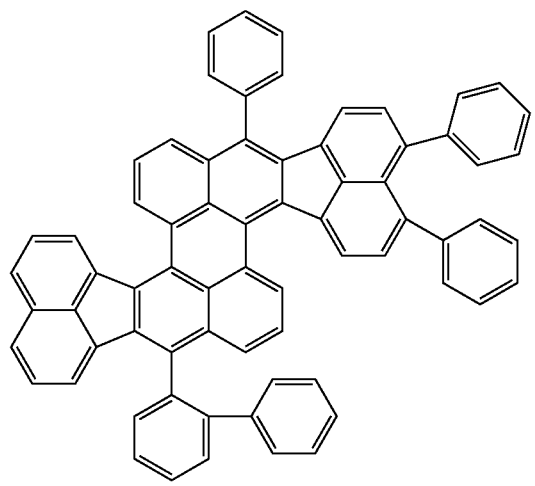
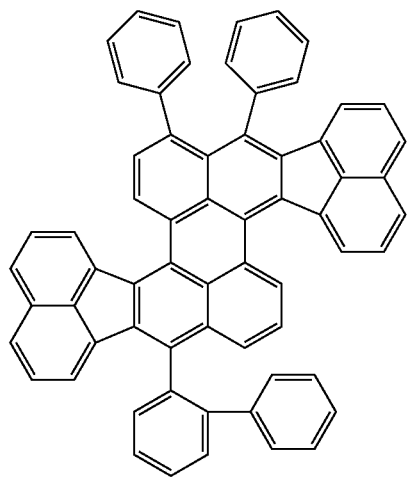
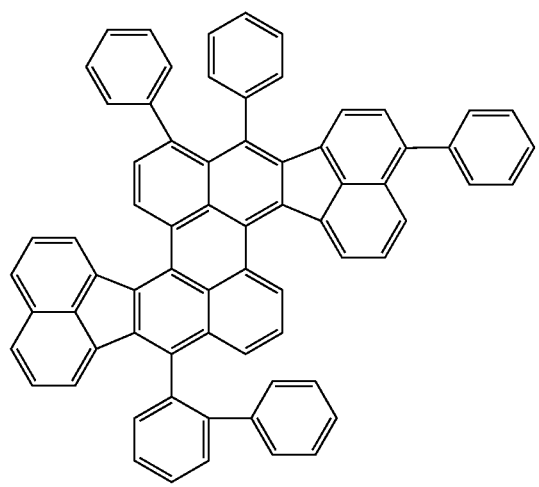
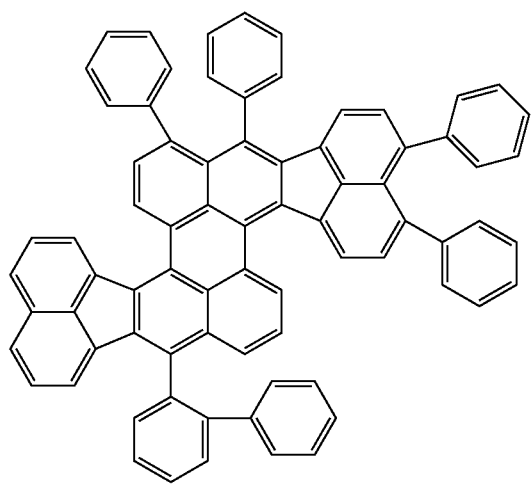

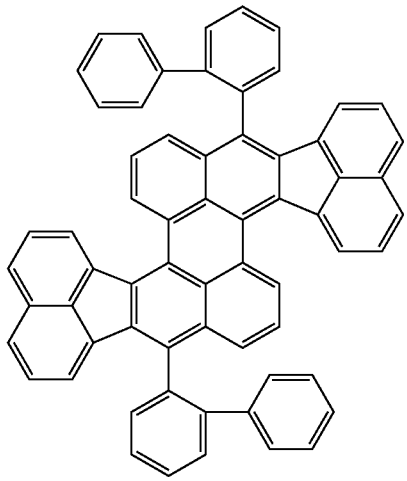

-continued
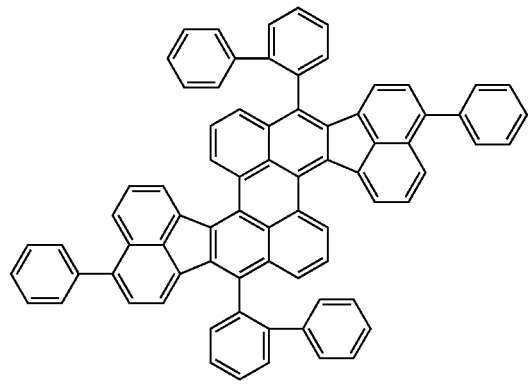
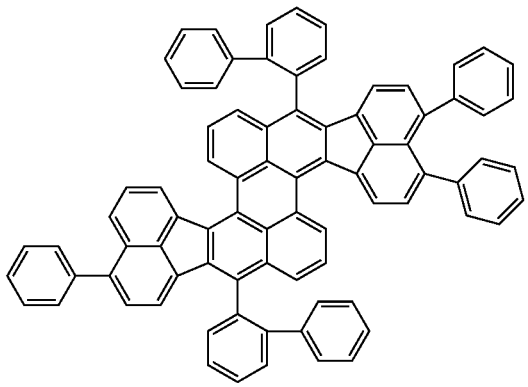
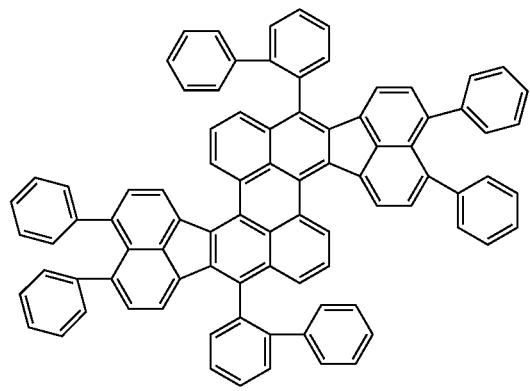
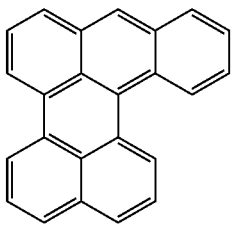
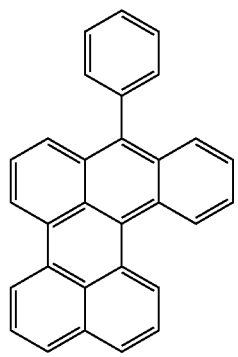
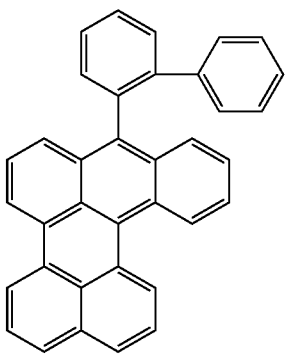
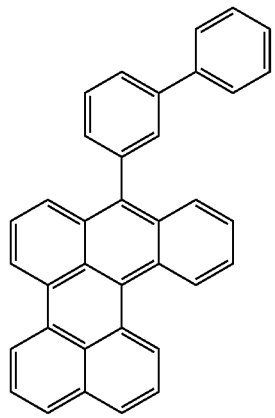
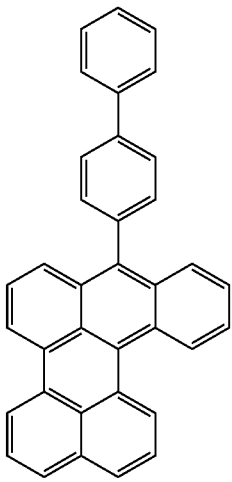

-continued
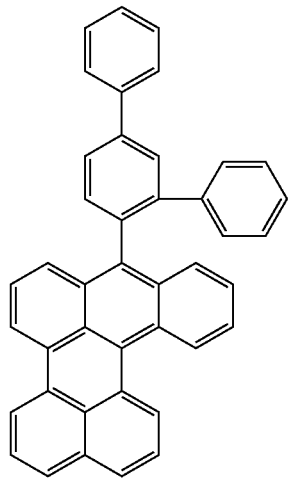
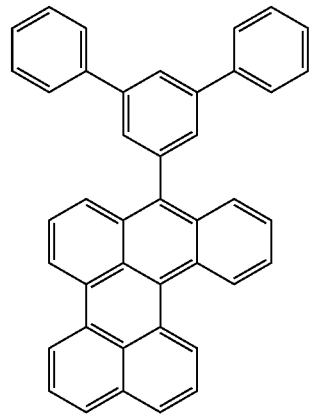
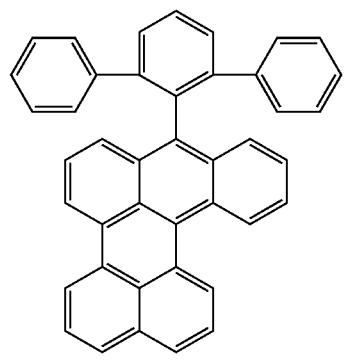
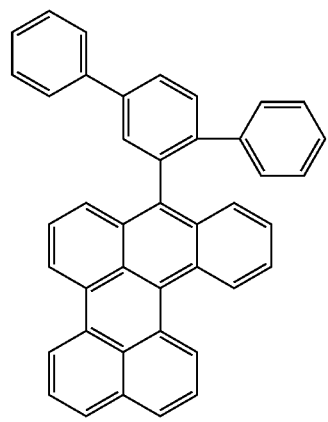
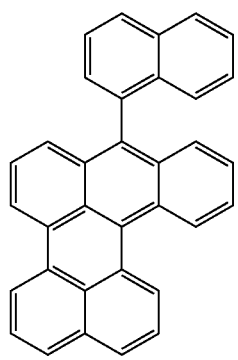
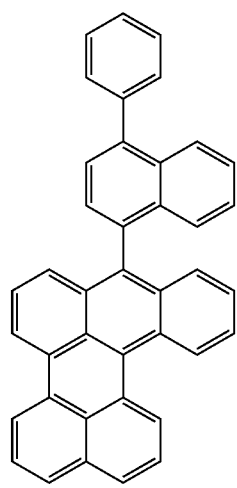

-continued
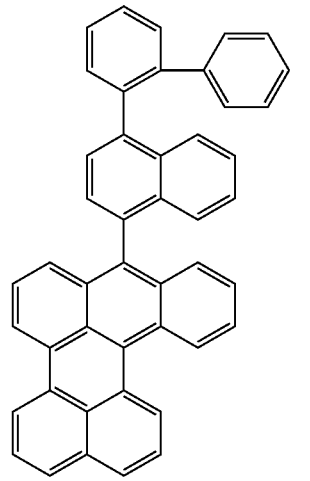
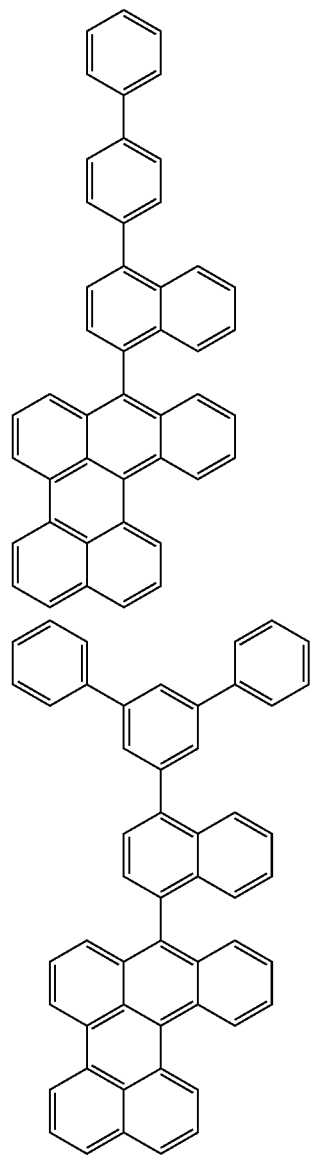
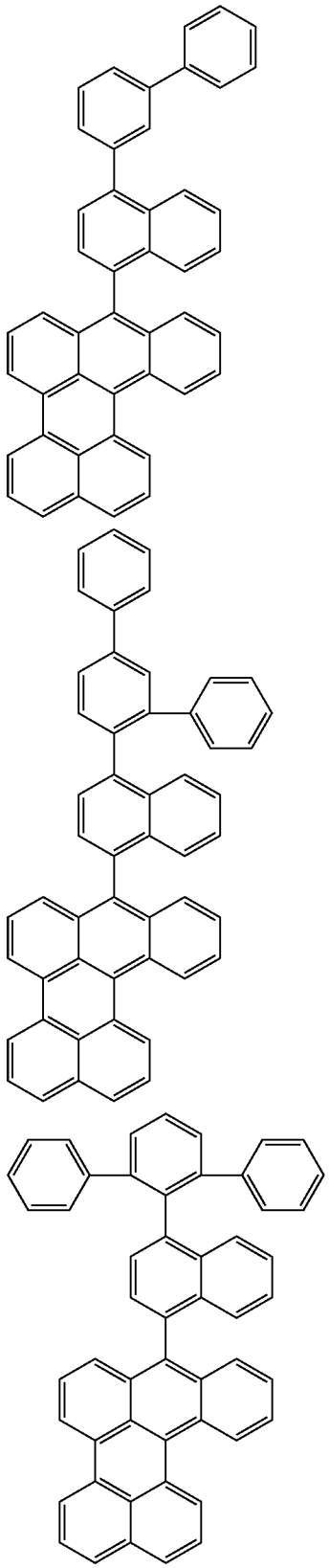

-continued
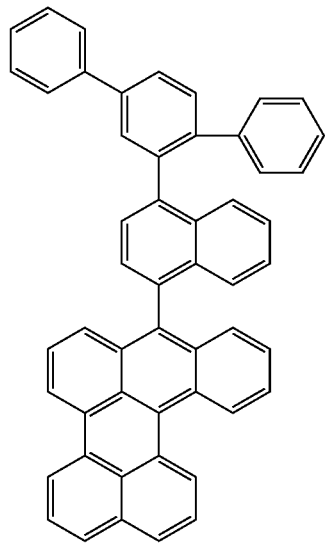
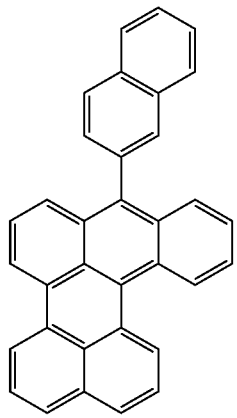
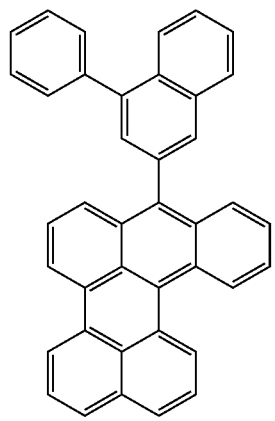
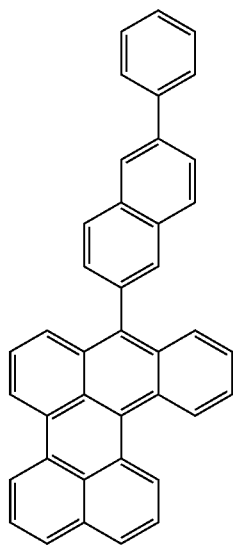
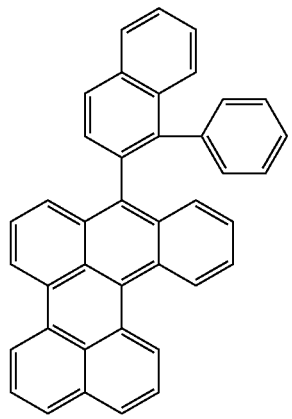
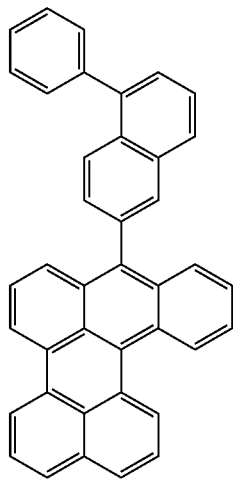

-continued
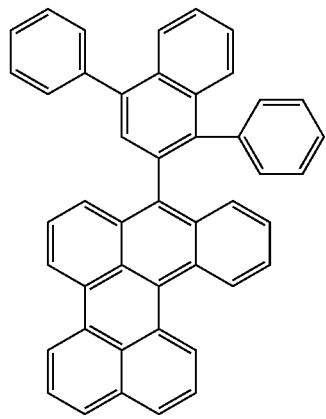
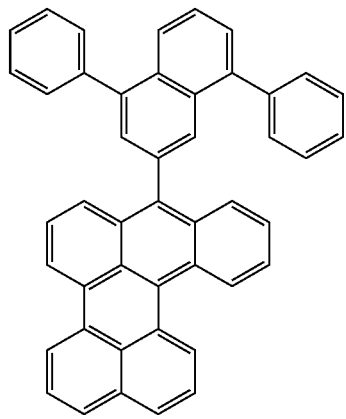
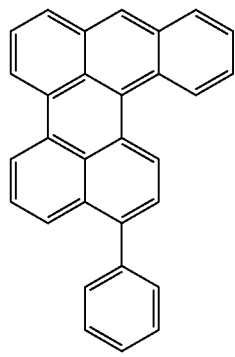
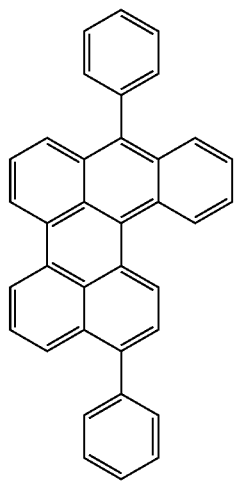
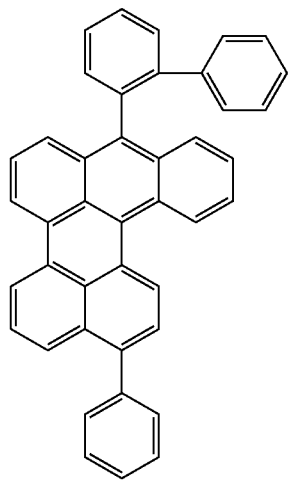
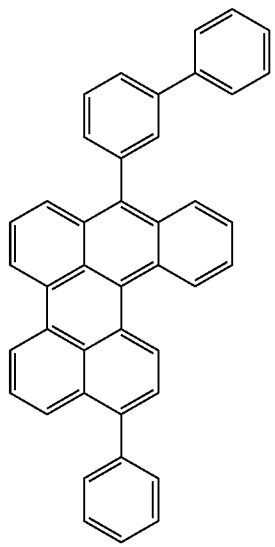

-continued
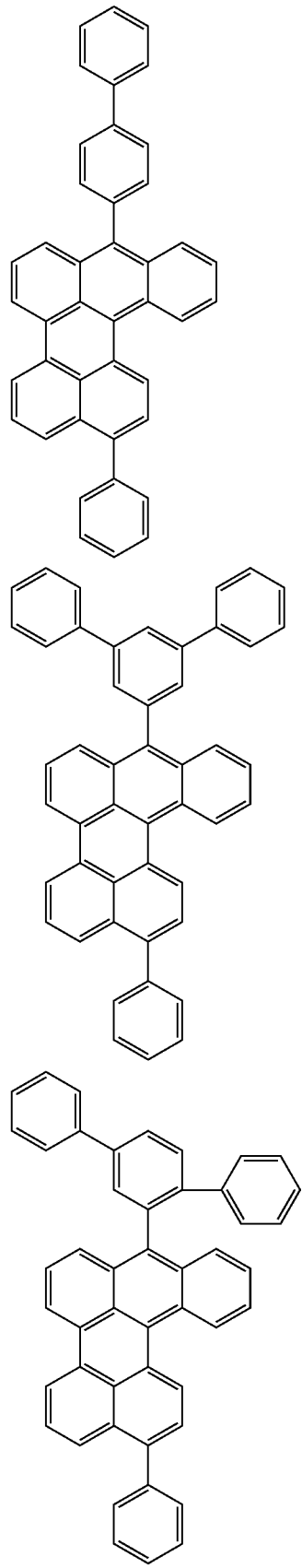
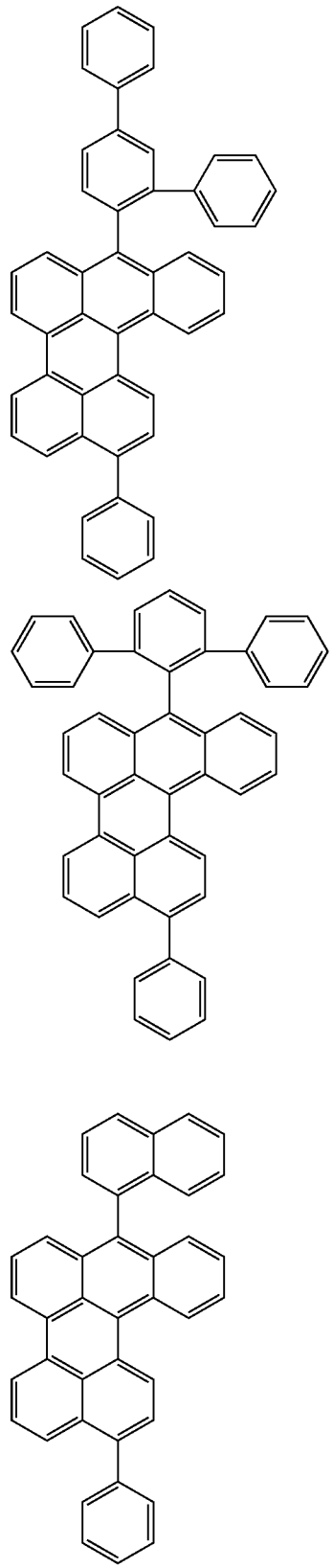

-continued
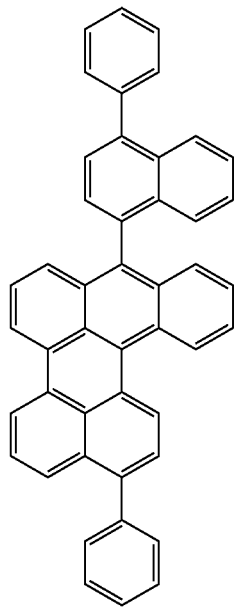
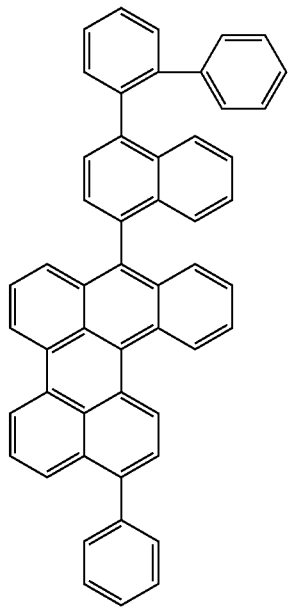
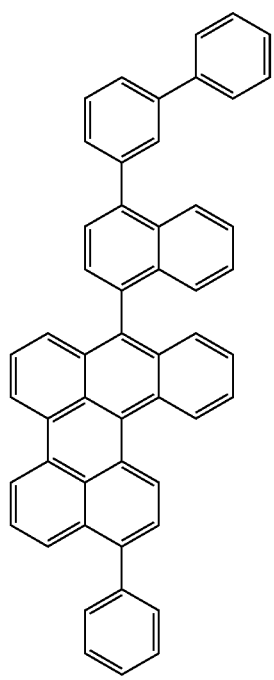
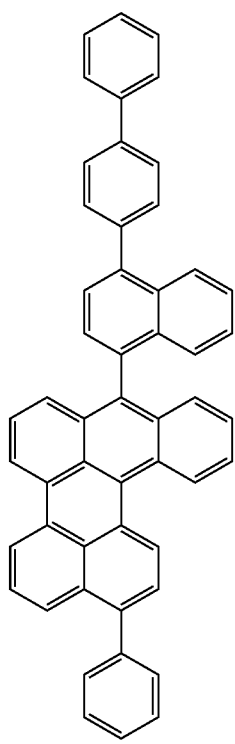

-continued
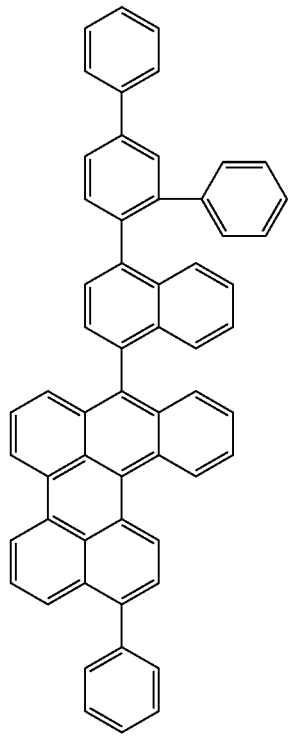
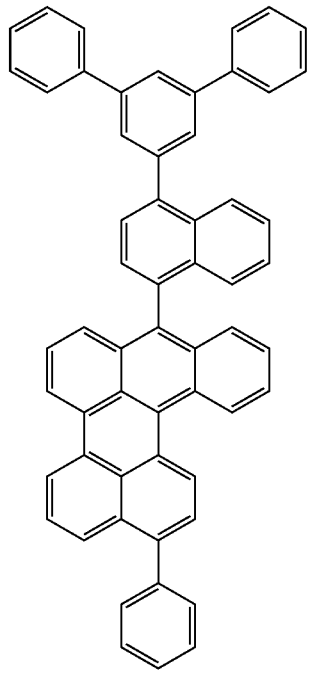
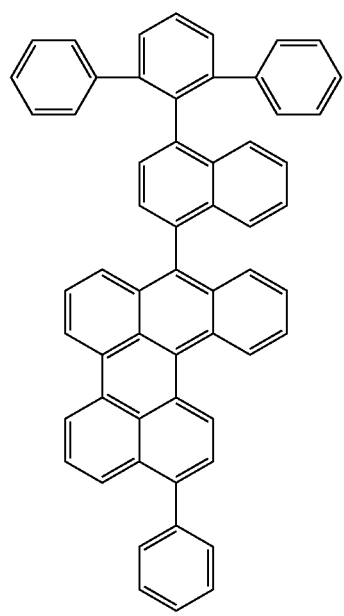
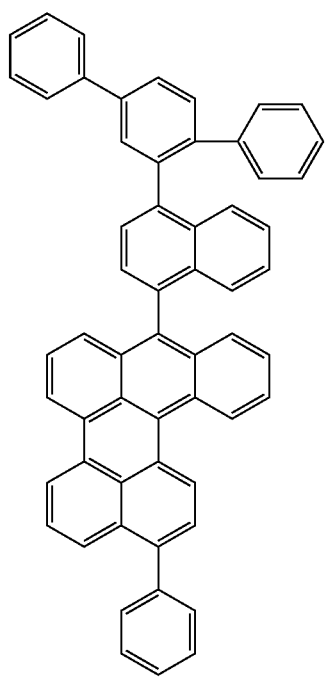

-continued
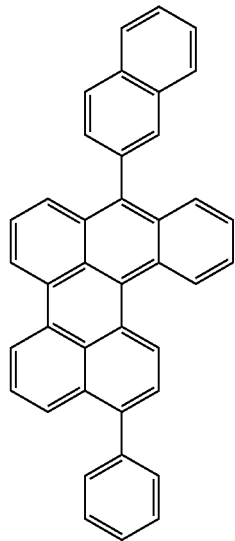
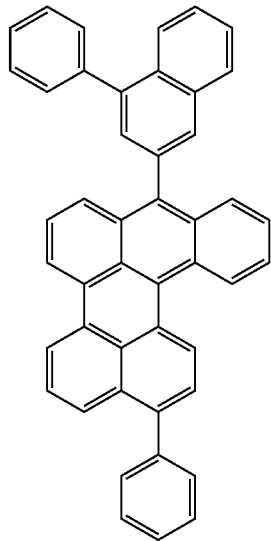
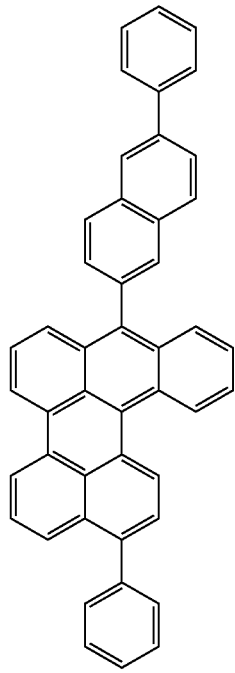
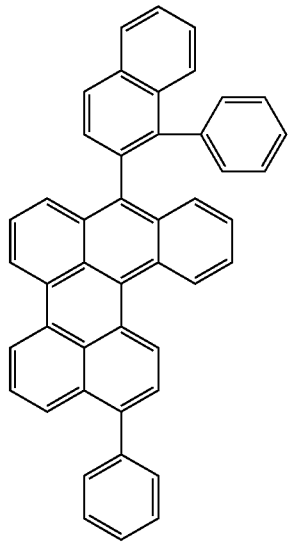

-continued
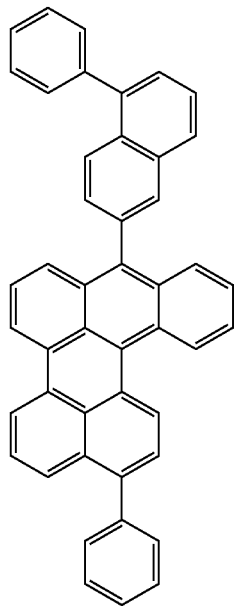
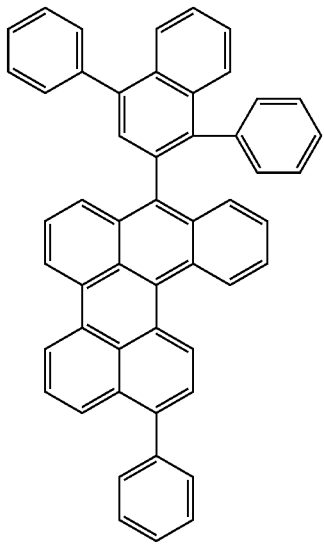
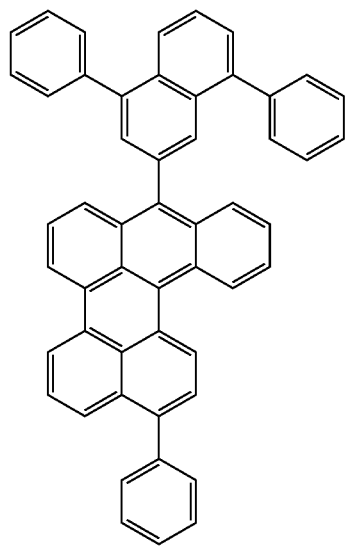
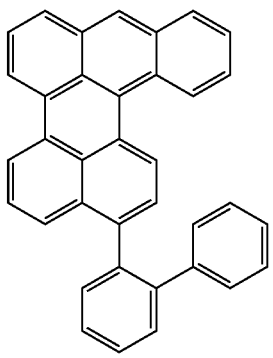
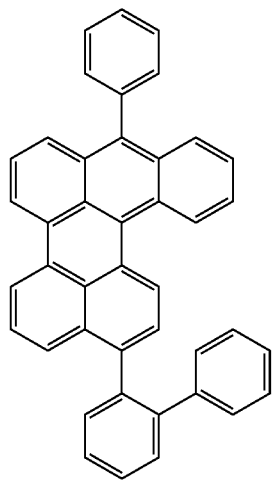
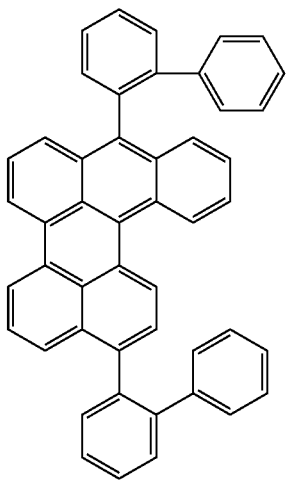

-continued
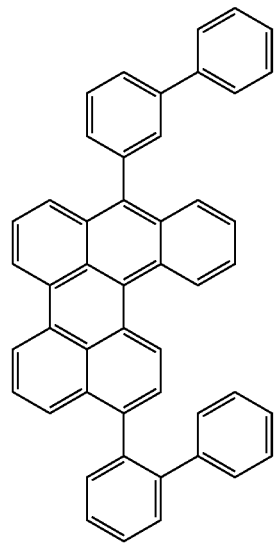
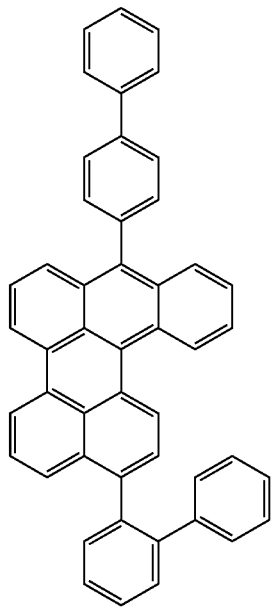
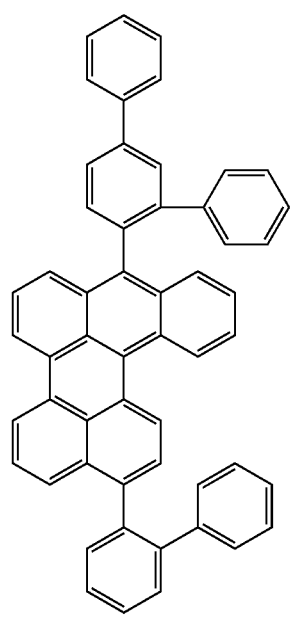
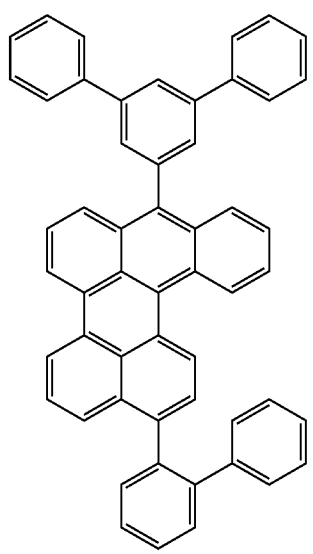

-continued
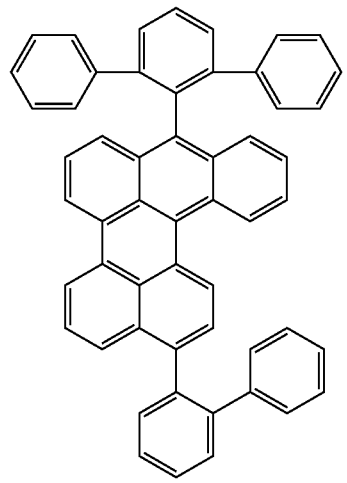
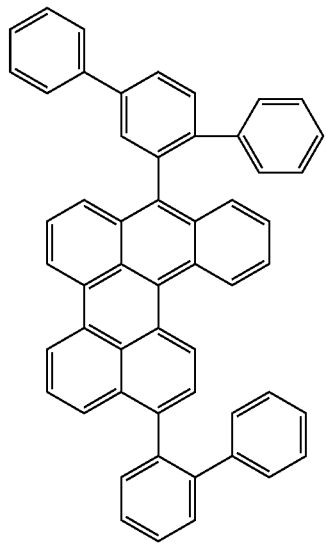
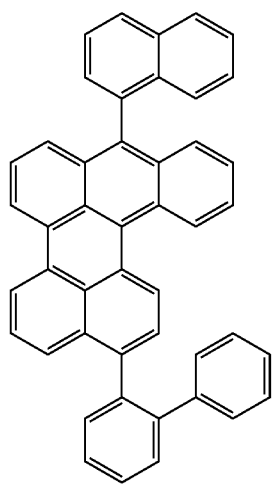
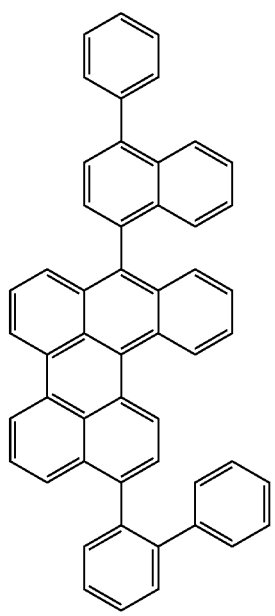

-continued
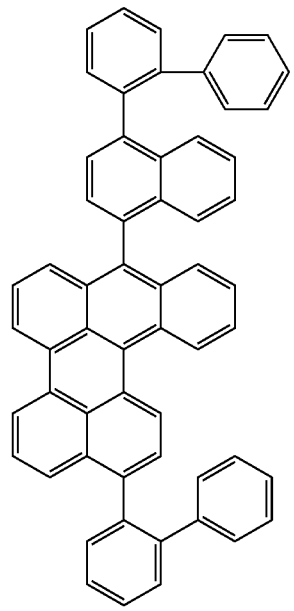
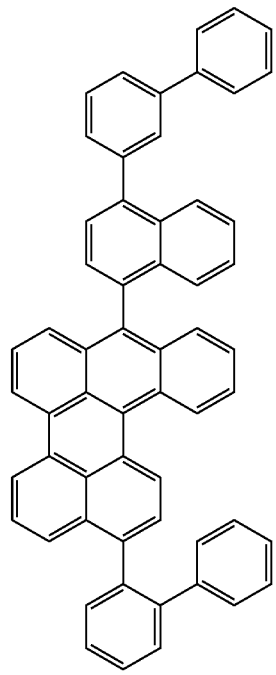
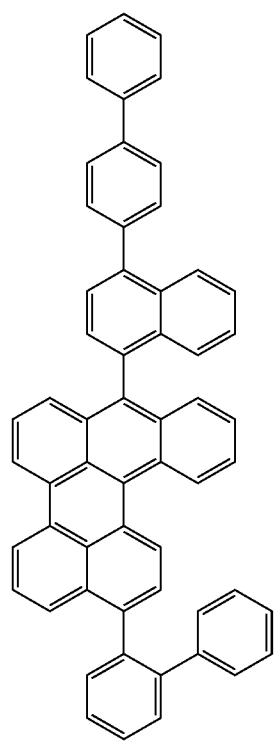
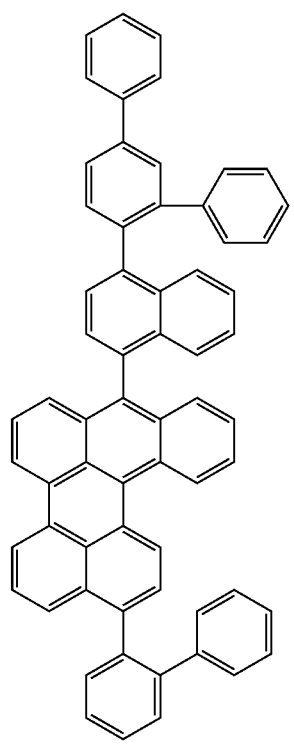

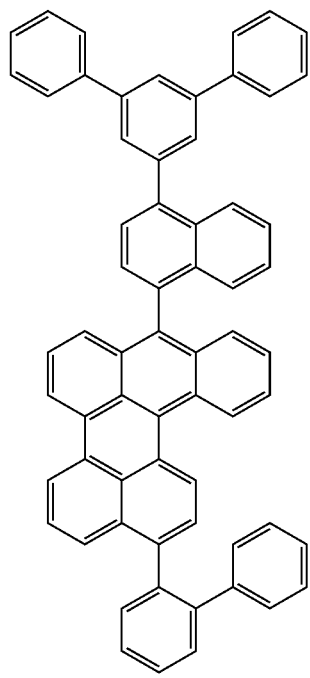
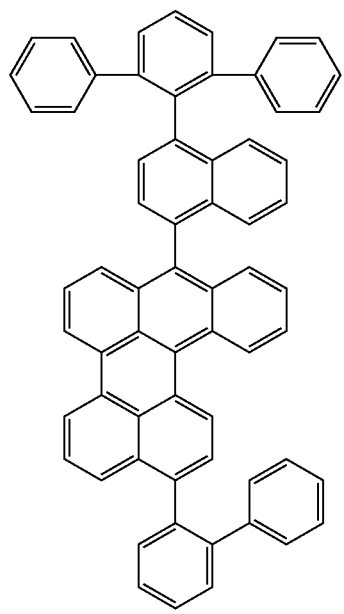
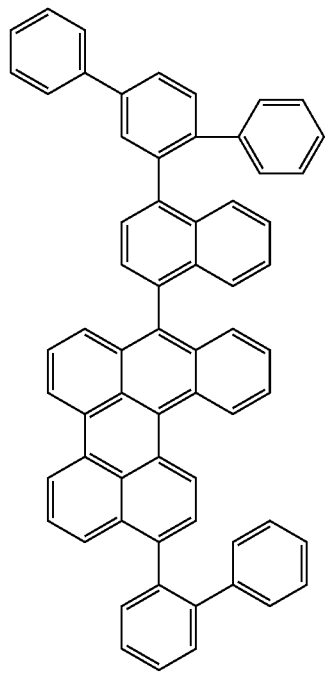
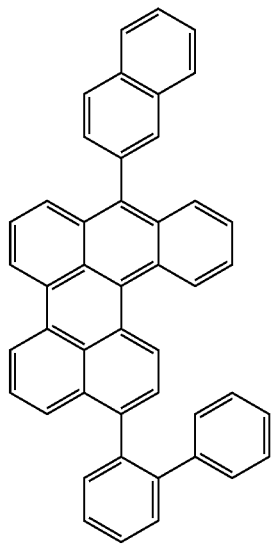

-continued
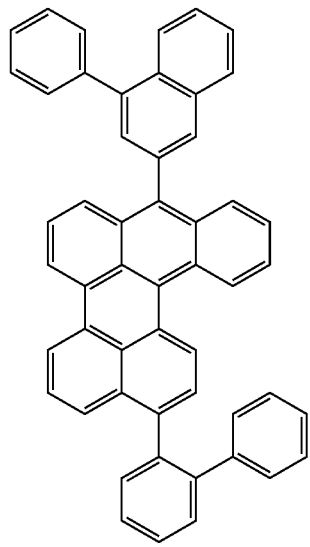
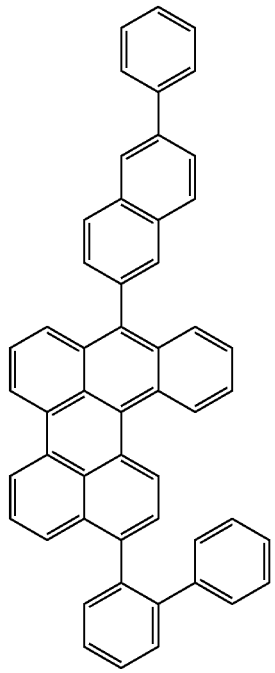
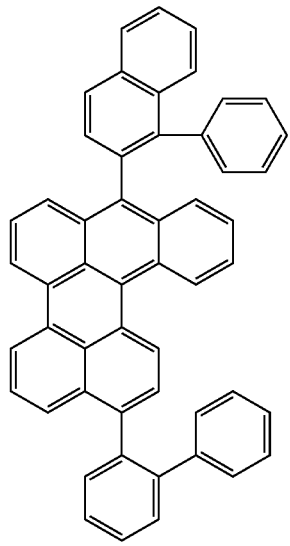
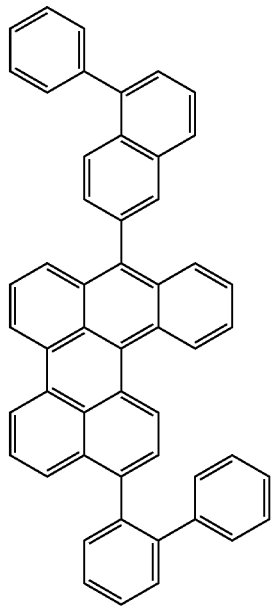

-continued
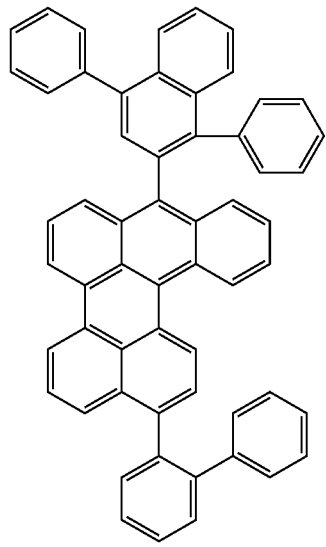

-continued
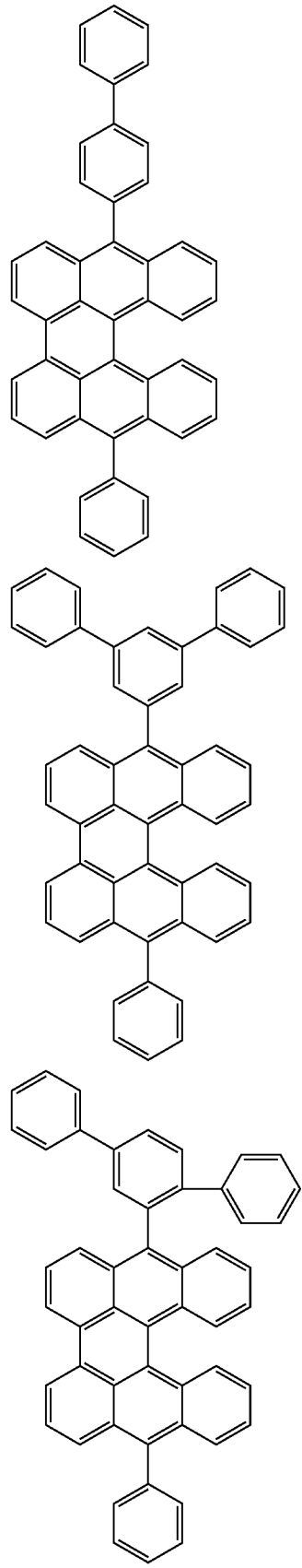
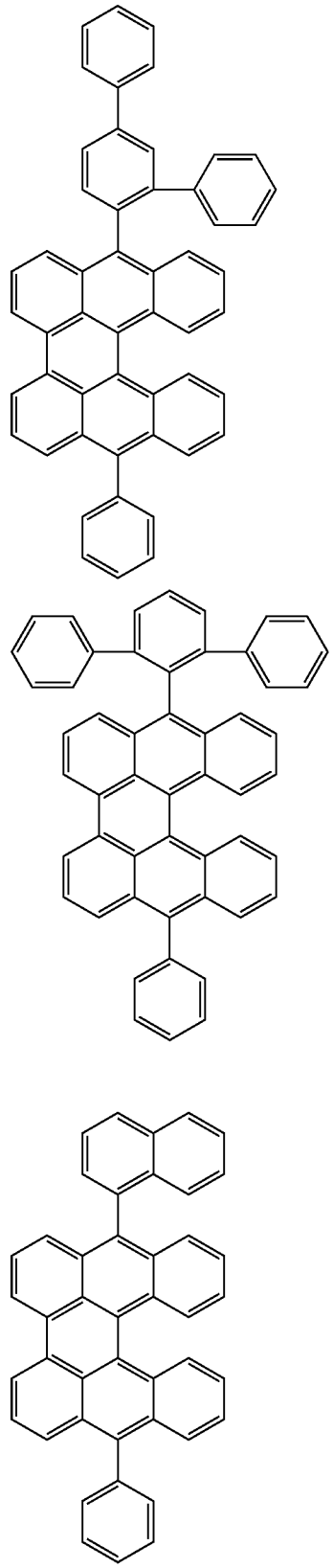

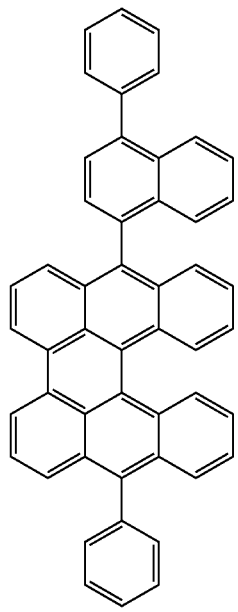
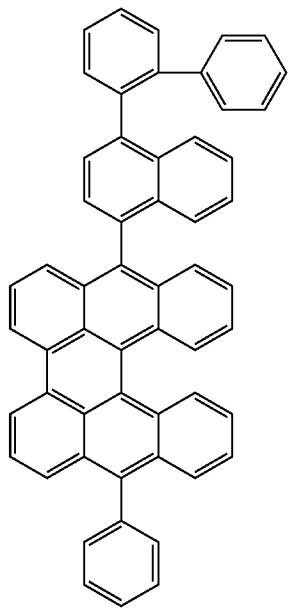
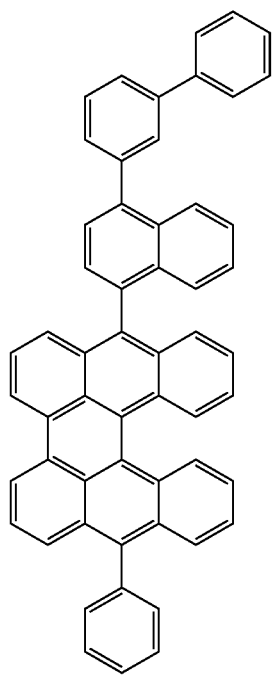
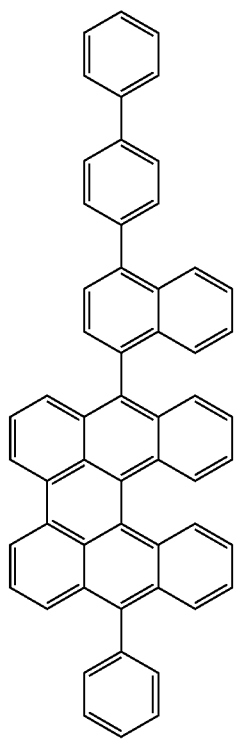

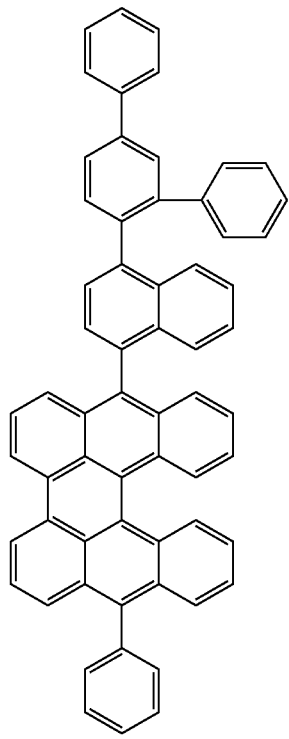
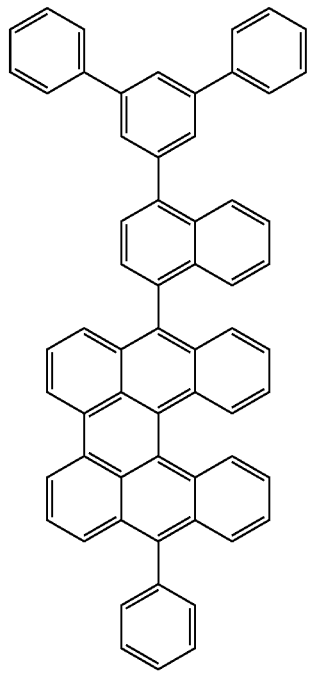
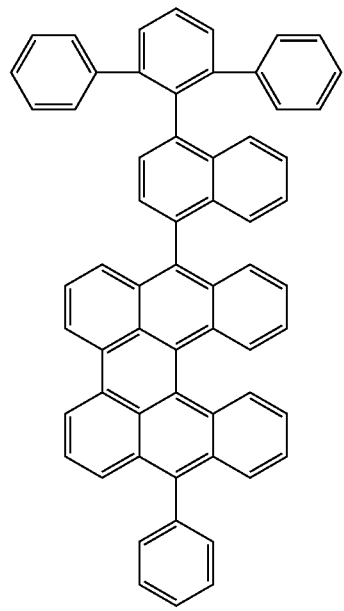
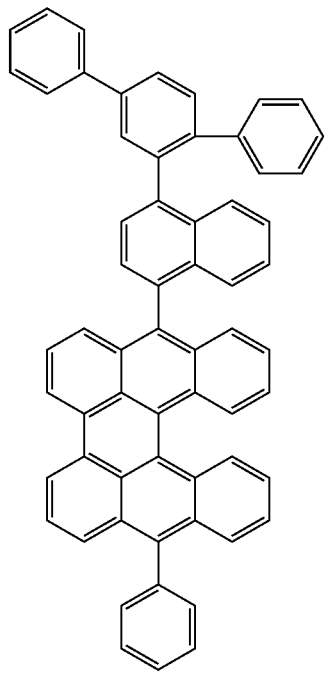

-continued
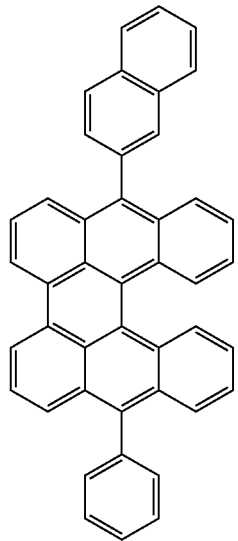
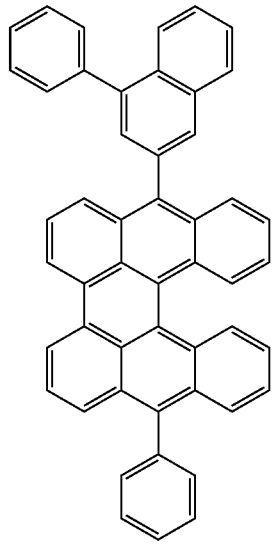
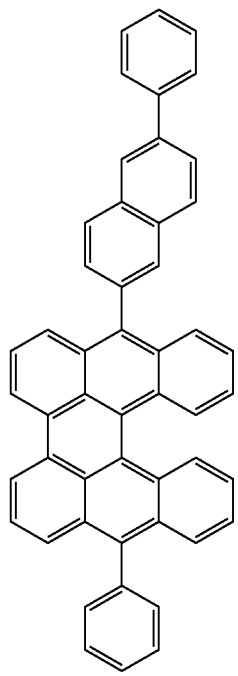
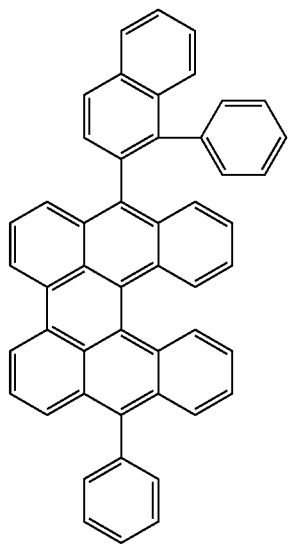

-continued
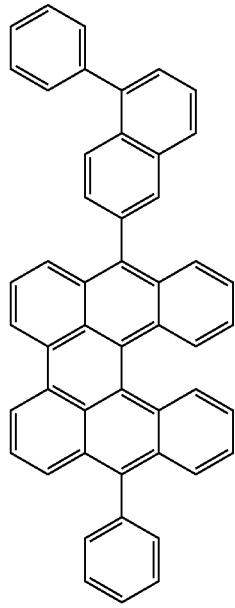
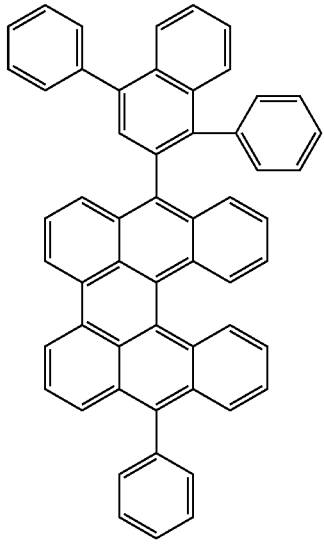
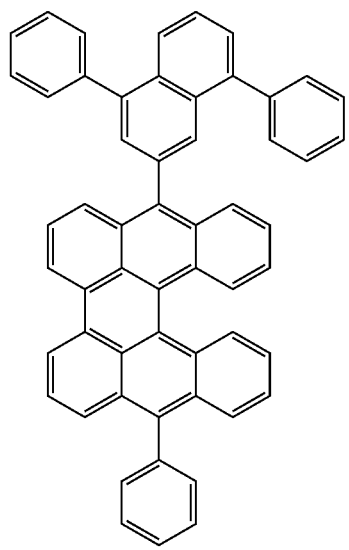
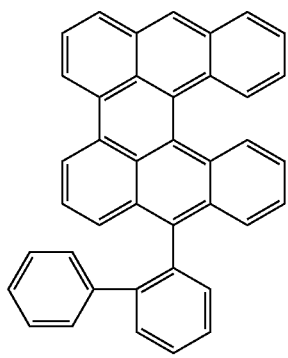
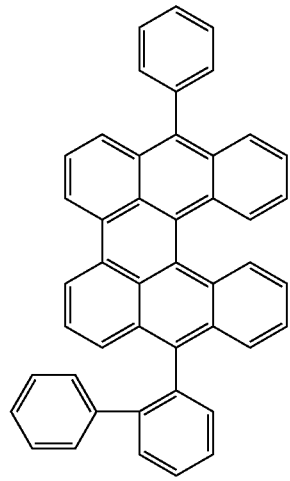
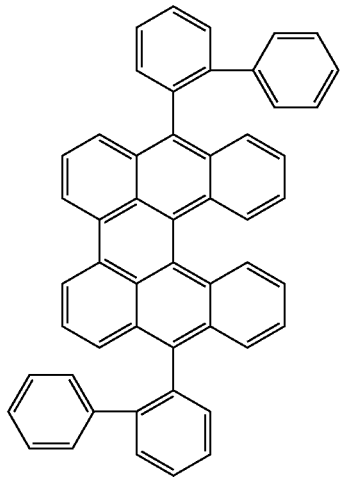

-continued
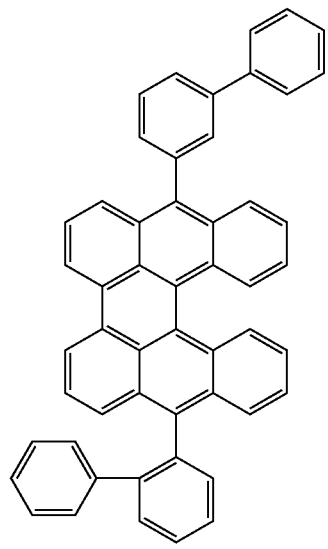
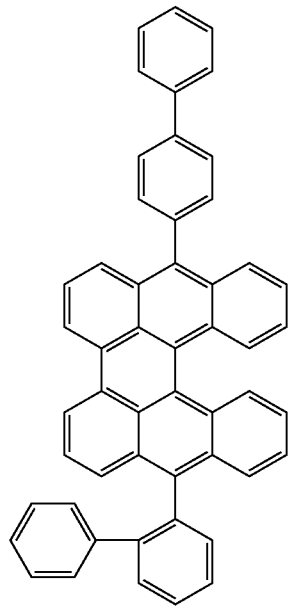
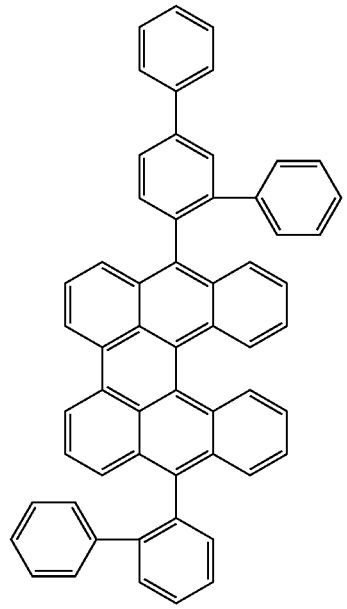
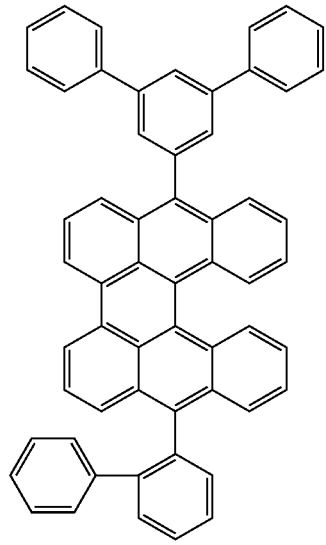

-continued
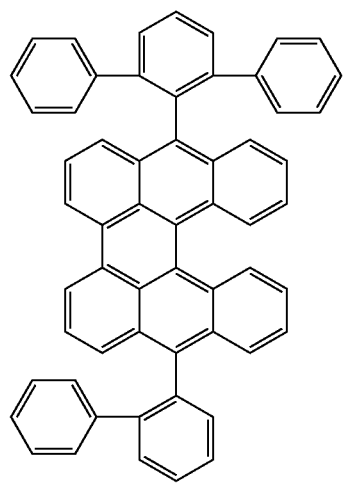
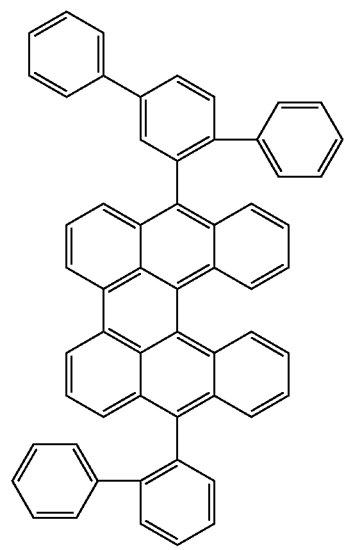
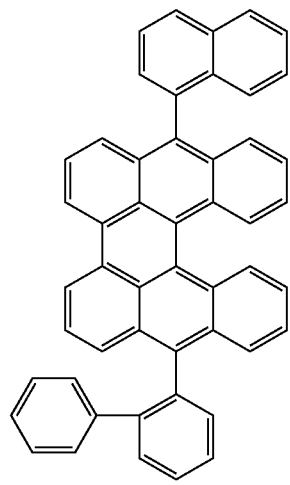
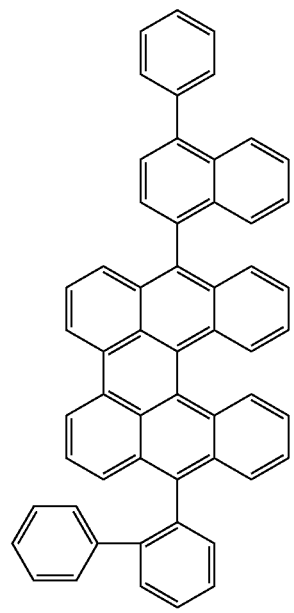

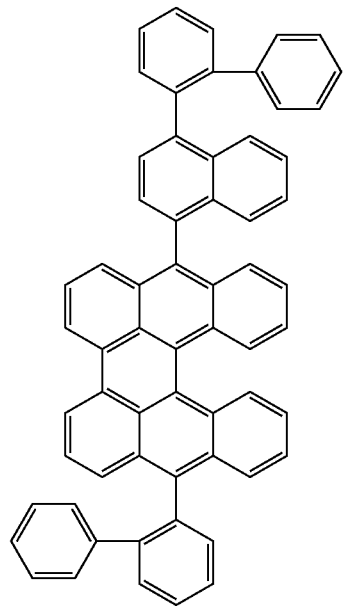
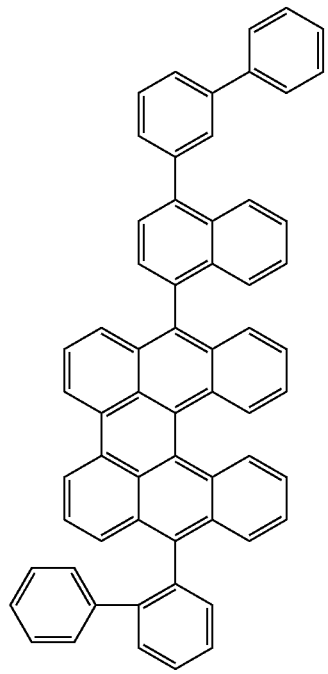
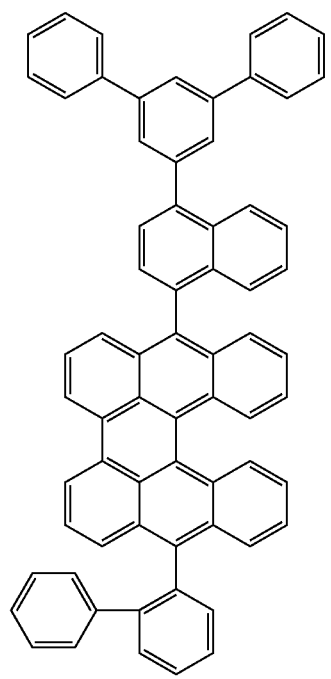
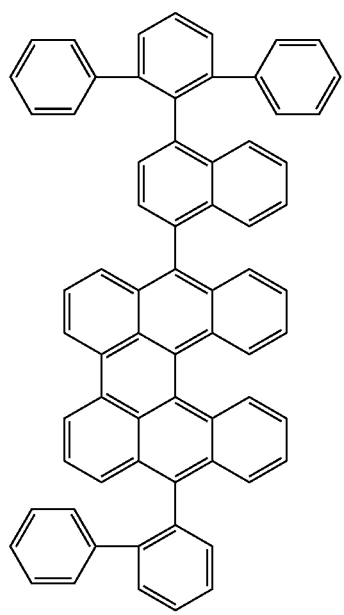

-continued
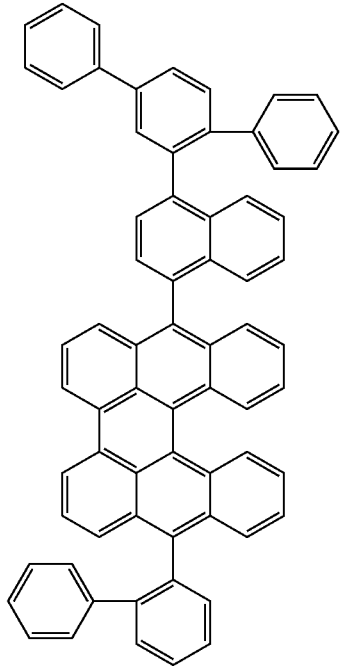
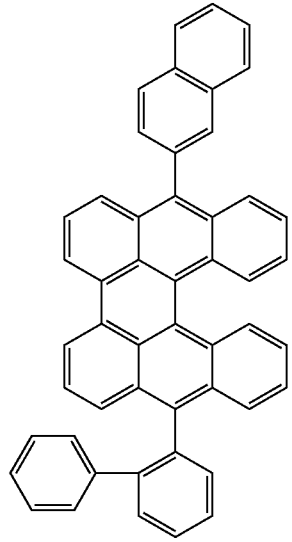
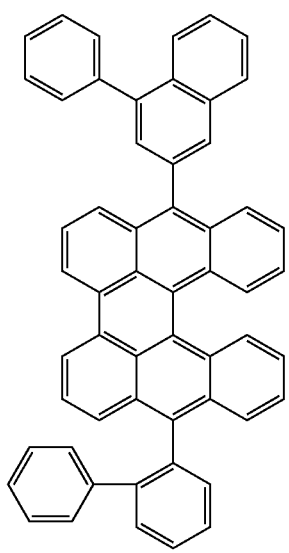
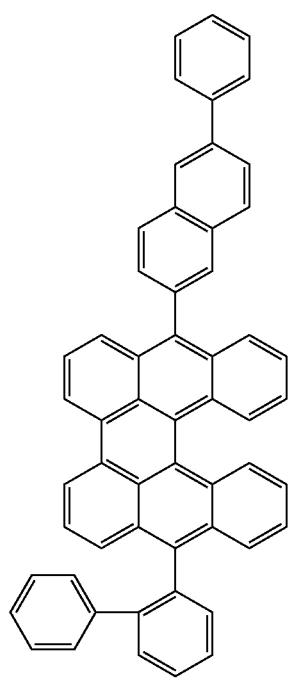

-continued
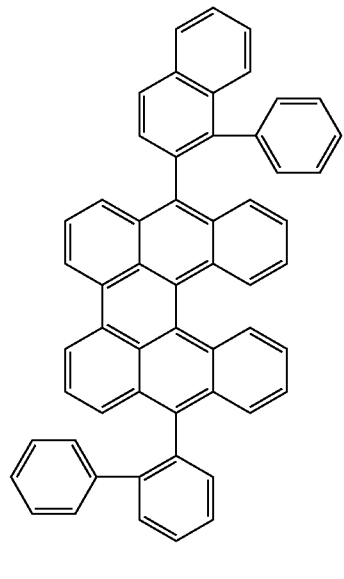

-continued
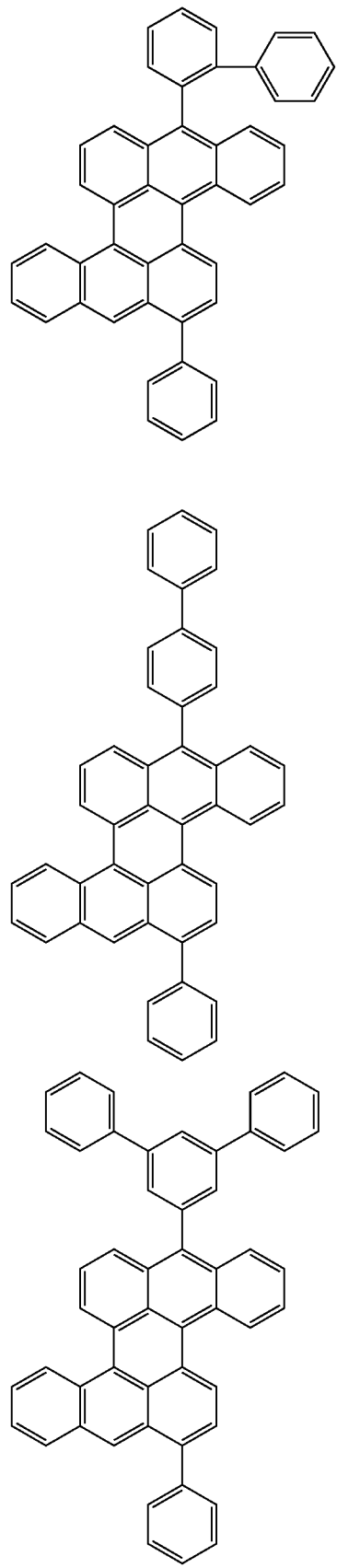
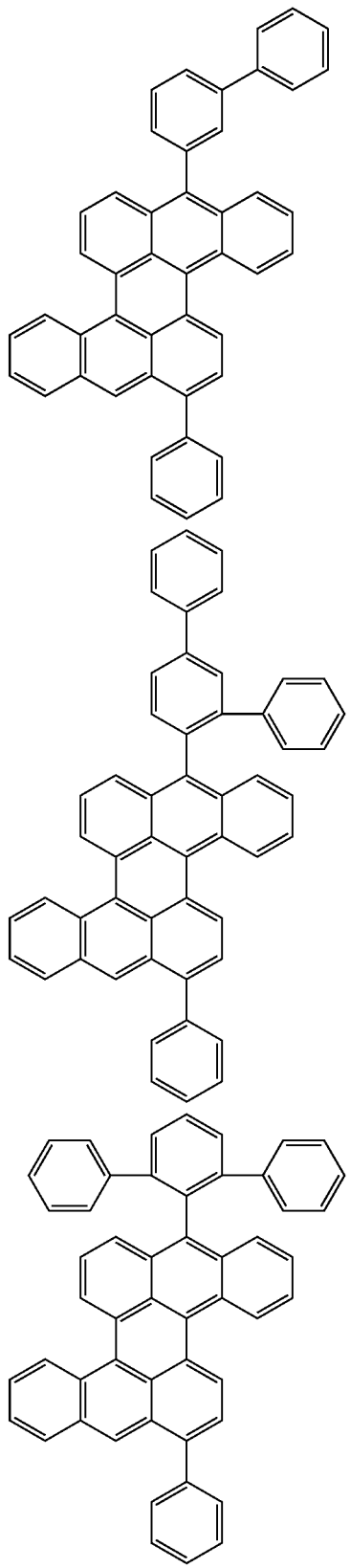

-continued
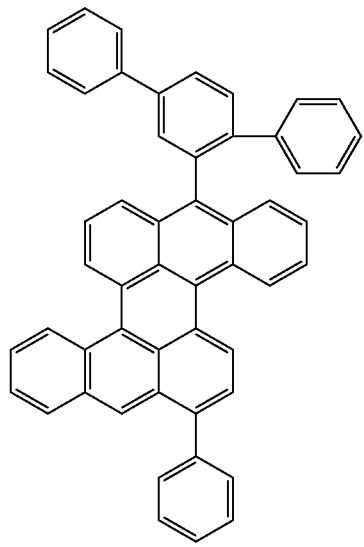
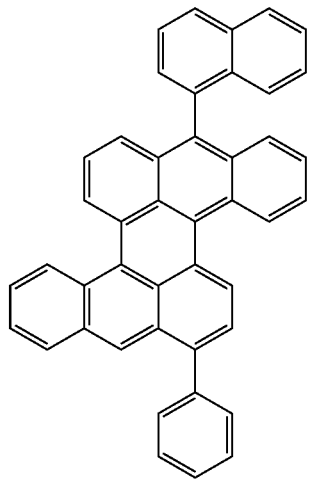
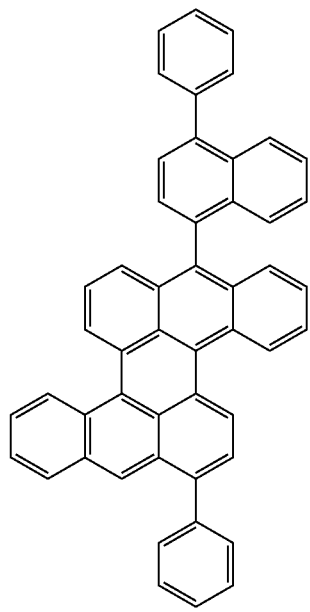
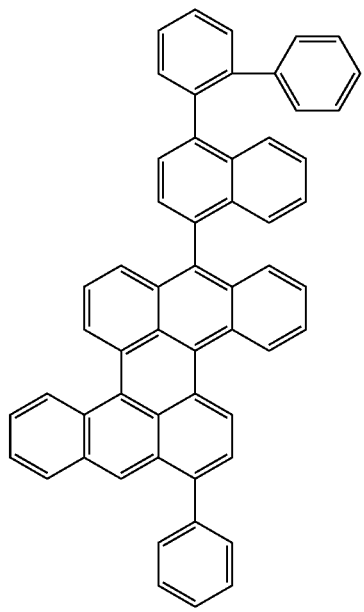

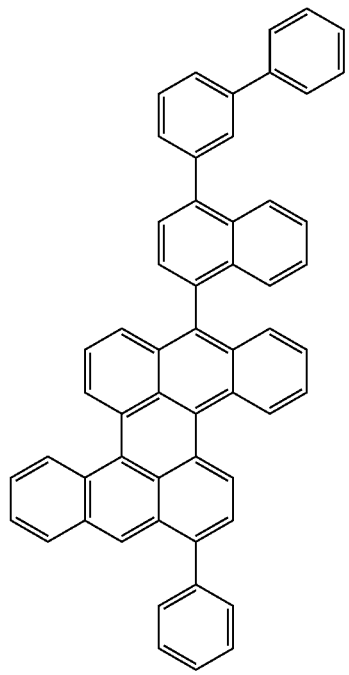
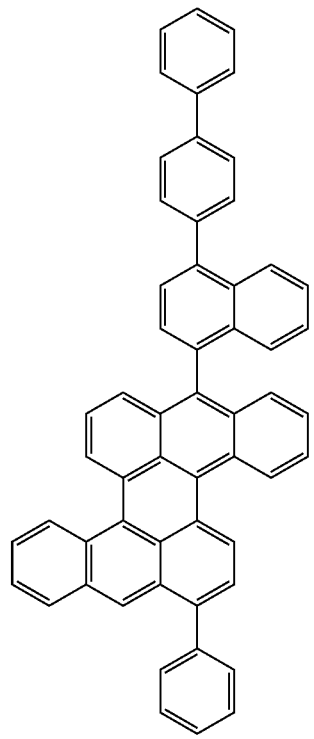
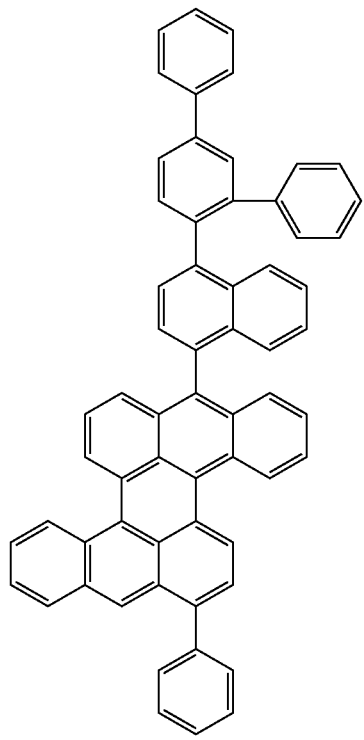
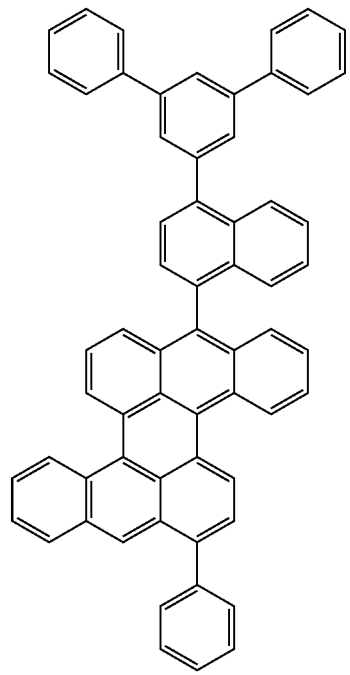

-continued
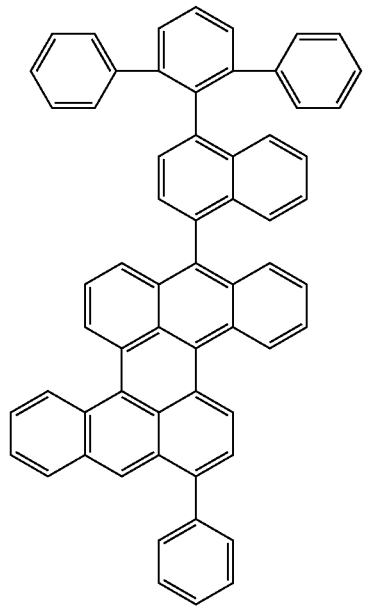
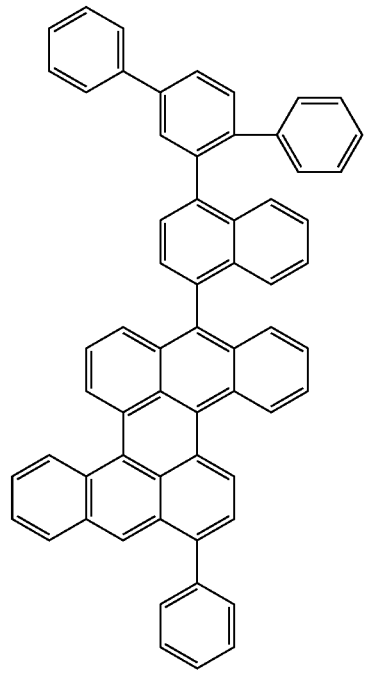
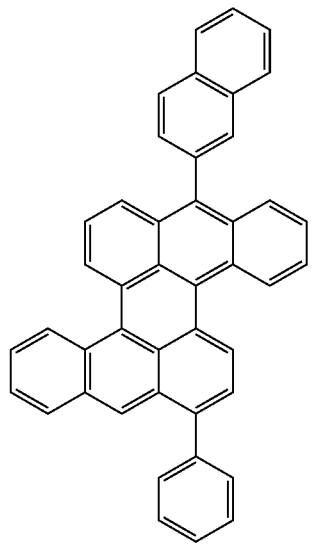
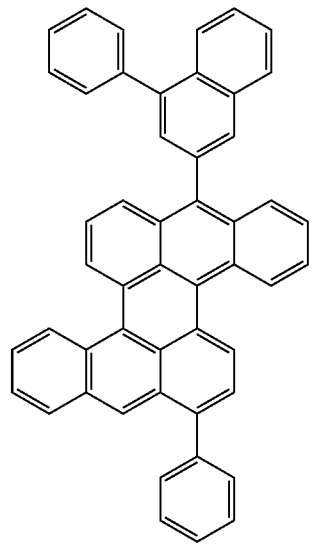

-continued
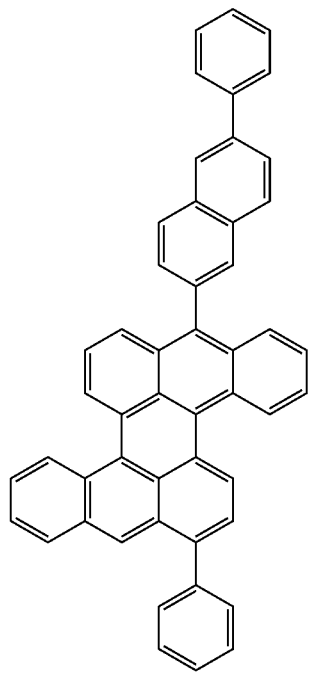
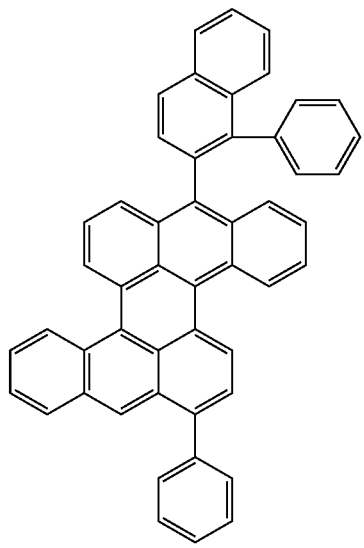
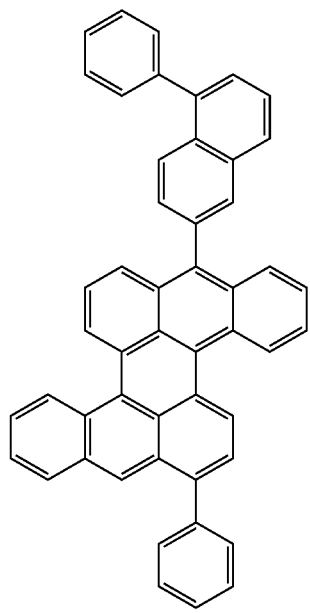
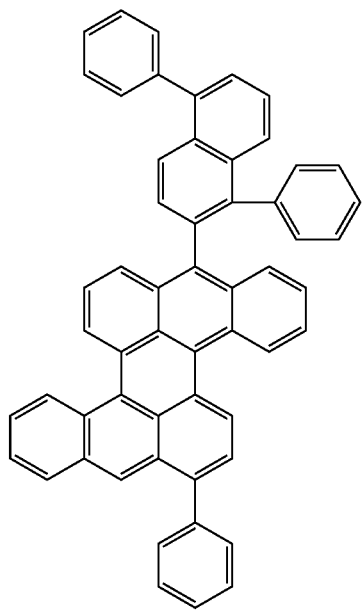

-continued
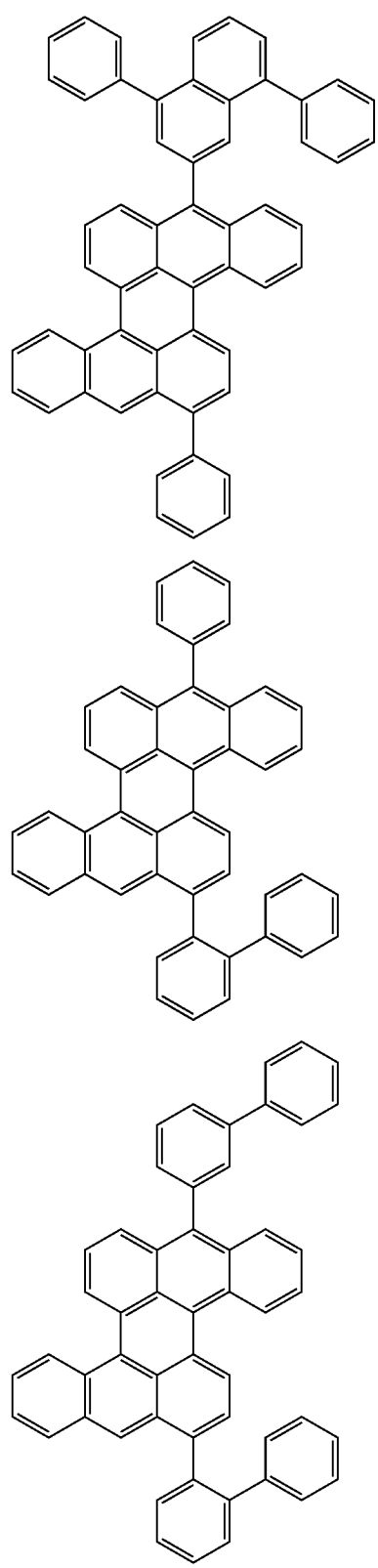
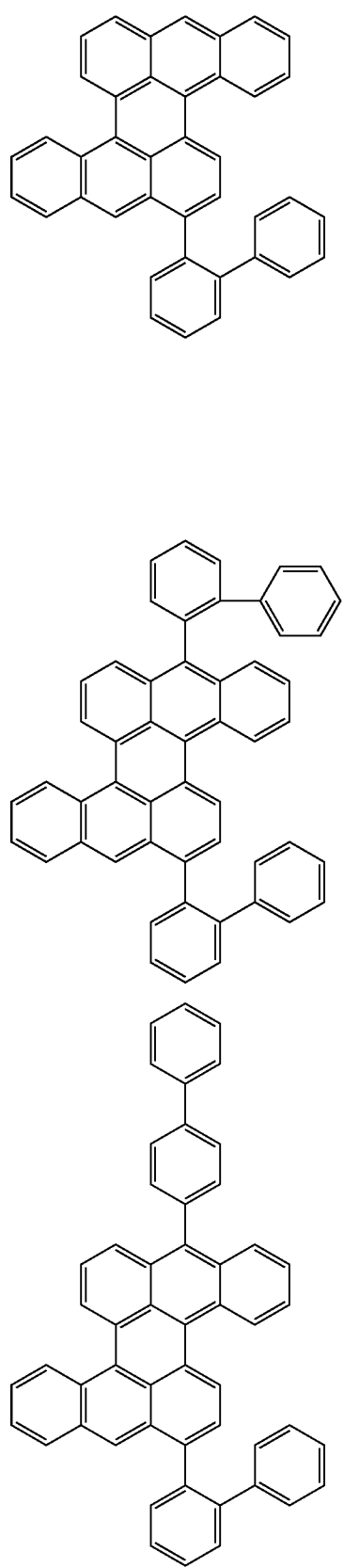

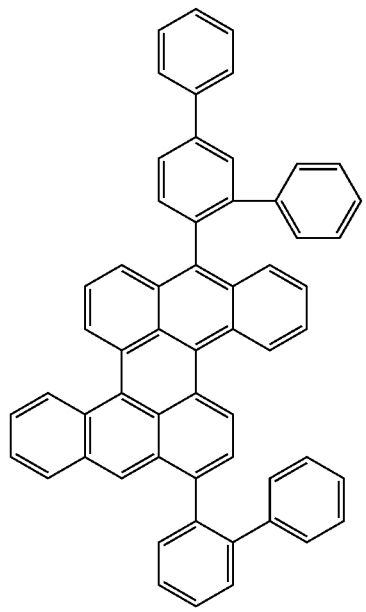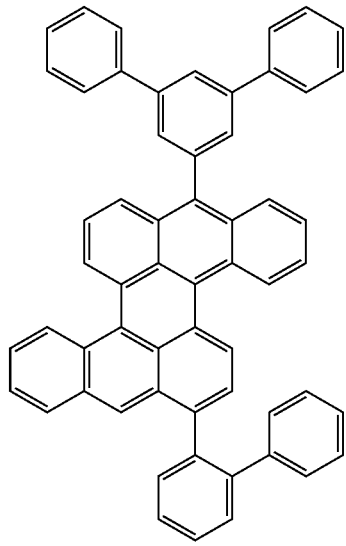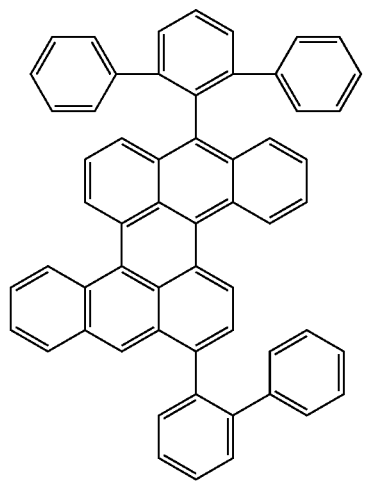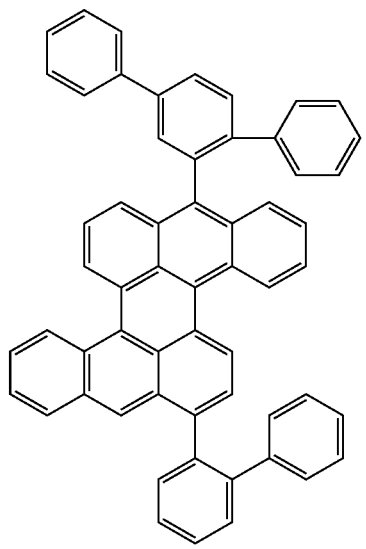

-continued
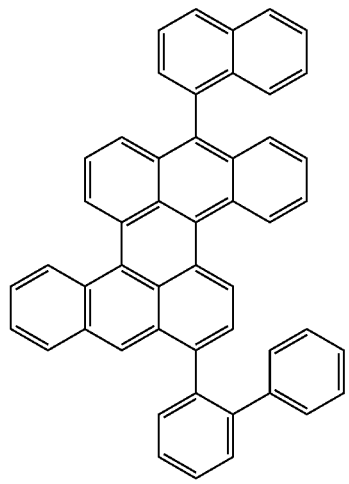 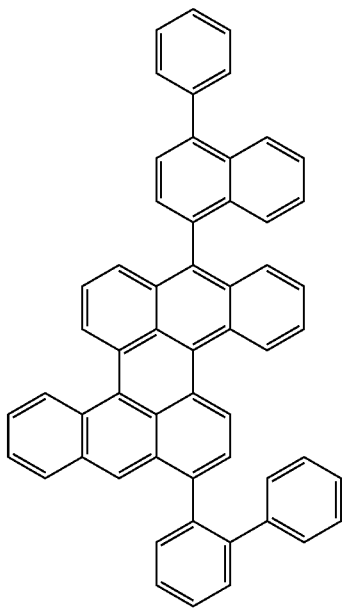
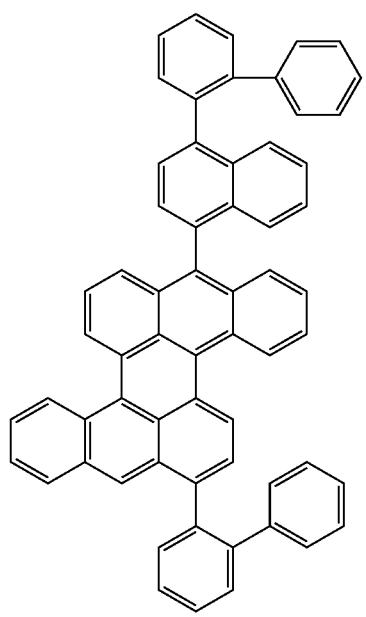 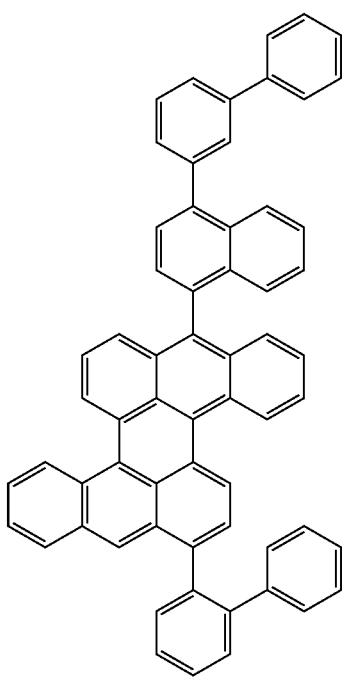

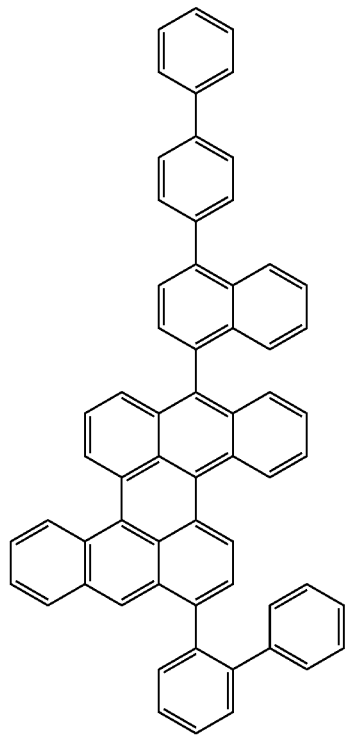
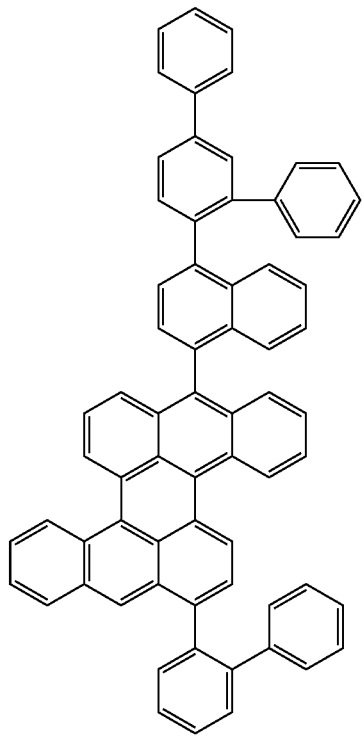
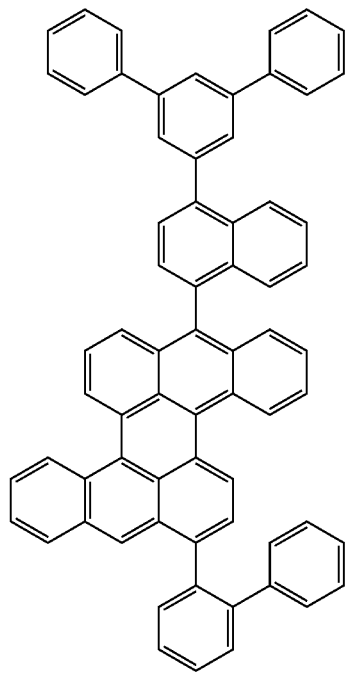
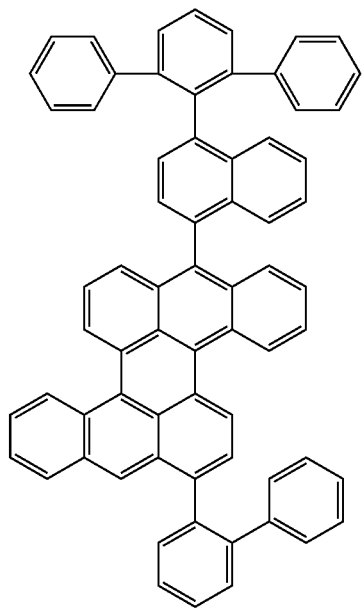

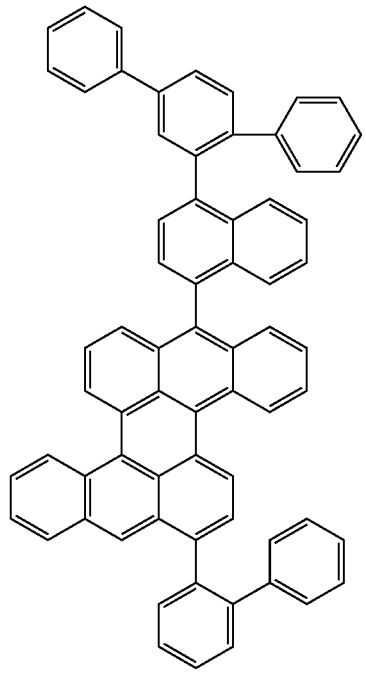
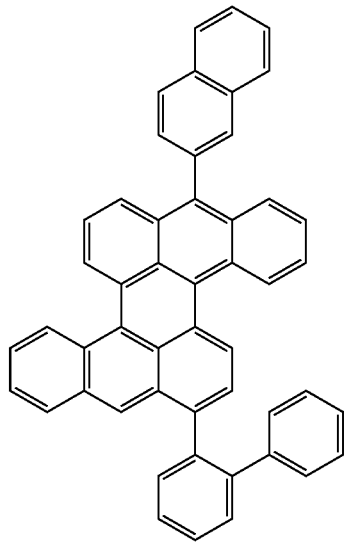
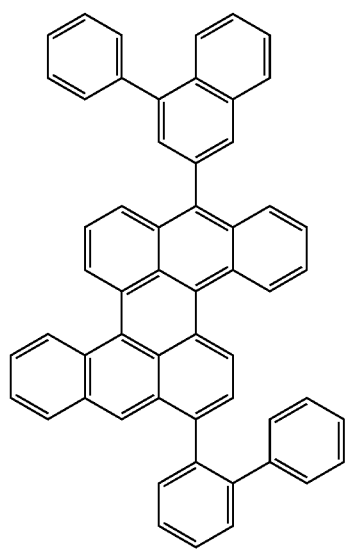
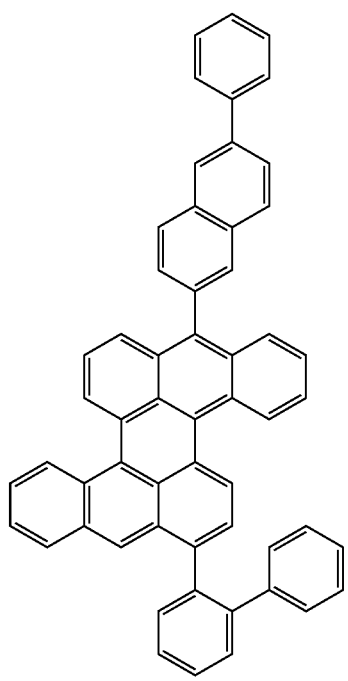

-continued
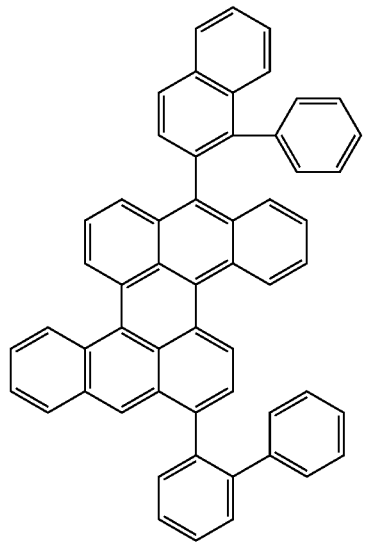
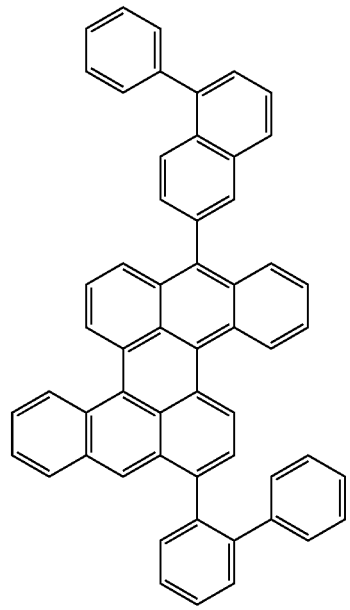
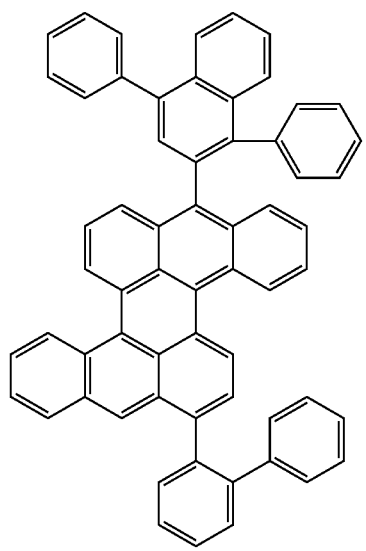
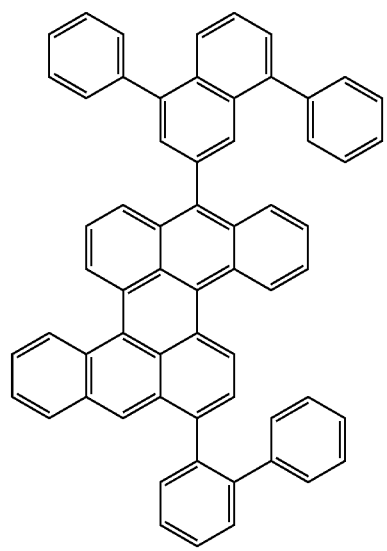
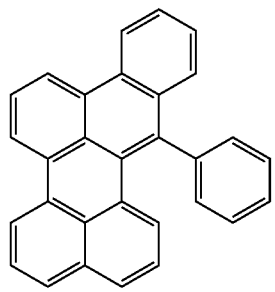
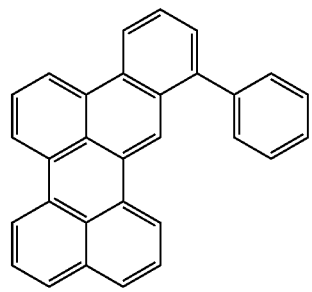

-continued
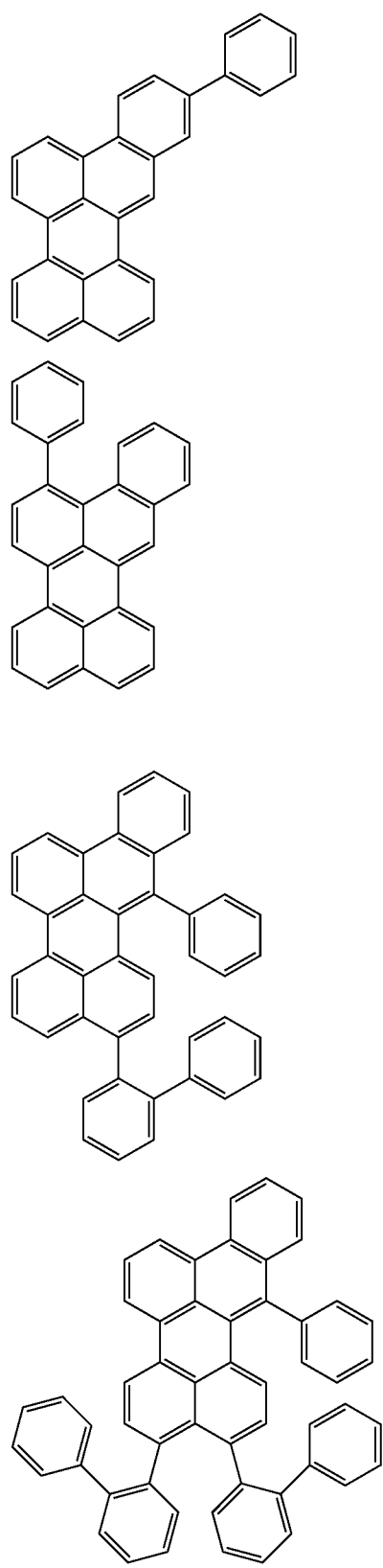
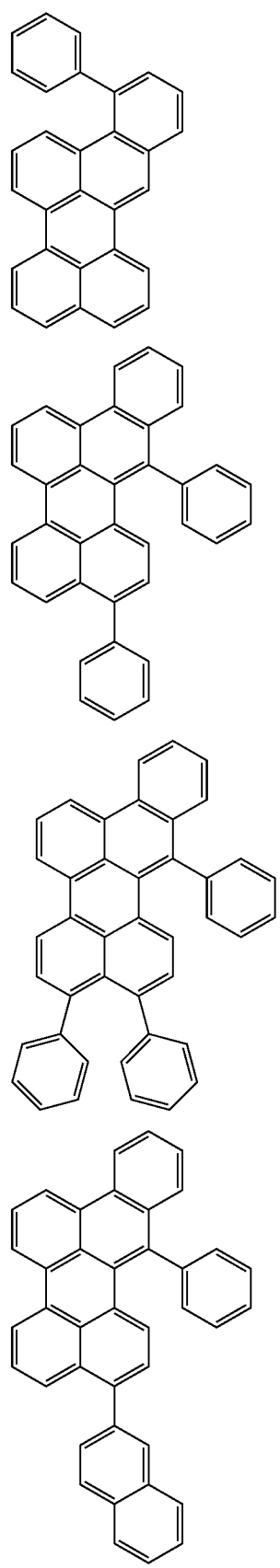

-continued
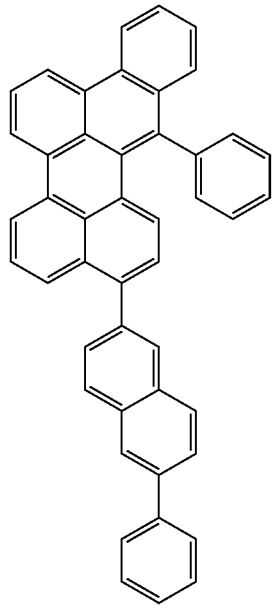
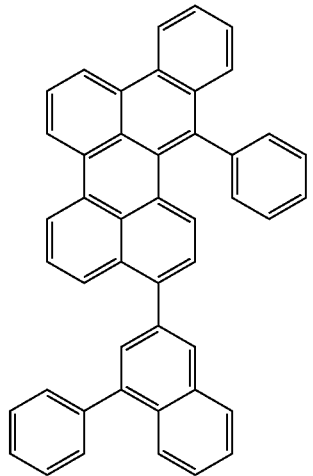
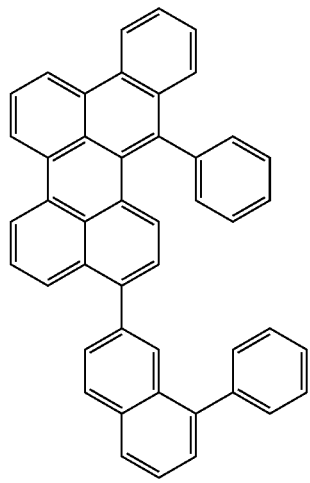
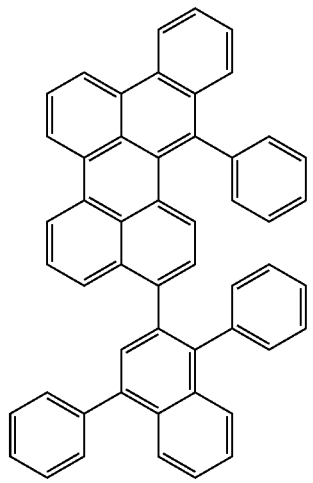
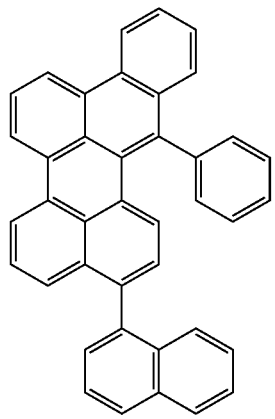
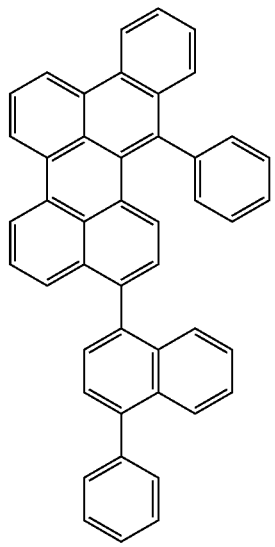

-continued
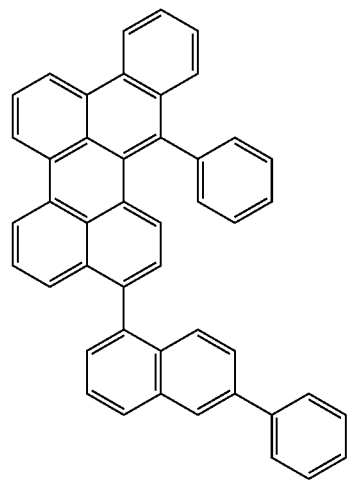
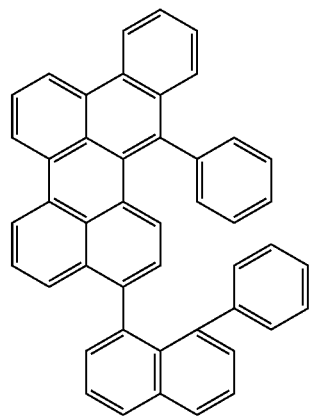
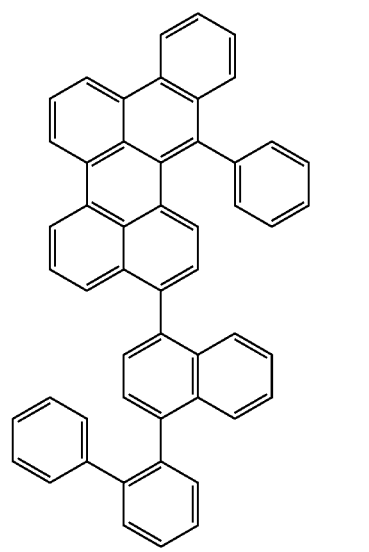
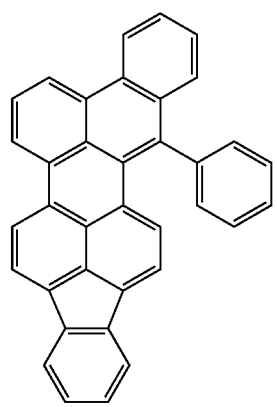
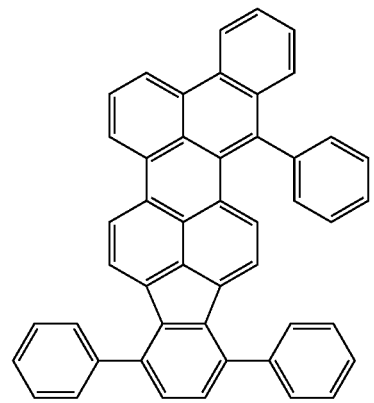
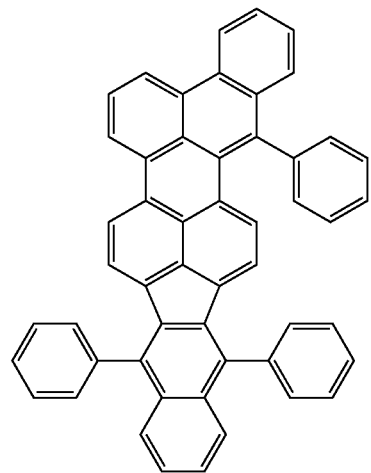

-continued
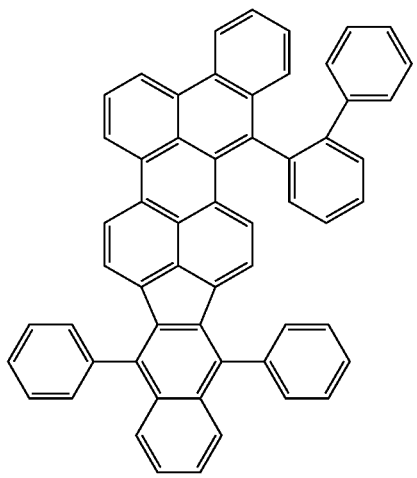
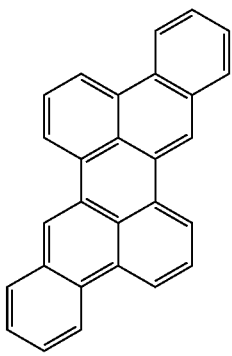
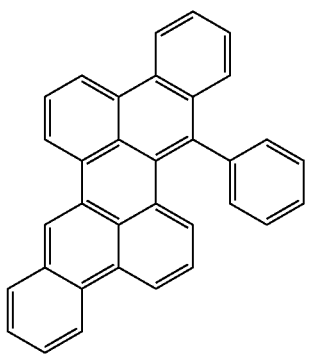
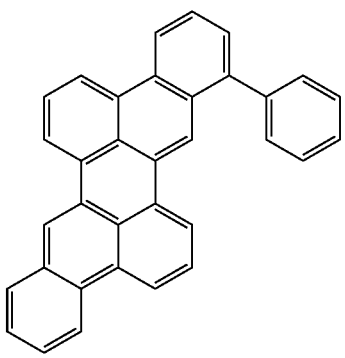
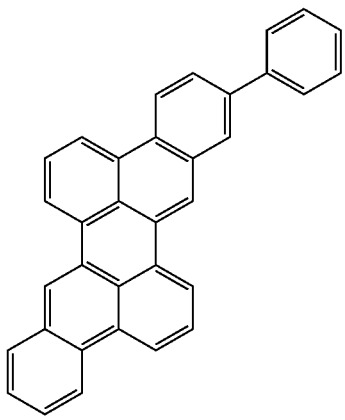
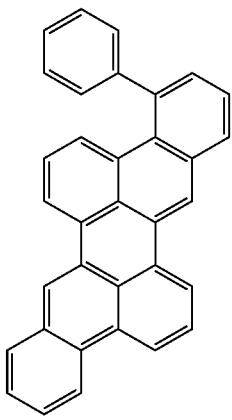
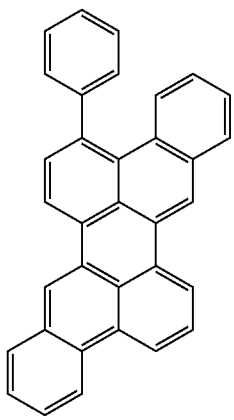
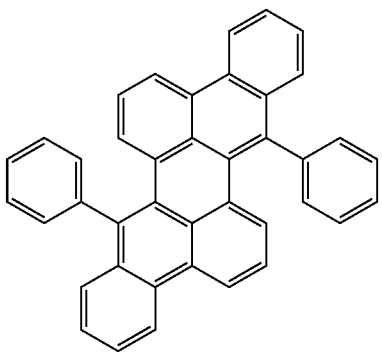

-continued
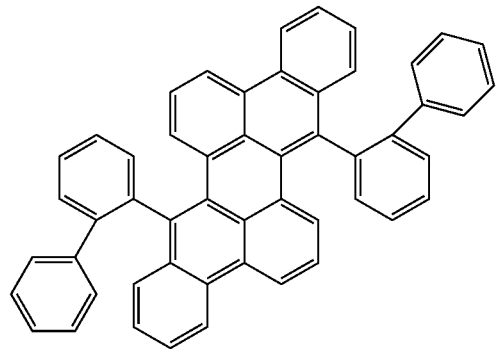 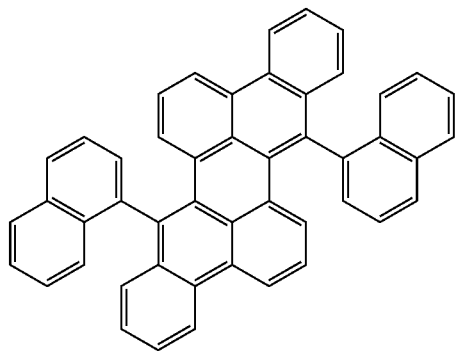
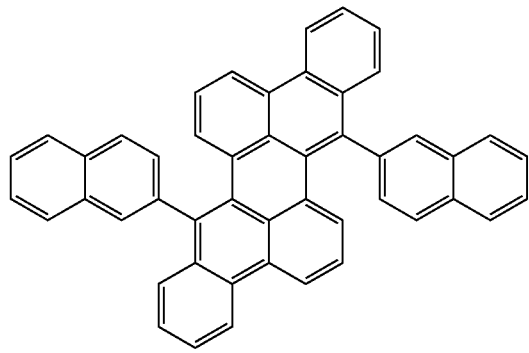 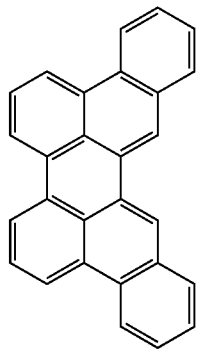
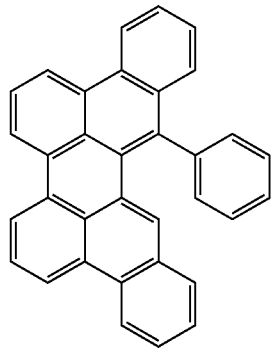 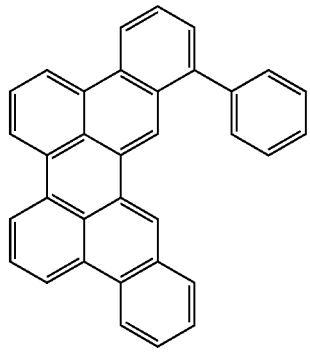
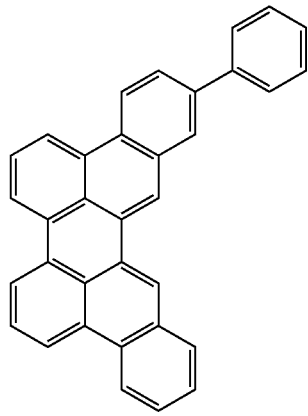 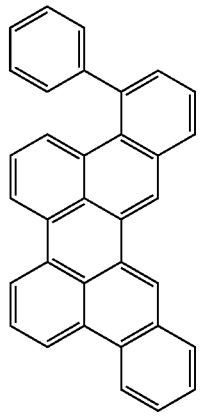

-continued
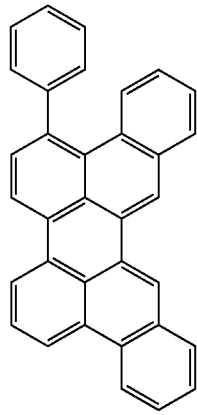

-continued
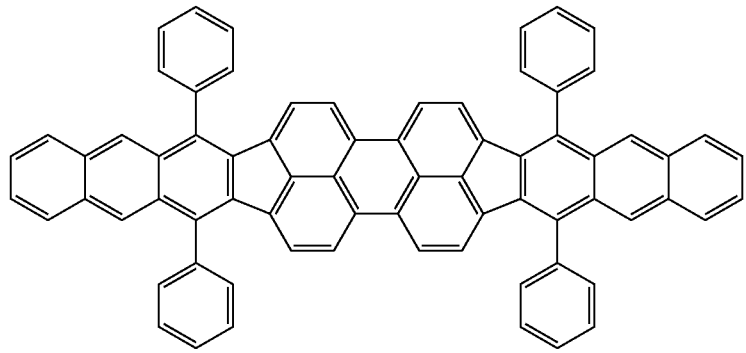
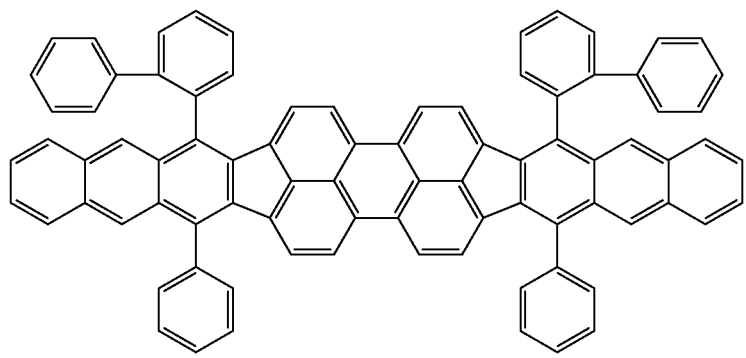
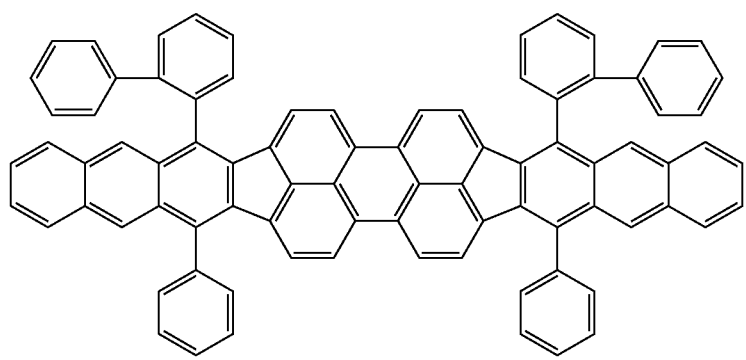
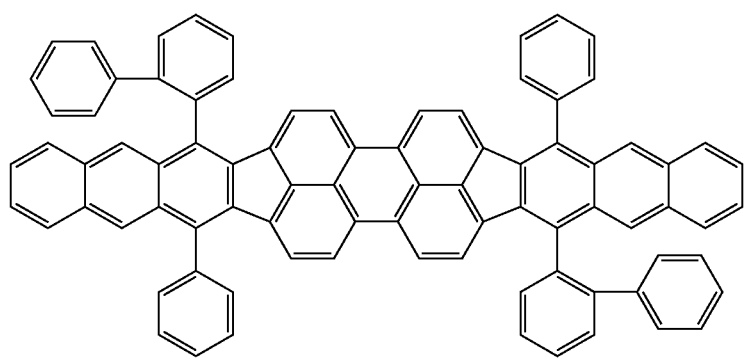

-continued
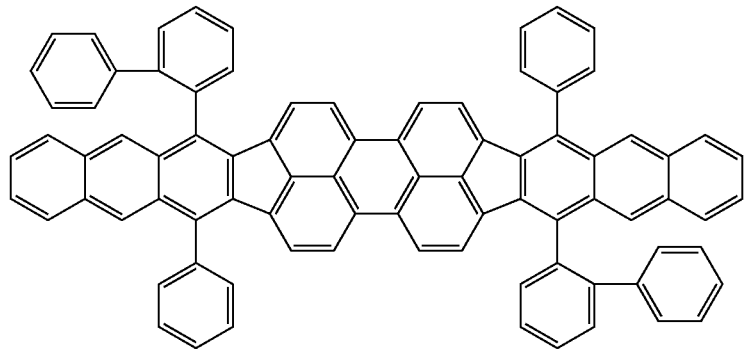
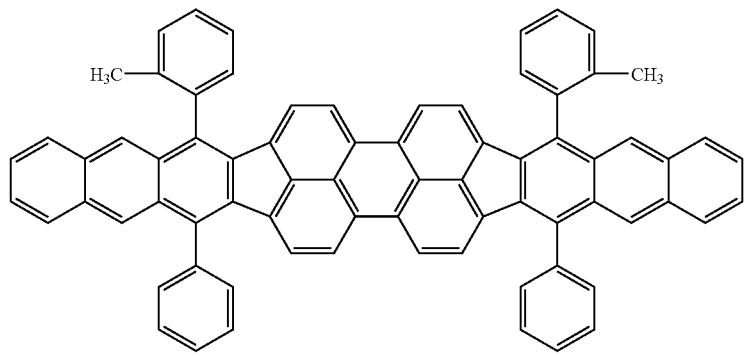
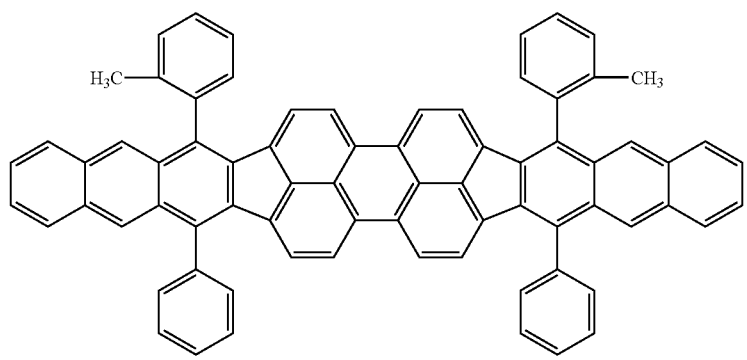
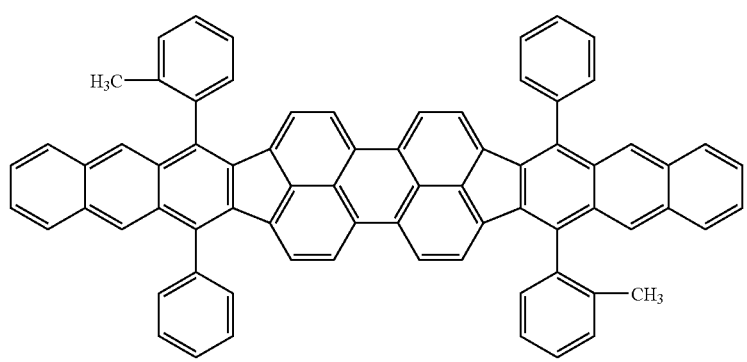

-continued
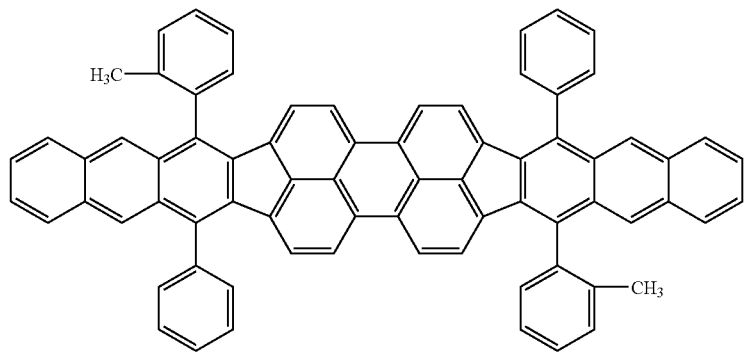
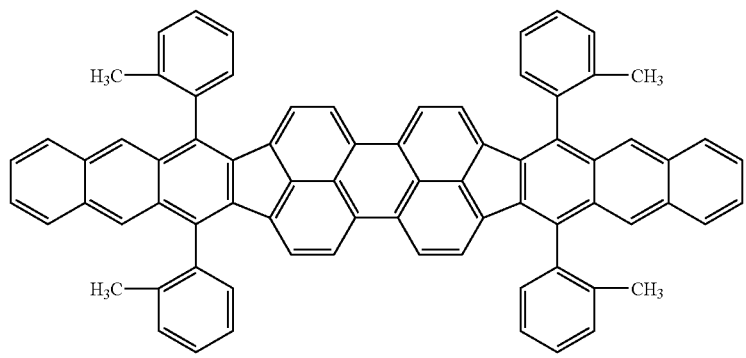
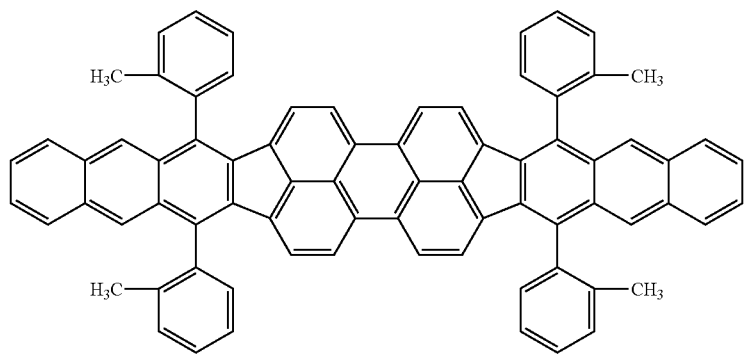
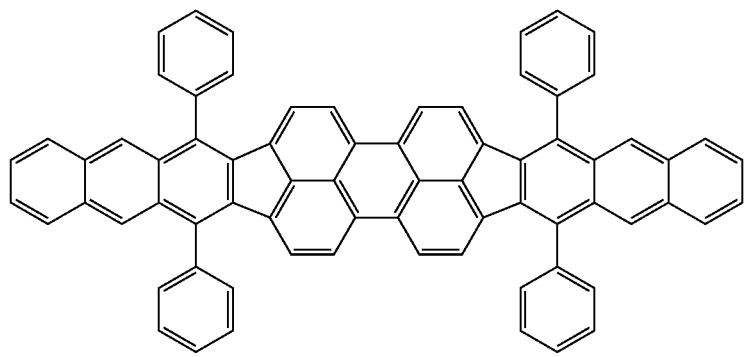

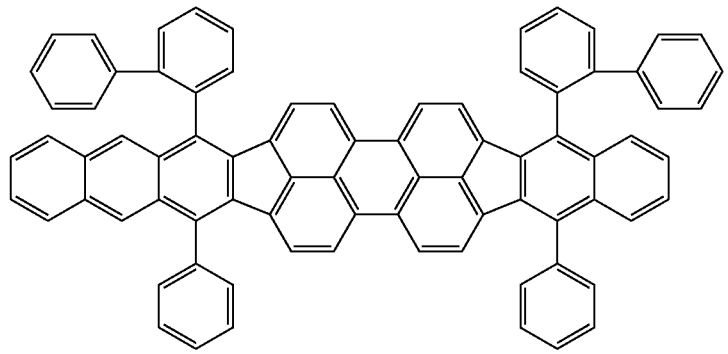
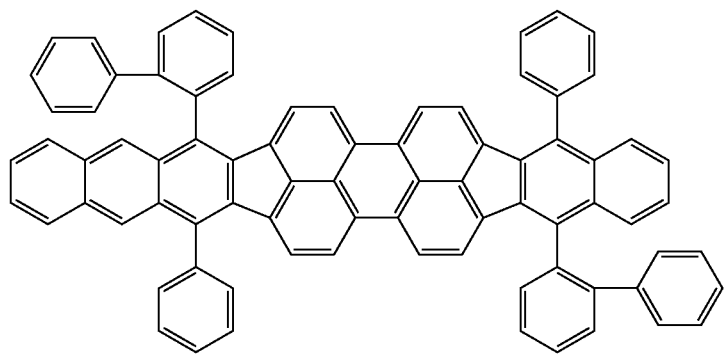
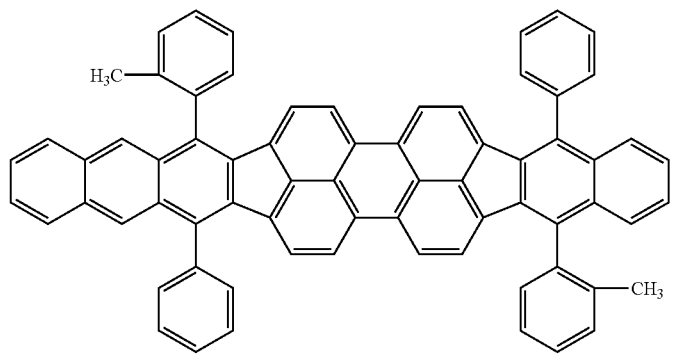
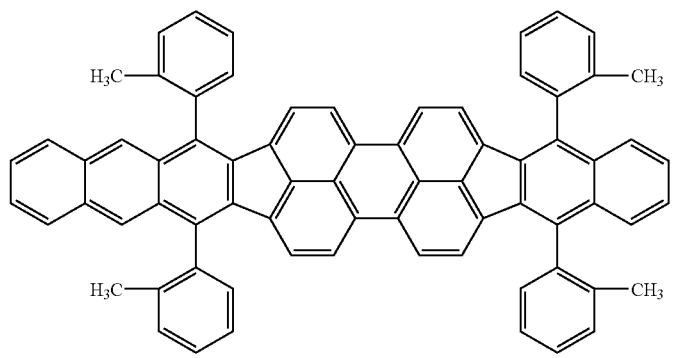

-continued
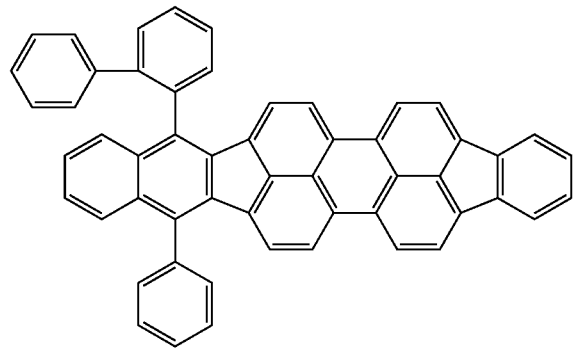
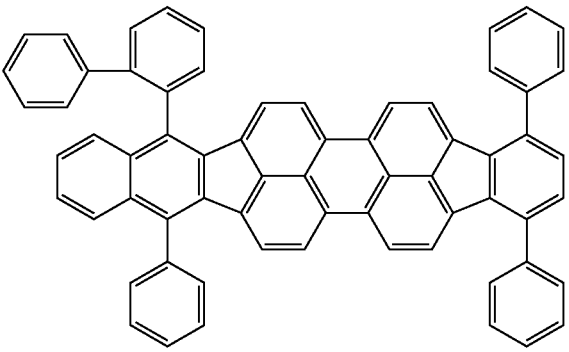
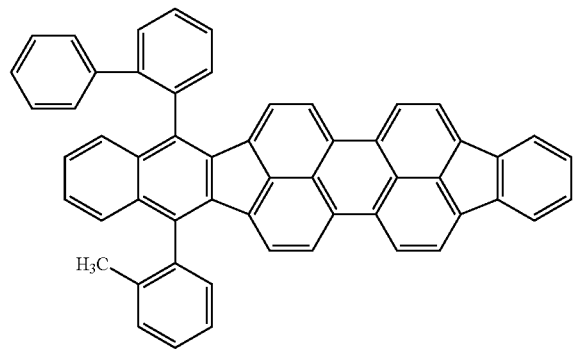
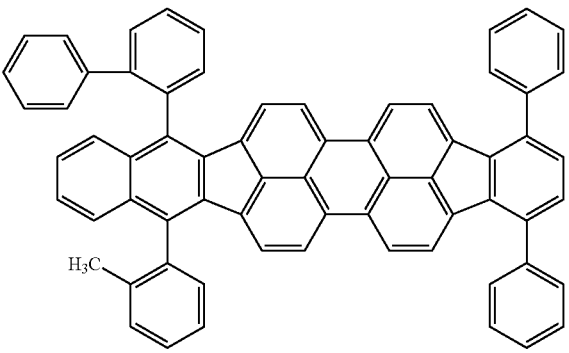
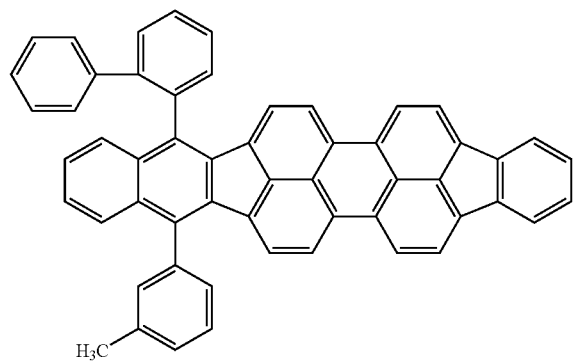
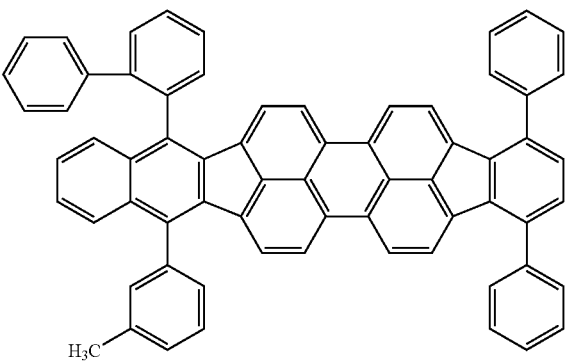
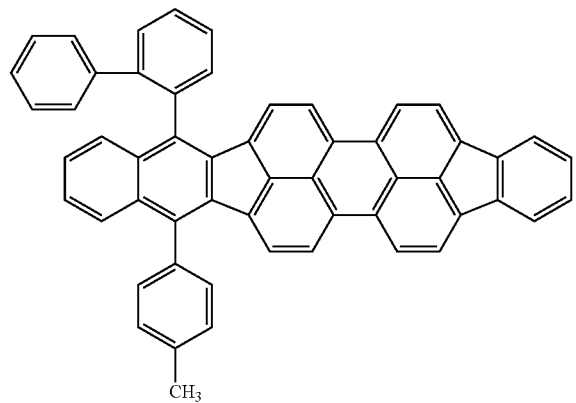
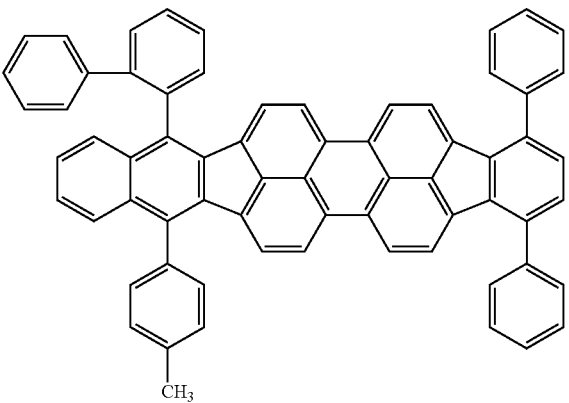

| 211 | 212 |
|---|---|
| 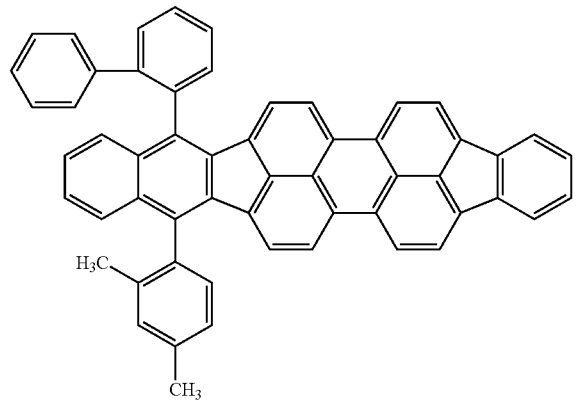 | 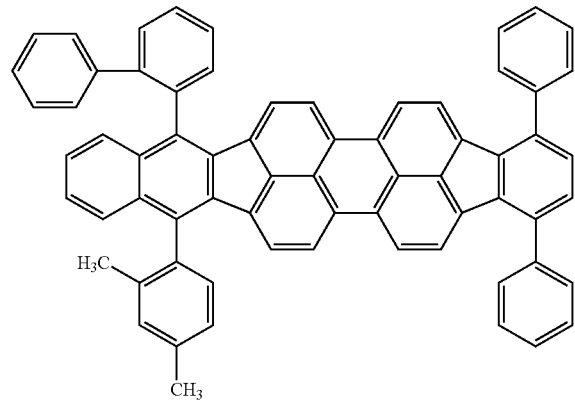 |
| 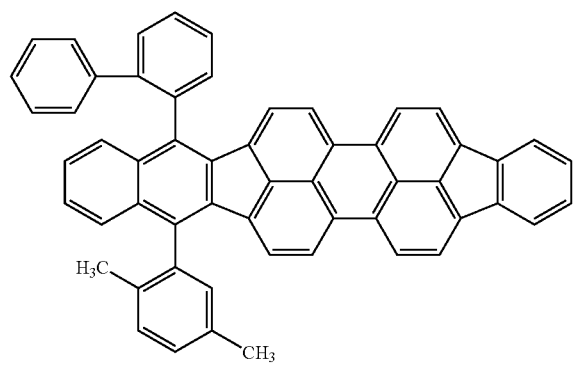 | 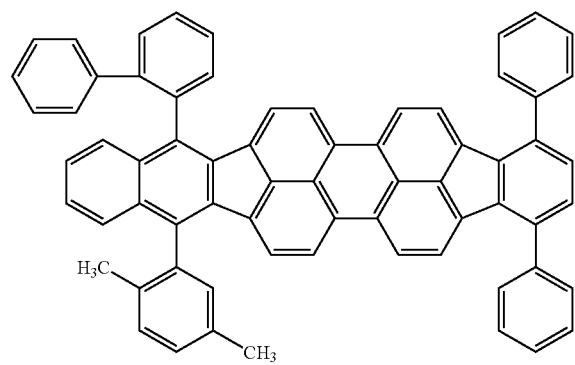 |
| 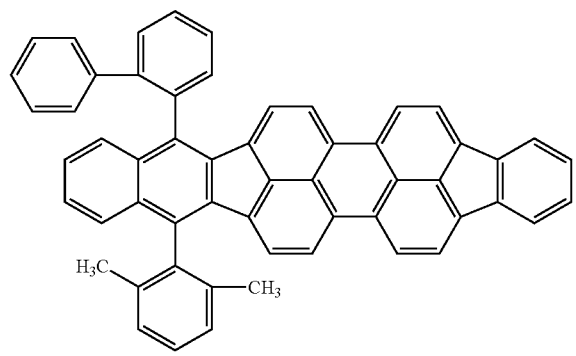 | 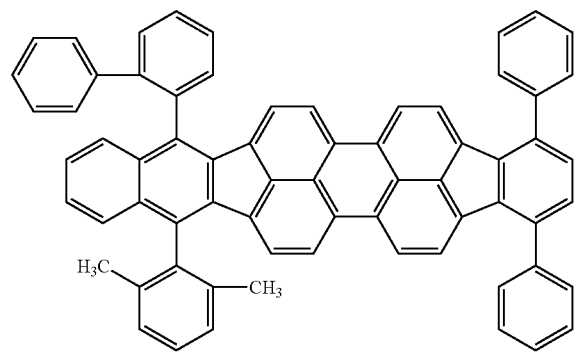 |
| 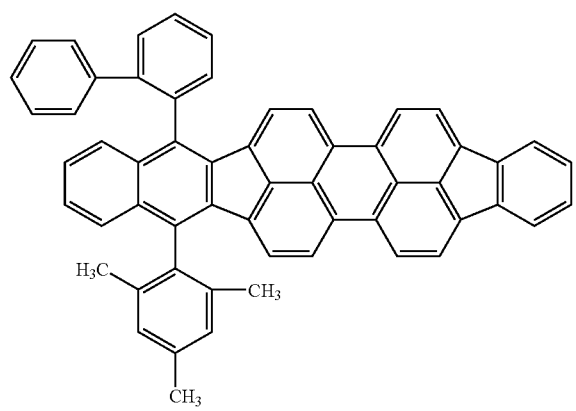 | 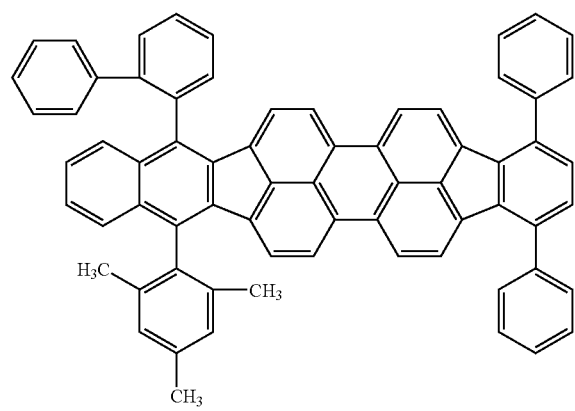 |

-continued
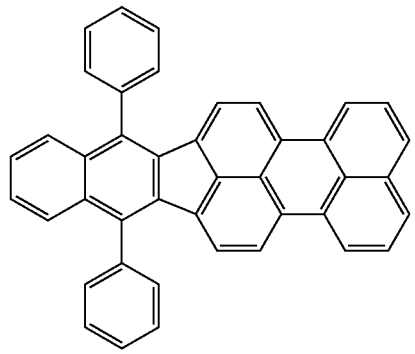
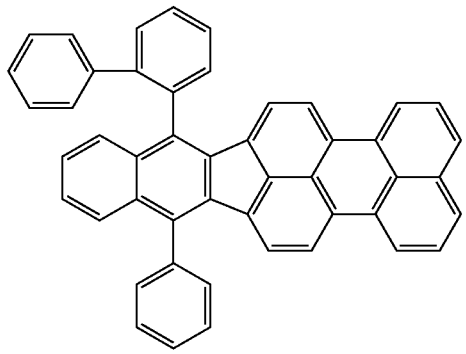
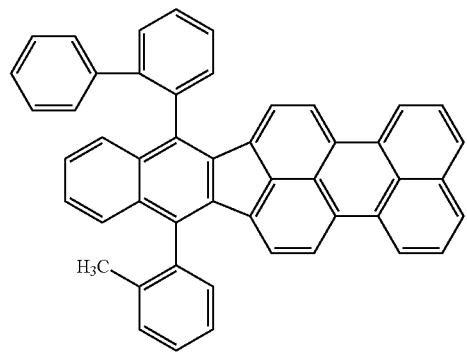
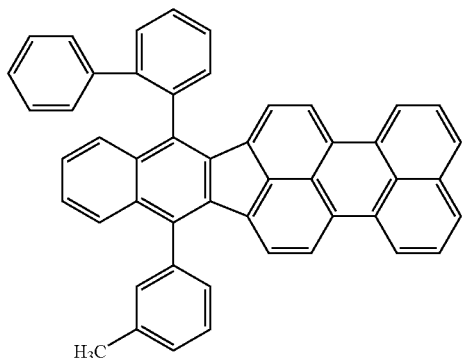
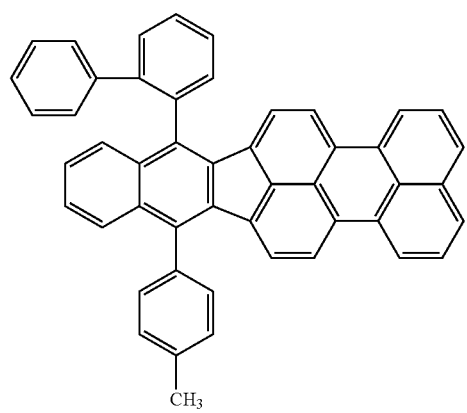
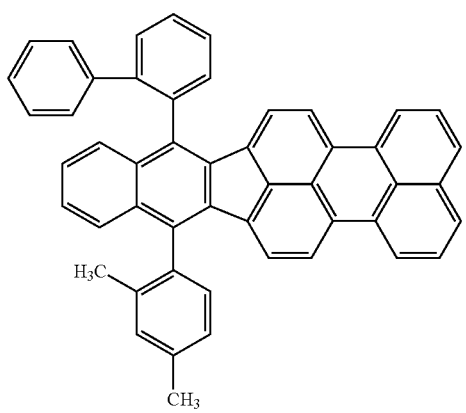
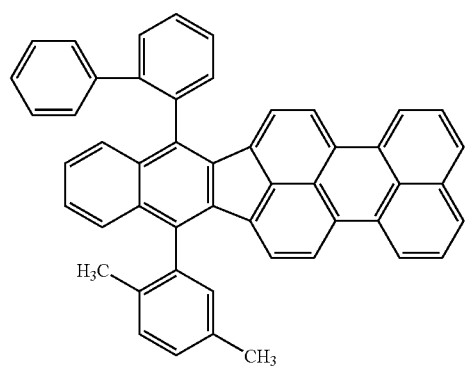
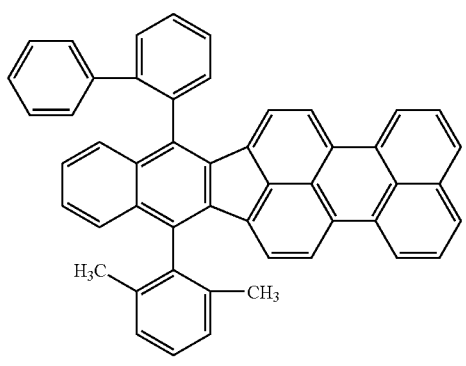

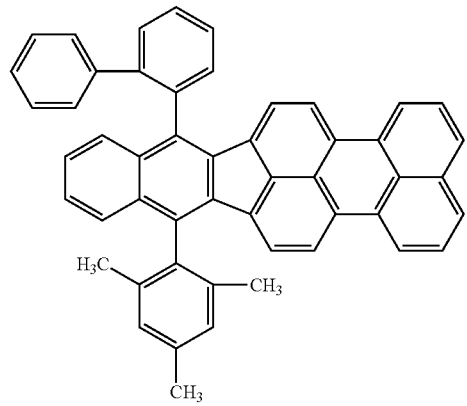
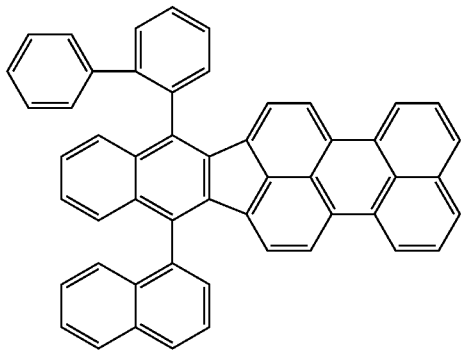
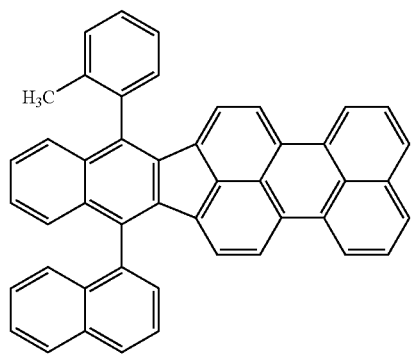
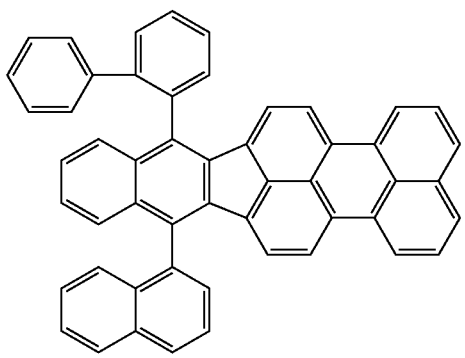
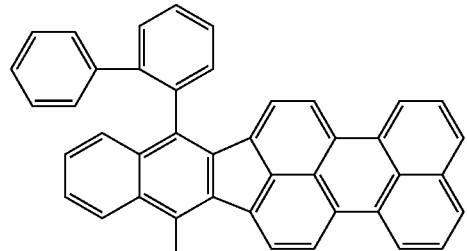
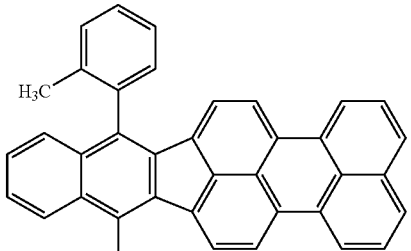
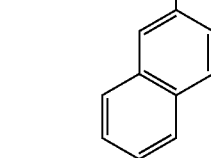
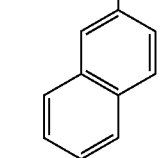
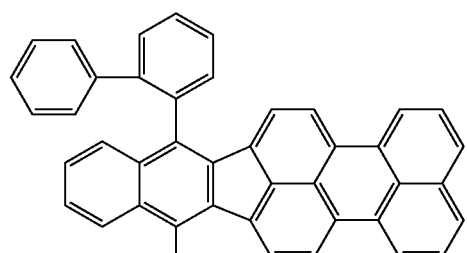
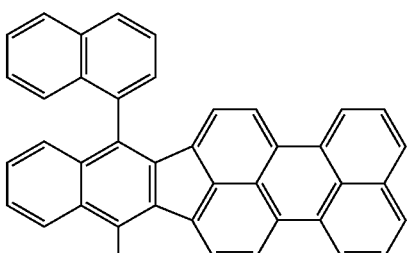
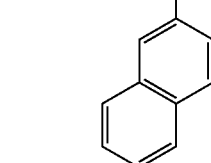
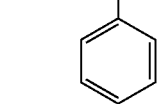

-continued
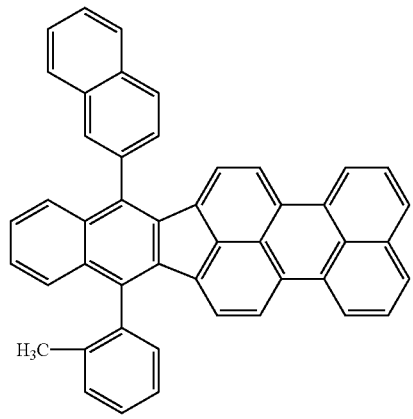
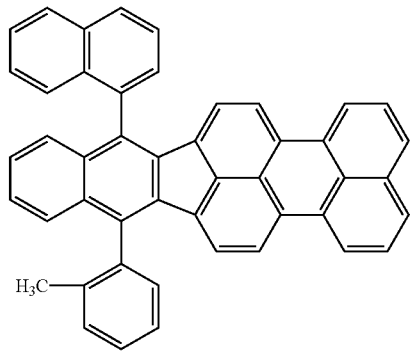
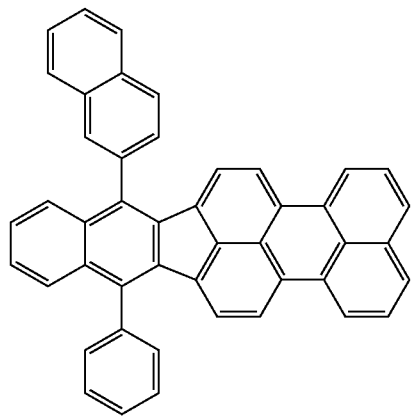
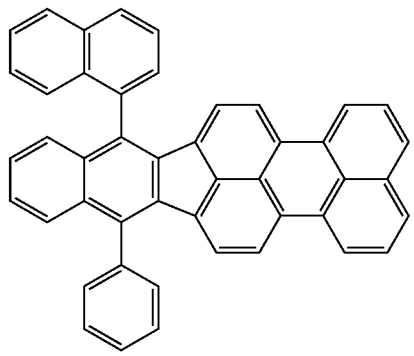
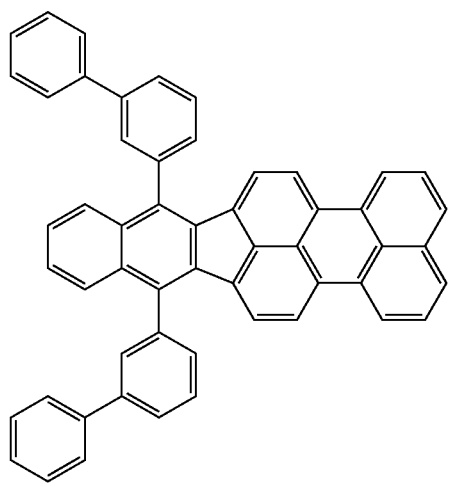
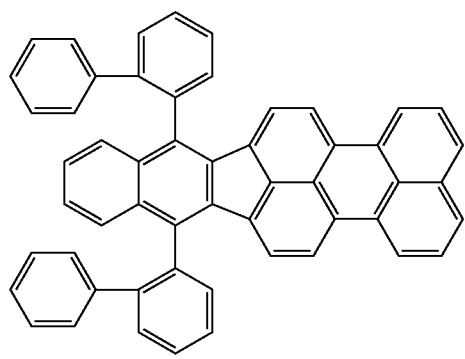

-continued
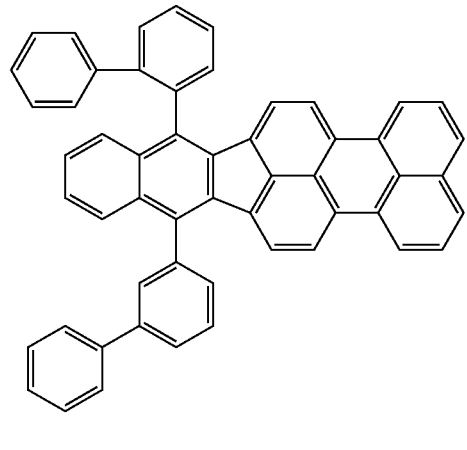
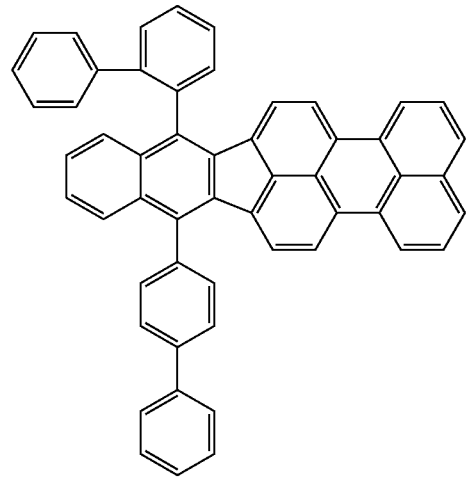
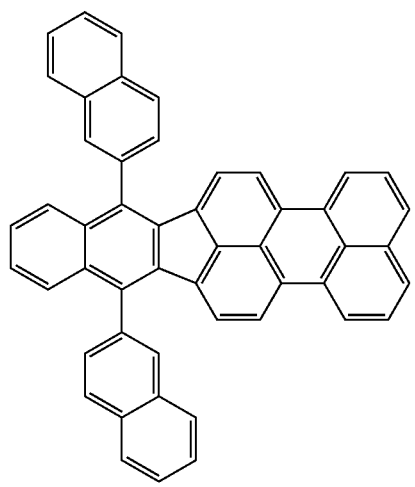
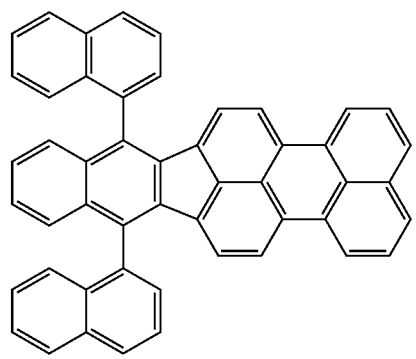
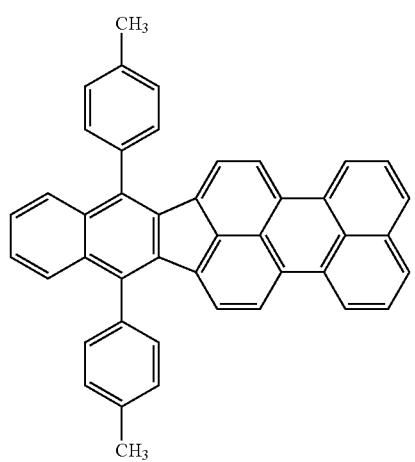
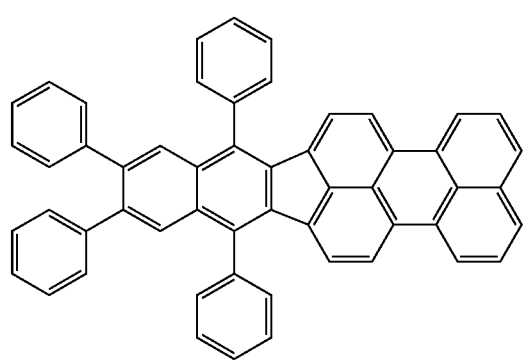

221
-continued
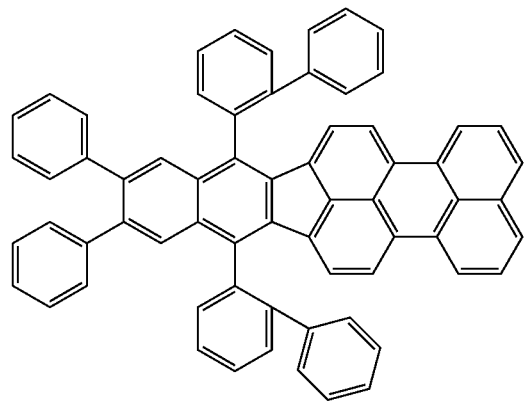
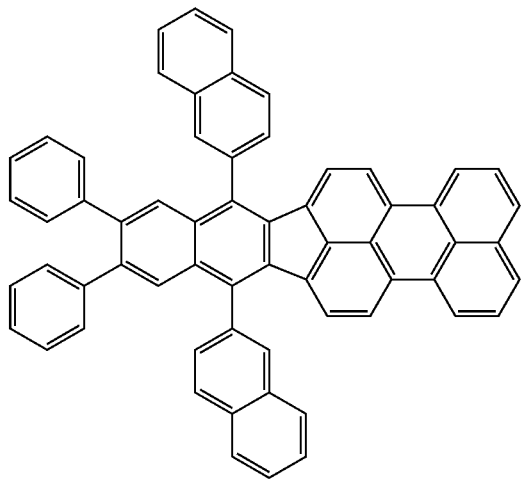
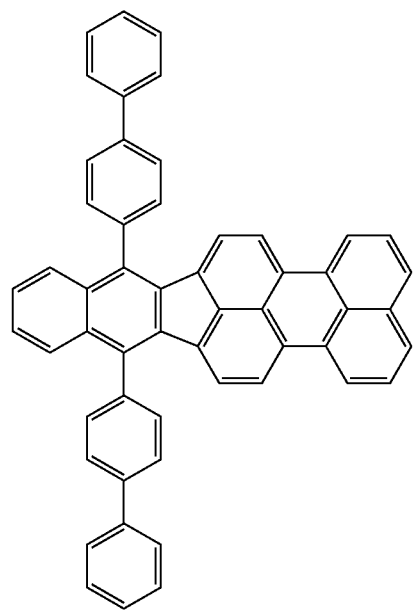
222
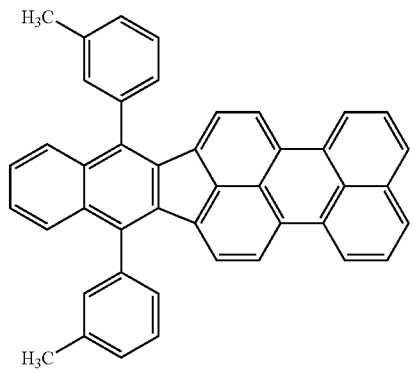
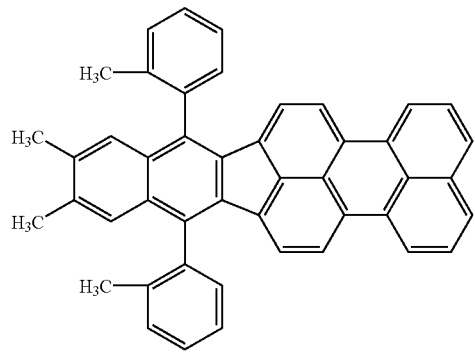
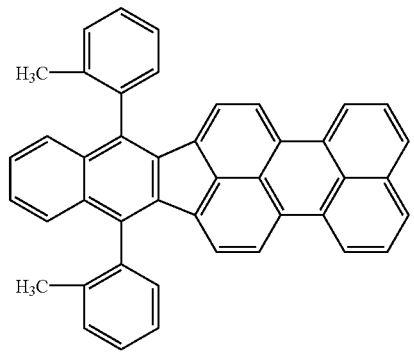

-continued
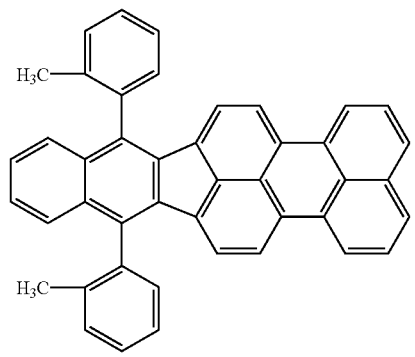
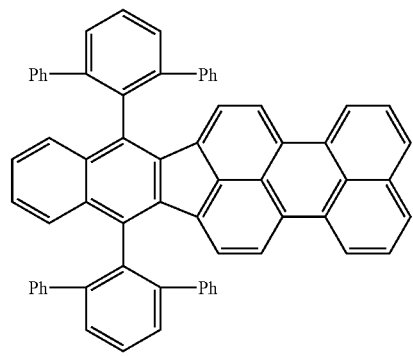
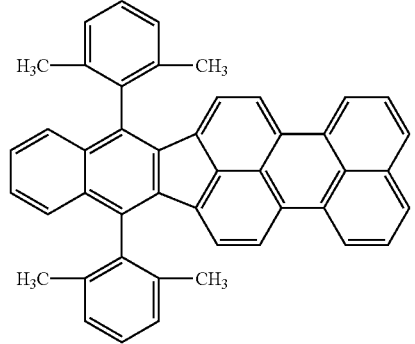
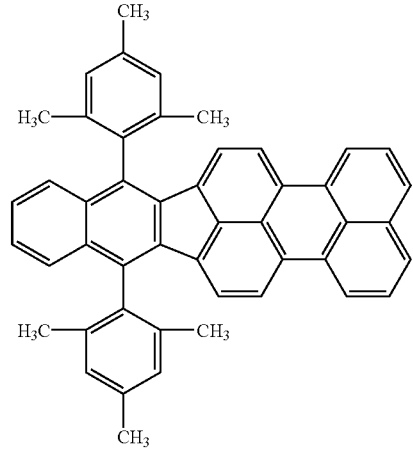
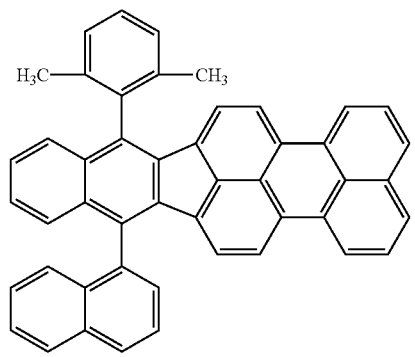
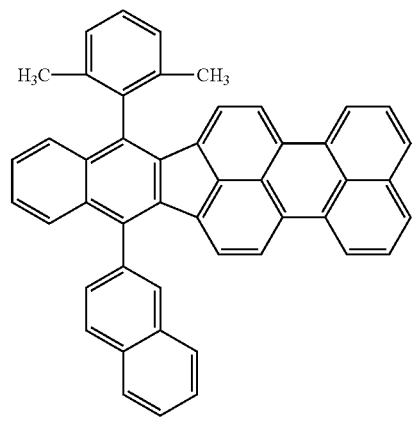
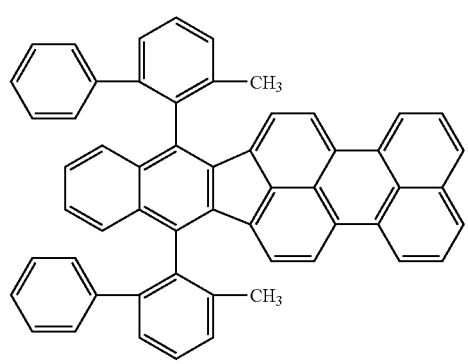
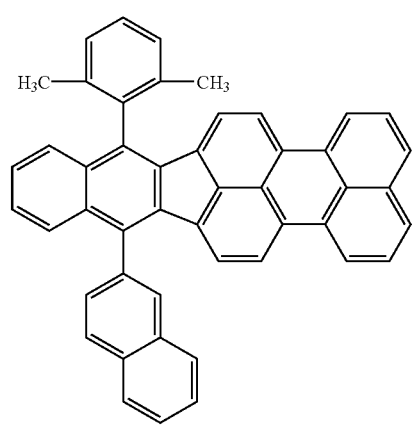

More preferred compounds are illustrated below.
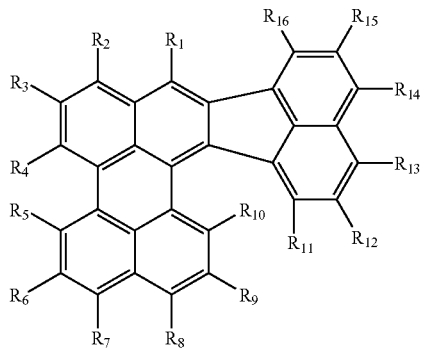
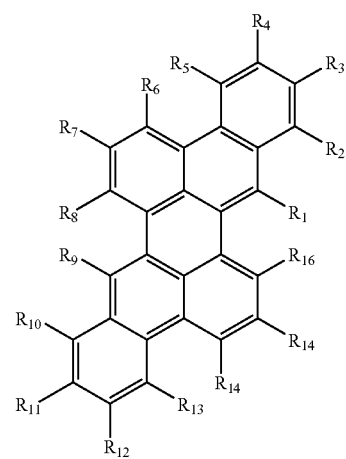
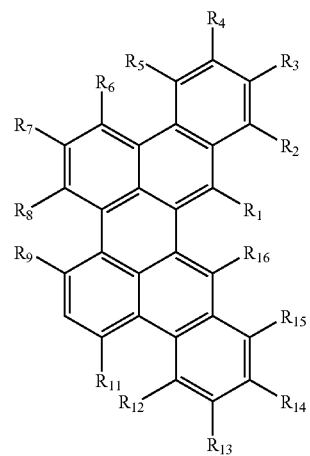
R = aryl or alkyl
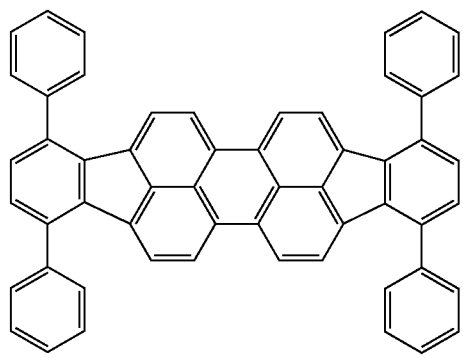
-continued
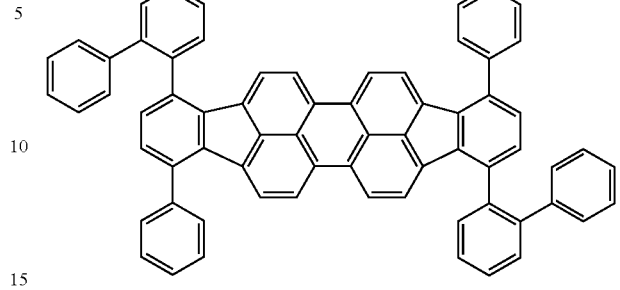
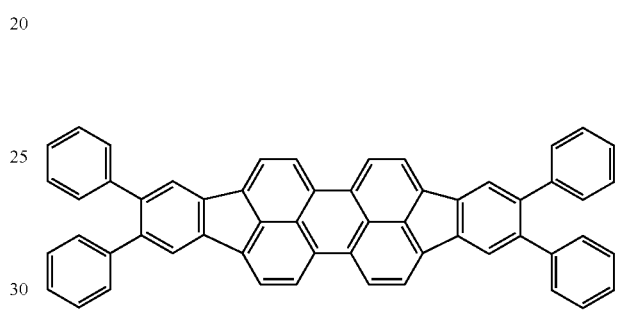
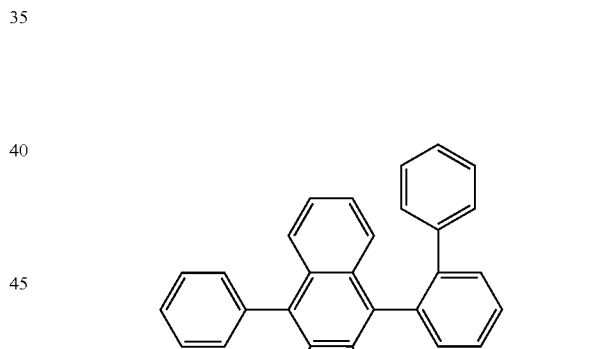
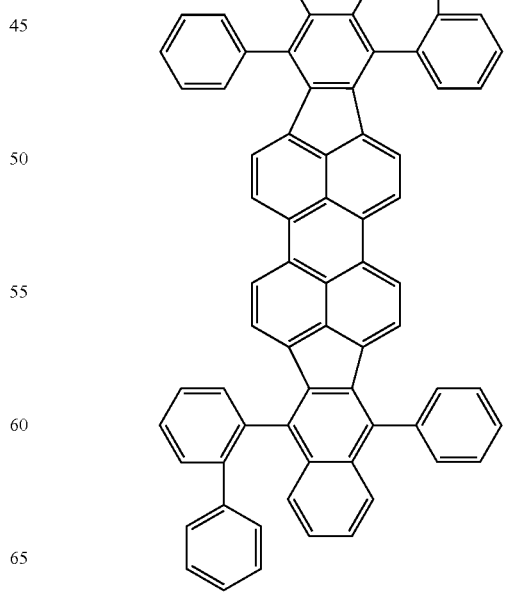

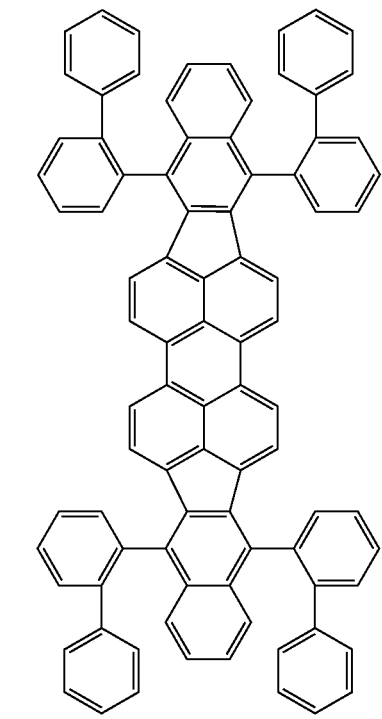

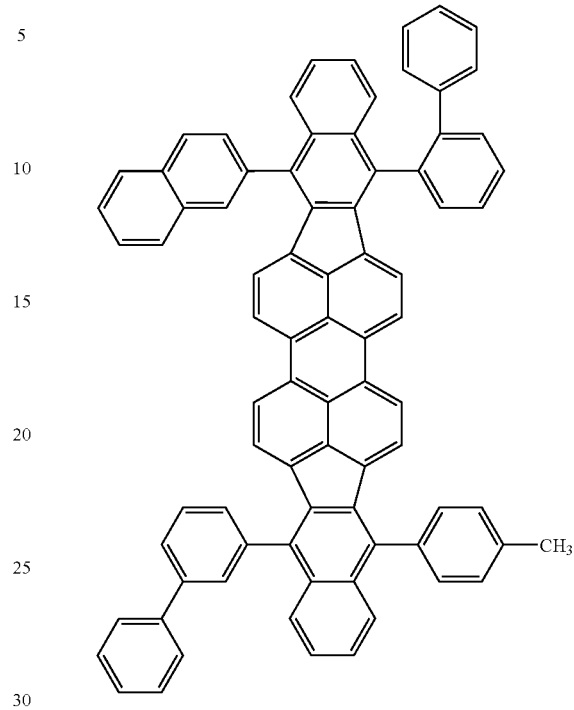

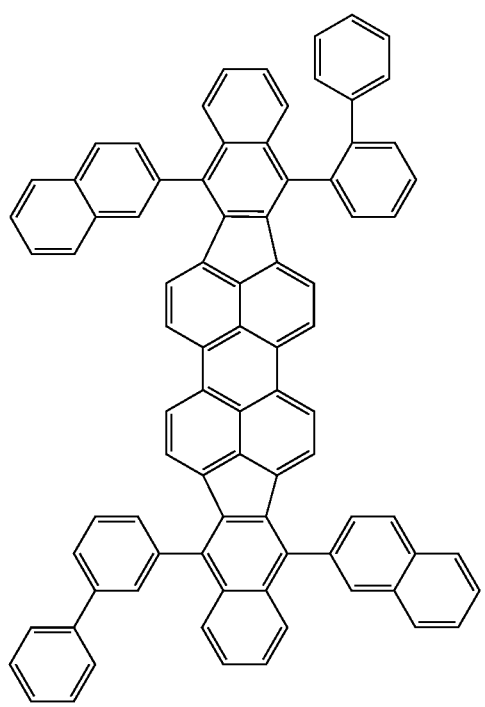

The diindeno[1,2,3-cd:1', 2', 3'-lm]perylene derivative of the above formula (6) should preferably have a vibration structure in both an excitation spectrum and a fluorescence spectrum. The presence of such a vibration structure is ascertainable by the appearance of two or more peaks in each of the spectra.

More preferably, a host material doped with the indenoperylene derivative prior to use has such a vibration structure.

The possession of a vibration structure leads to the manufacture of an organic EL device having improved temperature characteristics.

It is believed that a drop of EL luminous efficiency by temperature is due to thermal relaxation entailing a change of conformation in the excited state. Once a change of conformation in the excited state occurs, the overlap of molecular orbital function between the ground state and the excited state changes so that the fluorescence spectrum does not become a mirror image of the absorption spectrum. The fluorescence spectrum of a compound which can take a plurality of conformations in the excited state is the total of various vibration structures and thus becomes a broad spectrum apparently free of a vibration structure.

Accordingly, an organic compound which exhibits a vibration structure in the fluorescence spectrum and specifically, a compound whose vibration structure is a mirror image of the absorption spectrum experiences a minimal change of conformation in the excited state and therefore, when used as a luminescent material in an organic EL device, enables to produce a device having improved temperature characteristics as demonstrated by a minimal drop of EL luminous efficiency by temperature during driving.

For the same reason as above, the organic compound should preferably have a Stokes shift of up to 0.1 eV, especially up to 0.05 eV. The lower limit of Stokes shift is not critical although it is usually about 0.01 eV.

Another factor that governs the temperature characteristics of an organic EL device is the thermal excitation of carriers from the trap level. Especially in a doped light emitting layer, the dopant creates a trap level. Upon a temperature change, the hopping probability of carriers by thermal excitation changes. This sometimes results in changes of the carrier balance in the light emitting layer, leading to temperature dependent characteristics with a high efficiency. In contrast, the device of the invention has a minimized thermal change of the trapping of the light emitting layer, that is, minimized temperature dependence of efficiency.

In a preferred embodiment, the host material, especially at least one of the organic compounds of formula (I) shown later, in a light emitting layer has a greater electron affinity than an electron transporting layer and/or a hole transporting layer. If the host material in a light emitting layer has a greater electron affinity than an electron transporting layer and/or a hole transporting layer, the injection efficiency of electrons into the light emitting layer increases and electrons are blocked at the hole transporting layer interface, leading to an improvement in luminous efficiency and hence, device lifetime.

One class of organic compounds useful as the host material according to the invention have a basic skeleton of the following formula (I).

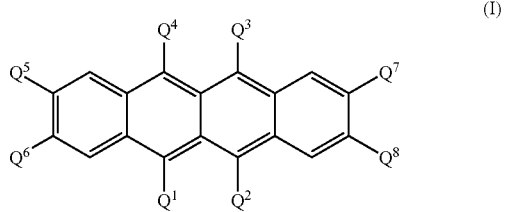

In the device of the invention, the use of the naphthacene derivative, preferably as the host material, helps induce strong light emission from the dopant.

Naphthacene derivatives belong to a class of preferable organic compounds, especially effective as the host material, among others. For example, the fluorescence intensity of a film of a naphthacene derivative (serving as the host material) doped with 1 wt % of a dibenzo[f,f']diindeno[1,2,3-cd:1', 2', 3'-lm]perylene derivative, as measured on photoexcitation, is about 3 times the fluorescence intensities of films of other organic compounds (e.g., Alq3) as the host.

The reason why such intense fluorescence is produced is presumably that the combination of a naphthacene derivative with the above dopant is an ideal combination that avoids interaction such as formation of an exciplex, and bipolar interaction between the respective molecules maintains a high intensity of fluorescence.

In the event of a red dopant, since the energy gap of a naphthacene derivative is relatively approximate to that of the dopant, an energy transfer phenomenon due to emission resorption takes place as well as energy transfer by electron exchange. This accounts for a high fluorescence intensity as well.

The combination with the above host material minimizes the concentration quenching of the dopant, which also contributes to a high fluorescence intensity.

In an exemplary organic EL device which was fabricated using the above doped film as a light emitting layer, a luminance of at least 600 cd/m$^2$ at maximum was obtained at a current density of 10 mA/cm$^2$, and the drive voltage at this time was as low as about 6 V. When operated at a current density of about 600 mA/cm$^2$, the device consistently produced a luminance of greater than about 20,000 cd/m$^2$. As compared with other organic compounds (e.g., Alq3) serving as the host, this provides a luminous efficiency greater by a factor of about 4 when assessed in terms of current efficiency, and because of possible driving at a lower voltage, a luminous efficiency greater by a factor of about 5 when assessed in terms of power efficiency. In the event of doping with a red dopant as in the above example, entailing the high efficiency of energy transfer from the host to the dopant, the device is characterized by a high chromatic purity in that only the dopant produces light emission, with little light emission from the host being observable.

It is believed that such a very high luminous efficiency exerted when organic EL devices are fabricated is due to the effects of an improved recombination probability of carriers in the light emitting layer and a singlet excitation state that the dopant forms as a result of energy transfer from the triplet excitation state of naphthacene, as well as the above-mentioned mechanism of providing a high fluorescence intensity.

As opposed to conventional organic EL devices whose drive voltage is increased by carrier trapping of the dopant, the inventive organic EL device using the above-mentioned light emitting layer has a very low drive voltage, because the order of carrier trapping of the dopant is low and high efficiency light emission is accomplished by the above-mentioned mechanism. Another probable reason is the ease of injection of carriers into the light emitting layer.

Since the naphthacene derivative is very stable and highly durable against carrier injection, the device fabricated using the above host-dopant combination has a very long lifetime. For example, an organic EL device having a light emitting layer of a specific naphthacene derivative doped with 1 wt % of a dibenzo[f,f']diindeno-[1,2,3-cd:1', 2', 3'-lm]perylene derivative is highly durable as demonstrated by its ability to sustain a luminance of at least 2,400 cd/m$^2$ over a period of 1,000 hours or longer, with an attenuation of less than about 1%, when driven at 50 mA/cm$^2$.

In organic EL devices as mentioned above, the dopant concentration ensuring a chromatic purity and maximum efficiency is about 1% by weight although dopant concentrations of about 2 or 3% by weight lead to devices which are practically acceptable albeit a drop of less than about 10%.

In formula (I), $Q^1$ to $Q^4$ are independently selected from among hydrogen and substituted or unsubstituted alkyl, aryl, amino, heterocyclic and alkenyl radicals. Preferred are aryl, amino, heterocyclic and alkenyl radicals. It is also desirable that $Q^2$ and $Q^3$ are these substituent radicals and $Q^1$ and $Q^4$ are hydrogen.

The aryl radicals represented by $Q^1$ to $Q^4$ may be monocyclic or polycyclic, inclusive of fused rings and a collection of rings. Those aryl radicals having 6 to 30 carbon atoms in total are preferred and they may have substituents.

Preferred examples of the aryl radical represented by $Q^1$ to $Q^4$ include phenyl, o-, m- and p-tolyl, pyrenyl, perylenyl, coronenyl, 1- and 2-naphthyl, anthryl, o-, m- and p-biphenylyl, terphenyl and phenanthryl.

The amino radicals represented by $Q^1$ to $Q^4$ may be selected from among alkylamino, arylamino, aralkylamino and analogous radicals. They preferably have aliphatic radicals having 1 to 6 carbon atoms in total and/or aromatic carbocyclic radicals having 1 to 4 rings. Illustrative examples include dimethylamino, diethylamino, dibutylamino, diphenylamino, ditolylamino, bisdiphenylylamino, and bisnaphthylamino radicals.

The heterocyclic radicals represented by $Q^1$ to $Q^4$ include 5- or 6-membered ring aromatic heterocyclic radicals containing O, N or S as a hetero atom, and fused polycyclic aromatic heterocyclic radicals having 2 to 20 carbon atoms.

The alkenyl radicals represented by $Q^1$ to $Q^4$ are preferably those having a phenyl radical as at least one substituent, such as 1- and 2-phenylalkenyl, 1,2- and 2,2-diphenylalkenyl, and 1,2,2-triphenylalkenyl although unsubstituted alkenyl radicals are acceptable.

Examples of the aromatic heterocyclic radicals and fused polycyclic aromatic heterocyclic radicals include thienyl, furyl, pyrolyl, pyridyl, quinolyl, and quinoxalyl radicals.

When $Q^1$ to $Q^4$ are substituted radicals, at least two of the substituents are preferably aryl, amino, heterocyclic, alkenyl or aryloxy radicals. These aryl, amino, heterocyclic and alkenyl radicals are as illustrated above for $Q^1$ to $Q^4$.

The aryloxy radicals to substitute on $Q^1$ to $Q^4$ are preferably those of aryl radicals having 6 to 18 carbon atoms in total, for example, o-, m- and p-phenoxy.

At least two of these substituents may form a fused ring. Also, these substituents may be further substituted ones, in which preferred substituents are as described above.

When $Q^1$ to $Q^4$ have substituents, it is preferred that at least two of the substituents have the above-described substituents. The position of substitution is not particularly limited and may be a meta, para or ortho position. $Q^1$ and $Q^4$, and $Q^2$ and $Q^3$ in the respective pairs are preferably identical although they may be different.

$Q^5$, $Q^6$, $Q^7$ and $Q^8$ are independently selected from among hydrogen and alkyl, aryl, amino, heterocyclic and alkenyl radicals which may have substituents.

The alkyl radicals represented by $Q^5$, $Q^6$, $Q^7$ and $Q^8$ are preferably those of 1 to 6 carbon atoms, which may be straight or branched. Preferred examples of the alkyl radical include methyl, ethyl, n- and i-propyl, n-, i-, sec- and tert-butyl, n-, i-, neo- and tert-pentyl.

The aryl, amino and alkenyl radicals represented by $Q^5$, $Q^6$, $Q^7$ and $Q^8$ are as illustrated above for $Q^1$ to $Q^4$. $Q^5$ and $Q^6$, and $Q^7$ and $Q^8$ in the respective pairs are preferably identical although they may be different.

It is preferred that rubrene wherein all $Q^1$ to $Q^4$ are phenyl and $Q^5$, $Q^6$, $Q^7$ and $Q^8$ are hydrogen be excluded.

The light emitting layer containing the host material and the dopant as mentioned above has functions of injecting holes and electrons, transporting them, and recombining holes and electrons to create excitons. The use of relatively electronically neutral compounds in the light emitting layer in addition to the compounds of the invention enables easy and well-balanced injection and transportation of electrons and holes.

The host material may be used alone or in admixture of two or more. When a mixture of two or more host materials is used, the mix ratio is arbitrary. The host material is preferably contained in an amount of 80 to 99.9%, more preferably 90 to 99.9%, even more preferably 95.0 to 99.5% by weight of the light emitting layer.

The thickness of the light emitting layer preferably ranges from the thickness corresponding to a single molecule layer to less than the thickness of an organic compound layer, for example, from 1 to 85 nm, more preferably 5 to 60 nm, and most preferably 5 to 50 nm.

Preferably the mix layer is formed by a co-deposition process of evaporating the compounds from distinct sources.

If both the compounds have equal or very close vapor pressure or evaporation temperature, they may be pre-mixed in a common evaporation boat, from which they are evaporated together. The mix layer is preferably a uniform mixture of both the compounds although the compounds can be present in island form. The light emitting layer is generally formed to a predetermined thickness by evaporating an organic fluorescent material or coating a dispersion thereof in a resin binder.

One exemplary construction of the organic EL light emitting device fabricated using the inventive compounds has on a substrate, a hole injecting electrode, a hole injecting and transporting layer, a light emitting and electron injecting and transporting layer, and an electron injecting electrode in the described order. If desired, a protective electrode, an auxiliary electrode and a sealing layer may be provided on the electron injecting electrode.

The organic EL device of the invention is not limited to the above exemplary construction and may have various other constructions. In another exemplary construction, the light emitting layer is provided singly and an electron injecting and transporting layer is interposed between the light emitting layer and the electron injecting electrode. Also, the light emitting layer may be mixed with the hole injecting and transporting layer, if desired.

The thicknesses of the light emitting layer, hole injecting and transporting layer, and electron injecting and transporting layer are not critical and vary with a particular formation technique. Usually each layer is about 5 to 500 nm thick, especially about 10 to 300 nm thick.

The thicknesses of the hole injecting and transporting layer and electron injecting and transporting layer are equal to or range from about 1/10 to 10 times the thickness of the light emitting layer although they depend on the design of a recombination/light emitting region. When the electron or hole injecting and transporting layer is divided into an injecting layer and a transporting layer, preferably the injecting layer is at least 1 nm thick and the transporting layer is at least 1 nm thick. The upper limit of thickness is generally about 500 nm for the injecting layer and about 500 nm for the transporting layer. The same applies when two injecting and transporting layers are provided.

The hole injecting and transporting layer has functions of facilitating injection of holes from the hole injecting electrode, transporting them stably, and blocking electrons. The electron injecting and transporting layer has functions of facilitating injection of electrons from the electron injecting electrode, transporting them stably, and blocking holes. These layers are effective for increasing the number of holes and electrons injected into the light emitting layer and confining holes and electrons therein for optimizing the recombination region to improve light emission efficiency.

In the hole injecting and transporting layer, there may be used various organic compounds as described, for example, in JP-A 63-295695, JP-A 2-191694, JP-A 3-792, JP-A 5-234681, JP-A 5-239455, JP-A 5-299174, JP-A 7-126225, JP-A 7-126226, JP-A 8-100172, and EPO 650955A1. Exemplary are tetraarylbenzidine compounds (triaryldiamines or triphenyl-diamines: TPD), aromatic tertiary amines, hydrazone derivatives, carbazole derivatives, triazole derivatives, imidazole derivatives, oxadiazole derivatives having an amino radical, and polythiophenes. Two or more of these compounds may be used, and on such combined use, they may be formed as a laminate of separate layers or mixed.

Where the hole injecting and transporting layer is formed separately as a hole injecting layer and a hole transporting layer, two or more compounds are selected in a proper combination from the compounds commonly used in hole injecting and transporting layers. In this regard, it is preferred to laminate layers in such an order that a layer of a compound having a lower ionization potential may be disposed adjacent the hole injecting electrode (ITO). It is also preferred to use a compound having good thin film forming ability at the hole injecting electrode surface. The order of lamination also applies where a plurality of hole injecting and transporting layers are provided. Such an order of lamination is effective for lowering the drive voltage and preventing current leakage and the development and growth of dark spots. Since evaporation is utilized in the manufacture of devices, films as thin as about 1 to 10 nm can be formed uniform and pinhole-free, which restrains any change in color tone of light emission and a drop of efficiency by re-absorption even if a compound having a low ionization potential and absorption in the visible range is used in the hole injecting layer. Like the light emitting layer, the hole injecting and transporting layer may be formed by evaporating the above-mentioned compounds.

In the electron injecting and transporting layer, there may be used quinoline derivatives including organic metal complexes having 8-quinolinol or a derivative thereof as a ligand such as tris(8-quinolinolato)aluminum (Alq3), oxadiazole derivatives, perylene derivatives, pyridine derivatives, pyrimidine derivatives, quinoxaline derivatives, diphenylquinone derivatives, nitro-substituted fluorene derivatives, etc. The electron injecting and transporting layer can also serve as the light emitting layer, and in such a case, the light emitting layer according to the invention is preferably employed. Like the light emitting layer, the electron injecting and transporting layer may be formed by evaporation or the like.

Where the electron injecting and transporting layer is formed separately as an electron injecting layer and an electron transporting layer, two or more compounds are selected in a proper combination from the compounds commonly used in electron injecting and transporting layers. In this regard, it is preferred to stack layers in such an order that a layer of a compound having a greater electron affinity may be disposed adjacent the electron injecting electrode. The order of stacking also applies where a plurality of electron injecting and transporting layers are provided.

In forming the hole injecting and transporting layer, the light emitting layer, and the electron injecting and transporting layer, vacuum evaporation is preferably used because homogeneous thin films are available. By utilizing vacuum evaporation, there is obtained a homogeneous thin film which is amorphous or has a crystal grain size of up to 0.1 µm. If the grain size is more than 0.1 µm, uneven light emission would take place and the drive voltage of the device must be increased with a substantial drop of hole injection efficiency.

The conditions for vacuum evaporation are not critical although a vacuum of $10^{-4}$ Pa or lower and a deposition rate of about 0.01 to 1 nm/sec are preferred. It is also preferred to successively form layers in vacuum because the successive formation in vacuum can avoid adsorption of impurities on the interface between the layers, thus ensuring better performance. Also, the drive voltage of a device can be reduced and the development and growth of dark spots be restrained.

In the embodiment wherein the respective layers are formed by vacuum evaporation, where it is desired for a single layer to contain two or more compounds, preferably boats having the compounds received therein are individually temperature controlled to achieve co-deposition.

The electron injecting electrode is preferably made of metals, alloys or intermetallic compounds having a work function of up to 4 eV. With a work function of more than 4 eV, the electron injecting efficiency lowers and consequently, the light emission efficiency lowers. Examples of the metal having a work function of up to 4 eV of which the electron injecting electrode film is constructed include alkali metals such as Li, Na and K, alkaline earth metals such as Mg, Ca, Sr and Ba, rare earth metals such as La and Ce, and Al, In, Ag, Sn, Zn, and Zr. Examples of the film-forming alloy having a work function of up to 4 eV include Ag—Mg (Ag: 0.1 to 50 at %), Al—Li (Li: 0.01 to 12 at %), In—Mg (Mg: 50 to 80 at %), and Al—Ca (Ca: 0.01 to 20 at %). These materials may be present alone or in combination of two or more. Where two or more materials are combined, their mixing ratio is arbitrary. It is also acceptable that an oxide or halide of an alkali metal, alkaline earth metal or rare earth metal is thinly deposited and a supporting electrode (auxiliary electrode or wiring electrode) of aluminum etc. is used.

The electron injecting electrode may be formed by evaporation or sputtering.

The electron injecting electrode may have at least a sufficient thickness to effect electron injection, for example, a thickness of at least 0.1 nm. Although the upper limit is not critical, the electrode thickness is typically about 0.1 to about 500 nm.

The hole injecting electrode is preferably formed of such a material to such a thickness that the electrode may have a transmittance of at least 80% of emitted light. Illustratively, oxide transparent conductive thin films are preferred. For example, materials based on tin-doped indium oxide (ITO), zinc-doped indium oxide (IZO), indium oxide ($In_2O_3$), tin oxide ($SnO_2$) or zinc oxide (ZnO) are preferable. These oxides may deviate somewhat from their stoichiometry. An appropriate proportion of $SnO_2$ mixed with $In_2O_3$ is 1 to 20%, more preferably 5 to 12% by weight. An appropriate proportion of ZnO mixed with $In_2O_3$ is 12 to 32% by weight.

The hole injecting electrode should preferably have a light transmittance of at least 80%, especially at least 90% in the light emission band, typically from 350 to 800 nm, and especially at each light emission. Since the emitted light is generally taken out through the hole injecting electrode, with a lower transmittance, the light emitted by the light emitting layer would be attenuated through the electrode, failing to provide a luminance necessary as a light emitting device. It is noted that only the side from which the emitted light exits has a transmittance of at least 80%.

The hole injecting electrode has at least a sufficient thickness to effect hole injection, preferably a thickness of 50 to 500 nm, especially 50 to 300 nm. Although the upper limit of the electrode thickness is not critical, a too thick electrode would have the risk of separation. Too thin an electrode would have problems with respect to film strength during fabrication, hole transporting ability, and resistance value.

In depositing the hole injecting electrode, a sputtering process is preferred. The sputtering process may be a high-frequency sputtering process using an RF power supply although a dc sputtering process is preferably used when the ease of control of physical properties of the hole injecting electrode being deposited and the flatness of the deposited film are taken into account.

A protective film may be formed if necessary. The protective film may be formed using an inorganic material such as SiOx or an organic material such as Teflon™. The protective film may be either transparent or opaque and have a thickness of about 50 to 1,200 nm. Apart from the reactive sputtering process mentioned above, the protective film may also be formed by an ordinary sputtering or evaporation process.

Further, a sealing layer is preferably provided on the device in order to prevent the organic layers and electrodes from oxidation. In order to prevent the ingress of moisture, the sealing layer is formed by attaching a sealing plate such as a glass plate to the substrate with an adhesive resin layer such as a commercially available low moisture absorption photo-curable adhesive, epoxy base adhesive, silicone base adhesive, or crosslinking ethylene-vinyl acetate copolymer adhesive sheet. Metal plates and plastic plates may also be used instead of the glass plate.

Transparent or translucent materials such as glass, quartz and resins are used as the substrate when the emitted light exits from the substrate side. The substrate may be provided with a color filter film, a fluorescent material-containing color conversion film or a dielectric reflecting film for controlling the color of light emission. In the case of the inversely stacked layer structure, the substrate may be either transparent or opaque. For the opaque substrate, ceramic and other materials may be used.

The color filter film used herein may be a color filter as used in liquid crystal displays and the like. The properties of a color filter may be adjusted in accordance with the light emission of the organic EL device so as to optimize the extraction efficiency and chromatic purity.

It is also preferred to use a color filter capable of cutting external light of short wavelength which is otherwise absorbed by the EL device materials and fluorescence conversion layer, because the light resistance and display contrast of the device are improved.

Also, an optical thin film such as a dielectric multilayer film may be used instead of the color filter.

The organic EL device of the invention is constructed, as shown in FIG. 1, for example, to have on a substrate 1, a hole injecting electrode (or anode) 2, a hole injecting layer 3, a hole transporting layer 4, a light emitting layer 5, an electron injecting and transporting layer 6, an electron injecting electrode (or cathode) 7 and optionally, a protective electrode 8 in the described order. The order of lamination may be inverse to the above-described order. The hole injecting layer 3, hole transporting layer 4 and electron injecting and transporting layer 6 may be omitted or either one of them may be a common layer to the light emitting layer 5. Each of these constituent layers may be adjusted optimum depending on the required function of the device.

The organic EL device of the invention is generally of the dc or pulse drive type while it can be of the ac drive type. The applied voltage is generally about 2 to 30 volts.

EXAMPLE

Synthesis Examples and Examples of the present invention are given below together with Comparative Examples for further illustrating the invention.

Example 1

Synthesis of 1-o-biphenylyl-3-phenylisobenzofuran

In Ar, 3.9 g (1.68E-2 mol) of o-bromobiphenyl was dissolved in 30 cm³ of tetrahydrofuran (THF) at −50° C. To the solution was added 10 cm³ of a nBuLi hexane solution (1.5 mol/l). After 2 hours, 3 g (1.4E-2 mol) of 3-phenylphthalide was added to the solution while it was kept cooled at −50° C. After 2 hours, the reaction solution was allowed to resume room temperature, and 10 cm³ of a 35% aqueous hydrochloric acid was added thereto. After 1 hour, toluene extraction was carried out using a separatory funnel, followed by thorough washing with distilled water. After the toluene solution was concentrated, the end product was isolated by silica gel chromatography (developer, toluene:hexane=1:4). There was obtained 4 g (80%) of a yellow viscous substance emitting bluish green fluorescence.

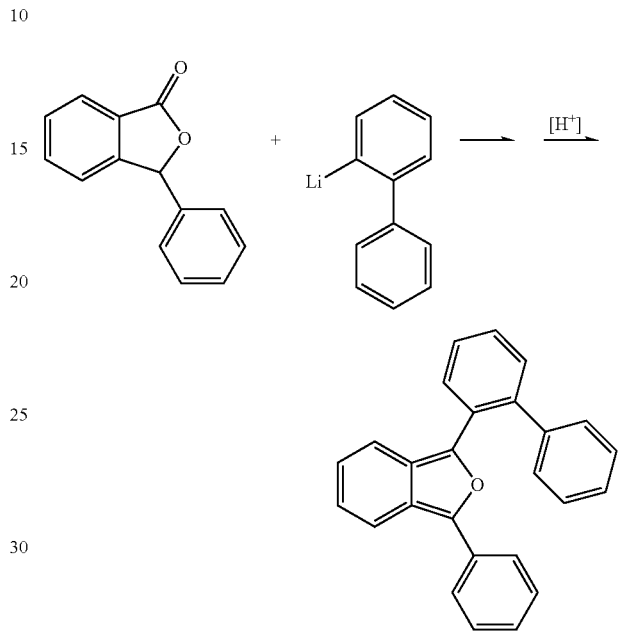

Synthesis of 3,4-dibromo-(7-o-biphenylyl-12-phenyl)-benzo[k]fluoranthene

In toluene, 2.2 g (6.45E-3 mol) of 1-o-biphenylyl-3-phenylisobenzofuran synthesized above and 2.0 g (6.45E-3 mol) of 5,6-dibromoacenaphthene were heated under reflux for 24 hours. At the end of reaction, the precipitate was recovered, obtaining an intermediate. 1.6 g (41%) The intermediate, 1.6 g, was dissolved in 150 cm³ of acetic acid by heating. To the solution, 20 cm³ of a 50% aqueous solution of HBr was added, and reaction effected at 120° C. for 30 minutes. After cooling, the precipitate was recovered. The end product was isolated by silica gel chromatography (developer, toluene:hexane=1:3). There was obtained 1.0 g (70%) of a yellow powder.

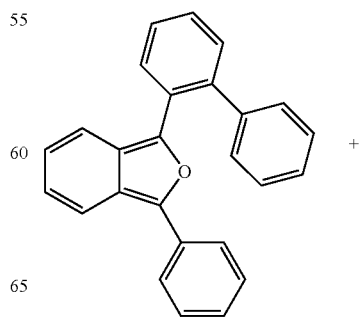

-continued

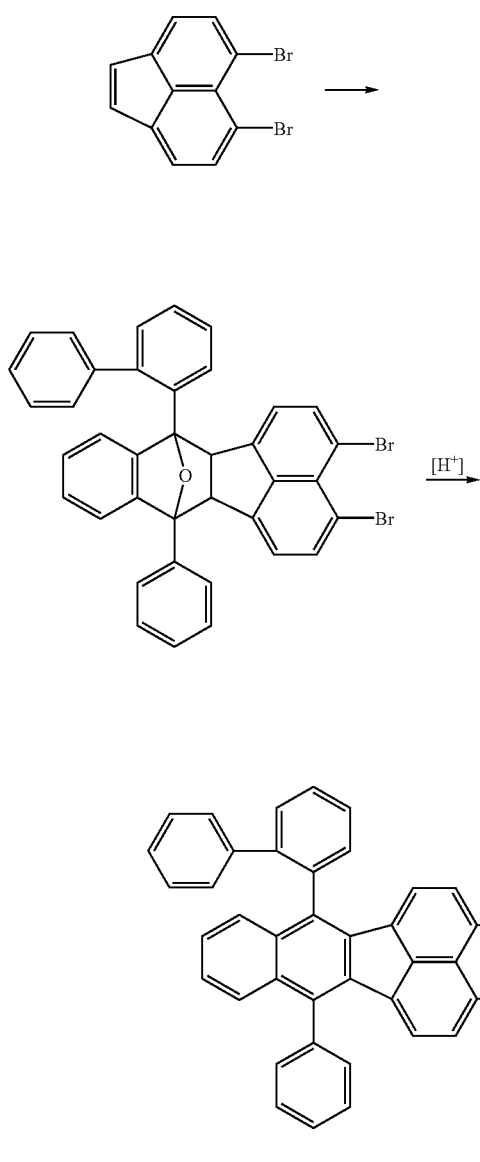

Synthesis of dibenzo-((bis-o-biphenylyl)(-diphenyl))-perifuranthene

In 30 cm³ of DMF was dissolved 1.0 g (1.57E-3 mol) of 3,4-dibromo-(7-o-biphenylyl-12-phenyl)benzo[k]fluoranthene synthesized above. To the solution, 0.52 g (1.9E-3 mol) of Ni(COD)$_2$, 1 ml of cyclooctadiene (COD) and 0.12 g (1.57E-3 mol) of bipyridine were added, and reaction effected at 60° C. for 12 hours.

At the end of reaction, 30 cm³ of 1N aqueous hydrochloric acid and 30 cm³ of methanol were added whereby the end compound was precipitated and recovered. The end compound was isolated by silica gel chromatography (developer, toluene:hexane=1:3). There was obtained 0.67 g (90%) of a bluish purple solid.

The compound in a dichloromethane solution exhibited fluorescence peaks (EM) at a wavelength of 602 and 652 nm. The compound in a dichloromethane solution exhibited fluorescence absorption peaks (EX) at a wavelength of 508, 547 and 593 nm.

Mass analysis: (M+1)$^+$=957

Sublimation purification temperature: 430° C.

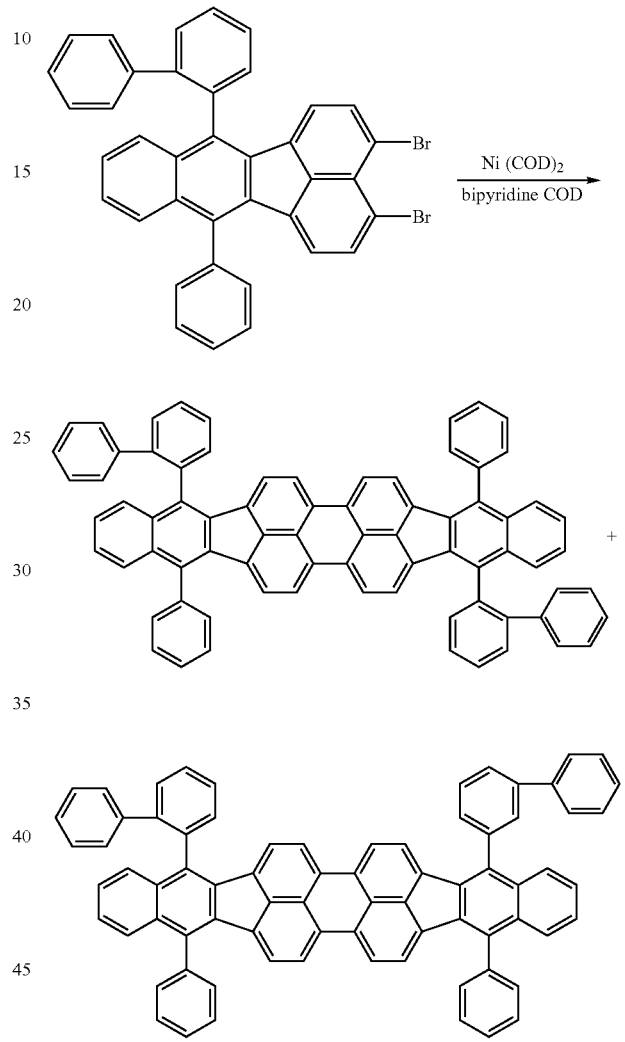

Example 2

Synthesis of 3,4-dibromofluoranthene Derivative

A series of 5,6-dibromofluoranthene derivatives are obtainable by effecting Diels-Alder reaction between 5,6-dibromoacenaphthylene and a butadiene derivative and then effecting dehydrogenation reaction with dichlorodicyanoquinone (DDQ).

In xylene, 5 g (1.6E-2 mol) of 5,6-dibromoace-naphthylene and 3.3 g (1.6E-2 mol) of 2,3-diphenylbutadiene were heated under reflux for 48 hours, obtaining 5.6 g (70%) of an intermediate.

In toluene were dissolved 5 g (9.6E-3 mol) of the intermediate and 2.2 g (9.6E-3 mol) of dichlorodicyano-quinone (DDQ). By effecting reaction at 120° C. for 24 hours, 3.0 g (60%) of 3,4-dibromo-8,9-diphenylfluoranthene was obtained.

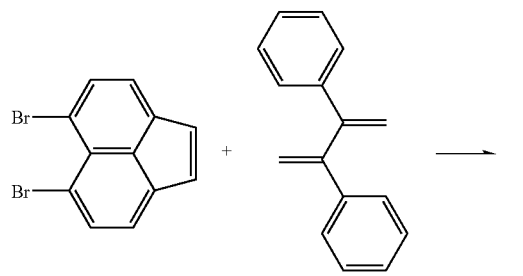

acidic. The reaction solution was allowed to resume room temperature, neutralized with aqueous NaHCO$_3$, and combined with distilled water. By vacuum distilling off the organic layer, the precipitate was recovered.

The recovered material was washed with a large volume of water by agitation, followed by filtration. The recovered material was dissolved in acetone, dried over MgSO$_4$, and precipitated again by adding hexane.

Yield 4 g (81%)

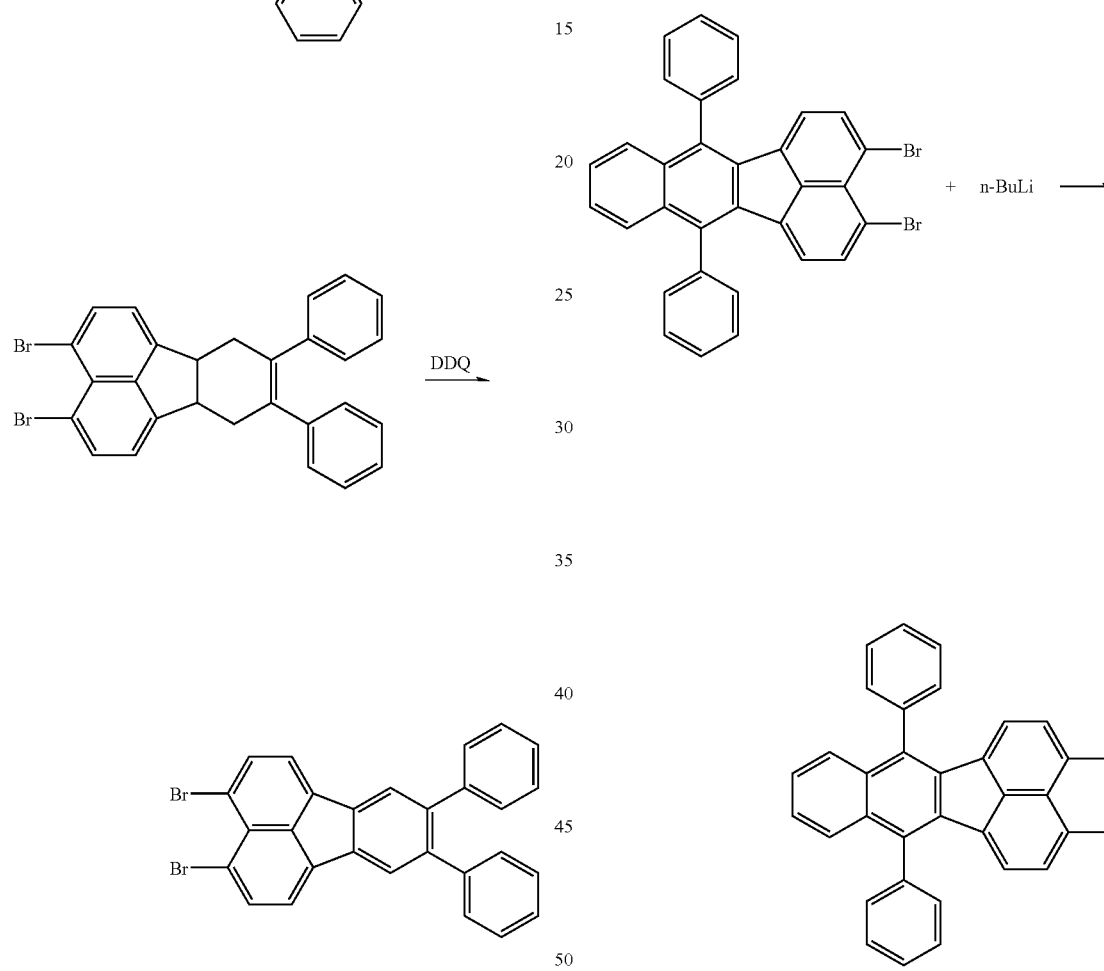

Synthesis Route of dibenzotetraphenylperifuranthene via Suzuki Coupling

Reaction (1)

In Ar, 5.6 g (1.0E-2 mol) of 3,4-dibromo(7,12-diphenyl)benzo[k]fluoranthene was dissolved in 100 cm$^3$ of dry THF, which was cooled at −40 to −50° C. To the solution, 14 cm$^3$ (1.0E-2×2.2 mol) of a nBuLi hexane solution (1.57 mol/l) was slowly added. The temperature was kept at −40 to −50° C. for 1 hour, after which 3.2 g (1.0E-2×2.2 mol) of triethyl borate was slowly added. After 2 hours, 50 cm$^3$ of distilled water was added. Thereafter, ~10% aqueous hydrochloric acid was added to the reaction solution until it turned weakly Reaction (2)

In nitrogen, 4 g (8.1E-3 mol) of (7,12-diphenyl)-benzo[k]fluoranthene-3,4-diboronic acid and 4.55 g (8.1E-3 mol) of 3,4-dibromobenzo[k]fluoranthene were dissolved in 150 cm$^3$ of a 1:1 solvent mixture of toluene and ethanol. Then 0.93 g (8.1E-3×2×0.05 mol) of tetrakis(triphenyl-phosphine)palladium(0) (Pd(PPh$_3$)$_4$) was added to the solution, which was heated at 85° C. in an oil bath. Then an aqueous solution of sodium carbonate which was previously prepared by dissolving 15 g of Na$_2$CO$_3$ in 50 cm$^3$ of distilled water was admitted into the solution, which was allowed to react overnight. The reaction was followed by extraction with chloroform and thorough washing with distilled water.

241

The product was column purified using silica gel.

Yield 5.2 g (80%)

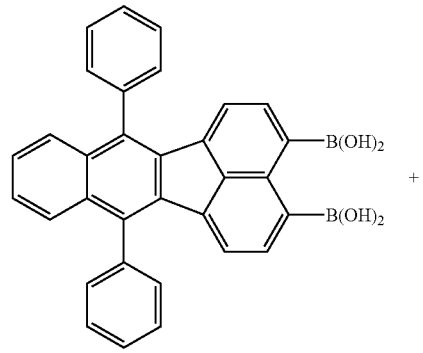

+

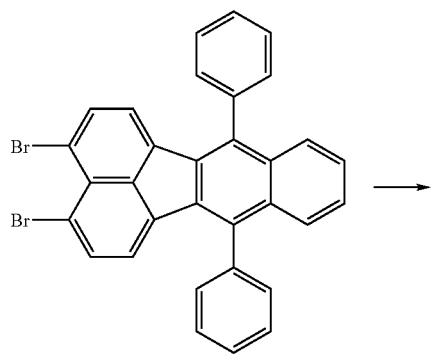

→

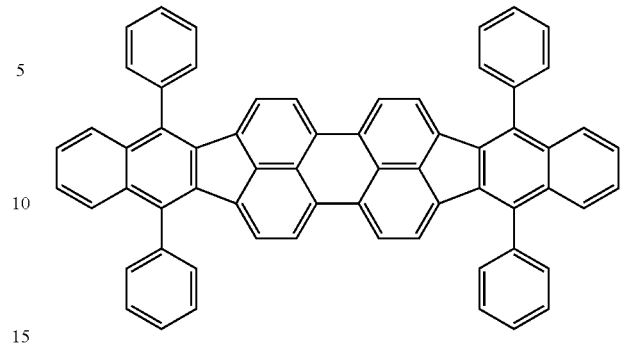

Example 3

Synthesis of dibenzotetraphenylperifuranthene

In 50 cm³ of DMF was dissolved 1.5 g (1.56E-3 mol) of 3,3'-dibromo-4,4'-bis((7,12-diphenyl)benzo[k]fluoranthene) of the formula shown below. To the solution, 0.52 g (1.9E-3 mol) of Ni(COD)$_2$, 1 ml of cyclooctadiene (COD) and 0.12 g (1.57E-3 mol) of bipyridine were added, and reaction effected at 80° C. for 12 hours.

Synthesis Example

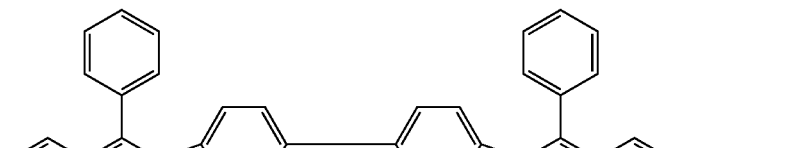

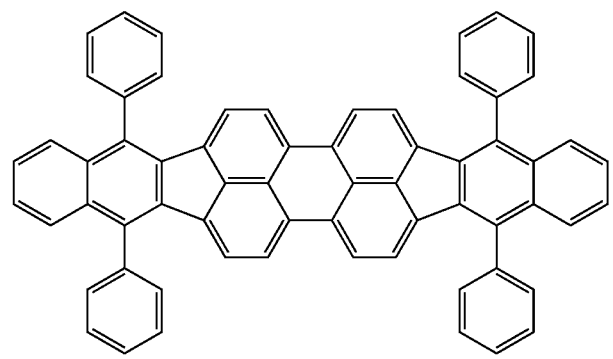

At the end of reaction, 30 cm³ of 1N aqueous hydrochloric acid and 30 cm³ of methanol were added whereby the end compound was precipitated and recovered. The end compound was isolated by silica gel chromatography (developer, toluene:hexane=1:3). There was obtained 1.1 g (90%) of a black solid.

The compound in a dichloromethane solution exhibited fluorescence peaks (EM) at a wavelength of 600 and 650 nm.

The compound in a dichloromethane solution exhibited fluorescence absorption peaks (EX) at a wavelength of 508, 546 and 591 nm.

Mass analysis: $(M+1)^+=805$

Sublimation purification temperature: 410° C.

Comparative Example

Synthesis of dibenzotetraphenylperifuranthene

A mixture of 2 g (5E-3 mol) of (7,12-diphenyl)-benzo[k]fluoranthene and 3 g (2.6E-2 mol) of cobalt fluoride (CoF₃) was suspended in 100 ml of trifluoroacetic acid, which was heated under reflux for 40 hours. At the end of reaction, the reaction solution was poured into cold water and extracted with dichloromethane. By drying over magnesium sulfate and removing the organic solvent, a black solid was obtained. It was purified by silica gel chromatography. There was obtained 1 g (50%) of a blackish purple solid.

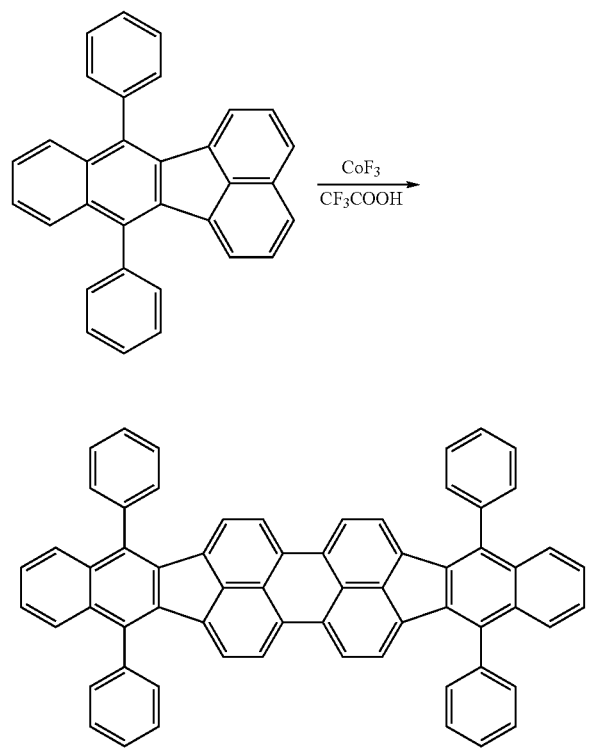

Synthesis of dibenzotetra(β-naphthyl)perifuranthene

A mixture of 2.52 g (5E-3 mol) of (7,12-bis(β-naphthyl)) benzo[k]fluoranthene and 3 g (2.6E-2 mol) of cobalt fluoride (CoF₃) was suspended in 100 ml of trifluoroacetic acid, which was heated under reflux for 40 hours. At the end of reaction, the reaction solution was poured into cold water and extracted with dichloromethane. By drying over magnesium sulfate and removing the organic solvent, a black solid was obtained. It was purified by silica gel chromatography. There was obtained 0.2 g (8%) of a blackish purple solid.

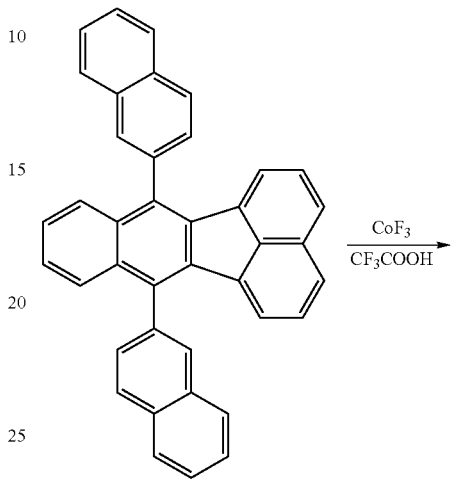

Synthesis of dibenzooctaphenylperifuranthene

A mixture of 2.79 g (5E-3 mol) of (7,9,10,12-tetraphenyl) benzo[k]fluoranthene and 3 g (2.6E-2 mol) of cobalt fluoride (CoF₃) was suspended in 100 ml of trifluoroacetic acid, which was heated under reflux for 40 hours. At the end of reaction, the reaction solution was poured into cold water and extracted with dichloromethane. By drying over magnesium sulfate and removing the organic solvent, a black solid was obtained. It was purified by silica gel chromatography. There was obtained 0.42 g (15%) of a blackish purple solid.

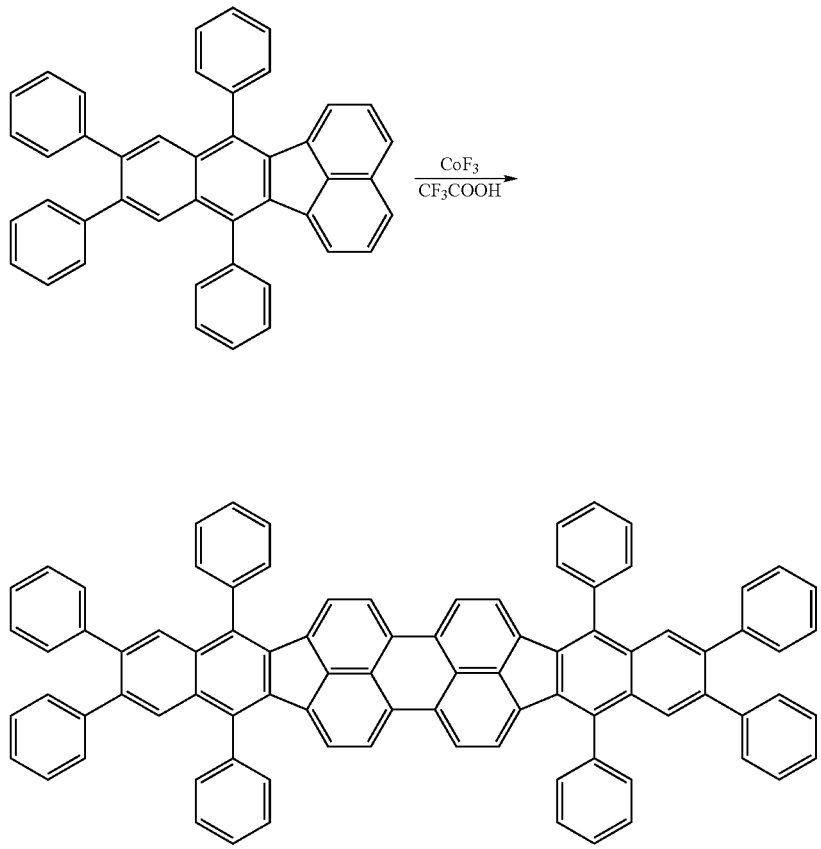

Example 4

On a glass substrate, a transparent ITO electrode thin film was deposited to a thickness of 100 nm by RF sputtering and patterned. The glass substrate having the transparent ITO electrode was subjected to ultrasonic washing with neutral detergent, acetone, and ethanol, pulled up from boiling ethanol, and dried. The transparent electrode surface was further cleaned with UV/O$_3$. Thereafter, the substrate was secured by a holder in a vacuum evaporation chamber, which was evacuated to a vacuum of $1 \times 10^{-5}$ Pa or lower.

With the vacuum kept, N,N'-diphenyl-N,N'-bis[N-(4-methylphenyl)-N-phenyl-(4-aminophenyl)]-1,1'-biphenyl-4,4'-diamine (ATP) of the structure shown below was evaporated at a deposition rate of 0.1 nm/sec. to a thickness of 50 nm, forming a hole injecting layer.

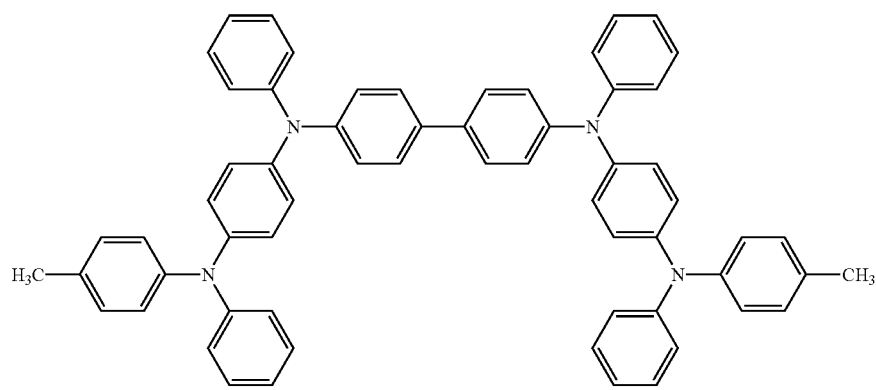

Then, N,N,N', N'-tetrakis(m-biphenyl)-1,1'-biphenyl-4,4'-diamine (TPD) of the structure shown below was evaporated at a deposition rate of 0.1 nm/sec to a thickness of 20 nm, forming a hole transporting layer.

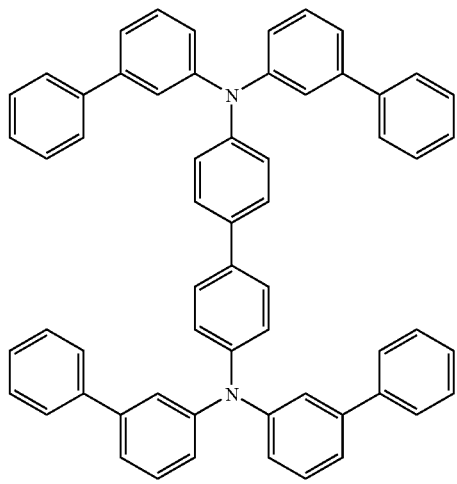

With the vacuum kept, a host material of the structure shown below and a mixture of dopants of the structure shown below were evaporated in a weight ratio of 99:1 and at an overall deposition rate of 0.1 nm/sec to a thickness of 40 nm, forming a light emitting layer.

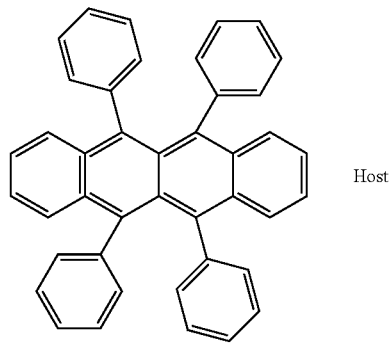
Host

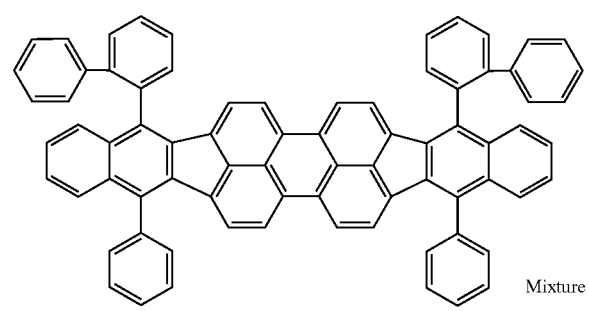
Mixture

-continued

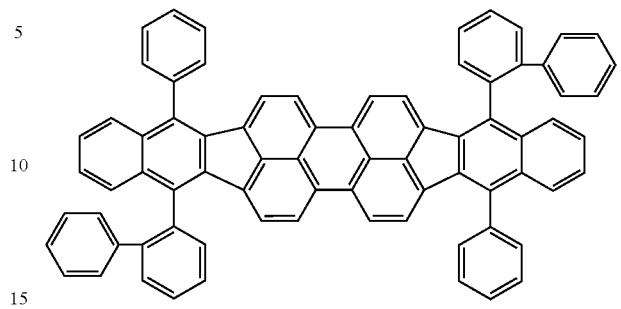

Next, with the vacuum kept, tris(8-quinolinolato)-aluminum of the structure shown below was evaporated at a deposition rate of 0.1 nm/sec to a thickness of 30 nm, forming an electron transporting laer.

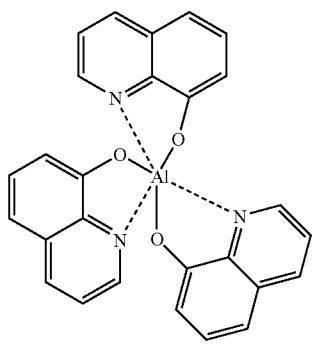

Next, with the vacuum kept, LiF was evaporated at a deposition rate of 0.01 nm/sec to a thickness of 0.3 nm, forming an electron injecting electrode. Finally, aluminum was evaporated to a thickness of 150 nm to form a protective electrode, completing an organic EL device.

A dc voltage was applied across the organic EL device. Initially, the device was found to produce light emission to a luminance of 630 cd/m$^2$ when operated at a current density of 10 mA/cm$^2$ and a drive voltage of 6.5 volts. The chromaticity coordinates (x, y) were (0.65, 0.35).

BENEFITS OF THE INVENTION

It is evident from the foregoing description that the invention provides a perylene derivative synthesis process featuring a satisfactory yield and improved preparation efficiency, perylene derivatives obtained by the process, and organic EL devices using the same.

What is claimed is:

1. A perylene derivative having a structure of the following formula (6):

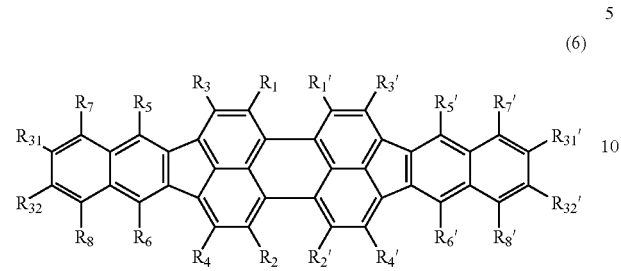

(6)

wherein $R_1$ to $R_8$, $R_{31}$ and $R_{32}$, and $R_{1'}$ to $R_{8'}$, $R_{31'}$ and $R_{32'}$, each are a hydrogen atom, a straight, branched or cyclic alkyl radical which may be substituted, a straight, branched or cyclic alkoxy radical which may be substituted, a straight, branched or cyclic alkylthio radical which may be substituted, a straight, branched or cyclic alkenyl radical which may be substituted, a straight, branched or cyclic alkenyloxy radical which may be substituted, a straight, branched or cyclic alkenylthio radical which may be substituted, a substituted or unsubstituted aralkyl radical, a substituted or unsubstituted aralkyloxy radical, a substituted or unsubstituted aralkylthio radical, a substituted or unsubstituted aryl radical, a substituted or unsubstituted aryloxy radical, a substituted or unsubstituted arylthio radical, a substituted or unsubstituted amino radical, a cyano radical, a hydroxyl radical, a —$COOM_1$ radical (wherein $M_1$ is a hydrogen atom, a straight, branched or cyclic alkyl radical which may be substituted, a straight, branched or cyclic alkenyl radical which may be substituted, a substituted or unsubstituted aralkyl radical, or a substituted or unsubstituted aryl radical), a —$COM_2$ radical (wherein $M_2$ is a hydrogen atom, a straight, branched or cyclic alkyl radical which may be substituted, a straight, branched or cyclic alkenyl radical which may be substituted, a substituted or unsubstituted aralkyl radical, a substituted or unsubstituted aryl radical, or an amino radical), or a —$OCOM_3$ radical (wherein $M_3$ is a straight, branched or cyclic alkyl radical which may be substituted, a straight, branched or cyclic alkenyl radical which may be substituted, a substituted or unsubstituted aralkyl radical, or a substituted or unsubstituted aryl radical), and at least two adjoining radicals selected from among $R_1$ to $R_8$, $R_{31}$ and $R_{32}$, and $R_{1'}$ to $R_{8'}$, $R_{31'}$ and $R_{32'}$, may bond or fuse together to form a substituted or unsubstituted carbocyclic aliphatic ring, aromatic ring or fused aromatic ring with the carbon atoms on which they substitute, wherein one of $R_5$ and $R_6$ is ortho-biphenylyl, and
wherein one of $R_{5'}$ and $R_{6'}$ is ortho-biphenylyl.

2. An organic EL device comprising a perylene derivative having a structure of the following formula:

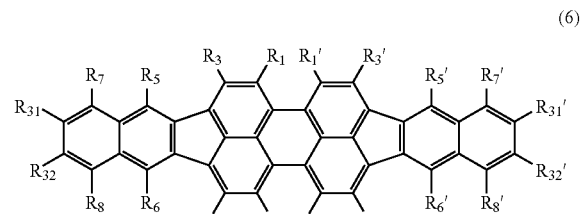

(6)

wherein $R_1$ to $R_8$, $R_{31}$ and $R_{32}$, and $R_{1'}$ to $R_{8'}$, $R_{31'}$ and $R_{32'}$, each are a hydrogen atom, a straight, branched or cyclic alkyl radical which may be substituted, a straight, branched or cyclic alkoxy radical which may be substituted, a straight, branched or cyclic alkylthio radical which may be substituted, a straight, branched or cyclic alkenyl radical which may be substituted, a straight, branched or cyclic alkenyloxy radical which may be substituted, a straight, branched or cyclic alkenylthio radical which may be substituted, a substituted or unsubstituted aralkyl radical, a substituted or unsubstituted aralkyloxy radical, a substituted or unsubstituted arlkylthio radical, a substituted or unsubstituted aryl radical, a substituted or unsubstituted aryloxy radical, a substituted or unsubstituted arylthio radical, a substituted or unsubstituted amino radical, a cyano radical, a hydroxyl radical, a —$COOM_1$ radical (wherein $M_1$ is a hydrogen atom, a straight, branched or cyclic alkyl radical which may be substituted, a straight, branched or cyclic alkenyl radical which may be substituted, a substituted or unsubstituted aralkyl radical, or a substituted or unsubstituted aryl radical), a —$COM_2$ radical (wherein $M_2$ is a hydrogen atom, a straight, branched or cyclic alkyl radical which may be substituted, a straight, branched or cyclic alkenyl radical which may be substituted, a substituted or unsubstituted arlkyl radical, a substituted or unsubstituted aryl radical, or an amino radical), or a —$OCOM_3$ radical (wherein $M_3$ is a straight, branched or cyclic akyl radical which may be substituted, a straight, branched or cyclic alkenyl radical which may be substituted, a substituted or unsubstituted aralkyl radical, or a substituted or unsubstituted aryl radical), and at least two adjoining radicals selected from among $R_1$ to $R_8$, $R_{31}$ and $R_{32}$, and $R_{1'}$ to $R_{8'}$, $R_{31'}$ and $R_{32'}$, may bond or fuse together to form a substituted or unsubstituted carbocyclic aliphatic ring, aromatic ring or fused aromatic ring with the carbon atoms on which they substitute, wherein one of $R_5$ and $R_6$ is ortho-biphenylyl, and
wherein one of $R_{5'}$ and $R_{6'}$ is ortho-biphenylyl.

* * * * *